US011555197B2

(12) United States Patent
Boddupalli et al.

(10) Patent No.: US 11,555,197 B2
(45) Date of Patent: Jan. 17, 2023

(54) CONTROL OF PHENOTYPE IN PLANTS

(71) Applicant: GREENVENUS, LLC, Davis, CA (US)

(72) Inventors: Sekhar Boddupalli, Davis, CA (US); Andrey Boukharov, Melrose, MA (US); Rio Stamler, Davis, CA (US); Zhongsen Li, Hockessin (DE); Arianne Tremblay, Davis, CA (US); Stephen Schauer, Rockville, MD (US); Shiv B. Tiwari, San Jose, CA (US); John Salmeron, Hillsborough, NC (US)

(73) Assignee: GREENVENUS, LLC, Davis, CA (US)

( * ) Notice: Subject to any disclaimer, the term of this patent is extended or adjusted under 35 U.S.C. 154(b) by 0 days.

(21) Appl. No.: 16/316,783

(22) PCT Filed: Jul. 25, 2017

(86) PCT No.: PCT/US2017/043650
§ 371 (c)(1),
(2) Date: Jan. 10, 2019

(87) PCT Pub. No.: WO2018/022574
PCT Pub. Date: Feb. 1, 2018

(65) Prior Publication Data

US 2019/0233834 A1 Aug. 1, 2019

Related U.S. Application Data

(60) Provisional application No. 62/366,402, filed on Jul. 25, 2016, provisional application No. 62/468,012, filed on Mar. 7, 2017, provisional application No. 62/467,958, filed on Mar. 7, 2017.

(51) Int. Cl.
*C12N 15/82* (2006.01)

(52) U.S. Cl.
CPC ....... *C12N 15/8217* (2013.01); *C12N 15/825* (2013.01); *C12N 15/827* (2013.01); *C12N 15/8218* (2013.01); *C12N 15/8273* (2013.01); *C12N 15/8274* (2013.01); *C12N 15/8281* (2013.01); *C12N 15/8282* (2013.01); *C12N 15/8283* (2013.01); *C12N 15/8286* (2013.01)

(58) Field of Classification Search
CPC .................................................. C12N 15/8217
USPC .......................................................... 800/290
See application file for complete search history.

(56) References Cited

U.S. PATENT DOCUMENTS 4,981,784 A 1/1991 Evans et al.
4,985,461 A 1/1991 Hsu et al.
5,117,057 A 5/1992 Hsu et al.
5,225,443 A 7/1993 Murphy et al.
5,378,726 A 1/1995 Yanagi et al.
5,530,028 A 6/1996 Lidert et al.
6,013,836 A 1/2000 Hsu et al.
6,015,709 A 1/2000 Natesan
6,117,680 A 9/2000 Natesan et al.
6,147,282 A 11/2000 Goff et al.
6,187,757 B1 2/2001 Clackson et al.
6,258,603 B1 7/2001 Carlson et al.
6,355,863 B1 3/2002 Yanofsky
6,379,945 B1 4/2002 Jepson et al.
6,479,653 B1 11/2002 Natesan et al.
6,509,152 B1 1/2003 Berlin et al.
6,649,595 B2 11/2003 Clackson et al.
6,723,531 B2 4/2004 Evans et al.
7,045,315 B2 5/2006 Evans et al.
7,091,038 B2 8/2006 Palli et al.
7,273,874 B2 9/2007 Graziani et al.
7,276,498 B2 10/2007 Graziani et al.
7,304,161 B2 12/2007 Hormann et al.
7,304,162 B2 12/2007 Hormann et al.
7,531,326 B2 5/2009 Kapitskaya et al.
7,563,879 B2 7/2009 Palli
7,601,508 B2 10/2009 Palli et al.
7,776,587 B2 8/2010 Palli et al.
7,807,417 B2 10/2010 Palli et al.
7,829,676 B2 11/2010 Zhang et al.
7,847,064 B2 * 12/2010 Beachy .............. C07K 14/4702
530/350
7,919,269 B2 4/2011 Zhang et al.
7,935,510 B2 5/2011 Palli et al.
8,021,878 B2 9/2011 Palli
8,030,067 B2 10/2011 Zhang et al.
8,076,454 B2 12/2011 Palli et al.
8,105,825 B2 1/2012 Dhadialla et al.
8,115,059 B1 * 2/2012 Palli ................... C12N 15/8216
800/288

(Continued)

FOREIGN PATENT DOCUMENTS

AU 765306 B2 9/2003
AU 2002306550 B2 10/2007

(Continued)

OTHER PUBLICATIONS

Andrés et al., "The genetic basis of flowering responses to seasonal cues," Nature Reviews Genetics 13(9):627-39 (2012).

(Continued)

*Primary Examiner* — Li Zheng

(74) *Attorney, Agent, or Firm* — Troutman Pepper Hamilton Sanders LLP (Rochester)

(57) ABSTRACT

The invention provides a compositions and methods for controlling phenotypic traits in plants. Genes of interest are placed under the control of a gene switch to allow inducible control or expression of a gene of interest "on-demand" by treatment of the plant with a chemical ligand.

16 Claims, 33 Drawing Sheets

Specification includes a Sequence Listing.

(56) References Cited

U.S. PATENT DOCUMENTS

| | | | | |
|---|---|---|---|---|
| 8,168,426 | B2 | 5/2012 | Dhadialla et al. | |
| 8,202,718 | B2 | 6/2012 | Palli et al. | |
| 8,236,556 | B2 | 8/2012 | Kapitskaya et al. | |
| 8,497,093 | B2 | 7/2013 | Palli | |
| 8,598,409 | B2 | 12/2013 | Kapitskaya et al. | |
| 2001/0044151 | A1 | 11/2001 | Carlson et al. | |
| 2002/0048792 | A1 | 4/2002 | Natesan et al. | |
| 2002/0110861 | A1 | 8/2002 | Dhadialla et al. | |
| 2002/0119521 | A1 | 8/2002 | Palli et al. | |
| 2004/0033600 | A1 | 2/2004 | Palli et al. | |
| 2004/0049037 | A1 | 3/2004 | Tice et al. | |
| 2004/0049437 | A1 | 3/2004 | Brikman et al. | |
| 2004/0096942 | A1 | 5/2004 | Kapitskaya et al. | |
| 2004/0171651 | A1 | 9/2004 | Hormann et al. | |
| 2004/0197861 | A1 | 10/2004 | Palli | |
| 2004/0235097 | A1 | 11/2004 | Zhang et al. | |
| 2005/0209283 | A1 | 9/2005 | Hormann et al. | |
| 2005/0228016 | A1 | 10/2005 | Michelotti et al. | |
| 2005/0266457 | A1 | 12/2005 | Palli et al. | |
| 2006/0014711 | A1 | 1/2006 | Evans et al. | |
| 2006/0020146 | A1 | 1/2006 | Hormann et al. | |
| 2006/0100416 | A1 | 5/2006 | Palli et al. | |
| 2007/0061912 | A1 | 3/2007 | Bisht et al. | |
| 2007/0161086 | A1 | 7/2007 | Palli et al. | |
| 2007/0298499 | A1 | 12/2007 | Beachy et al. | |
| 2009/0123441 | A1 | 5/2009 | Braughler et al. | |
| 2009/0136465 | A1 | 5/2009 | Merenick et al. | |
| 2009/0163592 | A1 | 6/2009 | Hormann et al. | |
| 2011/0212528 | A1 | 9/2011 | Palli et al. | |
| 2011/0257013 | A1 * | 10/2011 | Saijo .................... | C12N 15/827 504/187 |
| 2011/0268766 | A1 | 11/2011 | Beech et al. | |
| 2012/0167239 | A1 | 6/2012 | Palli et al. | |
| 2013/0195800 | A1 | 8/2013 | Roeth et al. | |
| 2014/0205625 | A1 | 7/2014 | Howard et al. | |
| 2014/0308247 | A1 | 10/2014 | Roeth et al. | |

FOREIGN PATENT DOCUMENTS

| | | | |
|---|---|---|---|
| AU | 2002248500 | B2 | 12/2007 |
| EP | 0234944 | B1 | 9/1987 |
| EP | 0461809 | B1 | 12/1994 |
| EP | 1266015 | B1 | 8/2006 |
| EP | 0965644 | B1 | 11/2007 |
| KR | 10-0563143 | B1 | 3/2006 |
| WO | 2002/029075 | A2 | 4/2002 |
| WO | 2001/070816 | A3 | 8/2002 |
| WO | 2002/066612 | A2 | 8/2002 |
| WO | 2002/066613 | A2 | 8/2002 |
| WO | 2002/066614 | A2 | 8/2002 |
| WO | 2002/066615 | A2 | 8/2002 |
| WO | 2003/027266 | A2 | 4/2003 |
| WO | 2003/027289 | A1 | 4/2003 |
| WO | 2004/078924 | A2 | 9/2004 |
| WO | 2005/108617 | A3 | 2/2006 |
| WO | 2009/114201 | A2 | 9/2007 |
| WO | 2008/036424 | A3 | 3/2008 |
| WO | 2009/045370 | A2 | 4/2009 |
| WO | 2009/048560 | A1 | 4/2009 |
| WO | 2010/042189 | A2 | 4/2010 |
| WO | 2010/101884 | A1 | 9/2010 |
| WO | 2008/153801 | A8 | 5/2011 |
| WO | 2011/057333 | A1 | 5/2011 |
| WO | 2011/119773 | A1 | 9/2011 |
| WO | 2012/122025 | A1 | 9/2012 |

OTHER PUBLICATIONS

Ando et al., "Twin Sister of FT, Gigantea, and Constans Have a Positive But Indirect Effect on Blue Light-Induced Stomatai Opening in Arabidopsis," Plant Physiol 162:1529 (2013).

Antoniewski et al., "The Ecdysone Response Enhancer of the Fbpl Gene of Drosophila melanogaster Is a Direct Target for the EcR/USP Nuclear Receptor," Molecular and Cellular Biology 14 (7) 4465-4474 (1994).

Auslander and Fussenegger, "From gene switches to mammalian designer cells: present and future prospects," Trends in Biotechnology 31(3):155-168 (2012).

Breaker, "Prospects for riboswitch discovery and analysis," Mol Cell 43(6):867-79 (2011).

Brent et al., "A eukaryotic transcriptional activator bearing the DNA specificity of a prokaryotic repressor," Cell 43(3):729-736 (1985).

Carlson et al., "The chemical and biological properties of methoxyfenozide, a new insecticidal ecdysteroid agonist," Pest Manag. Sci., 57(2):115-119 (2001).

Cherbas et al., "Identification of ecdysone response elements by analysis of the Drosophila Eip28/29 gene," Genes & Dev 5: 120-131 (1991).

Chiang et al., "Major flowering time gene, Flowering Locus C, regulates seed germination in *Arabidopsis thaliana*", Proceedings National Academy of Sciences, 106 (28): 11661-11666 (2009).

D'Avino et al., "The moulting hormone ecdysone is able to recognize target elements composed of direct repeats," Mol. Cell. Endocrinol. 113:1-9 (1995).

Dupont Pioneer. "Delayed Alfalfa Harvest." <http://www.pioneer.com/home/site/mobile/silage-zone/alfalfa_harvest/delayed-harvest/>. Webpage archived Nov. 12, 2015 on Archive.org.

Evans et al., "The steroid and thyroid hormone receptor superfamily," Science 240(4854):889-95 (1988).

Furth et al., "Temporal control of gene expression in transgenic mice by a tetracycline-responsive promoter," Proc. Natl. Acad. Sci. 91: 9302-9306 (1994).

Gossen et al., "Tight control of gene expression in mammalian cells by tetracycline-responsive promoters," Proc. Natl. Acad. Sci. 89(12):5547-5551 (1992).

Gossen et al., "Control of gene activity in higher eukaryotic cells by prokaryotic regulatory elements," TIBS 18(12):471-475 (1994).

Higgins et al., "Fast and sensitive multiple sequence alignments on a microcomputer," CABIOS Communications 5(2): 151-13 (1989).

International Search Report issued in PCT/US17/43650, dated Feb. 7, 2018.

Intrexon Corporation. "Intrexon's RheoSwitch® Precise Gene Expression Technology." Webpage copyright 2015, retrieved on Oct. 5, 2017 from <https://www.dna.com>.

Jung et al., "Flowering time control and applications in plant breeding," Trends Plant Sci 14(10):563-573 (2009).

Kim et al., "Design of TATA box-binding protein/zinc finger fusions for targeted Yegulation of gene expression," Proc. Natl. Acad. Sci. USA 94:3616 (1997).

Kimura et al., "A Flowering Integrator, SOC1, Affects Stomatai Opening in *Arabidopsis thaliana*," Plant Cell Physiol 56:640-649 (2015).

Li et al., "Suppression and restoration of male fertility using a transcription factor", Plant Biotechnology Journal, 5(2): 297-312 (2007).

Li et al., "Cas9-Guide RNA Directed Genome Editing in Soybean," Plant Physiology (169)2:960-970 (2015).

Mutasa-Göttens et al., "Bolting and flowering control in sugar beet: relationships and effects of gibberellin, the bolting gene B and vernalization," AoB Plants 2010:1-13 (2010).

Palli et al., "Improved ecdysone receptor-based inducible gene regulation system," Eur J Biochem 270:1308-1315 (2003).

Panguluri et al., "Functional characterization of ecdysone receptor gene switches in mammalian cells," FEBS J 273:5550-5563 (2006).

Paterson et al. "Risk of Gene Flow from Sorghum to 'Johnsongrass.'" Department of Soil and Crop Science, Texas A&M University. <http://www.nbiap.vt.edu/brarg/brasym96/paterson96.htm> Webpage archived on May 26, 2016 on Archive.org.

"Properties of Amino Acids." Jul. 30, 2020. Accessed on Apr. 12, 2021 at <https://chem.libretexts.org/@go/page/241691 >.

Reeck et al., "Homology" in proteins and nucleic acids: A terminology muddle and away out of it, Cell 50(5):667 (1987).

Sadowski et al., "GAL4-VP16 is an unusually potent transcriptional activator," Nature 335:563-564 (1988).

(56) References Cited

OTHER PUBLICATIONS

Shockett et al., "A modified tetracycline-regulated system provides autoregulatory, inducible gene expression in cultured cells and transgenic mice," Proc. Natl. Acad. Sci. 92: 6522-6526 (1995).
Sprenger-Haussels et al., "Transactivation properties of parsley proline-rich bZIP transcription factors," Plant J. 22(1):1-8 (2000).
Stotz et al., "Plant defensins: defense, development and application," Plant Signal Behav. 4(11):1010-1012 (2009).
Tavva et al., "Improvement of a monopartite ecdysone receptor gene switch and demonstration of its utility in regulation of transgene expression in plants," FEBS J 275:2161-2176 (2008).
Tiwari et al., "The Roles of Auxin Response Factor Domains in Auxin-Responsive Transcription," Plant Cell 15(2):533-543 (2003).
Tiwari et al., "Aux/IAA Proteins Contain a Potent Transcriptional Repression Domain," Plant Cell 16(2):533-543 (2004).
Tiwari et al., "The EDLL motif: a potent plant transcriptional activation domain from AP2/ERF transcription factors," The Plant Journal 70:855-865 (2012).
Upadhyay et al., "The EAR Motif Controls the Early Flowering and Senescence Phenotype Mediated by Over-Expression of S1ERF36 and Is Partly Responsible for Changes in Stomatai Density and Photosynthesis," PLOS ONE 9(7):1-9 (2014).
Wang et al., "Is genetic engineering ever going to take off in forage, turf and bioenergy crop breeding?," Annals of Botany 110:1317-1325 (2012).
Wang et al., "Bidirectional cross-kingdom RNAi and fungal uptake of external RNAs confer plant protection," Nat Plants 2(10):16151 (2016).
Weber et al., "A biotin-triggered genetic switch in mammalian cells and mice," Metabolic Engineering, 11(2):117-124 (2009).
Weber et al., "A synthetic time-delay circuit in mammalian cells and mice," Proc. Natl. Acad. Sci. U.S.A. 104, 2643-2648 (2007).
Wroblewski et al., "Optimization of Agrobacterium-mediated transient assays of gene expression in lettuce, tomato and *Arabidopsis*," Plant Biotechnol J. 3(2):259-73 (2005).
Wroblewski et al., "Silencing of the major family of NBS-LRR-encoding genes in lettuce results in the loss of multiple resistance specificities," The Plant Journal 51:803-818 (2007).
Yeoh et al., "Developing a method for customized induction of flowering," BMC Biotechnol 11:36 (2011).
Yoo et al., "Constans Activates Suppressor of Overexpression of Constans 1 through Flowering Locus T to Promote Flowering in *Arabidopsis*," Plant Physiol. 139:770-778 (2005).
Office Action for Argentina Patent Application No. 20170102086 and partial translation (dated Nov. 11, 2021).
Examination Report for Pakistan Patent Application No. 412/2017 (dated Sep. 5, 2019).

* cited by examiner

Complementation of Arabidopsis *ft* mutant late flowering phenotype

Create switchable mutations of other genes involved in flowering control

DNA construct for creating a switchable Arabidopsis *im* mutant using constitutive promoter + ligand → IM expression → normal green leaves

- Ligand → no IM expression → *im* mutant-like variegated leaves

Gene expression and flowering control using a cytotoxin gene

- Ligand → Barnase expression → no flowering

+ Ligand → Barstar expression → Barnase is inhibited > normal flowering

DNA construct for dowregulation of chalcone synthase A in petunia

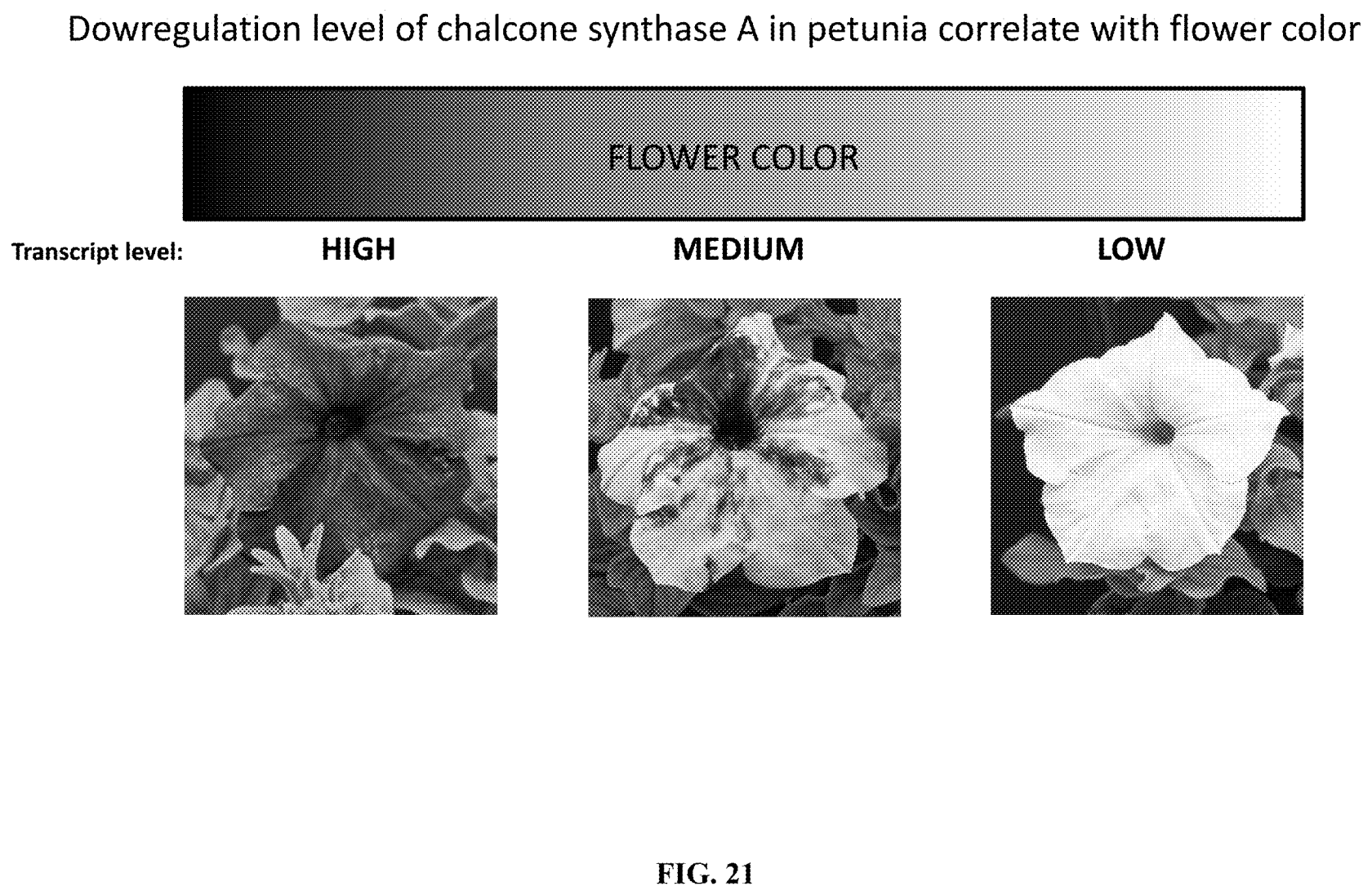

Dowregulation level of chalcone synthase A in petunia correlate with flower color

FLOWER COLOR

Transcript level: HIGH MEDIUM LOW

FIG. 21

Mtf (1mM) treated FS:ChsA RNAi plants showed a variety of flower color changes. Top row, before treatment. Bottom row, 22 days post-treatment.

Mtf (2mM) treated FS:ChsA RNAi plants showed a variety of flower color changes. Top row, before treatment. Bottom row, 6 days post-treatment.

Mtf (5mM) treated FS:ChsA RNAi plants showed a variety of flower color changes.
Top row, before treatment. Bottom row, 4 days post-treatment.

CONTROL OF PHENOTYPE IN PLANTS

This application is a national stage application under 35 U.S.C. § 371 of PCT Application No. PCT/US2017/043650, filed Jul. 25, 2017, which claims the priority benefit of U.S. Provisional Patent Application Ser. No. 62/467,958, filed Mar. 7, 2017; U.S. Provisional Patent Application Ser. No. 62/468,012, filed Mar. 7, 2017; and U.S. Provisional Patent Application Ser. No. 62/366,402, filed Jul. 25, 2016; which are hereby incorporated by reference in their entirety.

REFERENCE TO SEQUENCE LISTING

This application incorporates by reference a "Sequence Listing" (included below); this Sequence Listing is incorporated by reference in its entirety herein.

BACKGROUND OF THE INVENTION

In plants, the transition to flowering triggers global changes that can greatly influence vegetative organs in addition to initiating seed production (Andres F and Coupland G. (2012) Nature Reviews Genetics 13, 627-639). In crops harvested for vegetative tissues, flowering can lead to losses in yield or quality as plant metabolism is redirected. For example, in sugar beets high yields depend on a prolonged vegetative growing phase, and biennial varieties are bred to avoid early flowering (Mutasa-Göttens ES et al., (2010) AoB Plants, doi: 10.1093/aobpla/plq012). In alfalfa, a delay in flowering of five days can result in forage yield increase of 450 kg per acre (Dupont Pioneer: Delayed Alfalfa Harvest (URL pioneer.com/home/site/mobile/silage-zone/alfalfa harvest/delayed-harvest/). Alfalfa forage quality is also well-known to be inversely related to maturity, with Relative Feed Quality (RFQ) scores declining by five points for each day of delay in harvest after bud stage (Dupont Pioneer: Delayed Alfalfa Harvest (URL pioneer.com/home/site/mobile/silage-zone/alfalfa harvest/delayed-harvest/).

A second driver for flowering control is found in crops with high rates of out-crossing. In some cases, risks of gene flow to crop relatives have added to the cost and time requirements for development of genetically engineered (GE) varieties. For example, out-crossing to the noxious weed Johnsongrass has been a major barrier to development of GE sorghum (Paterson A H and Chandler M J, Texas A&M Soil and Crop Science (at URL nbiap.vt.edu/brarg/brasym96/paterson96.htm). Deregulation of ROUNDUP READY® herbicide-tolerant turf grass by SCOTTS MIRACLE-GRO® company took more than 10 years and only succeeded when a different molecular strategy was adopted (Wang Z-Y and Brummer CE. (2010) *Annals of Botany* doi: 10.1093/aob/mcs).

Control of seed production also has commercial implications for crops where farmer-saved seed can erode germplasm value and pose challenges to varietal stewardship. Use of a controllable flowering system would greatly reduce such risks to the seed company.

Breeders have been successful at exploiting natural variation to tailor flowering time for increased yields (Jung C and Müller A E (2009) *Trends Plant Sci.* 14: 563-573). However, as reproductive transition is still under control of the plant, there is need in the art for technology to induce flowering on demand, and the ability to "toggle" back and forth between vegetative and reproductive states. Controlled delay (inhibition) or prevention (absence) of flowering can lend the positive benefits described above. Moreover, since flowering is necessary for seed production and breeding, seed companies need the ability to restore flowering competency in non-flowering cultivars when desired.

Breeders and farmers also strive to improve or alter various traits in plants including color, aroma, sweetness, nutritional value, and many other traits. Selective cross-breeding has helped achieve desired changes over generations, but the advent of genetic engineering has led to direct control over expression or alteration of various genes in plants to achieve these ends. In most cases, however, the desired traits are expressed constitutively. They cannot be controlled over life cycle of the plant and often have some negative agronomic effects, e.g. decrease in yield or fitness, directly related to their constitutive expression.

Pest and disease protection is an important aspect of plant breeding and crop production. Various strategies have been implemented to have plants express a trait that enables them to resist infection and pests. These strategies fall in several categories: expression of proteins that promote plant innate immunity (e.g. NPR1, Defensin, flagelin); expression of proteins or RNA that disrupt pest recognition modules (disruption of sensitivity genes or plant receptors by RNAi, dsRNA or peptides), and expression of RNA or peptides that kill pests (e.g. Antimicrobial peptides, defensins, RNAi/dsRNA targeting pest genes).

In other systems, double-stranded RNA mediated post-transcriptional gene silencing is a conserved eukaryotic gene regulation mechanism, whereby dsRNA molecules are processed by a Dicer-like enzyme into dsRNA molecules 20-25 nt in length, termed siRNAs. Single stranded anti-sense RNAs derived from siRNAs associate with an RNA Induced Silencing Complex (RISC) and target homologous mRNA for degradation through the catalytic activity of Argonaut-like enzymes. This conserved gene-expression control module has been extensively exploited by scientists to uncover gene function in a multitude of organisms. In addition, there is an emerging body of evidence indicating that plant-pathogenic fungi will absorb and process exogenous dsRNA molecules resulting in gene silencing of essential endogenous genes for pathogen growth and virulence. A recent publication validates Host Induced Gene Silencing (HIGS) as a potent control strategy for generating resistance to the broad host range pathogen *Botrytis cinerea* (Wang et al. (2016) *Nature Plants* 2:16151).

However, while multiple plant genes have been identified that have direct anti-microbial activity or act as positive regulators of the innate immune system, constitutive expression of these genes typically results in a loss of fitness for the plant. Similarly, constitutive expression of dsRNA against pest genes may also burden plant growth and/or fitness. Moreover, constitutive expression of such genes can accelerate (or may lead to) development of resistance to the the plant pathogens and pests.

There is a need in the art to provide for controlled, "on-demand" expression of genes in plants which achieve desired ends while minimizing negative effects on the plants.

BRIEF SUMMARY OF THE INVENTION

The invention provides vectors and polynucleotides for controlled expression of traits in plants, plants transformed with polynucleotides to allow for controlled expression of traits and methods for making and using the same.

In some embodiments, control is exerted over a native plant gene for the trait to be controlled. In other embodiments, a plant gene is replaced with a polynucleotide used to transform the plant with control elements operatively linked to the inserted trait. In other embodiments, exogenous genes are inserted that inhibit native plant traits along with controlled genes to suppress the inhibition and inducibly restore function.

The invention provides a vector or polynucleotide comprising nucleic acids encoding:

(a) an ecdysone receptor-based (EcR-based) gene switch;

(b) a nucleic acid or protein which controls a gene of interest in a plant; and, (c) a regulatory element operably connected 5' of b), wherein the EcR-based gene switch binds said regulatory element in the presence of a chemical ligand.

The invention provides one or more vectors or polynucleotides comprising:

(a) a polynucleotide encoding an ecdysone receptor-based (EcR-based) gene switch or an ecdysone receptor-based (EcR-based) gene switch comprising a VGEvy ligand binding domain;

(b) a nucleic acid which controls a trait or traits in a plant; and, (c) a regulatory element operably connected 5' of b), wherein the gene switch induces expression of b) in the presence of a chemical ligand.

The vectors or polynucleotides may comprise genes of interest such as a gene for control or regulation of flowering, drought resistance, herbicide resistance, pest resistance, diseases resistance, type of floral color, intensity of floral color, floral aroma, accumulation of specific nutrients, fruit aroma, taste, nutritional value, or for expression of an exogenous gene.

In some cases the expression of the exogenous gene encodes a protein that has a toxic effect on the plant or imposes a metabolic burden on the plant during expression so controlled expression is desirable.

An EcR-based gene switch may have a ligand binding domain derived from *Choristoneura fumiferana* (Cf). It may also contain a heterologous (non-Cf) DNA-binding domain and a heterologous (non-Cf) transcriptional transactivation domain. In some embodiments, the DNA-binding domain is a Gal4 DNA binding domain, a LexA DNA binding domain, a transcription factor DNA binding domain, a Group H nuclear receptor DNA binding domain, a steroid/thyroid hormone nuclear receptor DNA binding domain, a bacterial LacZ DNA binding domain, an EcR DNA binding domain, an ARF DNA binding domain, a bZIP DNA binding domain, a homeodomain of a plant DNA binding domain, or a synthetic DNA binding domain. In some embodiments the transcriptional transactivation domain is a Group H nuclear receptor member transactivation domain, steroid/thyroid hormone nuclear receptor transactivation domain, synthetic or chimeric transactivation domain, polyglutamine transactivation domain, basic or acidic amino acid transactivation domain, a VP16 transactivation domain, a GAL4 transactivation domain, an NF-κB transactivation domain, a BP64 transactivation domain, a B42 acidic transactivation domain (B42AD), a p53 transactivation domain, a p65 transactivation domain (p65AD), an EDLL acidic transactivation domain from AP2/ERF, a glutamine-rich transactivation domain, an ARFs or CONSTANS proteins transactivation domain, a proline-rich transactivation domain from bZIP, or an analog, combination, or modification thereof.

In certain embodiments, the DNA-binding domain is a GAL4 transcription factor DNA-binding domain and the transcriptional transactivation domain is derived from a Simian Vacuolating Virus 40 or Simian Virus 40 (SV40) or comprises a herpes virus VP16 transcriptional transactivation domain.

In particular embodiments, the CfEcR ligand binding domain comprises one or more amino acid substitutions compared to wild-type (wt) CfEcR ligand binding domain (SEQ ID NO:19), and may comprise the polypeptide sequence of SEQ ID NO:2. An EcR-based gene switch may comprise the polypeptide sequence of SEQ ID NO:1.

For activation of the EcR-based gene switch, a chemical ligand is applied which may be a non-steroidal chemical ligand, such as, but not limited to a diacylhydrazine (DAH). An example of such a diacylhydrazine is methoxyfenozide.

The regulatory element is a recognition site for a DNA binding protein portion of an EcR-based gene switch operatively linked to a promoter.

In some embodiments, the vector or polynucleotide also has a nucleic acid sequence encoding a second gene switch and a second gene of interest. The second gene of interest is operatively linked to a second regulatory element operatively linked 5' of said second gene of interest wherein the second gene switch binds the second regulatory element in the presence of a second chemical ligand. In such embodiments, the second gene switch may be an ecdysone receptor (EcR) based gene switch, a rapamycin-based gene switch, a prokaryotic tetracycline repressor-based gene switch, a lactose repressor-operator-based gene switch, a cumate-based gene switch, or a biotin-based gene switch. The second chemical ligand may be the same or a different chemical ligand that is active for the EcR-based gene switch.

In some embodiments, the vector or polynucleotide may also have an AUX/IAA repression domain or an ERF-associated amphiphilic repression (EAR) domain.

Polynucleotides or vectors of the invention may be used to create a plant that contains these polynucleotides or vectors in which some or all of the vector or polynucleotide is integrated into the plant genome. The plant may be monocotyledonous or dicotyledonous.

The plant may be a flowering plant, a fruit or vegetable crop plant, a grain, a forage crop or a turf grass.

Examples of a fruit or vegetable crop are alfalfa sprouts, apples, apricots, artichokes, Asian pears, asparagus, atemoyas, avocados, bamboo shoots, bananas, beans, bean sprouts, beets, belgian endive, bitter melons, bell peppers, blackberries, blueberries, bok choy, boniato, boysenberries, broccoflowers, broccoli, broccolini, brussels sprouts, butter lettuce, cabbage, cantaloupe, carambola, carrots, casaba melons, cauliflower, celery, chayotes, cherimoyas, cherries, coconuts, coffee, collard greens, corn, cranberries, cucumbers, dates, eggplant, endive, escarole, feijoa, fennel, figs, garlic, gooseberries, grapefruit, grapes, green beans, green onions, collard greens, mustard greens, guava, hominy, honeydew melons, horned melons, iceberg lettuce, Jerusalem artichokes, jincama, kale, kiwifruit, kohlrabi, kumquats, leeks, lemons, lettuce, lima beans, limes, longan, loquats, lychees, madarins, malangas, marijuana, mandarin oranges, mangos, mulberries, mushrooms, napas, nectarines, okra, onions, oranges, papayas, parsnip, passion fruits, paw-paws, peaches, peanut, pears, sugar snap peas, green peas, peppers, persimmons, pineapples, plantains, plums, pomegranates, potatoes, prickly pears, pummelos, pumpkins, quince, radicchio, radishes, raspberries, red cabbage, rhubarb, romaine lettuce, rutabaga, shallots, snow peas, soybeans, spinach, sprouts, squash, strawberries, string beans, sweet potatoes, tangelo, tangerines, tomatillo, tomatoes, turnip, ugli fruit, watermelons, water chestnuts, watercress, waxed beans, yams, yellow squash, yuca/cassava, and zucchini squash.

Examples of flowering plants include, but are not limited to, African daisy, Agapanthus, Ageratum houstonianum, Alchemilla, Allium, Alyssum, Amaranthus, Amaryllis, Anemone, Angelonia, Anthurium, Artemisia, Asclepias syriaca, Aster, Astilbe, Astrantia, Aubreita deltoidea, baby's breath, bachelor button, balloon flower, bee balm, begonia, bellflower, blanketflower, Bergenia, black-eyed Susan, blanket flower, blazing star, bleeding heart, bluebell, blue-eyed grass, blue star flower, Bouvardia, Bougainvillea, broom, Buddleja, bush morning glory, buttercup, butterfly weed, butterfly bush, Calendula, California poppy, calla lily, Calliandra, Camellia, Campenula, candytuft, canna lily, cape primrose, cardinal flower, carnation, catmint, celosia, chrysanthemum, Clarkia, clover, clematis, cockscomb, columbine, coneflower, coral bells, Coreopsis, Cosmos, Cotoneaster, Crocus, creeping phlox, Crocosmia, crown imperial, cuckoo flower, Cyclamen, Dahlia, day lily, Delphinium, Echium, English bluebell, Erigeron, evening primrose, Euphorbia, flannel flower, flax flower, floss flower, forget-me-not, Forsythia, foxglove, frangipani, freesia, fuschia, gardenia, geranium, gas plant, Gaura, gayfeather, Gerbera, Gladiolus, globeflower, goldenrod, grape hyacinth, Gypsophila, heather, Hebe, Helenium, Heliotrope, Hellebore, hibiscus, hollyhock, honeysuckle, hosta, hyacinth, hydrangea, Hypericum, hardy geranium, hybrid tea roses, Iceland poppy, ice plant, Ilex, Impatiens, Ipheion uniflorum, iris, Ixia, Ixora, Jaborosa, Jacob's ladder, Jamesia americana, jasmine, Jupiter's beard, kaffir lily, Kalmia, kangaroo paw, Kerria, Knautia macedonica, Kniphofia, Kolkwitzia, lady's slipper, Lamium, Lantana, larkspur, Lavatera, lavender, Lechenaultia, lilac, lily, lily of the valley, Linaria, lisianthus, lobelia, loosestrife, lotus, lunaria, lupin, magnolia, Maltese cross, Mandevilla, Marguerite daisy, marigold, Matthiola, mayflower, Meconopsis, mimosa, Mina lobate, mock orange, monk's hood, moonflower, morning glory, Muscari, narcissus, nasturtiums, Nemesia, Nemophila, Nerine, New Guinea impatien, Nicotiana, Nierembergia, Nigella, Nolana, oleander, orchid, oriental lily, oriental poppy, Osteospermum, oyster plant, ox eye daisy, painted daisy, pansy, passion flower, peace lily, Pelargonium, Penstemon, peony, Persian buttercup, Peruvian lily, petunia, pincushion flower, pink lady's slipper, pointsettia, Polyanthus, poppy anemone, Portulaca grandiflora, Primula, Quaker ladies, Queen Anne's lace, Queen's cup, Queen of the meadow, quince, rain lily, Ranunculus, Rhododendron, rock rose, Rondeletia, rose, rose of Sharon, Salvia splendens, Saponaria, Scabiosa, Scaevola, scented geranium, Scilla, Sedum, shasta daisy, shrub roses, Silene, silver lace vine, snapdragon, snowball bush, snowdrop, snowflake, statice, strawflower, sun drop, sunflower, sweet pea, Syringa, tea rose, tiger flower, tiger lily, Tithonia, Trillium, Triteleia, Tritonia crocata, trumpet vine, tuberose, tulip, urn plant, Ursinia, Uva ursi, Verbena, Veronica incana, Vinca, Viola tri-colour, Violet, Virginia creeper, wallflower, wandflower, water lily, Watsonia, wax plant, Wedelia, Weigela, wild rose, wild violet, winter aconite, winterberry, winter jasmine, wishbone flower, wisteria, wooly violet, Xerophyllum, Xylobium, Xylosma, yarrow, yellow angel, yellow bell, yellow-eyed grass, yellowhorn, Zenobia, and zinnia.

Examples of grains are barley, buckwheat, bulgur wheat, corn, durum wheat, einkorn, emmer, farro, fonio, kamut, millet, oats, rice, rye, semolina wheat, sorghum, spelt, teff, triticale, wheat, bamboo shoots, barleygrass, lemongrass, molasses, rapadura, sugarcane, wheatgrass, Amaranth, Coxcomb, pitseed goosefoot, quinoa, chia, acacia seed, and wattleseed.

Examples of turf grasses are Kentucky bluegrass, perennial ryegrass, tall fescue, fine fescue, creeping bentgrass, creeping red fescue, hard fescue, chewings fescue, Bermudagrass, buffalograss, kikuyugrass, St. Augustine, and zoysia.

The invention also provides a vector or polynucleotide comprising nucleic acids encoding:

(a) an ecdysone receptor-based (EcR-based) gene switch;

(b) a nucleic acid or protein which controls flowering in plants; and, (c) a regulatory element 5' of b), wherein the EcR-based gene switch binds the regulatory element in the presence of a chemical ligand.

The invention also provides one or more vectors or polynucleotides comprising:

(a) a polynucleotide encoding an ecdysone receptor-based (EcR-based) gene switch or an ecdysone receptor-based (EcR-based) gene switch comprising a VGEvy ligand binding domain;

(b) a nucleic acid which controls flowering in plants; and, (c) a regulatory element 5' of b), wherein said gene switch induces expression of b) in the presence of a chemical ligand.

In some embodiments, the nucleic acid or protein that controls flowering is Gigantea (GI), Nuclear Factor Y (NFY), Constans (CO); protein farnesyltransferase (PFT), Agamous-Like 15 (AGL15), Flowering Locus (FT); Twin Sister of FT (TSF), bZIP transcription factor (FD), Flowering Locus T, Apetalal (AP1), Suppressor of Overexpression of CO1 (SOC1), Agamous-Like 24 (AGL24); Leafy (LFY), or Squamosa Promoter Binding Protein-Like 3a (SPL3). In particular embodiments, the nucleic acid or protein that controls flowering is the Flowering T Locus (FT).

An EcR-based gene switch may have a ligand binding domain derived from *Choristoneura fumiferana* (Cf). It may also contain a heterologous (non-Cf) DNA-binding domain and a heterologous (non-Cf) transcriptional transactivation domain. In some embodiments, the DNA-binding domain is a Gal4 binding DNA binding domain, a LexA DNA binding domain, a transcription factor DNA binding domain, a Group H nuclear receptor DNA binding domain, a steroid/thyroid hormone nuclear receptor DNA binding domain, a bacterial LacZ DNA binding domain, an EcR DNA binding domain, an ARF DNA binding domain, a bZIP DNA binding domain, a homeodomain of a plant DNA binding domain, or a synthetic DNA binding domain. In some embodiments the transcriptional transactivation domain is a Group H nuclear receptor member transactivation domain, steroid/thyroid hormone nuclear receptor transactivation domain, synthetic or chimeric transactivation domain, polyglutamine transactivation domain, basic or acidic amino acid transactivation domain, a VP16 transactivation domain, a GAL4 transactivation domain, an NF-κB transactivation domain, a BP64 transactivation domain, a B42 acidic transactivation domain (B42AD), p53 transactivation domain, a p65 transtransactivation domain (p65AD), an EDLL acidic transactivation domain from AP2/ERF, a glutamine-rich transactivation domain, an ARFs or CONSTANS proteins transactivation domain, a proline-rich transactivation domain from bZIP or an analog, combination, or modification thereof.

In certain embodiments, the DNA-binding domain is a GAL4 transcription factor DNA-binding domain and the transcriptional transactivation domain is derived from a Simian Vacuolating Virus 40 (SV40) or comprises a herpes virus VP16 transcriptional transactivation domain.

In particular embodiments, the CfEcR ligand binding domain comprises one or more amino acid substitutions compared to wild-type (wt) CfEcR ligand binding domain (SEQ ID NO:19), and may comprise the polypeptide sequence of SEQ ID NO:2. The EcR-based gene switch may comprise the polypeptide sequence of SEQ ID NO:1.

For activation of the EcR-based gene switch, a chemical ligand is applied which may be a non-steroidal chemical ligand, such as, but not limited to a diacylhydrazine. An example of such a diacylhydrazine is methoxyfenozide.

The regulatory element is a recognition site for a DNA binding protein portion of the EcR-based gene switch operatively linked to a promoter. In certain embodiments, the promoter is from a plant gene responsible for flowering. Examples of promoters that may be used include, but are not limited to, promoters for the genes APETALA1 (AP1), LEAFY (LFY), *Arabidopsis thaliana* FLOWERING PROMOTING FACTOR 1 (AtFPF1), UNUSUAL FLORAL ORGANS (UFO), TERMINAL FLOWER 1 (TFL1), SHOOT MERISTEMLESS (STM), upstream region of the HISTONE H4 (H4A748), *Arabidopsis thaliana* TRANSLATIONALLY CONTROLLED TUMOR PROTEIN (AtTCTP), or chlorophyll a/b binding protein.

In some embodiments, the vector or polynucleotide also has a nucleic acid sequence encoding a second gene switch and a second gene of interest. The second gene of interest is operatively linked to a second regulatory element operatively linked 5' of said second gene of interest wherein the second gene switch binds the second regulatory element in the presence of a second chemical ligand. In such embodiments, the second gene switch may be an ecdysone receptor (EcR) based gene switch, a rapamycin-based gene switch, a prokaryotic tetracycline repressor-based gene switch, a lactose repressor-operator-based gene switch, a cumate-based gene switch, or a biotin-based gene switch. The second chemical ligand may be the same or a different chemical ligand that is active for the EcR-based gene switch.

In some embodiments, the vector or polynucleotide may also have an AUX/IAA repression domain or an ERF-associated amphiphilic repression (EAR) domain.

The polynucleotides or vectors may be used to create a plant that contains these polynucleotides or vectors in which some or all of the vector or polynucleotide is integrated into the plant genome. The plant may be monocotyledonous or dictyledonous.

The invention also provides a vector or polynucleotide comprising nucleic acids encoding:

(a) an ecdysone receptor-based (EcR-based) gene switch;

(b) a protein or an RNA that inhibits a plant pathogen; and, (c) a regulatory element, wherein said EcR-based gene switch binds said regulatory element in the presence of a chemical ligand.

The invention also provides one or more vectors or polynucleotides comprising:

(a) a polynucleotide encoding an ecdysone receptor-based (EcR-based) gene switch or an ecdysone receptor-based (EcR-based) gene switch comprising a VGEvy ligand binding domain;

(b) a protein or an RNA that inhibits a plant pathogen; and, (c) a regulatory element, wherein said gene switch binds induces expression of b) in the presence of a chemical ligand.

The EcR-based gene switch may have a ligand binding domain derived from the *Choristoneura fumiferana* (Cf) EcR. It may also contain a heterologous (non-Cf) DNA-binding domain and a heterologous (non-Cf) transcriptional transactivation domain. In some embodiments, the DNA-binding domain is a Gal4 DNA binding domain, a LexA DNA binding domain, a transcription factor DNA binding domain, a Group H nuclear receptor DNA binding domain, a steroid/thyroid hormone nuclear receptor DNA binding domain, a bacterial LacZ DNA binding domain, an EcR DNA binding domain, an ARF DNA binding domain, a bZIP DNA binding domain, a homeodomain of a plant DNA binding domain, or a synthetic DNA binding domain. In some embodiments the transcriptional transactivation domain is a Group H nuclear receptor member transactivation domain, steroid/thyroid hormone nuclear receptor transactivation domain, synthetic or chimeric transactivation domain, polyglutamine transactivation domain, basic or acidic amino acid transactivation domain, a VP16 transactivation domain, a GAL4 transactivation domain, an NF-κB transactivation domain, a BP64 transactivation domain, a B42 acidic transactivation domain (B42AD), a p53 transactivation domain, a p65 transactivation domain (p65AD), an EDLL acidic transactivation domain from AP2/ERF, a glutamine-rich transactivation domain ARFs or CONSTANS proteins transactivation domain, a proline-rich transactivation domain from bZIP or an analog, combination, or modification thereof.

In certain embodiments, the DNA-binding domain is a GAL4 transcription factor DNA-binding domain and the transcriptional transactivation domain is derived from a Simian Vacuolating Virus 40 (SV40) or comprises a herpes virus VP16 transcriptional transactivation domain.

In particular embodiments, the CfEcR ligand binding domain comprises one or more amino acid substitutions compared to wild-type (wt) CfEcR ligand binding domain (SEQ ID NO:19), and may comprise the polypeptide sequence of SEQ ID NO:2. The EcR-based gene switch may comprise the polypeptide sequence of SEQ ID NO:1.

For activation of the EcR-based gene switch, a chemical ligand is applied which may be a non-steroidal chemical ligand, such as, but not limited to a diacylhydrazine. An example of such a diacylhydrazine is methoxyfenozide.

The regulatory element is a recognition site for a DNA binding protein portion of the EcR-based gene switch operatively linked to a promoter.

In some embodiments, the vector or polynucleotide also has a nucleic acid sequence encoding a second gene switch and a second gene of interest. The second gene of interest is operatively linked to a second regulatory element operatively linked 5' of said second gene of interest wherein the second gene switch binds the second regulatory element in the presence of a second chemical ligand. In such embodiments, the second gene switch may be an ecdysone receptor (EcR) based gene switch, a rapamycin-based gene switch, a prokaryotic tetracycline repressor-based gene switch, a lactose repressor-operator-based gene switch, a cumate-based gene switch, or a biotin-based gene switch. The second chemical ligand may be the same or a different chemical ligand that is active for the EcR-based gene switch.

In some embodiments, the vector or polynucleotide may also have an AUX/IAA repression domain or an ERF-associated amphiphilic repression (EAR) domain.

In some embodiments, the protein or RNA that inhibits a plant pathogen is a defensin family protein, including, but not limited to, a Defensin, a Snakin, a Hevein, a Thionin, a Lipid Transfer Protein, a Cyclotides, a Shepherins, an MBP-1, Vicilin-like peptide, an Impatiens family peptide, a Beta-Barrelin or a Knottin. Examples of proteins in the defensin family include Ah-AMP1, AX1, AX2, At-AFP1 (LCR67), AFP2B, Psd1, Psd2, J1-1, J1-2, Tk-AMP-D1, Tk-AMP-D1.1, Tk-AMP-D2, Tk-AMP-D3, Tk-AMP-D4, Tk-AMP-D5, Tk-AMP-D6, Tk-AMP-D6.1, Tm-AMP-D1.2, PhD1, PhD2, NaD1, MsDef1, MtDef2, MtDef4, MtDef5, Rs-AFP1, Rs-AFP2, Sa-AFP2, VrD1, Snakin-1 (StSN1), Snakin-2 (StSN2), AC-AMP1, AC-AMP2, Ar-AMP, EAFP1, EAFP2, Ee-CBP, Fa-AMP1, Fa-AMP2, IWF4, PN-AMP1, PN-AMP2, WjAMP1, Alpha-1-Purothionin, Alpha-2-Purothionin, Alpha-hordothionin, Beta-hordothjionin, BTH6, Pp-AMP1, Pp-AMP2, Tu-AMP-1, Tu-AMP2, VtA3, VtB, La-LTP (LJAFP), Ace-AMP1, Hy-LTP Cw-18 (PKG2316), Hy-LTP4.1 (LTP4.1)(CW21), IWF1 (Bv-LTP1), IWF2 (Bv-LTP2), Pa-LTP1, Circulin-A, Circulin-B, Cyclopsychotride-A, Kalata-B1, MiAMP2, MiAMP2b, MiAMP2c-1, MiAMP2c-2, MiAMP2c-3, MiAMP2d, Ib-AMP1, Ib-AMP2, Ib-AMP3, Ib-AMP4, MiAMP1 MJ-AMP1, MJ-AMP2, Mc-AMP1, and Pa-AMP1 (PAFP-S).

In some embodiments, the plant pathogen is a virus, a fungus, a bacterium, or an insect.

Examples of plant viruses include, but are not limited to, Tobacco mosaic virus, Tomato spotted wilt virus, Tomato yellow leaf curl virus, Cucumber mosaic virus, Potato virus Y, Cauliflower mosaic virus, African cassava mosaic virus, Plum pox virus, Brome mosaic virus, Potato virus X, Citrus tristeza virus, Barley yellow dwarf virus, Potato leafroll virus and Tomato bushy stunt virus.

Examples of fungal pathogens include, but are not limited to, *Alternaria, Botrytis, Fusarium, Pyricularia, Verticillium, Aspergillus, Saccharomyces, Trichophyton, Cercospora, Cladosporium, Leptosphaeria, Penicillium, Trichoderma, Septoria; Plectosphaerella, Colletotrichum, Bipolaris, Ascochyta, Phytophthora, Gibberella, Mycosphaerella, Neurospora, Phoma, Pythium, Rhizoctonia, Helinthosporium, Geotrichum, Sclerotinia, Clavibacter, Pyrenopkora, Nectria; Candida; Cryptococcus, Ceratocystis, Chalara*, and *Venturia*. In certain preferred embodiments, the pathogen is *Botrytis cinerea*.

Examples of bacterial pathogens include, but are not limited to, *Bacillus, Enterococcus, Staphylococcus, Clavibacter, Ralstonia, Listeria, Rhizobium, Erwinia, Escherichia, Pseudomonas, Agrobacterium, Sarcina, Ralstonia, Micrococcus, Proteus, Klebsiella, Salmonella, Serratia; Streptococcus*, and *Xanthomonas*. In certain preferred embodiments, the bacterial pathogen is *Erwinia amylovora*.

Examples of insect pathogens include, but are not limited to, *Spodoptera* and *Helicoverpa*. In certain preferred embodiments, the insect pathogen is *Spodoptera frugiperda*.

In some embodiments, the RNA has sufficient self-homology to form a double-stranded RNA (dsRNA). Such dsRNAs inhibit a gene of the virus, fungus, bacterium or insect such that the plant is resistant to the detrimental effects of the pathogen.

The invention also provides a vector or polynucleotide comprising nucleic acids encoding:

(a) a gene switch;

(b) a *Bacillus amyloliquefaciens* Barstar protein;

(c) a *Bacillus amyloliquefaciens* barnase ribonuclease; and (d) a regulatory element 5' of (b), wherein said gene switch binds said regulatory element in the presence of a chemical ligand.

The invention also provides one or more vectors or polynucleotides comprising nucleic acids encoding:

(a) a gene switch;

(b) a *Bacillus amyloliquefaciens* Barstar protein;

(c) a *Bacillus amyloliquefaciens* barnase ribonuclease; and (d) a regulatory element 5' of (b), wherein said gene switch induces expression of b) in the presence of a chemical ligand.

The invention also provides one or more vectors or polynucleotides comprising nucleic acids encoding:

(a) an EcR-based gene switch or an EcR-based gene switch comprising a VGEvy ligand binding domain;

(b) a *Bacillus amyloliquefaciens* Barstar protein;

(c) a *Bacillus amyloliquefaciens* barnase ribonuclease; and (d) a regulatory element 5' of (b), wherein said gene switch induces expression of b) in the presence of a chemical ligand.

In some embodiments, barnase is operatively linked to a plant promoter of a plant gene of interest to suppress expression of said plant gene of interest, such as, but not limited to a gene for flowering, drought resistance, herbicide resistance, pest resistance, diseases resistance, type of floral color, intensity of floral color, floral aroma, accumulation of specific nutrients, nutritional value, or for expression of an exogenous gene. In certain embodiments, the promoters provide tissue-specific expression such as in flower-specific expression. Examples of such plant promoters for tissue-specific expression in flower tissue include, but are not limited to, the promoters of plant genes such as, but not limited to APETALA1 (AP1), LEAFY (LFY), *Arabidopsis thaliana* FLOWERING PROMOTING FACTOR 1 (AtFPF1), UNUSUAL FLORAL ORGANS (UFO), TERMINAL FLOWER 1 (TFL1), SHOOT MERISTEMLESS (STM), upstream region of the HISTONE H4 (H4A748), *Arabidopsis thaliana* TRANSLATIONALLY CONTROLLED TUMOR PROTEIN (AtTCTP), and chlorophyll a/b binding protein.

In these embodiments of the invention, the gene switch may be an ecdysone receptor (EcR) based gene switch, a rapamycin-based gene switch, a prokaryotic tetracycline repressor-based gene switch, a lactose repressor-operator-based gene switch, a cumate-based gene switch, or a biotin-based gene switch. In certain embodiments, the gene switch is an ecdysone receptor (EcR)-based gene switch.

The gene switch may have a ligand binding domain derived from *Choristoneura fumiferana* (Cf) EcR. It may also contain a heterologous (non-Cf) DNA-binding domain and a heterologous (non-Cf) transcriptional transactivation domain. In some embodiments, the DNA-binding domain is a Gal4 binding DNA domain, a LexA DNA binding domain, a transcription factor DNA binding domain, a Group H nuclear receptor DNA binding domain, a steroid/thyroid hormone nuclear receptor DNA binding domain, a bacterial LacZ DNA binding domain, an EcR DNA binding domain, an ARF DNA binding domain, a bZIP DNA binding domain, a homeodomain of a plant DNA binding domain, or a synthetic DNA binding domain. In some embodiments the transcriptional transactivation domain is a Group H nuclear receptor member transactivation domain, steroid/thyroid hormone nuclear receptor transactivation domain, synthetic or chimeric transactivation domain, polyglutamine transactivation domain, basic or acidic amino acid transactivation domain, a VP16 transactivation domain, a GAL4 transactivation domain, an NF-κB transactivation domain, a BP64 transactivation domain, a B42 acidic transactivation domain (B42AD), a p65 transactivation domain (p65AD), an EDLL acidic transactivation domain from AP2/ERF, a glutamine-rich transactivation domain, an ARFs or CONSTANS proteins transactivation domain, a proline-rich transactivation domain from bZIP or an analog, combination, or modification thereof.

In certain embodiments, the DNA-binding domain is a GAL4 transcription factor DNA-binding domain and the transcriptional transactivation domain is derived from a Simian Vacuolating Virus 40 (SV40) or comprises a herpes virus VP16 transcriptional transactivation domain.

In particular embodiments, the gene switch is an EcR-based gene switch having a ligand binding domain derived from *Choristoneura fumiferana* (Cf). CfEcR ligand binding domain may comprise one or more amino acid substitutions compared to wild-type (wt) CfEcR ligand binding domain (SEQ ID NO:19), and may comprise the polypeptide sequence of SEQ ID NO:2. The EcR-based gene switch may comprise the polypeptide sequence of SEQ ID NO:1.

For activation of the EcR-based gene switch, a chemical ligand is applied. Such chemical ligands may be, for example, a non-steroidal chemical ligand, such as, but not limited to a diacylhydrazine. An example of such a diacylhydrazine is methoxyfenozide.

The regulatory element may be a recognition site for a DNA binding protein portion of the EcR-based gene switch operatively linked to a promoter.

In some embodiments, the vector or polynucleotide also has a nucleic acid sequence encoding a second gene switch and a second gene of interest. The second gene of interest is operatively linked to a second regulatory element operatively linked 5' of said second gene of interest wherein the second gene switch binds the second regulatory element in the presence of a second chemical ligand. In such embodiments, the second gene switch may be an ecdysone receptor (EcR) based gene switch, a rapamycin-based gene switch, a prokaryotic tetracycline repressor-based gene switch, a lactose repressor-operator-based gene switch, a cumate-based gene switch, or a biotin-based gene switch. The second chemical ligand may be the same or a different chemical ligand that is active for the EcR-based gene switch.

In some embodiments, the vector or polynucleotide may also have an AUX/IAA repression domain or an ERF-associated amphiphilic repression (EAR) domain.

The polynucleotides or vectors may be used to create a plant that contains these polynucleotides or vectors in which some or all of the vector or polynucleotide is integrated into the plant genome. The plant may be monocotyledonous or dictyledonous.

The plant may be a flowering plant, a fruit or vegetable crop plant, a grain, or a turf grass.

Examples of a fruit or vegetable crop are alfalfa sprouts, apples, apricots, artichokes, Asian pears, asparagus, atemoyas, avocados, bamboo shoots, bananas, beans, bean sprouts, beets, belgian endive, bitter melons, bell peppers, blackberries, blueberries, bok choy, boniato, boysenberries, broccoflowers, broccoli, broccolini, brussels sprouts, butter lettuce, cabbage, cantaloupe, carambola, carrots, casaba melons, cauliflower, celery, chayotes, cherimoyas, cherries, coconuts, coffee, collard greens, corn, cranberries, cucumbers, dates, eggplant, endive, escarole, feijoa, fennel, figs, garlic, gooseberries, grapefruit, grapes, green beans, green onions, collard greens, mustard greens, guava, hominy, honeydew melons, horned melons, iceberg lettuce, Jerusalem artichokes, jincama, kale, kiwifruit, kohlrabi, kumquats, leeks, lemons, lettuce, lima beans, limes, longan, loquats, lychees, madarins, malangas, marijuana, mandarin oranges, mangos, mulberries, mushrooms, napas, nectarines, okra, onions, oranges, papayas, parsnip, passion fruits, paw-paws, peaches, peanut, pears, sugar snap peas, green peas, peppers, persimmons, pineapples, plantains, plums, pomegranates, potatoes, prickly pears, pummelos, pumpkins, quince, radicchio, radishes, raspberries, red cabbage, rhubarb, romaine lettuce, rutabaga, shallots, snow peas, soybeans, spinach, sprouts, squash, strawberries, string beans, sweet potatoes, tangelo, tangerines, tomatillo, tomatoes, turnip, ugli fruit, watermelons, water chestnuts, watercress, waxed beans, yams, yellow squash, yuca/cassava, and zucchini squash.

Examples of flowering plant include, but are not limited to, African daisy, Agapanthus, Ageratum houstonianum, Alchemilla, Allium, Alyssum, Amaranthus, Amaryllis, Anemone, Angelonia, Anthurium, Artemisia, Asclepias syriaca, Aster, Astilbe, Astrantia, Aubreita deltoidea, baby's breath, bachelor button, balloon flower, bee balm, begonia, bellflower, blanketflower, Bergenia, black-eyed Susan, blanket flower, blazing star, bleeding heart, bluebell, blue-eyed grass, blue star flower, Bouvardia, Bougainvillea, broom, Buddleja, bush morning glory, buttercup, butterfly weed, butterfly bush, Calendula, California poppy, calla lily, Calliandra, Camellia, Campenula, candytuft, canna lily, cape primrose, cardinal flower, carnation, catmint, celosia, chrysanthemum, Clarkia, clover, clematis, cockscomb, columbine, coneflower, coral bells, Coreopsis, Cosmos, Cotoneaster, Crocus, creeping phlox, Crocosmia, crown imperial, cuckoo flower, Cyclamen, Dahlia, day lily, Delphinium, Echium, English bluebell, Erigeron, evening primrose, Euphorbia, flannel flower, flax flower, floss flower, forget-me-not, Forsythia, foxglove, frangipani, freesia, fuschia, gardenia, geranium, gas plant, Gaura, gayfeather, Gerbera, Gladiolus, globeflower, goldenrod, grape hyacinth, Gypsophila, heather, Hebe, Helenium, Heliotrope, Hellebore, hibiscus, hollyhock, honeysuckle, hosta, hyacinth, hydrangea, Hypericum, hardy geranium, hybrid tea roses, Iceland poppy, ice plant, Ilex, Impatiens, Ipheion uniflorum, iris, Ixia, Ixora, Jaborosa, Jacob's ladder, Jamesia americana, jasmine, Jupiter's beard, kaffir lily, Kalmia, kangaroo paw, Kerria, Knautia macedonica, Kniphofia, Kolkwitzia, lady's slipper, Lamium, Lantana, larkspur, Lavatera, lavender, Lechenaultia, lilac, lily, lily of the valley, Linaria, lisianthus, lobelia, loosestrife, lotus, lunaria, lupin, magnolia, Maltese cross, Mandevilla, Marguerite daisy, marigold, Matthiola, mayflower, Meconopsis, mimosa, Mina lobate, mock orange, monk's hood, moonflower, morning glory, Muscari, narcissus, nasturtiums, Nemesia, Nemophila, Nerine, New Guinea impatien, Nicotiana, Nierembergia, Nigella, Nolana, oleander, orchid, oriental lily, oriental poppy, Osteospermum, oyster plant, ox eye daisy, painted daisy, pansy, passion flower, peace lily, Pelargonium, Penstemon, peony, Persian buttercup, Peruvian lily, petunia, pincushion flower, pink lady's slipper, pointsettia, Polyanthus, poppy anemone, Portulaca grandiflora, Primula, Quaker ladies, Queen Anne's lace, Queen's cup, Queen of the meadow, quince, rain lily, Ranunculus, Rhododendron, rock rose, Rondeletia, rose, rose of Sharon, Salvia splendens, Saponaria, Scabiosa, Scaevola, scented geranium, Scilla, Sedum, shasta daisy, shrub roses, Silene, silver lace vine, snapdragon, snowball bush, snowdrop, snowflake, statice, strawflower, sun drop, sunflower, sweet pea, Syringa, tea rose, tiger flower, tiger lily, Tithonia, Trillium, Triteleia, Tritonia crocata, trumpet vine, tuberose, tulip, urn plant, Ursinia, Uva ursi, Verbena, Veronica incana, Vinca, Viola tri-colour, Violet, Virginia creeper, wallflower, wandflower, water lily, Watsonia, wax plant, Wedelia, Weigela, wild rose, wild violet, winter aconite, winterberry, winter jasmine, wishbone flower, wisteria, wooly violet, Xerophyllum, Xylobium, Xylosma, yarrow, yellow angel, yellow bell, yellow-eyed grass, yellowhorn, Zenobia, and zinnia.

Examples of grain are barley, buckwheat, bulgur wheat, corn, durum wheat, einkorn, emmer, farro, fonio, kamut, millet, oats, rice, rye, semolina wheat, sorghum, spelt, teff, triticale, wheat, bamboo shoots, barleygrass, lemongrass, molasses, rapadura, sugarcane, wheatgrass, Amaranth, Coxcomb, pitseed goosefoot, quinoa, chia, acacia seed, and wattleseed.

Examples of turf grass are Kentucky bluegrass, perennial ryegrass, tall fescue, fine fescue, creeping bentgrass, creeping red fescue, hard fescue, chewings fescue, Bermudagrass, buffalograss, kikuyugrass, St. Augustine, and zoysia.

The invention also provides a vector or polynucleotide comprising nucleic acids encoding:

(a) an ecdysone receptor-based (EcR-based) gene switch;

(b) an immutans variegation mutant (IM); and, (c) a regulatory element 5' of b), wherein said EcR-based gene switch binds said regulatory element in the presence of a chemical ligand.

The invention also provides one or more vectors or polynucleotides comprising:

a) a polynucleotide encoding an ecdysone receptor-based (EcR-based) gene switch or an ecdysone receptor-based (EcR-based) gene switch comprising a VGEvy ligand binding domain;

b) an immutans variegation mutant (IM) nucleic acid; and, c) a regulatory element 5' of b), wherein said gene switch induces expression of b) in the presence of a chemical ligand The EcR-based gene switch may have a ligand binding domain derived from *Choristoneura fumiferana* (Cf) EcR. It may also contain a heterologous (non-Cf) DNA-binding domain and a heterologous (non-Cf) transcriptional transactivation domain. In some embodiments, the DNA-binding domain is a Gal4 DNA binding domain, a LexA DNA binding domain, a transcription factor DNA binding domain, a Group H nuclear receptor DNA binding domain, a steroid/thyroid hormone nuclear receptor DNA binding domain, a bacterial LacZ DNA binding domain, an EcR DNA binding domain, an ARF DNA binding domain, a bZIP DNA binding domain, a homeodomain of a plant DNA binding domain, or a synthetic DNA binding domain. In some embodiments the transcriptional transactivation domain is a Group H nuclear receptor member transactivation domain, steroid/thyroid hormone nuclear receptor transactivation domain, synthetic or chimeric transactivation domain, polyglutamine transactivation domain, basic or acidic amino acid transactivation domain, a VP16 transactivation domain, a GAL4 transactivation domain, an NF-κB transactivation domain, a BP64 transactivation domain, a B42 acidic transactivation domain (B42AD), a p53 transactivation domain, a p65 transactivation domain (p65AD), an EDLL acidic transactivation domain from AP2/ERF, a glutamine-rich transactivation domain, an ARFs or CONSTANS proteins transactivation domain, a proline-rich transactivation domain from bZIP or an analog, combination, or modification thereof.

In certain embodiments, the DNA-binding domain is a GAL4 transcription factor DNA-binding domain and the transcriptional transactivation domain is derived from a Simian Vacuolating Virus 40 (SV40) or comprises a herpes virus VP16 transcriptional transactivation domain.

In particular embodiments, the CfEcR ligand binding domain comprises one or more amino acid substitutions compared to wild-type (wt) CfEcR ligand binding domain (SEQ ID NO:19), and may comprise the polypeptide sequence of SEQ ID NO:2. The EcR-based gene switch may comprise the polypeptide sequence of SEQ ID NO:1.

For activation of the EcR-based gene switch, a chemical ligand is applied which may be a non-steroidal chemical ligand, such as, but not limited to a diacylhydrazine. An example of such a diacylhydrazine is methoxyfenozide.

The regulatory element is a recognition site for a DNA binding protein portion of the EcR-based gene switch operatively linked to a promoter.

In some embodiments, the vector or polynucleotide also has a nucleic acid sequence encoding a second gene switch and a second gene of interest. Thesecond gene of interest is operatively linked to a second regulatory element operatively linked 5' of said second gene of interest wherein the second gene switch binds the second regulatory element in the presence of a second chemical ligand. In such embodiments, the second gene switch may be an ecdysone receptor (EcR) based gene switch, a rapamycin-based gene switch, a prokaryotic tetracycline repressor-based gene switch, a lactose repressor-operator-based gene switch, a cumate-based gene switch, or a biotin-based gene switch. The second chemical ligand may be the same or a different chemical ligand that is active for the EcR-based gene switch.

In some embodiments, the vector or polynucleotide may also have an AUX/IAA repression domain or an ERF-associated amphiphilic repression (EAR) domain.

The polynucleotides or vectors may be used to create a plant that contains these polynucleotides or vectors in which some or all of the vector or polynucleotide is integrated into the plant genome. The plant may be monocotyledonous or dictyledonous.

The invention provides a vector or polynucleotide comprising nucleic acids encoding:

(a) an ecdysone receptor-based (EcR-based) gene switch;

(b) a nucleic acid or protein which controls a gene of interest in a plant; and, (c) a regulatory element operably connected 5' of b), wherein said EcR-based gene switch binds said regulatory element in the presence of a chemical ligand.

The invention provides one or more vectors or polynucleotides comprising:

(a) a polynucleotide encoding an ecdysone receptor-based (EcR-based) gene switch or an ecdysone receptor-based (EcR-based) gene switch comprising a VGEvy ligand binding domain;

(b) a nucleic acid which controls a trait or traits in a plant; and, (c) a regulatory element operably connected 5' of b), wherein said gene switch induces expression of b) in the presence of a chemical ligand.

The invention also provides a method of reducing environmental risk of pollen drift from genetically engineered plants to wild plant species wherein polynucleotides or vectors of the invention are introduced to genetically engineered plants to control, inhibit and prevent cross-pollination of wild plant species. In some embodiments, the genetically engineered plants are forage crops or turfgrass.

The invention also provides a method of improving crop yield comprising introduction of polynucleotides or vectors of the invention into crop plants. In some embodiments, the crop plants are fruits or vegetables. The fruits and vegetables may be any of those described above. In some particular embodiments, the fruits are oranges or any other citrus fruit, pears, cherries, avocados, strawberries, pineapples, or apples.

The invention also provides a method of generating plants with "on-demand" resistance to pests or biological stressors comprising introduction of polynucleotides or vectors of the invention into said plants. In some embodiments, the biological stressors are drought, or herbicides.

The invention also provides a method of generating precise control of flowering in high value fruits, vegetables or other plant produce to aid in harvest timing, comprising introduction of polynucleotides or vectors of the invention into said plants. In some embodiments, the fruits are oranges or any other citrus fruit, pears, cherries, avocados, strawberries, pineapples, or apples.

The invention also provides a method of controlling flowering in plants wherein commercial value is derived from the flower, comprising introduction of polynucleotides or vectors of the invention into said plants.

The invention also provides a method of controlling plant traits, such as but not limited to, color and aroma, in fruits and flowers, comprising introduction of polynucleotides or vectors of the invention into said plants.

The invention also provides a method of increasing plant-based production of high-value active pharmaceutical ingredients, comprising introduction of polynucleotides or vectors of the invention into said plants.

The invention also provides a method of generating increased efficiency or effectiveness in methods of commercial seed production, comprising introduction of polynucleotides or vectors of the invention into said plants.

The invention also provides a method of controlling when a crop plant flowers to increase biomass production, comprising introduction of polynucleotides or vectors of the invention into said plants. In some embodiments, forage crop quality may be improved, such as by reduced lignin.

The invention also provides a method of controlling timing of fruiting and seed production in plants, comprising introduction of polynucleotides or vectors of the invention into said plants.

The invention provides a method of controlling or regulating flowering in plants comprising introducing into the plant a vector or polynucleotide comprising nucleic acids encoding:

(a) an ecdysone receptor-based (EcR-based) gene switch;

(b) a nucleic acid or protein which controls a gene of interest in a plant; and, (c) a regulatory element operably connected 5' of (b), wherein said EcR-based gene switch binds said regulatory element in the presence of a chemical ligand and contacting the plant with a non-steroidal chemical ligand when one desires to express the gene of interest.

The invention provides a method of controlling or regulating flowering in plants comprising introducing into the plant one or more vectors or polynucleotides comprising:

(a) a polynucleotide encoding an ecdysone receptor-based (EcR-based) gene switch or an ecdysone receptor-based (EcR-based) gene switch comprising a VGEvy ligand binding domain;

(b) a nucleic acid which controls or regulates flowering in a plant;

(c) a regulatory element operably connected 5' of (b), wherein said gene switch induces expression of b) in the presence of a non-steroidal chemical ligand; and (d) contacting the plant with the non-steroidal chemical ligand to regulate flowering.

The chemical ligand may be a diacylhydrazine, such as, for example, methoxyfenozide.

BRIEF DESCRIPTION OF THE DRAWINGS

FIG. 4 shows transgenic T1 plants produced by transforming *Arabidopsis* late-flowering ft mutant with constructs ID14 (left) and ID16 (right). Left—EcR-based gene switch plants (ID14) exhibit late-flowering phenotype in the absence of switch activating ligand; right—control plants (ID16) overexpress FT and exhibit premature flowering.

FIG. 21 shows petunia flowers of varying purple color in relation to the amount of ChsA transcript present in the plant cell (not to scale). At low levels of transcript (right picture) flowers are white in color; at intermediate levels of transcript (middle picture) flowers are variegated with white and purple color; at high levels of transcript (left picture) flowers are purple.

DETAILED DESCRIPTION OF THE INVENTION

Figure 1:
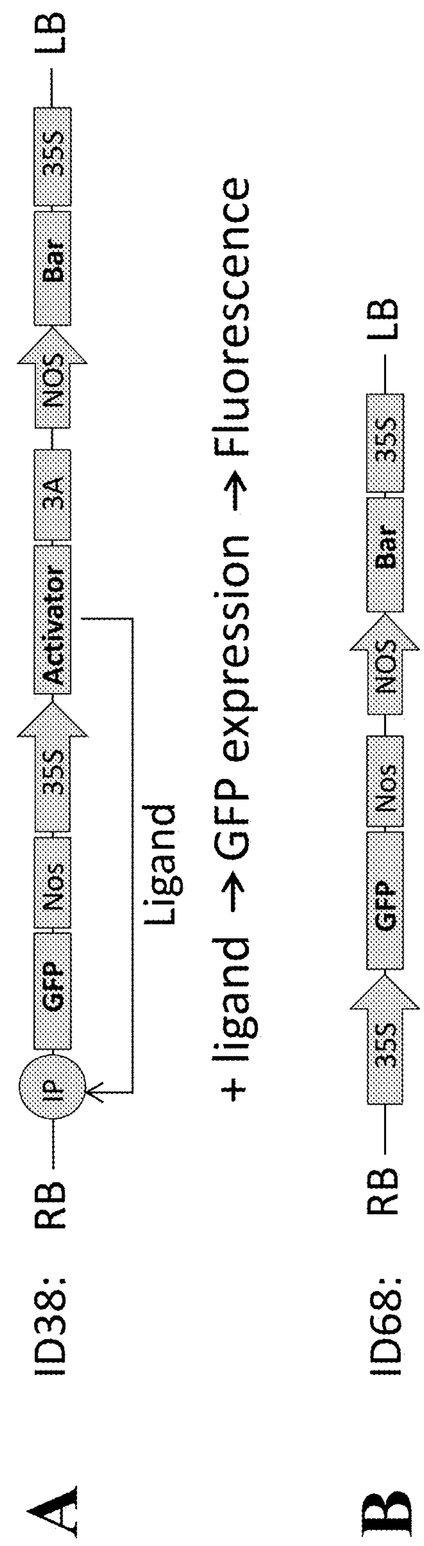
FIG. 1 shows DNA constructs for controlled expression of green fluorescent protein reporter gene (GFP). Panel A shows ID38 which was constructed to express GFP under the control of a switch that may be activated by addition of ligand; Panel B shows ID68, a construct that serves as a control expressing GFP constitutively.

All journal articles or other publications, patents and patent applications referred to herein are expressly incorporated by reference as if each individual journal article, publication, patent, or patent application was specifically and individually indicated to be incorporated by reference. In the event of a conflict between a disclosure in the present application compared to a disclosure incorporated by reference, the disclosure in the present application controls.

The present invention comprises compositions and methods useful for chemically-regulated control of flowering in dicotyledonous plants.

Definitions

In this disclosure, a number of terms and abbreviations are used. The following definitions are provided to be helpful in understanding the scope and practice of the present invention.

As used herein, "EcR-based gene switch" is a chimeric (i.e., three-part heterologous) polypeptide comprised of a transcriptional transactivator domain, a DNA-binding domain and an EcR (ecdysone receptor-derived) ligand binding domain.

As used herein, "LB" refers to the left T-DNA border of a vector.

As used herein, "35S" refers to a cauliflower mosaic virus terminator when shown as a rectangular box in the figures.

As used herein, "35S promoter" refers to the promoter from the cauliflower mosaic virus containing TATA Box elements. In the figures "35S" refers to the full 35S promoter when shown as an arrow-shaped polygon.

As used herein, "NPTII" refers to the neomycin phosphotransferase II gene product which, when expressed, confers resistance to the antibiotic Kanamycin.

As used herein, "IP" (i.e., Inducible Promoter) refers to sequences comprising DNA binding site sequences (such as repeated (5×) GAL4 binding site sequences) and a promoter region (such as a 35S minimal promoter) that is responsive to the Activator.

As used herein, "GFP" refers to Green Fluorescent Protein.

As used herein, "Activator" refers to an EcR-based gene switch polypeptide containing a transactivation domain, a DNA-binding domain and a ligand binding domain.

As used herein, "TM" refers to the immutans gene product which is encoded by the immutans gene, im.

As used herein, "RB" refers to the right T-DNA border of a vector.

As used herein, "U6" refers to a small nuclear RNA subunit involved in RNA processing. As used herein when shown describing a construct with an arrow icon, the U6 promoter is being shown.

As used herein, "gRNA" refers to guide RNA, a nucleic acid moiety that recruits and directs nuclease activity in the CRISPR-Cas9 system. The gRNA may be composed of two molecules that form a partial double-stranded molecule including a transactivating CRSPR RNA (tacrRNA) portion and a CRISPR RNA (crRNA) portion, or it may be a nucleic acid molecule single guide RNA (sgRNA) that consists of both the crRNA and tracrRNA as a single construct.

As used herein, "Cas9" refers to the Cas9 endonuclease which is the nuclease that cleaves DNA in the CRISPR-Cas9 system.

As used herein, "IM Pro" refers to the immutans promoter.

As used herein, "TM CDS" refers to the immutans coding DNA sequence.

As used herein, "PDS" refers to phytoene desaturase which, when reduced, leads to photobleaching in plants and loss of green pigment due to reduced PDS levels.

As used herein, "FT" refers to the Flowering Locus T, a floral integrator that activates flowering in *Arabidopsis thaliana* and in many other plants.

As used herein, "FT Pro" refers to the flowering locus T promoter.

As used herein, "5' FT" refers to the 5' region of the gene encoding the Flowering Locus T.

As used herein, "FT CDS" refers to the Flowering Locus T coding DNA sequence.

As used herein, wt: means "wild-type."

As used herein, "Bar" refers to the bar gene (phosphinothricin N-acetyltransferase) which confers phosphinothricin (PPT)-resistance.

As used herein, "Barstar" refers to a small protein from *Bacillus amyloliquefaciens* which inhibits barnase, resulting in flowering.

As used herein, "Barnase" refers to the barnase ribonuclease from *Bacillus amyloliquefaciens* which, when expressed in plants, suppresses flowering.

As used herein, "NOS" refers to the nopaline synthase promoter from *Agrobacterium tumefaciens*

As used herein, "E9" refers to the 3' end (untranslated region) of the small subunit of *Pisum sativum* ribulose-1,5-biphosphate carboxylase (rbc).

As used herein, "AP1" refers to Apetalal," one of three gene products of plants that are involved in the activity of APETALA3 (AP3) and PISTILLATA (PI) which are needed for floral meristem formation in *Arabidopsis* and other plants. As used herein when shown describing a construct with an arrow icon, the AP1 promoter is being shown.

As used herein, "3A" refers to the 3' end of the small subunit of *Pisum sativum* ribulose-1,5-biphosphate carboxylase (rbc) poly-A (untranslated) region.

As used herein, "VGEvy" refers to a modified ecdysone receptor-based gene switch, for example, but not limited to the monopartite gene switch polypeptide VGEvy (E68V/V184I1/Y204E) as shown in SEQ ID NO:1 (the (E68V/V184I/Y204E) numbering is with respect to the ligand-binding domain shown in SEQ ID NO:2).

As used herein, "LFY" refers to "Leafy," one of three gene products of plants that are involved in the activity of APETALA3 (AP3) and PISTILLATA (PI) which are needed for proper development of flowers in *Arabidopsis* and other plants. As used herein when shown describing a construct with an arrow icon, the LFY promoter is being shown.

As used herein, "UFO" refers to "Unusual Floral Organs," one of three gene products of plants that are involved in the activity of APETALA3 (AP3) and PISTILLATA (PI) which are needed for proper development of flowers in *Arabidopsis* and other plants. As used herein when shown describing a construct with an arrow icon, the UFO promoter is being shown.

As used herein, "GUS" refers to β-glucuronidase which is used in assays to detect expression as expression of GUS allows cleavage of substrates such as 5-bromo-4-chloro-3-indolyl glucuronide and p-nitrophenyl β-D-glucuronide to provide a blue color.

As used herein, "H4A" refers to the histone 4 gene cluster. As used herein when shown describing a construct with an arrow icon, the H4A promoter is being shown.

As used herein, "ft" refers to the gene encoding the Flowering Locus T (FT) protein.

The term "about" or "approximately" means a value or number encompassing more than and/or less than the exact value or number indicated as would be understood by one of ordinary skill in the relevant art in the context of the subject matter in which the term "about" or "approximately" is used. For example, depending on the subject matter context, "about" or "approximately" could mean within 20%, within 10%, within 5%, or even within 1% of a given value, number or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (e.g., nucleic acid or protein) that has been removed from its original environment (the environment in which it is naturally present).

For example, a polynucleotide present in the natural state in a plant or an animal is not isolated. The same polynucleotide is "isolated" if it is separated from the adjacent nucleic acids in which it is naturally present. The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" or "polynucleotide" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmid DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alfa, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" when referring to a polynucleotide will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 8, 10, 12, 15, 18, 20 to 25, 30, 40, 50, 70, 80, 100, 200, 500, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, optionally including regulatory sequences preceding (5' noncoding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

Heterologous" DNA refers to DNA not naturally located in the cell, or in a chromosomal site of the cell. Preferably, the heterologous DNA includes a gene or polynucleotides foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head"

may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as PBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited, to retrovirus, adeno-associated virus, pox, baculovirus, vaccinia, herpes simplex, Epstein-Barr, adenovirus, geminivirus, and caulimovirus vectors. Non-viral vectors include, but are not limited to, plasmids, liposomes, electrically charged lipids (cytofectins), DNAprotein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include, one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include, but are not limited to: genes providing resistance to ampicillin, streptomycin, gentamycin, kanamycin, hygromycin, bialaphos herbicide, sulfonamide, glyphosate and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include, but are not limited to: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase or transcription factors.

A coding sequence is "under the control" of transcriptional and translational control sequences in a cell when RNA polymerase transcribes the coding sequence into mRNA, which is then RNA spliced (if the coding sequence contains introns) and translated into the protein encoded by the coding sequence.

Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domain of a polypeptide. This DNA element may be, for example,palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of natural ecdysone receptor polypeptides include, but are not limited to: RRGG/TTCANTGAC/ACYY (see Cherbas L., et al., (1991), Genes Dev. 5, 120-131); AGGTCAN$_{(n)}$AGGTCA, where N$_{(n)}$ can be one or more spacer nucleotides (see D'Avino P P., et al., (1995) *Mol. Cell. Endocrinol.* 113:1-9); and GGGTTGAATGAATTT (see Antoniewski C., et al., (1994) *Mol. Cell Biol.* 14:4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a, response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include, but are not limited to, origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host, the cloned gene, i.e., the inserted nucleic acid sequence, is usually placed under the control of control elements such as a promoter, a minimal promoter, an enhancer, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

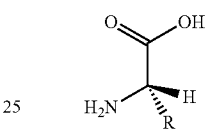

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of 10, 15, 20, 30 to 40, 50, 100, 200 or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

"signal sequence" is included at the beginning of the coding sequence of a protein to be expressed on the surface of a cell. This sequence encodes a signal peptide, N-terminal to the mature polypeptide that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al. (1987) *Cell* 50:667). As used herein, the term "homologous" in all its grammatical forms and spelling variations refers to the relationship between proteins that possess a "common evolutionary origin," including proteins from superfamilies and homologous proteins from different species (Reeck et al., supra). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are thus nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410; see also www ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, N.J. (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., J. Mol. Biol. 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized," as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codonbias of the host cell. The skilled artisan appreciates the likelihood of successful gene expression if codon usage is biased towards those codons favored by the host. Determination of preferred codons can be based on a survey of genes derived from the host cell where sequence information is available.

A. The EcR-Based Gene Switch

The invention provides an ecdysone-receptor (EcR)-based gene switch system for controlled expression of phenotypic traits in plants. In particular, the invention provides a system for controlling expression of genes in plants which can be turned "on" or "off" as desired. For example, in some applications, the invention provides control of flowering, disease resistance, flower color, nutritional value, and expression of desirable traits. In some embodiments, for example, it will be desirable to turn flowering off, such as, for example, when growing alfalfa so that the biomass and quality of the alfalfa is increased. In other applications, turning flowering on will be desirable such as for seed harvest.

In certain embodiments, the invention comprises use of an EcR based gene switch to control gene expression in plants (the plants may be monocotyledonous or dicotyledonous). In certain embodiments, the EcR-based gene switch comprises a ligand binding domain derived from an ecdysone receptor polypeptide of *Choristoneura fumiferana* (Cf) (also known as spruce budworm).

In certain embodiments, the EcR-based gene switch is a heterologous chimeric polypeptide comprised of a transcriptional transactivator domain (AD), a DNA-binding domain (DBD) and an EcR ligand binding domain (LBD). The DBD is characterized by the presence of two cysteine zinc fingers, between which are two amino acid motifs, the P-box and the D-box, which confer specificity for response elements. These domains may be either native, modified, or chimeras of different domains of heterologous receptor proteins. The EcR, like a subset of the nuclear receptor family, also possesses regions responsible for heterodimerization properties. Because the domains of nuclear receptors are modular in nature, the LBD, DBD, and AD may be interchanged.

In another embodiment, the transcription factor comprises an AD, a DBD that recognizes a response element associated with the protein or polynucleotide of interest whose expression is to be modulated; and a Group H nuclear receptor LBD. In certain embodiments, the Group H nuclear receptor LBD comprises one or more substitution mutations.

The DNA binding domain can be any DNA binding domain (DBD) with a known response element, including synthetic and chimeric DNA binding domains, or analogs, combinations, or modifications thereof. In one embodiment, the DNA binding domain is selected from the group consisting of a GAL4 DBD, a LexA DBD, a transcription factor DBD, a Group H nuclear receptor member DBD, a steroid/thyroid hormone nuclear receptor superfamily member DBD, a bacterial LacZ DBD, an EcR DBD and a plant DBD (such as, but not limited to ARFs, a bZIP DBD, plant homeodomain families of DNA binding domains or synthetic DNA-binding proteins generated through directed evolution (e.g., SELEX) as described in Tiwari et al. (2003) *Plant Cell,* 15:533-543).

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p53 transactivtion domain (p53AD), a p65 transactivation domain (p65AD), cREL, a plant transactivation domain such as, but not limited to an EDLL acidic transactivation domain from the AP2/ERF family, a glutamine-rich transactivation domain from ARFs and CONSTANS proteins, a proline-rich domains from a bZIP family (as described in Tiwari, S. B. et al. (2012) *Plant J.* 70:855-865; Tiwari, S. B. et al. (2003) *Plant Cell* 15(2):533-543; Sprenger-Haussels, M. and B. Weisshaar (2000) *Plant J.* 22(1):1-8) or an analog, combination, or modification thereof.

In some embodiments, the EcR-based gene switch is comprised of an AD, DBD and LBD from three different species of organisms. In certain embodiments, the transcriptional transactivator domain is a herpes virus VP16 polypeptide or an SV40 virus transcriptional transactivator domain. In certain embodiments, the DNA-binding domain comprises a Gal4 transcription factor DNA binding polypeptide.

In certain embodiments, an EcR-based gene switch of the invention comprises the substitution mutated CfEcR polypeptide designated herein as Evy (E68V/V184I/Y204E); as shown in SEQ ID NO:2. In certain embodiments, an EcR-based gene switch of the invention comprises the monopartite gene switch polypeptide designated herein as VGEvy (E68V/V184I/Y204E) as shown in SEQ ID NO:1 (numbering of with respect to E68V/V184I/Y204E is with respect to the ligand binding domain shown in SEQ ID NO:2).

In certain embodiments, the invention comprises biologically active polypeptides fragments of VGEvy (E68V/V184I/Y204E (SEQ ID NO:1)) or Evy (E68V/V184I/Y204E (SEQ ID NO:12)) and polypeptides at least 80% identical, at least 85% identical, at least 90% identical, at least 95% identical, at least 97% identical, at least 98% identical, at least 99% identical, or 100% identical to SEQ ID NO:1 or SEQ ID NO:2 provided E68V, V184I, and Y204E are unchanged.

In certain embodiments, the invention comprises polynucleotides encoding VGEvy (E68V/V184I/Y204E (SEQ ID NO:1)) or Evy (E68V/V184I/Y204E (SEQ ID NO:2)) polypeptides, as well as polynucleotides encoding polypeptides at least 80% identical, at least 85% identical, at least 90% identical, at least 95% identical, at least 97% identical, at least 98% identical, at least 99% identical, or 100% identical to SEQ ID NO:1 or SEQ ID NO:2 provided that the coding sequences do not change E68V, V184I, or Y204E.

In some embodiments, the EcR-based gene switch is activated by methoxyfenozide. Methoxyfenozide is a diacylhydrazine (organic chemical) compound which acts as a molt accelerating compound in insects. It is specifically effective against a broad range of lepidopterous (e.g., caterpillar) insect species. Methoxyfenozide is also identified as: 3-methoxy-2-methylbenzoic acid 2-(3,5-dimethylbenzoyl)-2-(1,1-dimethylethyl)hydrazide and as Benzoic acid, 3-methoxy-2-methyl-,2-(3,5-dimethylbenzoyl)-2-(1,1-dimethylethyl) hydrazide. See, for example, Carlson et al., "The chemical and biological properties of methoxyfenozide, a new insecticidal ecdysteroid agonist" *Pest Manag. Sci.,* 57(2):115-119 (February 2001) which is hereby incorporated by reference in its entirety. See also the NCBI (United States National Center for Biotechnology Information (U.S. National Library of Medicine 8600 Rockville Pike, Bethesda Md., 20894 USA)) PubChem Substance Database which contains descriptions of samples, from a variety of sources. The description for methoxyfenozide includes links to additional compositional, safety, structural and supplier information.

It will be understood that any phenotypic trait could be put under the control of an EcR-based gene switch system of the invention. Non-limiting examples of phenotypic traits include stress resistance (abiotic, such as drought, or biotic such as pests and diseases); biofactory traits, such as the production of high value compounds (active pharmaceutical ingredients, biopolymers, etc.) in plants when it is necessary to control the timing of compound accumulation (switching it on before harvesting) because of the fitness cost; tunable traits such as type and intensity of color and aroma in flowers, and controlled accumulation of specific nutrients in fruits and vegetables such as differentiating taste and nutritional value to satisfy different groups of consumers. Timing of expression can be important such that one may select to turn on genes at the proper time in the plant's life. For example, but not by way of limitation, *Erwinia amylovora*, the causative agent of fire blight in apples and pears, attacks the trees at the time of flowering and will infect the fruit. A gene switch to produce an antibacterial protein or dsRNA against *E. amylovora* can be induced by applying the chemical ligand at the time of flowering to inhibit fire blight. In another non-limiting example, the ability to change the color of cotton filaments had not been possible due to the inability of being able to control the timing of color expression. With the gene switch of the invention, one may time expression of color in cotton filaments to alter the color of cotton at the time of boll formation.

B. Additional Gene Switch Systems for use Alone or in Combination.

In some embodiments of the invention, at least one other gene switch sytem is included. Other gene switches that may be used in the invention may be any gene switch that regulates gene expression by addition or removal of a specific ligand or other gene switch activator (e.g., light, heat, cold, etc). In one embodiment, the gene switch is one in which the level of gene expression is dependent on the level of ligand that is present. Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety.

In one aspect of the invention, the gene switch is an EcR-based gene switch. Examples of such systems include, without limitation, the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/US2002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. application Ser. No. 10/468,193 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. application Ser. No. 14/001,943 (U.S. Pub. No. 20140308247), each of which is incorporated by reference in its entirety.

In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709; 6,117,680; 6,479,653; 6,187,757; and 6,649,595.

In one embodiment, the gene switch comprises a single transcription factor sequence encoding a ligand-dependent transcription factor complex under the control of a switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

1. Ecdysone-Based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans (1988) *Science* 240:889). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

| Transactivation | DNA-Binding Domain | Hinge | Ligand Binding Domain | Transactivation |
|---|---|---|---|---|
| A/B | C | D | E | F |

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

Ecdysone receptor (878aa) from *Drosophila melanogaster* (Fruit fly) (SEQ ID NO:20)

```
1 MKRRWSNNGG FMRLPEESSS EVTSSSNGLV LPSGVNMSPS SLDSHDYCDQ DLWLCGNESG

61 SFGGSNGHGL SQQQQSVITL AMHGCSSTLP AQTTIIPING NANGNGGSTN GQYVPGATNL

121 GALANGMLNG GFNGMQQQIQ NGHGLINSTT PSTPTTPLHL QQNLGGAGGG GIGGMGILHH

181 ANGTPNGLIG VVGGGGGVGL GVGGGGVGGL GEQHTPRSDS VNSISSGRDD LSPSSSLNGY
```

-continued

```
241 SANESCDAKK SKKGPAPRVQ EELCLVCGDR ASGYHYNALT CEGCKGFFRR SVTKSAVYCC

301 KFGRACEMDM YMRRKCQECR LKKCLAVGGER PECVVPENQC AMKRREKKAQ KEKDKMTTSP

361 SSQHGGNGSL ASGGGQDFVK KEILDLMTCE PPQHATIPLL PDEILAKCQA RNIPSLTYNQ

421 LAVIYKLIWY QDGYEQPSEE DLRRIMSQPD ENESQTDVSF RHITEITILT VQLIVEFAKG

481 LPAFTKIPQE DQITLLKACS SEVMMLRMAR RYDHSSDSIF FANNRSYTRD SYKMAGMADN

541 IEDLLHFCRQ MFSMKVDNVE YALLTAIVIF SDRPGLEKAQ LVEAIQSYYI DTLRIYILNR

601 HCGDSMSLVF YAKLLSILTE LRTLGNQNAE MCFSLKLKNR KLPKFLEEIW DVHAIPPSVQ

661 SHLQITQEEN ERLERAERMR ASVGGAITAG IDCDSASTSA AAAAAQHQPQ PQPQPQPSSL

721 TQNDSQHQTQ PQLQPQLPPQ LQGQLQPQLQ PQLQTQLQPQ IQPQPQLLPV SAPVPASVTA

781 PGSLSAVSTS SEYMGGSAAI GPITPATTSS ITAAVTASST TSAVPMGNGV GVGVGVGGNV

841 SMYANAQTAM ALMGVALHSH QEQLIGGVAV KSEHSTTA
```

In one embodiment, the ecdysone receptor ligand binding domain is selected from the group consisting of an invertebrate ecdysone receptor ligand binding domain, an Arthropod ecdysone receptor ligand binding domain, a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm *Choristoneura fumiferana* EcR ecdysone receptor ligand binding domain, a beetle *Tenebrio molitor* ecdysone receptor ligand binding domain, a *Omphisa fuscidentalis* (Bamboo caterpillar) ecdysone receptor ligand, a *Locusta migratoria* (locust) ecdysone receptor ligand, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain and a leafhopper *Nephotetix cincticeps* ecdysone receptor ligand binding domain.

In another embodiment, the ecdysone receptor ligand binding domain is the *Choristoneura fumiferana* ecdysone receptor ligand binding domain, for which the amino acid sequence is set forth in SEQ ID NO:19.

In another embodiment, the ecdysone receptor ligand binding domain is an analog of the *Choristoneura fumiferana* ecdysone receptor ligand binding domain that retains at least 80%, 85%, 90%, 95%, 96%, 97%, 98% 99% or 100% of the in vitro *Christoneura fumiferana* ecdysone receptor ligand binding activity of the *Choristoneura fumiferana* ecdysone receptor ligand binding domain. In vitro ecdysone receptor ligand binding assays are well known to those of ordinary skill in the art. For example, see WO 02/066612.

In another embodiment, the ecdysone receptor ligand binding domain analog is an ecdysone receptor ligand binding domain disclosed in WO 02/066612, US 2006/0100416, WO 05/108617 and 2005/0266457. In another embodiment, the ecdysone receptor ligand binding domain analog is the V1071/Y127E substitution mutant of SEQ ID NO:19.

In certain embodiments an ecdysone receptor ligand binding domain analog is a monopartite EcR gene switch. In some embodiments the monopartite EcR is derived from *Choristoneura fumiferana* EcR (CfEcR) containing two substitutions: V395I and Y415E (vy), of CfEcR (CfEcRvy) (Tavva (2008) *FEBS J.* 275:2161-2176). In some embodiments, the ecdysone receptor gene switch is the same EcR-based gene switch as the first EcR-based gene switch. In some embodiments, a single EcR-based gene switch is used to regulate inducible expression of two different genes of interest, wherein said gene switch and and said two different genes of interest may be part of a single polynucleotide or vector or may be parts of two or three different polynucleotides or vectors.

The DBD may be characterized by the presence of two cysteine zinc fingers, between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises an AD, a DBD that recognizes a response element associated with the protein or polynucleotide of interest whose expression is to be modulated; and a Group H nuclear receptor LBD. In certain embodiments, the Group H nuclear receptor LBD comprises a substitution mutation.

The DNA binding domain can be any DNA binding domain (DBD) with a known response element, including synthetic and chimeric DNA binding domains, or analogs, combinations, or modifications thereof. In one embodiment, the DNA binding domain is selected from the group consisting of a GAL4 DBD, a LexA DBD, a transcription factor DBD, a Group H nuclear receptor member DBD, a steroid/thyroid hormone nuclear receptor superfamily member DBD, a bacterial LacZ DBD, an EcR DBD, and a plant DBD (such as, but not limited to ARFs, bZIP, plant homeodomain families of DNA binding domains or synthetic DNA-binding proteins generated through directed evolution (e.g., SELEX) as described in Tiwari et al. (2003) *Plant Cell,* 15:533-543).

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p53 transactivation domain (p53AD), a p65 transactivation domain (p65AD), a plant activation domain such as, but not limited to an EDLL acidic transactivation domain from the AP2/ERF family, a glutamine-rich transactivation domain from ARFs and CONSTANS proteins, a proline-rich transactivation domain from a bZIP family member (as described in Tiwari, S. B. et al. (2012) *Plant* 1 70:855-865; Tiwari, S. B. et al. (2003) *Plant Cell* 15(2):533-543; Sprenger-Haussels, M. and B. Weisshaar (2000) *Plant J.* 22(1):1-8) or an analog, combination, or modification thereof.

The vectors and polynucleotides of the invention may also contain a transcription repression domain such as an AUX/IAA protein with an LxLxL domain, such as those described in Tiwari, S. B. et al. (2004) *Plant Cell* 16(2):533-543. Examples include, but are not limited to: TELRLGLPG (SEQ ID NO: 37), TELRLGLPE (SEQ ID NO:38), TELCLGLPG (SEQ ID NO:39), TELTLGLPG (SEQ ID NO:40), TELTLALPG (SEQ ID NO:41), TDLRLGLSF (SEQ ID NO:42), TELDLALGL (SEQ ID NO:43), SELELGLGL (SEQ ID NO:44), MELDLGLSL (SEQ ID NO:45), IELGLTLSL (SEQ ID NO:46), IDLGLDLRT (SEQ ID NO:47), VNLSLSLTF (SEQ ID NO:48), KKLELKLGP (SEQ ID NO:49), KKLELRLHR (SEQ ID NO:50), and KRLELRLAP (SEQ ID NO:51). The repression domain may also be an ERF-associated amphiphilic repression (EAR) domain such as a SIERF36, or SIERF.F.1 (Accssion No. SGN-U564952) as described in Upadhyay, R. K. et al. (2014) *PLOS One* 9(7): e101995. Examples include NtERF3 (IDLDLNLAP) (SEQ ID NO:52), AtERF4 (LDLELNLPP) (SEQ ID NO:53), and AtSUPR (QDLDLELRL) (SEQ ID NO:54).

A transcription repressor domain may be used in conjunction with a constitutively expressed gene to inhibit a trait of interest (e.g., flowering). For example, but not by way of limitation, a plant may be transformed to include a gene that inhibits flowering such as miR156 which produces dsRNA that inhibits SPL which controls flowering in plants. The transformed plant may also comprise a gene switch of the invention that contains a repressor domain such as LxLxL from an AUVIAA protein. Upon application of an activating chemical ligand, the gene switch binds to the DNA responsive element and the repressor domain represses expression of miR156 and flowering is turned back on.

In one embodiment, the first transcription factor sequence encodes a polypeptide comprising a AD, a DBD that recognizes a response element associated with the gene of interest whose expression is to be controlled; and a Group H nuclear receptor LBD, and the second transcription factor sequence encodes a transcription factor comprising a nuclear receptor LBD selected from a vertebrate retinoid X receptor (RXR), an invertebrate RXR, an ultraspiracle protein (USP), or a chimeric nuclear receptor comprising at least two different nuclear receptor ligand binding domain polypeptide fragments selected from a vertebrate RXR, an invertebrate RXR, and a USP (see WO 01/70816A2 and US2004/0096942A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the sequence of the gene of interest whose expression is to be controlled, and a second transcription factor sequence encoding a second polypeptide comprising an AD and a nuclear receptor LBD, wherein one of the nuclear receptor LBDs is a Group H nuclear receptor LBD. In one embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In one embodiment, a vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, an invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, a chimeric RXR LBD comprises at least two polypeptide fragments selected from a vertebrate species RXR polypeptide fragment, an invertebrate species RXR polypeptide fragment, or a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment. Such chimeric RXR LBDs are disclosed, for example, in WO 2002/066614.

In one embodiment, a chimeric RXR ligand binding domain comprises at least one vertebrate species RXR polypeptide fragment and one invertebrate species RXR polypeptide fragment.

In another embodiment, a chimeric RXR ligand binding domain comprises at least one vertebrate species RXR polypeptide fragment and one non-Dipteran/non-Lepidopteran invertebrate species RXR homolog polypeptide fragment.

In a specific example, binding of the ligand to the LBD of a Group H nuclear receptor and its nuclear receptor LBD partner enables expression of a sequence of a gene of interest. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the plant for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors. Another advantage of two-hybrid systems is that they allow choice of a promoter used to drive the gene expression according to a desired end result. Such double control may be particularly important, especially when cytotoxic proteins are produced, because both the timing of expression as well as the cells wherein expression occurs may be controlled. When genes, operably linked to a suitable promoter, are introduced into the cells of the plant, expression of the exogenous genes is controlled by the presence of the system of this invention. Promoters may be constitutively or inducibly regulated or may be tissue-specific (that is, expressed only in a particular type of cells) or specific to certain developmental stages of the plant.

In certain embodiments a chimeric protein is used comprising an acidic domain of human Herpes Simplex virus as the transactivation domain, "V" fused to a GAL4 DNA-binding domain derived from *Saccharomyces cerevisia*, "G," and a *Choristoneura fumiferana* ecdysone receptor, "E," as the ligand binding domain (together, "VGE"). In other embodiments, the ecdysone receptor ligand binding portion of VGE is a E68V\V184I\Y204E (evy) substitution mutant with respect to the wild type EcR portion of the VGE construct (mutations shown underlined below (shown in Figures and dicussed herein as "VGEvy") Numbering of the mutations is based on the EcR portion of the molecule shown below in italics.

(FKBP) domain and at least one protein domain heterologous thereto, wherein the FKBP domain comprises a peptide sequence selected from:

(1) a naturally occurring FKBP (2) a variant of a naturally occurring FKBP in which up to 10 amino acid residues have been deleted, inserted, or replaced with substitute amino acids, and (3) an FKBP encoded by a DNA sequence which selectively hybridizes to a DNA sequence encoding an FKBP of (1) or (2);

(b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:

(4) a naturally occurring FRB domain, (5) a variant of a naturally occurring FRB domain in which up to 10 amino acid residues have been deleted, inserted, or replaced with substitute amino acids, and (6) an FRB domain encoded by a DNA sequence which selectively hybridizes to a DNA sequence encoding an FRB of (4) or (5).

In this gene switch system, each of the first polynucleotide and the second polynucleotide are under the control of one or more switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

```
                                                                  SEQ ID NO: 1
MAPPTDVSLG DELHLDGEDV AMAHADALDD FDLDMLGDGD SPGPGFTPHD SAPYGALDMA   60

DFEFEQMFTD ALGIDEYGGK LLGTSRRISG GEFGGMKLLS SIEQACDICR LKKLKCSKEK  120

PKCAKCLKNN WECRYSPKTK RSPLTRAHLT EVESRLERLE QLFLLIFPRE DLDMILKMDS  180

LQDIKALLTG LFVQDNVNKD AVTDRLASVE TDMPLTLRQH RISATSSSEE SSNKGQRQLT  240

VSGGSRRISR PECVVPETQC AMKRKEKKAQ KEKDKLPVST TTVDDHMPPI MQCEPPPPEA  300

ARIHEVVPRF LSDKLLVTNR QKNIPQLTAN QQFLIARLIW YQDGYEQPSD EDLKRITQTW  360

QQADDENEES DTPFRQITEM TILTVQLIVE FAKGLPGFAK ISQPDQITLL KACSSEVMML  420

RVARRYDAAS DSILFANNQA YTRDNYRKAG MAEVIEDLLH FCRCMYSMAL DNIHYALLTA  480

VVIFSDRPGL EQPQLVEEIQ RYYLNTLRIY ILNQLSGSAR SSVIYGKILS ILSELRTLGM  560

QNSNMCISLK LKNRKLPPFL EEIWDVADMS HTQPPPILES PTNL                   584
```

2. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises (a) a first polynucleotide encoding a first chimeric protein which binds to rapamycin or an analog thereof and which comprises at least one FK506-binding protein In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757 B1, 6,649,595 B1, 6,509,152 B1, 6,479,653 B1, and 6,117,680 B1.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

3. Procaryotic Repressor/Operator Based Gene Switch System

In some embodiments, the present invention provides gene switch system comprising (a) a first polynucleotide coding for a transactivator fusion protein comprising a prokaryotic tetracycline ("tet") repressor and a eucaryotic transcriptional activator protein domain; and (b) a second polynucleotide coding for a gene of interest, wherein said second polynucleotide is operably linked to a minimal promoter and at least one tet operator sequence. The first polynucleotide coding for a transactivator fusion protein may comprise a switch promoter as described elsewhere herein. The expression of the lethal protein is up-regulated in the absence of tetracycline. (see, e.g., Gossen et al. (1992) *Proc. Natl. Acad. Sci.* 89: 5547-5551; Gossen et al. (1993) *TIBS* 18: 471-475; Furth et al. (1994) *Proc. Natl. Acad. Sci.* 91: 9302-9306; and Shockett et al. (1995) *Proc. Natl. Acad. Sci.* 92: 6522-6526). The TetO expression system is disclosed in U.S. Pat. No. 5,464,758 B 1.

In another embodiment, the gene switch system comprises the lactose ("Lac") repressor-operator systems from the bacterium *Escherichia coli*. The gene switch system of the present invention may also comprise (a) a first polynucleotide coding for a transactivator fusion protein comprising a prokaryotic lac I repressor and a eucaryotic transcriptional activator protein domain; and (b) a second polynucleotide coding for a gene of interest, wherein said second polynucleotide is operably linked to a gene switch promoter. In the Lac system, a lac operon is inactivated in the absence of lactose, or synthetic analogs such as isopropyl-b-D-thiogalactoside.

Additional gene switch systems include, but are not limited to, those described in the following: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S Pat. No. 6,258,603; US20050209283; US20050228016; US20060020146; EP0965644; U.S. Pat. Nos. 7,304,162; 7,304,161; MX234742; KR10-0563143; AU765306; AU2002-248500; and AU2002-306550.

4. Other Gene Switches

In another aspect of the invention, gene expression cassettes of the invention incorporate a cumate switch system, which works through the CymR repressor that binds the cumate operator sequences with high affinity. (SparQ™ Cumate Switch, System Biosciences, Inc.) The repression is alleviated through the addition of cumate, a non-toxic small molecule that binds to CymR. This system has a dynamic inducibility, can be finely tuned and is reversible and inducible.

In another aspect of the invention, gene expression cassettes of the invention incorporate a riboswitch, which is a regulatory segment of a messenger RNA molecule that binds an effector, resulting in a change in production of the proteins encoded by the mRNA. An mRNA that contains a riboswitch is directly involved in regulating its own activity in response to the concentrations of its effector molecule. Effectors can be metabolites derived from purine/pyrimidine, amino acid, vitamin, or other small molecule co-factors. These effectors act as ligands for the riboswitch sensor, or aptamer. Breaker, RR. Mol Cell. (2011) 43(6): 867-79.

In another aspect of the invention, gene expression cassettes of the invention incorporate the biotin-based gene switch system, in which the bacterial repressor protein TetR is fused to streptavidin, which interacts with the synthetic biotinylation signal AVITAG that is fused to VP16 to activate gene expression. Biotinylation of the AVITAG peptide is regulated by a bacterial biotin ligase BirA, thus enabling ligand responsiveness. Weber et al. (2007) Proc. Natl. Acad. Sci. U.S.A. 104, 2643-2648; Weber et al. (2009) Metabolic Engineering, 11(2):117-124.

Additional gene switch systems which may be used as part of the present invention are well known in the art, including but not limited to those described in Auslander and Fussenegger (2012) *Trends in Biotechnology* 31(3):155-168, incorporated herein by reference.

5. Combination of the Gene Switch Systems

The present invention provides nucleic acid compositions, modified cells, and plants comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more genes of interest, upon binding to one or more ligands. Within the scope of the present invention are any numbers of and/or combinations of gene switch systems.

In certain embodiments, there may be a combination of two or more gene switch systems. In some embodiments, the combination is (1) an EcR-based gene switch and (2) a dual-switch ecdysone receptor based gene expression system. In other embodiments, the combination may be (1) an EcR-based gene switch and (2) a rapamycin based gene switch. Alternatively, the combination of gene switch systems may be two identical rapamycin based gene switch systems disclosed above. Any possible combinations of the gene switch systems are within the scope of the invention.

C. Ligands

As used herein, the term "ligand," as applied to gene switches (e.g., EcR based gene switches), describes small and soluble molecules having the capability of activating a gene switch to stimulate expression of a polypeptide encoded therein. The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazie), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, published as US 2009/0163592, and PCT Appl. No. PCT/US2008/006757, both of which are incorporated herein by reference in their entireties.

For example, a ligand for the edysone receptor based gene switch may be selected from any suitable ligands. Both naturally occurring ecdysone or ecdyson analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 B1, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057 B 1. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkyl-N'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I Formula I

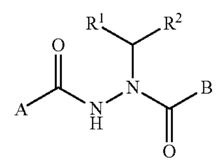

wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

or pharmaceutically acceptable salts, hydrates, crystalline forms or amorphous forms thereof.

In another embodiment, the ligand may be enantiomerically enriched compounds of Formula II Formula II

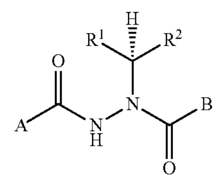

wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S;

or pharmaceutically acceptable salts, hydrates, crystalline forms or amorphous forms thereof.

In certain embodiments, the ligand may be enantiomerically enriched compounds of Formula III Formula III

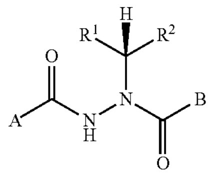

wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly R;

or pharmaceutically acceptable salts, hydrates, crystalline forms or amorphous forms thereof.

In one embodiment, a ligand may be (R)-3,5-dimethylbenzoic acid N-(1-tert-butyl-butyl)-N'-(2-ethyl-3-methoxybenzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a gene of interest. See U.S. application Ser. No. 12/155,111, published as US 2009/0163592, filed May 29, 2008, which is fully incorporated by reference herein.

The ligands used in the present invention may form salts. The term “salt(s)” as used herein denotes acidic and/or basic salts formed with inorganic and/or organic acids and bases. In addition, when a compound of Formula I, II or III contains both a basic moiety and an acidic moiety, zwitterions (“inner salts”) may be formed and are included within the term “salt(s)” as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. Nos. 6,649,595 B2 and 6,187,757. See also U.S. Pat. Nos. 7,276,498 and 7,273,874.

The ligands described herein may be administered alone or as part of a pharmaceutical composition comprising an agrochemical acceptable carrier. In one embodiment, the pharmaceutical composition is in the form of a solution, a suspension, or a spray composition.

The term “ecdysone receptor-based,” with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain. Examples of ecdysone-responsive systems are described in U.S. Pat. Nos. 7,091,038 and 6,258,603.

D. Regulatory Elements for the Polynucleotides or Vectors

Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, plant promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in Saccharomyces); AOX1 promoter (useful for expression in Pichia); β-lactamase, lac, ara, tet, tryp, $1P_L$, $1P_R$, T7, tac, and trc promoters (useful for expression in *Escherichia coli*); and light regulated-, seed specific-, pollen specific-, ovary specific-, pathogenesis or disease related-, cauliflower mosaic virus 35S, CMV 35S minimal, cassava vein mosaic virus (CsVMV), APETALA1 (AP1), LEAFY (LFY), *Arabidopsis thaliana* FLOWERING PROMOTING FACTOR 1 (AtFPF1), UNUSUAL FLORAL ORGANS (UFO), TERMINAL FLOWER 1 (TFL1), SHOOT MERISTEMLESS (STM), upstream region of the HISTONE H4 (H4A748), *Arabidopsis thaliana* TRANSLATIONALLY CONTROLLED TUMOR PROTEIN (AtTCTP), Cestrum yellow leaf curling virus (CmYLCV), Cotton leaf curl Gezira virus (ClCuGB-5), pepper huasteco yellow vein virus (PHYVV) and peanut chlorotic streak virus (PC1SV), chlorophyll a/b binding protein, ribulose 1,5-bisphosphate carboxylase, shoot-specific, root specific, chitinase, stress inducible, rice tungro bacilliform virus, plant superpromoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long termnal repeat (LTR) of Rous sarcoma virus (RSV), the promoters of the E1A or major late promoter (MLP) genes of adenoviruses, the cytomegalovirus early promoter, the herpes simplex virus (HSV) thymidine kinase (TK) promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter, and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, β-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In some embodiments of the invention, the promoter is selected from the group consisting of a cauliflower mosaic virus 35S promoter, a cassava vein mosaic virus promoter, and a cauliflower mosaic virus 35S minimal promoter, an elongation factor 1 alpha (EF1) promoter, a phosphoglycerate kinase (PGK) promoter, a ubiquitin (Ubc) promoter, and an albumin promoter provided that the promoter selected is active in the plant into which it is introduced.

In addition, these expression sequences may be modified by addition of enhancer or regulatory sequences and the like. Enhancers that may be used in embodiments of the invention include but are not limited to: tobacco mosaic virus enhancer, cauliflower mosaic virus 35S enhancer, tobacco etch virus enhancer, ribulose 1,5-bisphosphate carboxylase enhancer, rice tungro bacilliform virus enhancer, and other plant and viral gene enhancers, and the like.

Termination control regions, i.e., terminator or polyadenylation sequences, may also be derived from various genes native to the preferred hosts. Optionally, a termination site may be unnecessary, however, in some embodiments, it is preferred if included. In some embodiments of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, nopaline synthase (nos), cauliflower mosaic virus (CaMV), octopine synthase (ocs), *Agrobacterium*, viral, and plant terminator sequences, or the like.

The polynucleotide or vectors of the invention may also include a repression domain such as LxLxL from an AUX/IAA protein, such as those described in Tiwari, S. B. et al. (2004) *Plant Cell* 16(2):533-543. Examples include, but are not limited to, TELRLGLPG (SEQ ID NO: 37), TELRLGLPE (SEQ ID NO:38), TELCLGLPG (SEQ ID NO:39), TELTLGLPG (SEQ ID NO:40), TELTLALPG (SEQ ID NO:41), TDLRLGLSF (SEQ ID NO:42), TELDLALGL (SEQ ID NO:43), SELELGLGL (SEQ ID NO:44), MELDLGLSL (SEQ ID NO:45), IELGLTLSL (SEQ ID NO:46), IDLGLDLRT (SEQ ID NO:47), VNLSLSLTF (SEQ ID NO:48), KKLELKLGP (SEQ ID NO:49), KKLELRLHR (SEQ ID NO:50), and KRLELRLAP (SEQ ID NO:51). The repression domain may also be an ERF-associated amphiphilic repression (EAR) domain such as a SIERF36, or SIERF.F.1 (Accssion No. SGN-U564952) as described in Upadhyay, R. K. et al. (2014) *PLOS One* 9(7): e101995. Examples include, but are not limited to, NtERF3 (IDLDLNLAP) (SEQ ID NO:52), AtERF4 (LDLELNLPP) (SEQ ID NO:53), and AtSUPR (QDLDLELRL) (SEQ ID NO:54).

E. Control of Flowering and Biomass

Controlled flowering addresses a major regulatory concern of potential gene flow from GE crops to closely related weeds. It enables development of beneficial traits (e.g. drought tolerance, resistance to pests and diseases, herbicide resistance) in plant species prone to outcrossing (e.g. in turfgrass). Controlled flowering also improves trait stewardship by controlling seed production, creates opportunity to achieve dramatic increase in yield and vigor through development of hybrid seeds in crops where it is not currently possible or economical; improves yield and quality of crops where natural switch to flowering is undesirable (bolting in vegetables (e.g. broccoli, lettuce, spinach), declined nutritional quality of forage crops (e.g. alfalfa)); and improves yield and decreases costs in crops where synchronized flowering/fruit setting is desirable (e.g. pineapples).

Figure 10:
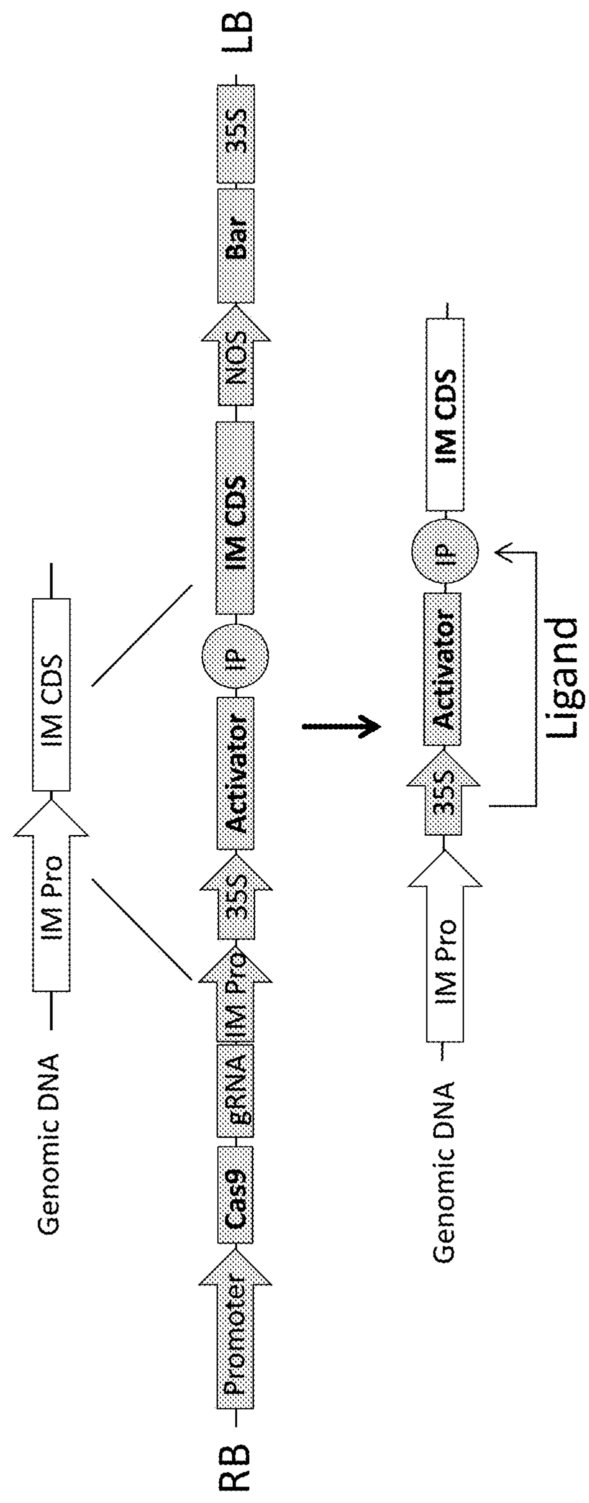
FIG. 10 shows a representative, hypothetical construct containing a CRISPR and an EcR-based gene switch for regulating expression of IM with a strong promoter (35S) that is inserted into the genome of the plant by CRISPR to place the EcR-based gene switch-controlled IM in the native position of wt IM with the strong heterologous promoter.

Flowering is controlled by various genes illustrated in FIG. 10. As used herein genes responsible for flowering may include, but are not limited to, any of these genes such as but not limited to the following (with gene identifiers in parentheses): CONSTANS (CO, AT5G15840), FLOWERING LOCUS D (FD, AT3G10390) or (At4g35900), SUPPRESSOR OF OVEREXPRESSION OF CO1 (SOC1, AT2G45660), TWIN SISTER OF FT (TSF, AT4G20370), LEAFY (LFY, AT5G61850), APETALA1 (AP1, AT1G69120), SPL3 (At2g33810); SPL9 (At2g42200); SUC2 (At1g22710); FLC (At5g10140); β-TUBULIN-2 (At5g62690); FT (At1g65480); FUL (At5g60910); AGL42 (At5g62165); TFL1 (At5g03840); FloweringMIR156a (At2g25095).

F. Controlled Resistance to Disease

Another use of the gene switch systems of the invention is the controlled delivery of compounds for pest and disease protection whereby a combination of novel pest and/or disease control chemistries are expressed only after application of ligand spray or activator substance. By way of illustration, but not limitation, multiple plant genes have been identified that have direct anti-microbial activity or act as positive regulators of the innate immune system; constitutive expression of these genes typically results in a loss of fitness for the plant. Precision control of defense related gene expression through switch ligand-dependent transcription activation enables transgenic disease resistance while reducing the metabolic or fitness cost associated with producing a transgene constitutively. In some embodiments, it is desireable to limit the expression of these antimicrobial compounds or positive regulators to key time points with the highest disease pressure. This can not only reduce the stress of constitutive expression of a transgene, but can also reduce the accumulation of novel chemistries in the environment. Moreover, expressing multiple chemistries with distinct modes of action and limiting their accumulation in the environment, reduces the long-term risk of resistant populations of insects or diseases developing in the field.

Examples of antimicrobial peptides that can be expressed in embodiments of the invention include defensins. Defensins are small, stable cysteine-rich peptides produced by plants that form part of the plant's innate immune system. Defensins are known to have antifungal activity and have also been shown to have activity against insects and some have antimicrobial activity (Stotz, H. U. et al. (2009) *Plant Signal Behay.* 4(11):1010-1012). For example, it has been demonstrated that wasabi defensin (WT1) imparted increased resistance to *Magnaporthe grisea, Erwinia carotovora* and *Botrytis cinerea* in rice, potato and orchid, while chili defensin (cdef1) has been shown to impart resistance to *Phytophthora infestans* and *Fusarium* sp. in tomatoes (Stotz et al. (2009)). Expression of dahlia defensin (Dm-AMP1) has been demonstrated to impart resistance to *Magnaporthe oryzae* and *Rhizoctonia solani* in rice and *Phytophthora palmivora* in papaya (Stotz et al. (2009)).

Examples of antifungal defensins that may be used in the invention include, but are not limited to Defensins, such as Ah-AMP1, AX1, AX2, At-AFP1 (LCR67), AFP2B, Psd1, Psd2, J1-1, J1-2, Tk-AMP-D1, Tk-AMP-D1.1, Tk-AMP-D2, Tk-AMP-D3, Tk-AMP-D4, Tk-AMP-D5, Tk-AMP-D6, Tk-AMP-D6.1, Tm-AMP-D1.2, PhD1, PhD2, NaD1, MsDef1, MtDef2, MtDef4, MtDef5, Rs-AFP1, Rs-AFP2, Sa-AFP2 and VrD1, which have activity against *Alternaria, Botrytis, Fusarium, Pyricularia, Verticillium, Aspergillus, Saccharomyces, Trichophyton, Cercospora, Cladosporium, Leptosphaeria, Penicillium, Trichoderma*, and *Septoria*; Snakins, such as Snakin-1 (StSN1), Snakin-2 (StSN2), which have activity against *Botrytis* (e.g., *Botrytis cinerea*), *Fusarium, Plectosphaerella, Colletotrichum, Bipolaris*, and *Aspergillus*; Heveins, such as AC-AMP1, AC-AMP2, Ar-AMP, EAFP1, EAFP2, Ee-CBP, Fa-AMP1, Fa-AMP2, IWF4, PN-AMP1, PN-AMP2, and WjAMP1 which have activity against *Alternaria, Ascochyta, Botrytis* (e.g., *Botrytis cinerea*), *Colletotrichum, Fusarium, Trichoderma, Verticillium, Phytophthora, Gibberella, Mycosphaerella, Neurospora, Phoma, Pythium, Rhizoctonia, Helinthosporium, Geotrichum*, and *Saccharomyces*; Thionins, such as Alpha-1-Purothionin, Alpha-2-Purothionin, Alpha-hordothionin, β-hordothjionin, BTH6, Pp-AMP1, Pp-AMP2, Tu-AMP-1, Tu-AMP2, VtA3, and VtB, which have activity against *Fusarium, Sclerotinia, Phytophtora, and Geotrichum*; Lipid Transfer Proteins such as La-LTP (LJAFP), Ace-AMP1, Hy-LTP Cw-18 (PKG2316), Hy-LTP4.1 (LTP4.1)(CW21), IWF1 (Bv-LTP1), IWF2 (Bv-LTP2), and Pa-LTP1, which have activity against *Fusarim, Pythium, Sclerotium, Alternaria, Ascockyta, Aspergillus, Bipolaris, Botrytis* (e.g., *Botrytis cinerea*), *Cerospora, Colletotrichum, Penicillium, Pyricularia, Rhizoctonia, Saccharomyces, Sclerotinia, Trichoderma, Verticillium, Clavibacter, Pyrenopkora*, and *Nectria*; Cyclotides, such as Circulin-A, Circulin-B, Cyclopsychotride-A, Kalata-B1, which are active against *Candida*; Shepherins, such as Shepherin I and Shepherin II, which are active against *Candida, Cryptococcus, Saccharomyces, Alternaria, Aspergillus*, and *Fusarium*; MBP-1 family peptides, which are active against *Alternaria Fusarium, Sclerotinia*, and *Aspergillus*; Vicilin-like peptides such as MiAMP2, MiAMP2b, MiAMP2c-1, MiAMP2c-2, MiAMP2c-3, and MiAMP2d, which are active against *Alternaria, Ceratocystis, Cercospora, Chalara, Fusarium, Leptosphaeria, Sclerotinia, Verticillium, Saccharomyces*, and *Phytophthora*; Impatiens family peptides such as Ib-AMP1, Ib-AMP2, Ib-AMP3, and Ib-AMP4, which have activity against *Alternaria, Botrytis* (e.g., *Botrytis cinerea*), *Cladosporium, Fusarium, Penicillium, Trichoderma*, and *Verticillium*; β-Barrelin, such as MiAMP1 which has activity against *Saccharomyces*; knottins family peptides, such as MJ-AMP1, MJ-AMP2, Mc-AMP1, and Pa-AMP1 (PAFP-S), which have activity against *Alternaria, Ascochyta, Botrytis* (e.g., *Botrytis cinerea*), *Cercospora, Colletotrichum, Fusarium, Nectria, Phoma, Pyrenophora, Pyricularia, Rhizoctonia, Verticiliium*, and *Venturia*.

Some defensins have antimicrobial activity. Examples of defensins family peptides with antimicrobial activity that may be used in the invention include, but are not limited to Defensins, such as Ah-AMP1, AX1, AX2, Cp-thionin-2, Fabatin-1, Fabatin-2, and VrD1, which have activity against Gram-positive bacteria (e.g., *Bacillus, Enterococcus*, and *Staphylococcus*); Snakins, such as Snakin-1 (StSN1), Snakin-2 (StSN2), and ZmGASA-like, which have activity against Gram-positive bacteria (e.g., *Clavibacter, Ralstonia, Listeria*, and *Rhizobium*) *Erwinia* (e.g., *Erwinia amylovora*), *Escherichia*, and *Pseudomonas*; Heveins, such as AC-AMP1, AC-AMP2, Fa-AMP1, Fa-AMP2, PN-AMP1, PN-AMP2, and WjAMP1 which have activity against Gram positive bacteria (e.g., *Bacillus, Clavibacter*) and *Escherichia*; Thionins, such as Pp-AMP1, Pp-AMP2, Tu-AMP-1, Tu-AMP2, which have activity against *Erwinia, Agrobacterium, Clavibacter* and *Curtobacterium*; Lipid Transfer Proteins such as La-LTP, Ace-AMP1, Lc-LTP1, Lc-LTP2, Lc-LTP3, Lc-LTP4, Lc-LTP5, Lc-LTP6, Lc-LTP7, Lc-LTP8, Pa-LTP1 which have activity against Gram positive bacteria (e.g., *Bacillus, Staphylococcus, Sarcina*), *Pseudomonas, Ralstonia, Agrobacterium*, and *Escherichia*; Cyclotides, such as Circulin-A, Circulin-B, Cyclopsychotride-A, Kalata-B1, which are active against Gram positive bacteria (e.g., *Staphylococcus, Micrococcus*), *Pseudomonas, Proteus, Klebsiella*, and *Escherichia*; Shepherins, such as Shepherin I and Shepherin II, which are active against Gram positive bacteria (e.g., *Bacillus, Staphylococcus, Streptococcus*), *Erwinia, Escherichia, Pseudomonas, Salmonella*, and *Serratia*; MBP-1 family peptides, which are active against Gram positive bacteria (e.g., *Clavibacter*), and *Escherichia*; Vicilin-like peptides such as MiAMP2, MiAMP2b, MiAMP2c-1, MiAMP2c-2, MiAMP2c-3, and MiAMP2d, which are active against Gram positive bacteria (e.g., *Clavibacter*); Impatiens family peptides such as Ib-AMP1, and Ib-AMP4, which have activity against Gram positive bacteria (e.g., *Bacillus, Micrococcus, Staphylococcus, Streptococcus*) *Xanthomonas, Erwinia, Escherichia, Proteus*, and *Pseudomonas*; knottins family peptides, such as MJ-AMP1, MJ-AMP2, Mc-AMP1, and Pa-AMP1 (PAFP-S), which have activity against Gram positive bacteria (e.g., *Bacillus, Sarcina*, and *Staphylococcus*).

Some defensins have activity against insects. These include, for example, but not by way of limitation, defensins such as VrD1, which has activity against *Spodoptera frugiperda*; Cyclotides such as Circulin-B, Kalata-B1, and Kalata-B2, which have activity against *Helicoverpa.*

G. Control of Other Traits

Controlled gene expression using the polynucleotides or vectors of the invention may be applied to any trait of interest. Various phenotypic traits include stress resistance (e.g., drought and herbicides), tunable traits such as type and intensity of color and aroma in flowers, and controlled accumulation of specific nutrients in fruits and vegetables such as differentiating taste and nutritional value to satisfy different groups of consumers. Timing of expression can be important such that one may select to turn on genes at the proper time in the plant's life, and even the production of high value compounds (exogenous active pharmaceutical ingredients, biopolymers, etc.). In some embodiments it is necessary to control the timing of compound accumulation (switching it on right before harvesting) because of the fitness cost. In other embodiments, the control of expression is timed in the life of the plant and in various plant tissues using tissue-specific prototers to express the gene of interest at specific stages of the plant (e.g., flowering, seed production) in order to achieve the goal desired by the grower.

H. Uses of Controlled Traits

Uses of the control of flowering include, but are not limited to, improvement in crop yield and quality in conjunction with lower cost profile for select fruits and vegetables; increased biomass production in forage crops by prolonging vegetative state; on-demand resistance for environmental and biological stressors such as drought, pests and disease; development of beneficial traits in plant species prone to outcrossing such as turfgrass; enhanced plant production of high-value compounds including active pharmaceutical ingredients and biopolymers; approach to reduce potential environmental impact from GMO crops addressing significant global concerns; regulated accumulation of specific nutrients in fruits and vegetables providing an ability to adjust the taste or nutritional value to satisfy market demands; tune traits such as color and aroma in flowers, as well as provide florists ability to have flowering occur onsite lowering lost productivity commonplace in the industry; and more efficient and effective commercial seed production of plants.

Examples of these crops that may be controlled using the compositions and methods of the invention include, but are not limited to, alfalfa sprouts, apples, apricots, artichokes, Asian pears, asparagus, atemoyas, avocados, bamboo shoots, bananas, beans, bean sprouts, beets, belgian endive, bitter melons, bell peppers, blackberries, blueberries, bok choy, boniato, boysenberries, broccoflowers, broccoli, broccolini, brussels sprouts, butter lettuce, cabbage, cantaloupe, carambola, carrots, casaba melons, cauliflower, celery, chayotes, cherimoyas, cherries, coconuts, coffee, collard greens, corn, cotton, cranberries, cucumbers, dates, eggplant, endive, escarole, feijoa, fennel, figs, garlic, gooseberries, grapefruit, grapes, green beans, green onions, collard greens, mustard greens, guava, hominy, honeydew melons, horned melons, iceberg lettuce, Jerusalem artichokes, jincama, kale, kiwifruit, kohlrabi, kumquats, leeks, lemons, lettuce, lima beans, limes, longan, loquats, lychees, madarins, malangas, mandarin oranges, mangos, marijuana, mulberries, mushrooms, napas, nectarines, okra, onions, oranges, papayas, parsnip, passion fruits, paw-paws, peaches, peanut, pears, sugar snap peas, green peas, peppers, persimmons, pineapples, plantains, plums, pomegranates, potatoes, prickly pears, pummelos, pumpkins, quince, radicchio, radishes, raspberries, red cabbage, rhubarb, romaine lettuce, rutabaga, shallots, snow peas, soybeans, spinach, sprouts, squash, strawberries, string beans, sweet potatoes, tangelo, tangerines, tomatillo, tomatoes, turnip, ugli fruit, watermelons, water chestnuts, watercress, waxed beans, yams, yellow squash, yuca/cassava, and zucchini squash.

Examples of flowers that may be controlled using the compositions and mthods of the invention include, but are not limited to African daisy, Agapanthus, Ageratum houstonianum, Alchemilla, Allium, Alyssum, Amaranthus, Amaryllis, Anemone, Angelonia, Anthurium, Artemisia, Asclepias syriaca, Aster, Astilbe, Astrantia, Aubreita deltoidea, baby's breath, bachelor button, balloon flower, bee balm, begonia, bellflower, blanketflower, Bergenia, black-eyed Susan, blanket flower, blazing star, bleeding heart, bluebell, blue-eyed grass, blue star flower, Bouvardia, Bougainvillea, broom, Buddleja, bush morning glory, buttercup, butterfly weed, butterfly bush, Calendula, California poppy, calla lily, Calliandra, Camellia, Campenula, candytuft, canna lily, cape primrose, cardinal flower, carnation, catmint, celosia, chrysanthemum, Clarkia, clover, clematis, cockscomb, columbine, coneflower, coral bells, Coreopsis, Cosmos, Cotoneaster, Crocus, creeping phlox, Crocosmia, crown imperial, cuckoo flower, Cyclamen, Dahlia, day lily, Delphinium, Echium, English bluebell, Erigeron, evening primrose, Euphorbia, flannel flower, flax flower, floss flower, forget-me-not, Forsythia, foxglove, frangipani, freesia, fuschia, gardenia, geranium, gas plant, Gaura, gayfeather, Gerbera, Gladiolus, globeflower, goldenrod, grape hyacinth, Gypsophila, heather, Hebe, Helenium, Heliotrope, Hellebore, hibiscus, hollyhock, honeysuckle, hosta, hyacinth, hydrangea, Hypericum, hardy geranium, hybrid tea roses, Iceland poppy, ice plant, Ilex, Impatiens, Ipheion uniflorum, iris, Ixia, Ixora, Jaborosa, Jacob's ladder, Jamesia americana, jasmine, Jupiter's beard, kaffir lily, Kalmia, kangaroo paw, Kerria, Knautia macedonica, Kniphofia, Kolkwitzia, lady's slipper, Lamium, Lantana, larkspur, Lavatera, lavender, Lechenaultia, lilac, lily, lily of the valley, Linaria, lisianthus, lobelia, loosestrife, lotus, lunaria, lupin, magnolia, Maltese cross, Mandevilla, Marguerite daisy, marigold, Matthiola, mayflower, Meconopsis, mimosa, Mina lobate, mock orange, monk's hood, moonflower, morning glory, Muscari, narcissus, nasturtiums, Nemesia, Nemophila, Nerine, New Guinea impatien, Nicotiana, Nierembergia, Nigella, Nolana, oleander, orchid, oriental lily, oriental poppy, Osteospermum, oyster plant, ox eye daisy, painted daisy, pansy, passion flower, peace lily, Pelargonium, Penstemon, peony, Persian buttercup, Peruvian lily, petunia, pincushion flower, pink lady's slipper, pointsettia, Polyanthus, poppy anemone, Portulaca grandiflora, Primula, Quaker ladies, Queen Anne's lace, Queen's cup, Queen of the meadow, quince, rain lily, Ranunculus, Rhododendron, rock rose, Rondeletia, rose, rose of Sharon, Salvia splendens, Saponaria, Scabiosa, Scaevola, scented geranium, Scilla, Sedum, shasta daisy, shrub roses, Silene, silver lace vine, snapdragon, snowball bush, snowdrop, snowflake, statice, strawflower, sun drop, sunflower, sweet pea, Syringa, tea rose, tiger flower, tiger lily, Tithonia, Trillium, Triteleia, Tritonia crocata, trumpet vine, tuberose, tulip, urn plant, Ursinia, Uva ursi, Verbena, Veronica incana, Vinca, Viola tri-colour, Violet, Virginia creeper, wallflower, wandflower, water lily, Watsonia, wax plant, Wedelia, Weigela, wild rose, wild violet, winter aconite, winterberry, winter jasmine, wishbone flower, wisteria, wooly violet, Xerophyllum, Xylobium, Xylosma, yarrow, yellow angel, yellow bell, yellow-eyed grass, yellowhorn, Zenobia, and zinnia.

Examples of grains that may be controlled using the compositions and methods of the invention include, but are not limited to barley, buckwheat, bulgur wheat, corn, durum wheat, einkorn, emmer, farro, fonio, kamut, millet, oats, rice, rye, semolina wheat, sorghum, spelt, teff, triticale, wheat, bamboo shoots, barleygrass, lemongrass, molasses, rapadura, sugarcane, wheatgrass, Amaranth, Coxcomb, pitseed goosefoot, quinoa, chia, acacia seed, and wattleseed.

Examples of turf grass that may be controlled using the compositions and mthods of the invention include, but are not limited to Kentucky bluegrass, perennial ryegrass, tall fescue, fine fescue, creeping bentgrass, creeping red fescue, hard fescue, chewings fescue, Bermudagrass, buffalograss, kikuyugrass, St. Augustine, and zoysia.

Examples of forage crops that may be controlled using the compositions and methods of the invention include but are not limited to alfalfa, alsike clover, annual lespedeza, birdsfoot trefoil, crownvetch, ladino clover, red clover, Sericea lespedeza, sweetclover, white Dutch clover, big bluestem, caucasian bluestem, Indiangrass, little bluestem, pearl millet, side-oats grama, switchgrass, and triticale.

In certain preferred embodiments, the plants are potato, sugar beet, alfalfa, silage corn hay, pear apple, pineapple, orange, grapefruit, coffee, soybeans, snapbeans, kidney beans, zinnias, turfgrass, sorghum, rice, wheat, barley, green bean, red bean, potato, oat and millet; *Arabidopsis*, Chinese cabbage, radish, red pepper, strawberry, tomato, watermelon, cucumber, cabbage, melon, squash, stone-leek, onion, ginseng, tobacco, marijuana, cotton, sesame, sugar cane, sugar beet, wild sesame, peanut, rape, peach, date, western Actinidia, grape, persimmon, plum, apricot, banana, ryegrass, red clover, orchard grass and tall fescue, maize, miscanthus, and switchgrass.

In some embodiments, flower color may be controlled on demand using the gene switch strategies of the invention. For example, a gene responsible for flower color such as chalcone synthase A of petunias which is responsible for purple color can be influenced using a gene switch system in which a dsRNA is expressed in the petunia when provided with ligand. The dsRNA has the effect of inhibiting chalcone synthase A and the flowers will not be deep purple, instead, the flowers will have low level of purple color with increased amounts of the dsRNA. At high levels, the flowers will be white. Similarly, other genes responsible for flower color, aroma, and other traits can be targeted and operatively linked to the gene switch system of the invention for on-demand expression or inhibition of a trait.

Methods of Making the Polynucleotides or Vectors

Various non-limiting arrangements and types of the vector elements are illustrated in the Examples Section and in the Figures, but other types of promoters, activators, terminators, etc., and arrangements of the elements (5' or 3' of one another) can be made to achieve desired outcomes as will be apparent to one of skill in the art.

The polynucleotide vectors of the invention may be made by methods that are well-known in the art. DNA construct may also be made such that elements for gene editing may be containing both an EcR-based gene switch and gene editing elements such as zinc-finger nucleases, TALENs or CRISPR elements. For example, but not by way of limitation, CRISPR elements (Cas9 and gRNA elements) may be incorporated into a vector such that the vector targets a locus in the genome of the plant and the CRISPR-Cas9 and guide RNA elements direct transformation of the plant through homology directed recombination (HDR) to insert the gene switch between the gene of interest promoter and its coding sequence to create an insertional mutation of gene of interest to create a gene under the control of a gene switch of the invention, while the other components of the DNA construct including the CRISPR-Cas9 and gRNA elements are not integrated at the locus. Application of the activating ligand turns the gene back on to restore normal function.

In other methods, homologous recombination may be used to replace the endogenous gene of interest (e.g., a gene responsible for flowering) or an exogenous gene to be controlled by a gene switch into a predetermined locus in the plant. In this way, the endogenous plant gene will be controllable by application of the chemical ligand "on-demand."

In some embodiments of the invention, control of a plant gene, (e.g., for flowering) may be accomplished by introducing *Bacillus amyloliquefaciens* Barnase into the plant. Barnase ("BActerial RiboNucleASE") is a nuclease that has been shown to inhibit gene expression as it degrades nucleic acid and prevents expression in plants. Barnase may be expressed in the method of the invention by using tissue-specific promoters to limit Barnase expression to a particular tissue to inhibit the targeted gene of interest. Generalized expression of Barnase could be lethal to the plant. As an example, one could target a gene for flowering using a flowering-specific promoter to limit the expression of Barnase to flower tissue. Barnase may be operatively linked to a flower-specific promoter (e.g., LFY, AP1, H4A, etc.). Floral-meristem controlled expression of Barnase should prevent flowering in the plant. To control flowering, an EcR-based gene switch of the invention may be introduced with *Bacillus amyloliquefaciens* Barstar which is operatively linked to a regulatory element 5' of of Barstar wherein said EcR-based gene switch binds said regulatory element in the presence of the activating chemical ligand. Barstar is an inhibitor of Barnase and controlled expression of the Barstar inhibitor allows the plant to flower. Introduction of Barnase under the control of a plant tissue-specific promoter may be on the same polynucleotide or vector of the invention or on a separate polynucleotide or vector.

Other ways of accomplishing control include providing a vector or polynucleotide to direct expression of an inhibitor of an endogenous gene of interest constitutively such that the trait is turned off in the plant. The gene switch of the invention may be introduced with a gene to override the repressor of expression. By way of example and not by way of limitation, a plant may be made to constitutively express miR156 to inhibit SPL and thereby inhibit flowering in the plant. The plant may also be transformed with a gene switch of the invention to control a mutant form of SPL that has altered codon usage so the miR156 molecule cannot hybridize with it to prevent expression. Application of ligand leads to expression of the SPL (same amino acid sequence, but altered mRNA sequence) and the SPL protein produced therefrom leads to flowering in the plant.

Vectors may be introduced into the desired host cells by methods known in the art, e.g., *Agrobacterium*-mediated transformation, transfection, electroporation, microinjection, transduction, cell fusion, DEAE dextran, the flower dipping method, use of a gene gun (biolistics) and the like. The EcR-based gene switch may be introduced into the plant separately from the gene to be controlled and inserted to control the native gene of interest. Alternatively, the native gene to be controlled may be replaced with the gene switch and control elements on the polynucleotide or vector of the invention.

It will be understood that the above description is intended to be illustrative of the invention and is not limiting. Those of skill in the art may make various modifications without departing from the spirit of the invention, which is defined by the appended claims.

EXAMPLES

Example 1

Transform wild type *Arabidopsis* to introduce inducible GFP reporter: DNA construct ID38, which is shown diagrammatically in FIG. 1A, may be used to transform wild type (wt) *Arabidopsis*. The construct contains both the inducible promoter (IP) composed of 5 GAL4 regulatory elements (GAL4-RE) placed upstream of the minimal CaMV-35S promoter and the multidomain activator (AP—activator protein or Activator) gene (VGE$_{CE}$68V/V184I/204E) under the control of CaMV-35S strong constitutive promoter. In addition, the construct contains the Nos:Bar gene to allow selection of transgenic plants with glufosinate-ammonium that is the active ingredient of herbicide formulations sold under different brand names including LIBERTY® 280SL and BASTA® herbicides.

GFP gene will not be expressed until methoxyfenozide (activator ligand—AL) is provided to mobilize the activator proteins for binding to the GAL4-RE and switching on the IP. Methoxyfenozide is the active ingredient of INTREPID® 2F commercial insecticide. Since GFP expression can be conveniently monitored in live plants under a fluorescence microscope, the transgenic *Arabidopsis* can be used to study the dosage, timing, and half life time of the ligand application. The DNA construct ID68, shown diagrammatically in FIG. 1B, containing GFP under control of strong constitutive promoter CaMV-35S may be used to transform wt *Arabidopsis* to produce positive control plants that will express GFP constitutively.

Figure 2:
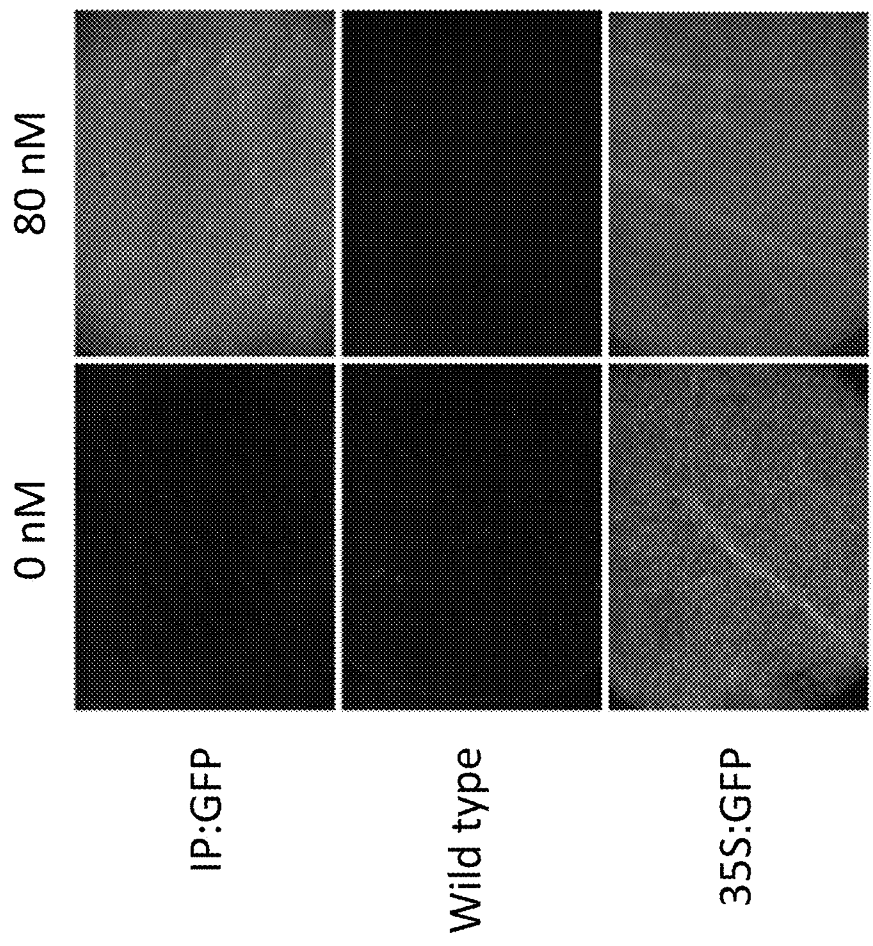
FIG. 2 shows fluorescence in detached *arabidopsis* leaf disks obtained from ID38 plants (top row); wild type plants (middle row) and ID68 plants (bottom row). Fluorescence was assessed after 48 hours in water (left column) or 80 nM solution of methoxyfenozide (right column) added to activate GFP expression.

Briefly, the DNA constructs shown in FIG. 1 were built following standard molecular cloning procedures and transformed into disarmed *Agrobacterium tumefaciens* strain AGL1. Wild type (wt) *Arabidopsis* plants were then transformed separately with the *Agrobacterium* strains carrying constructs ID38 and ID68 by flower dipping method. T1 seeds were harvested and germinated in soil. 5 day old T1 seedlings were sprayed with LIBERTY® 280SL herbicide to kill off non-transgenic plants. Selected transgenic plants were analyzed by quantitative PCR (qPCR) and PCR to check transgene copy numbers and transgene intactness. Specific primers for Bar gene (Bar-F1/Bar-R1/Bar-T1) and endogenous PDS gene as control (AtPDS-F1/AtPDS-R1/AtPDS-T1) were used (Primers used in the PCR assays are shown in Table 1). Events with single copy of the transgenes were grown in growth chambers under 16 hours long day photoperiod to evaluate phenotypes. Plants transformed with the positive control DNA construct 35S:GFP (ID68) showed strong GFP expression in leaves. No GFP expression was observed in plants transformed with the DNA construct IP:GFP (ID38). Leaf samples were collected from the plants and incubated on media containing the ligand methoxyfenozide at different concentrations to induce gene expression. GFP expression was induced with as low as 16 nM methoxyfenozide in 24 hr in the transgenic plants samples with IP:GFP but not in the wt control as shown in FIG. 2. Plants transformed with the 35S:GFP construct expressed GFP constitutively either with or without ligand induction.

Example 2

Transform *Arabidopsis* Mutants to Achieve Inducible Restoration of Wild-Type Phenotype:

A. FT Mutant

DNA construct ID14, shown diagrammatically in FIG. 3A, is similar to that described in Example 1, except that the GFP is replaced with a wt FLOWERING LOCUS T (FT, AT1G65480) gene and may be used to transform a homozygous ft late flowering *Arabidopsis* mutant. Transgenic FT gene may similarly be turned on by applying methoxyfenozide ligand to give a dominant phenotype restoring late flowering to normal flowering. The advantage of using the late flowering ft mutant is to simplify phenotype analysis. The flowering time of transgenic plants can be compared to wt and ft plants grown side by side under the same long day or short day condition with or without applying methoxyfenozide ligand. DNA construct ID16, shown diagrammatically in FIG. 3B, containing FT under the direct control of CaMV-35S promoter may be used to transform ft mutant *Arabidopsis* to produce positive control plants that will express FT constitutively. Overexpression of FT under a strong constitutive promoter such as 35S will induce premature early flowering.

Figure 3:
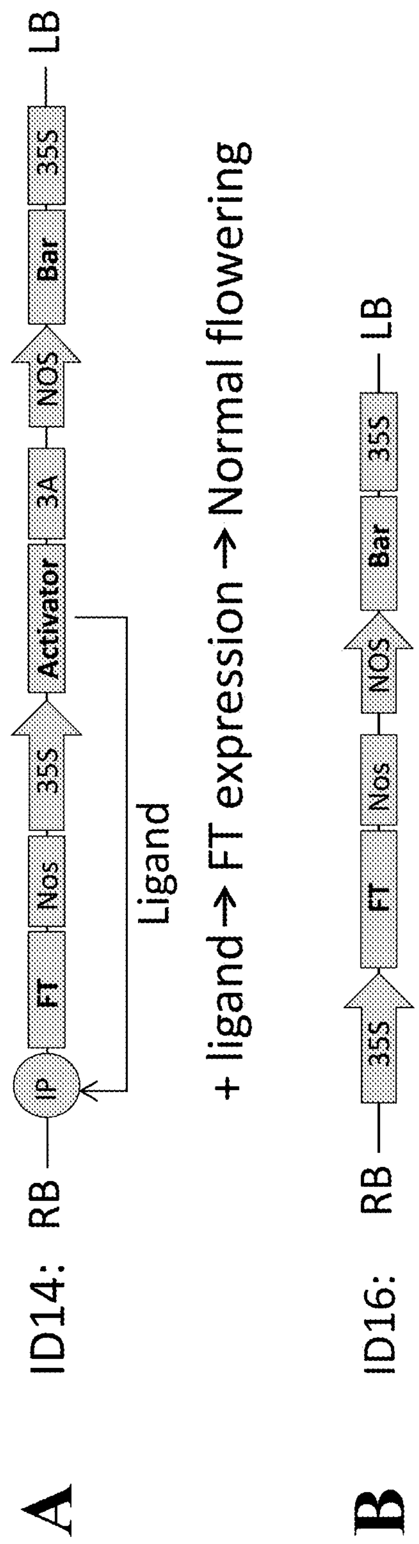
FIG. 3 shows a DNA construct for controlled expression of the flowering locus T gene (FT). Panel A shows ID14 which was constructed to express FT under the control of a switch that may be activated by addition of ligand; Panel B shows ID16, a construct that constitutively expresses FT (control).
Figure 4:
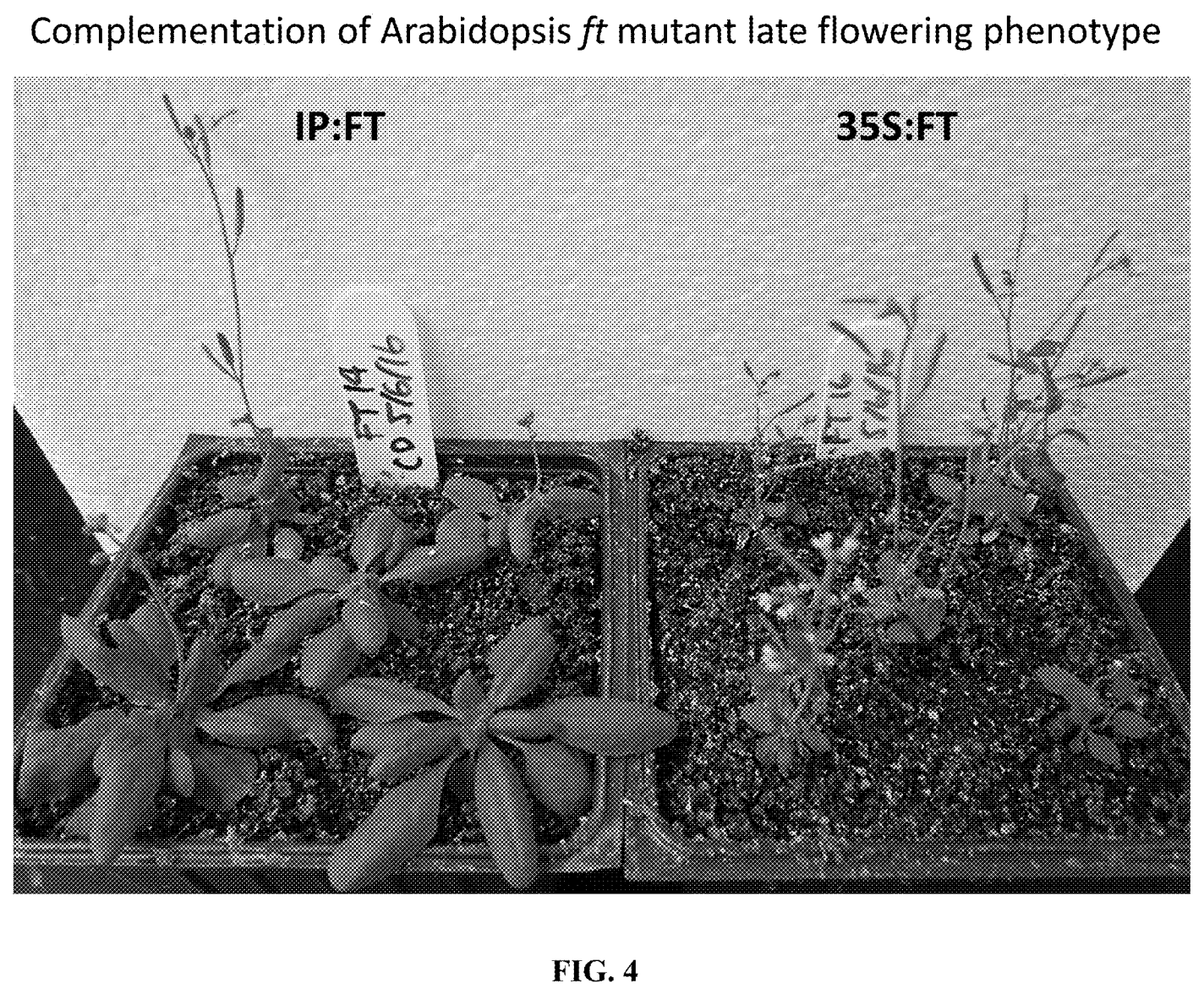

Briefly, the DNA constructs shown in FIG. 3 were transformed into homozygous ft mutant *Arabidopsis* by flower dipping method. T1 seeds were harvested and germinated in soil. 5 days old T1 seedlings were sprayed with LIBERTY® 280SL herbecide to kill off non-transgenic plants. Selected transgenic plants were analyzed by Bar-specific quantitative PCR (qPCR) to check transgene copy number. Events with low copy number of the transgenes were grown in growth chambers to evaluate phenotypes. In the absence of ligand methoxyfenozide some of the transgenic plants with IP:FT construct (ID14) showed the expected late flowering behavior just like the ft mutant and null segregants, while others showed early flowering, suggesting that the IP:FT cassette in these plants might be able to express enough FT to induce early flowering even in the absence of ligand induction. Plants transformed with the ID16 construct overexpressed FT constitutively that resulted in extremely early flowering and stunted phenotype as shown in FIG. 4. Non-flowering IP:FT plants were selected and sprayed with the ligand methoxyfenozide which induced flowering and allowed for normal seed set. Select T1 plants were grown to maturity and seeds were used to generate T2 and T3 progeny plants. Further detailed evaluation of the transgenic lines were done in T2 and T3 generation plants (as described in Example 7).

B. IM Mutant.

Figure 5:
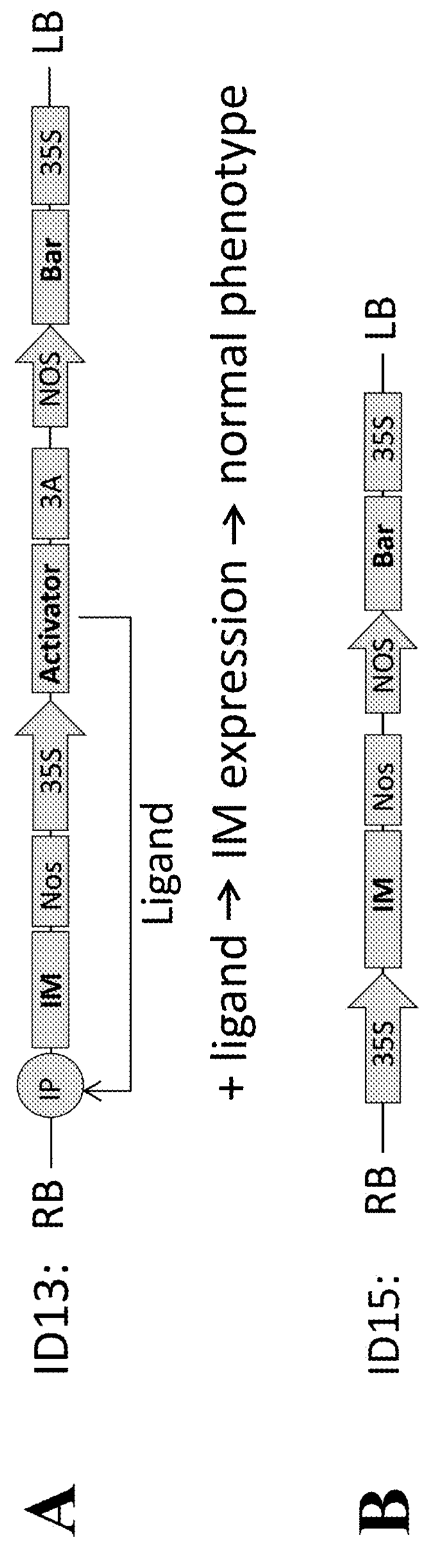
FIG. 5 shows a DNA construct for controlled expression of the immutans gene (IM). Panel A shows ID13 which may be constructed to express IM under the control of a switch that may be activated by addition of ligand; Panel B shows ID15, a construct that constitutively expresses IM (control).

DNA construct ID13, shown diagrammatically in FIG. 5A, is similar to that described in Example 1 except that the GFP is replaced with a wt IMMUTANS (IM) gene (AT4G22260). This construct may be used to transform *Arabidopsis* homozygous immutans variegation mutant (im) CS3639 as obtained from Aridopsis Biological Resource Center (ABRC). Transgenic wt IM gene may similarly be turned on by applying methoxyfenozide ligand to give a dominant phenotype where the white-green variegated leaves are restored to normal green leaves. The advantage of using the non-lethal variegation im mutant is to simplify phenotype analysis by the visual observation of leaf colors.

Alternatively, a recessive lethal albino T-DNA insertion mutant of the phytoene desaturase gene (PDS, locus AT4G14210) can be restored by expressing the wt PDS under the EcR-based gene switch control.

DNA construct ID15, shown diagrammatically in FIG. 5B, containing wt IM under direct control of CaMV-35S promoter may be used to transform im mutant *Arabidopsis* to produce positive control plants that will express IM constitutively.

Briefly, the DNA construct shown in FIG. 5A may be transformed into homozygous im *Arabidopsis* by flower dipping method. T1 seeds are then harvested and germinated in soil. 5 days old T1 seedlings are sprayed with LIBERTY®

280SL herbicide to kill off non-transgenic plants. Selected transgenic plants are analyzed by quantitative PCR (qPCR) and PCR to check transgene copy numbers and transgene intactness. Events with single intact copy of the transgenes are grown in growth chambers to observe phenotypes. In the absence of methoxyfenozide ligand the transgenic plants with IP:IM construct should have variegated leaves just like the im mutant plants. Selected plants may then be sprayed with the ligand methoxyfenozide and newly grown leaves should no longer be variegated due to EcR-based gene switch system driving expression of IM. Plants transformed with the construct in FIG. 5B would overexpress IM constitutively and would produce normal green leaves.

Example 3

Targeting genes in plants by inserting EcR-based gene switch to control a phenotypic trait. One could also take advantage of the recent CRISPR gene targeting technology (Li et al. (2015) *Plant Physiol.* 169:960-970) to introduce inducibility to a plant gene. For example, a flowering control gene such as the FLOWERING LOCUS T (FT) florigen gene may be targeted by inserting EcR-based gene switch system between the FT promoter and coding sequence of the FT gene. The interruption of the key flowering gene FT will likely create a late flowering mutant that can be restored by turning the same FT gene expression back on by the EcR-based gene switch when appropriate ligand is applied. The native FT promoter is appointed to express the activator (AP) to mimic the natural expression profile of the FT gene and minimize potential pleiotropic effects from the overexpression of FT if using a strong constitutive promoter such as 35S.

Figure 6:
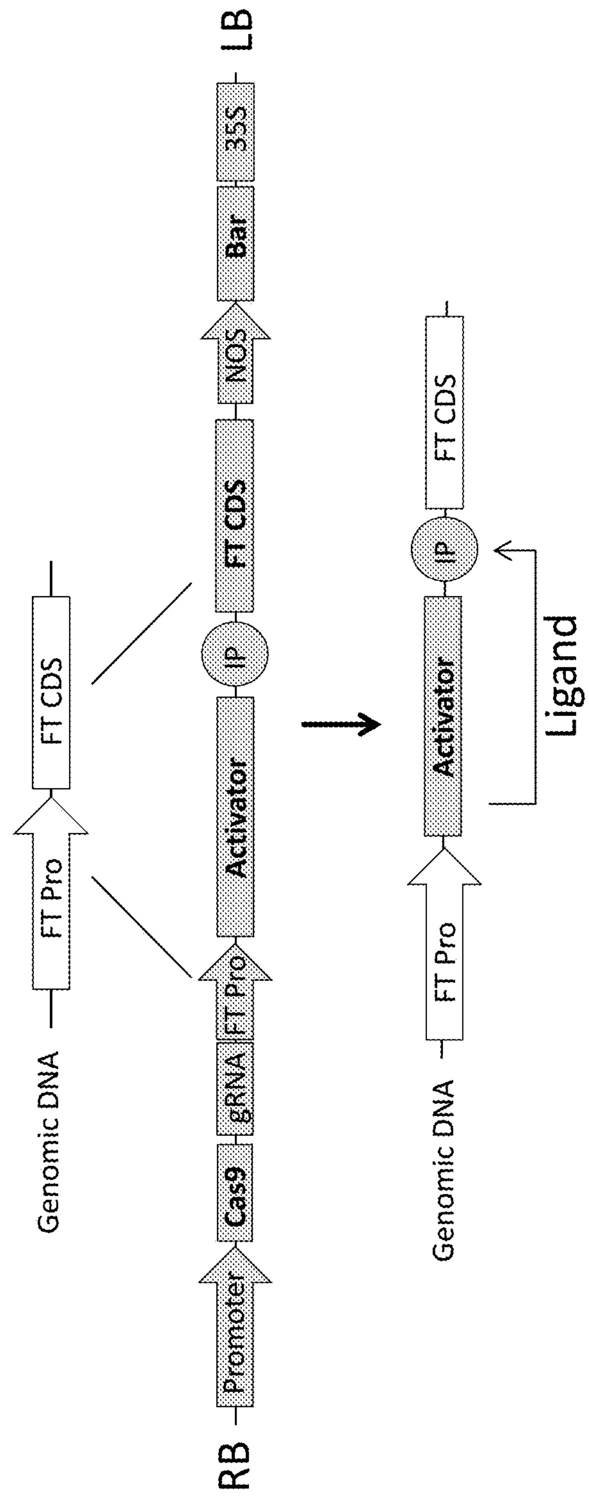
FIG. 6 shows a representative, hypothetical construct containing a CRISPR and an EcR-based gene switch for regulating expression of the flowering locus T gene (FT) with a native FT promoter (FT Pro) that is inserted into the genome of the plant by CRISPR to place the EcR-based gene switch-controlled FT in the native position of wt FT with the native FT promoter.

A DNA construct, such as shown diagrammatically in FIG. 6, containing both an EcR-based gene switch and CRISPR elements (Cas9+gRNA) targeting the FLOWERING LOCUS T (AT1G65480) gene is transformed into wt *Arabidopsis*. CRISPR mediated gene targeting through homology directed recombination (HDR) places the Activator+IP elements between the FT promoter and its coding sequence to create an insertional mutation of FT gene that leads to a late flowering phenotype. Other components of the DNA construct including the Promoter:Cas9+gRNA and Nos:Bar expression cassettes will not be integrated at the FT locus. Application of the methoxyfenozide ligand turns the FT gene back on and restores the late flowering FT mutation to normal flowering.

Briefly, a DNA construct as illustrated in FIG. 6 (middle) is transformed into wt *Arabidopsis* by flower dipping method. T1 seeds are harvested and germinated in soil. 5 days old T1 seedlings are sprayed with LIBERTY® 280SL herbicide to ensure than only transgenic plants survive. Transformants are analyzed by qPCR to check transgene copy number. Events with single copy of the transgenes are grown in growth chambers to evaluate genotypes. FT locus is further analyzed by PCR to check the targeted FT for gene interruption, and the targeted insertion site is sequenced to confirm that the insertion does not change the FT coding sequence. Events with an HDR insertion of the transgene or indel at the FT target site are grown in growth chambers to observe phenotypes. The majority of transgenic events with randomly integrated transgenes are discarded. Since ft is a recessive mutation, no late flowering phenotype occurs in hemizygous T1 generation.

T2 seeds are germinated into plants and homozygous transgenic plants identified by qPCR are then grown in growth chambers to evaluate for late flowering phenotype. Some of the plants are sprayed with methoxyfenozide and some are not (controls). The flowering time of sprayed and untreated plants are compared to wt and ft plants grown side by side under the same conditions. Typically, *Arabidopsis* plants flower in ~4 weeks of initiation in soil under long day (16 hours) photoperiod. Plants showing a delay or absence of flowering in the absence of methoxyfenozide ligand and normal flowering in the presence of the ligand should be insertional mutants and may be selected for further analysis of EcR switch controlled flowering and FT gene expression level.

Example 4

Targeting Genes in Plants by Inserting an Enhanced EcR-Based Gene Switch to Control a Phenotypic Trait.

Figure 7:
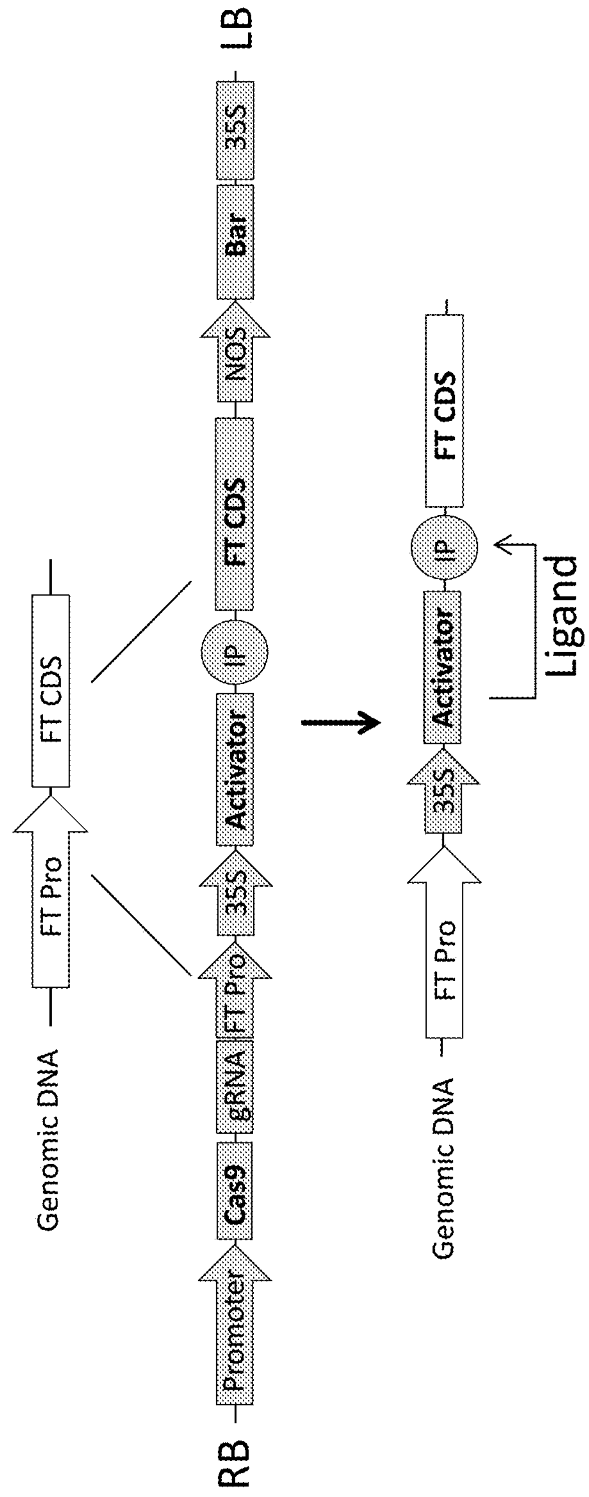
FIG. 7 shows a representative, hypothetical construct containing a CRISPR and an EcR-based gene switch for regulating expression of FT gene with a strong constitutive promoter (35S) that is inserted into the genome of the plant by CRISPR to place the EcR-based gene switch-controlled FT in the native position of wt FT with the strong heterologous promoter.

In another embodiment using CRISPR gene targeting technology, a DNA construct shown diagrammatically in FIG. 7, containing both an EcR-based gene switch using a strong 35S promoter and CRISPR elements (Cas9+gRNA) targeting the FLOWERING LOCUS T (AT1G65480) gene is transformed into wt *Arabidopsis*. The only difference between the two DNA constructs in FIG. 6 and FIG. 7 is that the latter has the 35S promoter expressing the Activator protein. CRISPR mediated gene targeting through homology directed recombination (HDR) places the 35S:Activator+IP elements between the FT promoter and its coding sequence to create an insertional mutation of FT gene that leads to a late flowering phenotype. Other components of the DNA construct including the Promoter:Cas9+gRNA and Nos:Bar expression cassettes will not be integrated at the FT locus. The 35S promoter is appointed to express more EcR-based gene switch proteins to trigger the switch for overexpression of the FT gene. Application of the methoxyfenozide ligand turns the FT gene on at higher level than the wt to convert theft late flowering mutation to early flowering.

Briefly, a DNA construct as illustrated in FIG. 7 (middle) is transformed into wild type *Arabidopsis* by flower dipping method. T1 seeds are harvested and germinated in soil. 5 day old T1 seedlings are sprayed with LIBERTY® 280SL herbicide to ensure that only transgenic plants survive. The transgenic plants are analyzed by PCR analyses to check the targeted FT site for gene interruption, to determine transgene copy number, and to sequence the targeted insertion site to confirm correct insertion that does not alter the FT gene coding sequence. Events with an HDR insertion of the transgene or indel at the FT target site are grown in growth chambers to observe phenotypes. The majority of transgenic events with randomly integrated transgenes are discarded. Since ft is a recessive mutation, no late flowering phenotype occurs in hemizygous T1 generation.

T2 seeds are germinated into plants and homozygous transgenic plants identified by qPCR are then grown in growth chambers to evaluate for late flowering phenotype. Some of the plants are sprayed with methoxyfenozide and some are not (controls). The flowering time of sprayed and untreated plants are compared to wt and ft plants grown side by side under the same conditions. Typically, *Arabidopsis* plants flower in ~4 weeks of initiation in soil under long day (16 hours) photoperiod. Plants showing a delay or absence of flowering in the absence of methoxyfenozide ligand and early or normal flowering in the presence of the ligand are identified and analyzed for EcR switch controlled FT gene expression and flowering.

Figure 8:
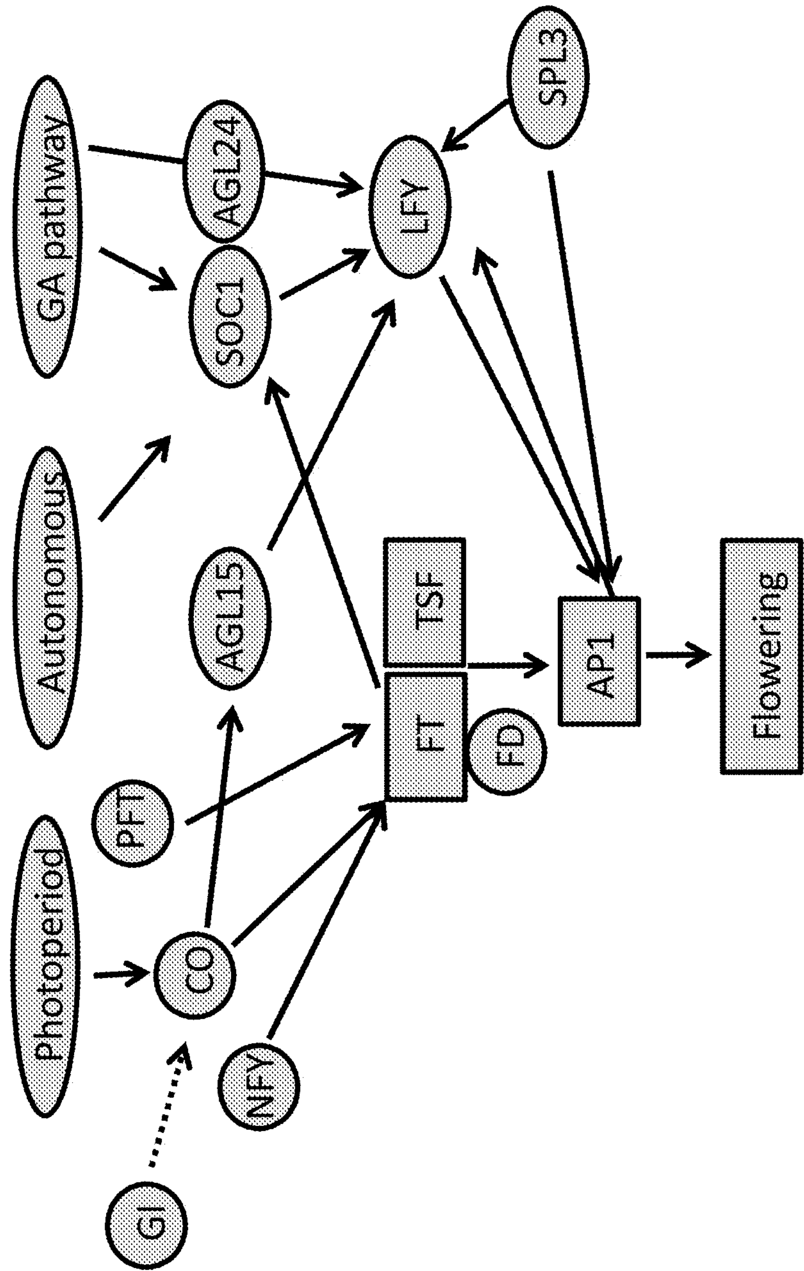
FIG. 8 shows a diagram showing interaction of other genes in flowering control that may be used in creating switchable mutations; GI, GIGANTEA; NFY, Nuclear Factor Y; CO, CONSTANS; PFT, protein farnesyltransferase; AGL15, AGAMOUS-LIKE 15; FT, FLOWERING LOCUS T; TSF, TWIN SISTER OF FT; FD, bZIP transcription factor; AP1, APETALA1; SOC1, SUPPRESSOR OF OVEREXPRESSION of CO1; AGL24, AGAMOUS-LIKE 24; LFY, LEAFY; SPL3, SQUAMOSA PROMOTER BINDING PROTEIN-LIKE 3. The diagram illustrates a range of interacting regulators using *arabidopsis* genes as an example. The orthologs of these genes from other plants may be equally useful in creating switchable control of the flowering.

Other flowering genes such as CONSTANS (CO, AT5G15840), FLOWERING LOCUS D (FD, AT3G10390), SUPPRESSOR OF OVEREXPRESSION OF CO 1 (SOC1, AT2G45660), TWIN SISTER OF FT (TSF, AT4G20370), LEAFY (LFY, AT5G61850), and APETALA1 (AP1, AT1G69120) upstream or downstream of the major regulatory component FT as illustrated in FIG. 8 can be similarly targeted to control flowering (Ando et al. (2013) *Plant Physiol* 162:1529-1538; Kimura et al. (2015) *Plant Cell Physiol* 56:640-649; Yeoh et al. (2011) *BMC Biotechnol* 11:36, 2011; Yoo et al., (2005) *Plant Physiol.* 139:770-778).

Similarly, any selected endogenous gene involved in other pathways can be knocked out by inserting a similar switch to create mutants in which the interrupted genes can be turned back on by applying the corresponding ligand.

Example 5

Targeting Genes in Plants by Inserting an EcR-Based Gene Switch to Control a Phenotypic Trait.

One could also take advantage of the recent CRISPR gene targeting technology (Li et al. (2015) *Plant Physiol.* 169: 960-970), to gain control over a particular phenotype by targeting an endogenous locus such as the endogenous IMMUTANS gene. This may be targeted to insert an EcR-based gene switch system (e.g., an Activator gene and GAL4 binding motifs) between the IM promoter and its full-length coding sequence. The insertion will likely create an immutans variegation mutant by interrupting the IM gene expression. Simultaneously, the inserted EcR-based gene switch system can be used to turn on the downstream IM gene to restore the mutation. The native IM promoter may be appointed to express the Activator with expression profile mimicking natural expression of the IM gene. In addition, a stronger constitutive promoter, such as 35S may be used to express more EcR-based gene switch Activator proteins to trigger the switch as a positive control.

Figure 9:
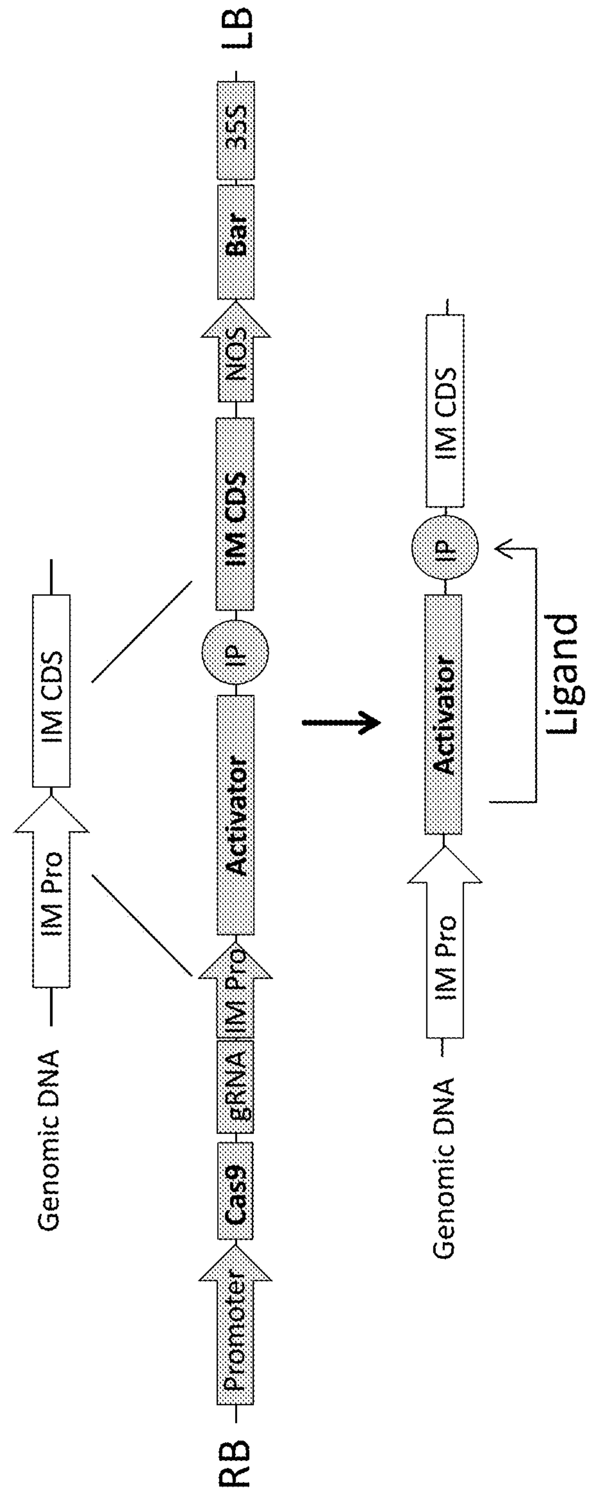
FIG. 9 shows a representative, hypothetical construct containing a CRISPR and EcR-based gene switch for regulating expression of IM that is inserted into the genome of the plant by CRISPR to place the EcR-based gene switch-controlled IM in the native position of wild-type (wt) IM.

Briefly, DNA constructs as shown in FIG. 9 may be transformed into wild type *Arabidopsis*. Harvested T1 seeds may be germinated in soil for one week before spraying with LIBERTY® 280SL herbicide to select transgenic seeds. Transformants are analyzed by PCR (PCR) to check the targeted IMMUTANS site for gene interruption, to check transgene copies, and to sequence the targeted insertion site. The majority of transgenic events with randomly integrated transgenes and indels at the target site are discarded. Events with HR-based insertion of the transgene will be further cultivated in growth chambers to observe phenotypes. Since immutans is a recessive mutation, no variegation phenotype is expected in hemizygous T1 generation.

T2 seeds may be germinated in soil for one week before spraying with LIBERTY® 280SL herbicide to select transgenic seedlings. The selected seedlings are further cultivated with or without applications of methoxyfenozide ligand to develop into plants that may display variegation phenotype in the absence of methoxyfenozide and normal green leaves in the presence of methoxyfenozide.

DNA constructs as illustrated in FIG. 10 may similarly be transformed and analyzed as positive controls to show the effect of a stronger constitutive promoter to express Activator proteins sufficient to trigger the EcR-based gene switch system if desired.

Example 6

Modify a Plant Trait Through Controlled Expression of a Cytotoxin Gene:

The ribonuclease barnase from *Bacillus amyloliquefaciens* has been proven an effective transgene for ablating floral tissues in many plant systems. It can be used to block transition to flowering in transgenic plants. To avoid general phytotoxicity, expression of barnase can be restricted to floral progenitor cells, and a number of early floral stage-specific promoters have been identified and validated in *Arabidopsis* to enable such tissue-specific barnase expression. These promoters are selected for vector construction to drive barnase expression to block flower initiation. There is also another well studied small protein from *Bacillus amyloliquefaciens*—barstar—which is an extremely potent inhibitor of barnase function. The gene for barstar can be fused to the EcR-based gene switch to achieve controlled expression of barstar by the activator protein which could be expressed under a tissue-specific or constitutive promoter. In the presence of methoxyfenozide ligand inducer, barstar expression is turned on and the resulting barstar protein inhibits barnase ribonuclease function thus restoring the flowering.

Figure 11:
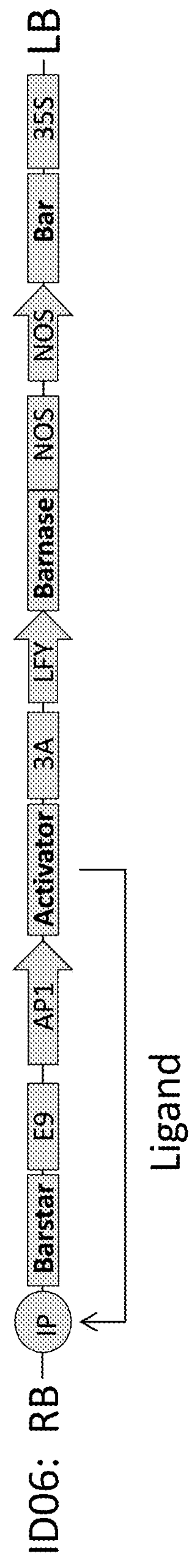
FIG. 11 shows a vector construct to provide constant expression of the barnase ribonuclease from *Bacillus amyloliquefaciens* in flower primordia to suppress flowering and EcR-based gene switch for regulating expression of barstar which inhibits barnase. Addition of the ligand methoxyfenozide turns on transcription of barstar, resulting in flowering.

A vector ID06, illustrated diagrammatically in FIG. 11, was constructed to provide constant expression of the barnase ribonuclease from *Bacillus amyloliquefaciens* in flower primordia to suppress flowering. The DNA construct (ID06) was transformed into wild type *Arabidopsis* by flower dipping method. T1 seeds were harvested and germinated in soil. Seven day old T1 seedlings were sprayed with LIBERTY® 280SL herbicide and 37 transgenic plants resistant to the herbicide survived. Transformants were analyzed by quantitative PCR (qPCR) to check transgene copy numbers. Thirteen percent of transgenic events contained only one copy of the transgene. All events were grown in growth chambers to evaluate phenotypes. The transgenic plants containing ID06 DNA construct should express the cytotoxic ribonuclease barnase in flower primordia which prevents formation of flowers. Indeed, at 7 weeks of age when wild type *Arabidopsis* flowered and developed siliques with seeds (FIG. 12A, on the left), the Barnase/IP:Barstar transgenic plants (shown on FIG. 12A, on the right, and on FIG. 12B) did not develop any normal flowers. Instead of flowers, the Barnase/IP:Barstar plants have elongated small leaves that could have derived from sepals as shown in the inset picture of FIG. 12B.

Figure 12:
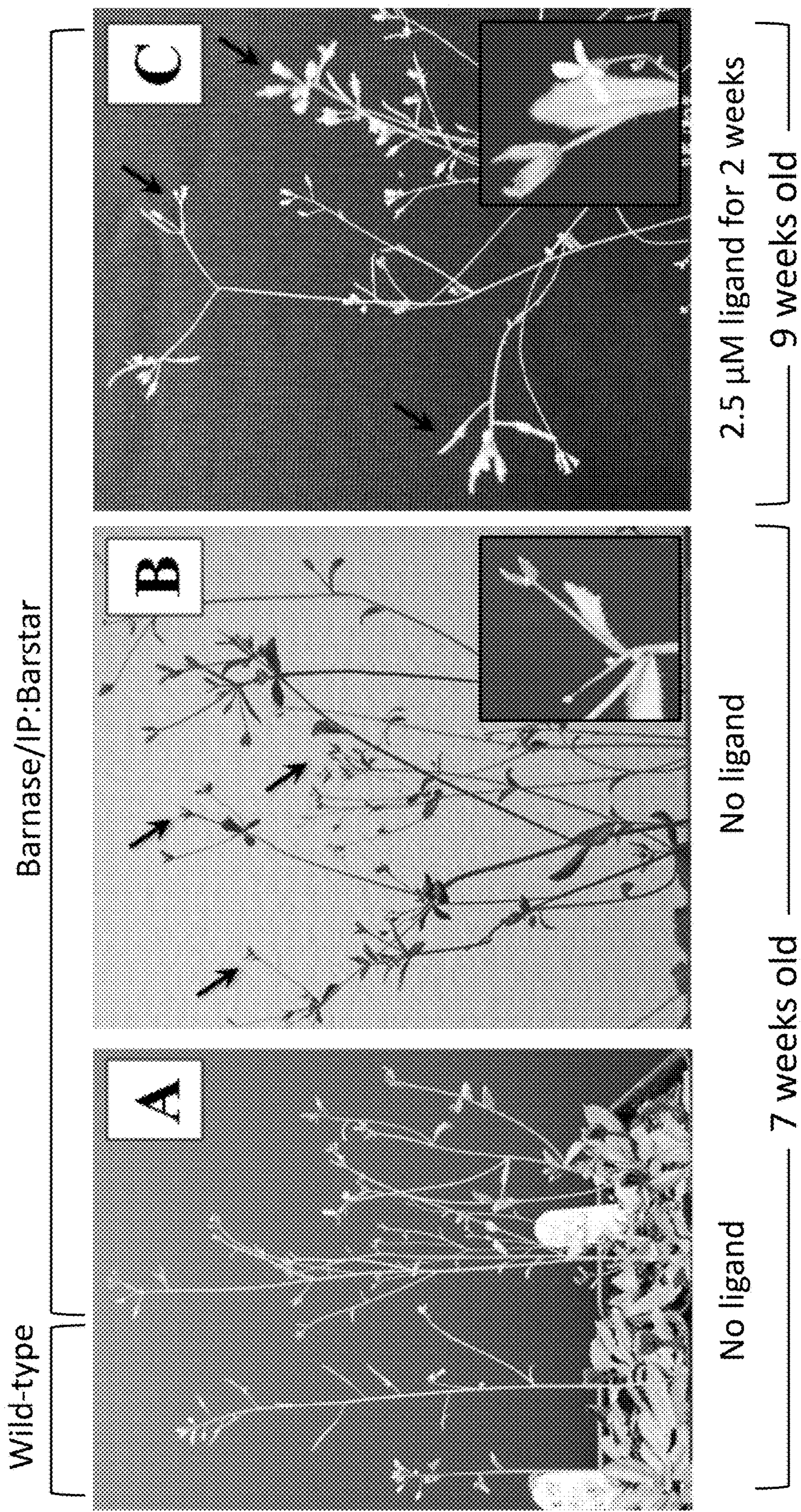
FIG. 12 shows how plants expressing barnase exhibit inhibition of flowering and induction of barstar restores flowering; Panel A shows wild type *Arabidopsis* on the left and Barnase/Barstar plants on the right before addition of ligand; Panel B shows a close up of the Barnase/Barstar plant in A (magnified in inset); Panel C shows flowering Barnase/Barstar plants treated with 2.5 μM ligand (magnified in inset).
Figure 13:
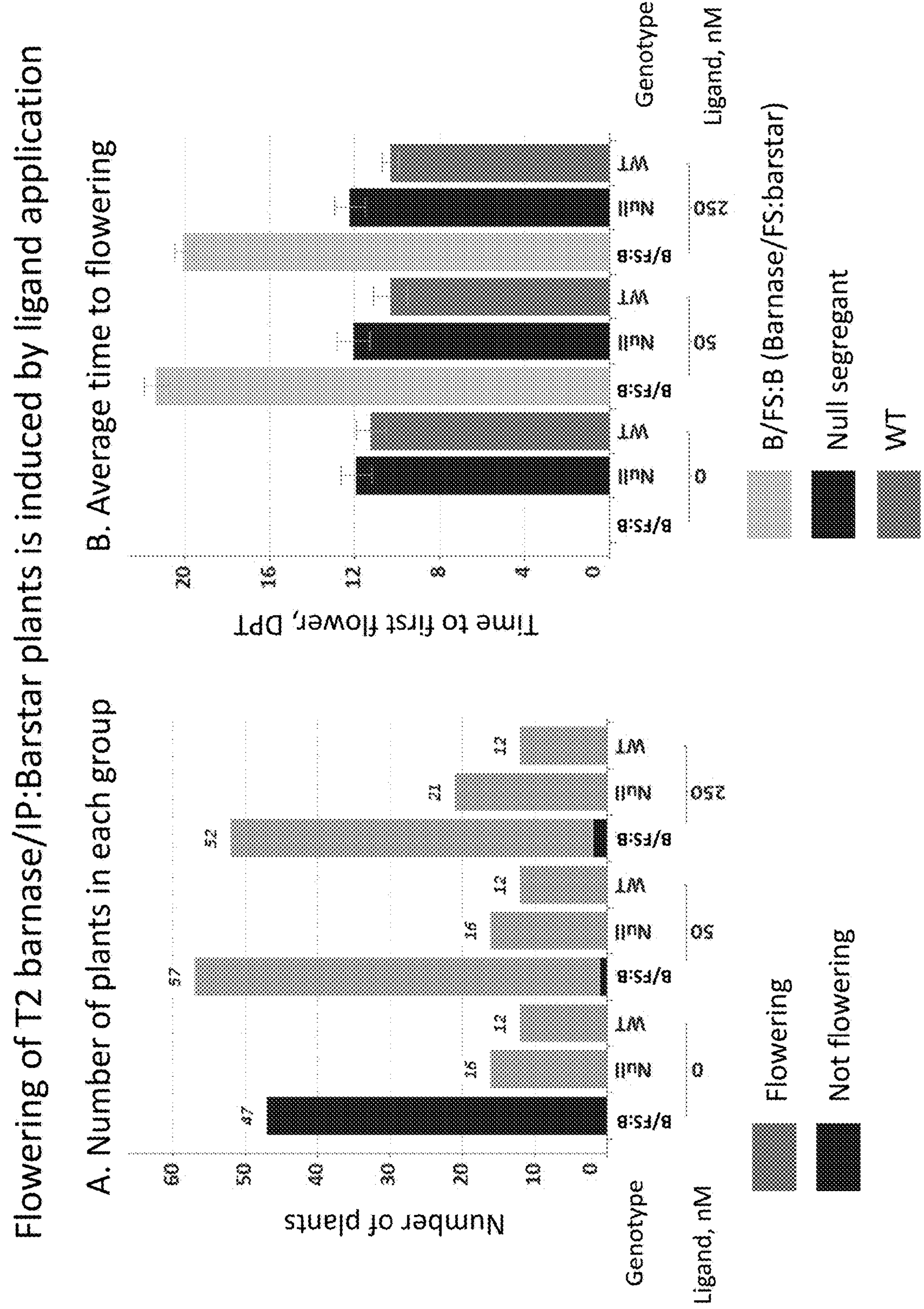
FIG. 13 shows how plants expressing barnase exhibit inhibition of flowering and induction of barstar restores flowering. Panel A shows number of plants in 3 genotype groups—transgenic ID06 plants with Barnase/IP:barstar construct (B/FS:B), ID06 null segregants (Null) and wild type *Arabidopsis* (WT)—treated with methoxyfenozide ligand at different concentrations: 0 nm (control), 50 nM and 250 nM. Each bar corresponds to the total number of plants in the group and shows the number of plants that did and did not flower. Panel B shows average time after treatment started (DPT—days post-treatment) before the first flower was observed in the same groups of plants. The error bars are Standard Error of the Mean.

The seven week old non-flowering plants were then sprayed with the ligand methoxyfenozide (2.5 μM) to turn on barstar expression and restore flowering. Ligand applications were performed every other day until all flowers had developed. As early as seven days after ligand application, flower buds and flowers appear as shown in FIG. 12C. T1 plants were grown to maturity and most of them produced siliques and seeds in quantities comparable to wild-type plants. T2 seeds were harvested for further evaluation of the transgenic lines on T2 plants.

Multiple T2 plants from six independent single copy transgenic ID06 events along with wt *arabidopsis* control plants were grown for three weeks. At three weeks plants from each line were divided in 3 treatment groups of 12 plants in each. The treatment was applied every other day for 30 days. The plants in group A were sprayed with plain water, in group B—with 50 nM solution of methoxyfenozide, and in group C—with 250 nM solution of methoxyfenozide. Before start of the treatment leaf tissue was collected from each plant for DNA extraction and genotype assessment by qPCR to identify homozygous, heterozygous and null segregant plants.

Plants were assessed as to whether they ever flowered (yes/no at the end of experiment, day 51) and the time to start flowering defined as the number of days after the first application of methoxyfenozide (days post-treatment: DPT) until the first flower bud appears. As can be seen on FIG.

13A none of the plants with ID06 transgene construct (labeled B/FS:B genotype) flowered in the absence of inducer ligand (methoxyfenozide), while almost all B/FS:B plants treated with either 50 nM or 250 nM methoxyfenozide developed flowers (56 of 57 plants, and 50 of 52 plants, respectively). All the null segregants and wild-type plants flowered irrespectively of whether or not they were sprayed with methozyfenozide.

here was a 8-10 days delay in the time to start flowering between ligand-treated transgenic (ID06) and non-transgenic (null segregants and wild-type) plants. This delay reflects the timing of expression of activator protein (AP) under AP1 floral promoter, and the lag in ligand reaching to and interacting with AP. Expressing AP under strong constitutive promoter, e.g., CaMV-35S could shorten the delay.

Methoxyfenozide had the same effect on flowering when applied as either 50 nM or 250 nM solution indicating that minimal effective concentration could be lower than 50 nM.

Figure 14:
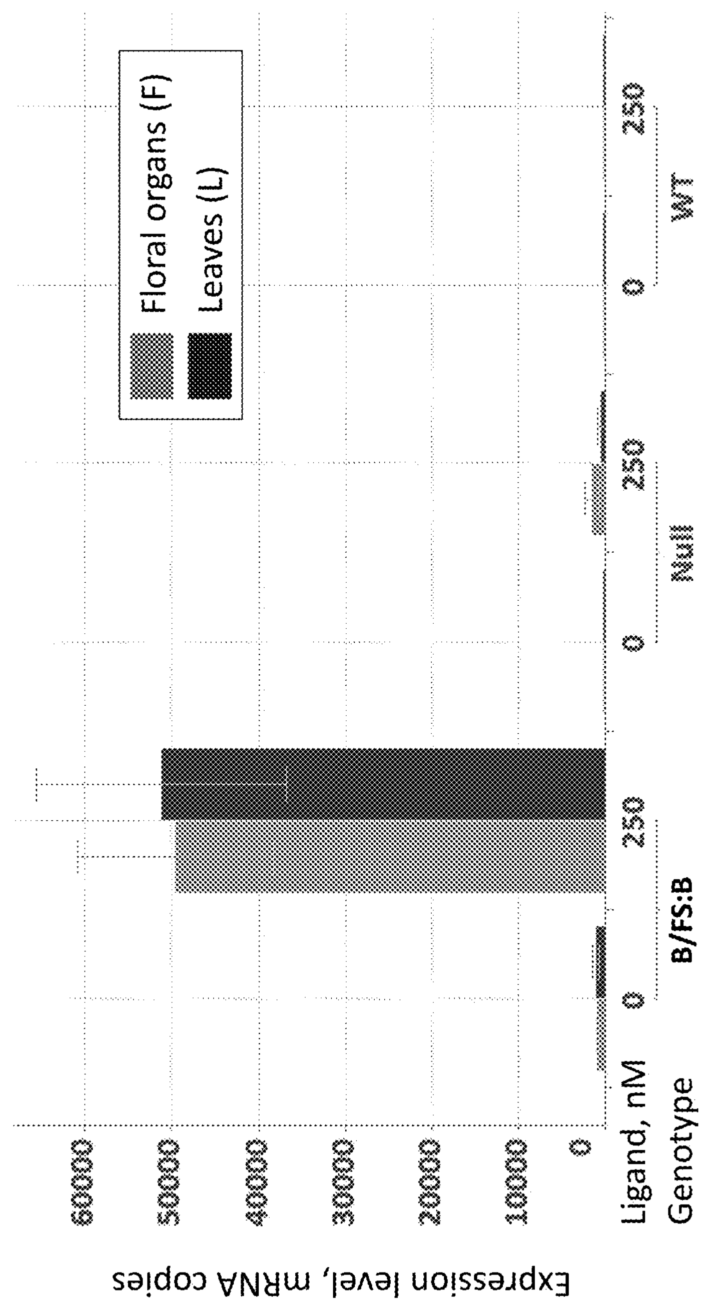
FIG. 14 shows induction of expression of barstar gene in floral organs and leaves of transgenic ID06 plants with barnase/IP:barstar constructs (B/FS:B), ID06 null segregants (Null) and wild type *Arabidopsis* plants (WT) when plants are treated with 250 nM methoxyfenozide ligand. 0 nM ligand represents water treatment control.

Barnase expression was assessed by qRT-PCR of the leaf and floral tissues sampled from plants treated with 250 nM activating ligand and from plants treated with water. As can be seen on FIG. 14 the expression of barstar is tightly controlled by EcR-based switch in both sampled tissues with expression barely detectable in the absence of ligand and dramatically increased by the ligand.

Example 7

Complementation of Late Flowering Through the Ectopic Expression of FT Gene.

Two DNA vectors ID14 and ID16 (described in FIG. 3) were constructed to transform late flowering ft mutant *Arabidopsis* line CS184 acquired from TAIR, The *Arabidopsis* Information Resource (at URL address *arabidopsis*.org). ID14, shown diagrammatically in FIG. 3A, incorporates EcR-based gene switch to control expression of the wt FT transgene by activator ligand, while ID16, shown diagrammatically in FIG. 3B, constitutively overexpresses the wt FT transgene and serves as a positive control for complementation of ft mutant phenotype.

Fifty-five T1 transgenic plants with ID were obtained. Thirty-two of those flowered in 2 weeks indicating uncontrollable expression of the FT gene resulting in early flowering possibly due to corruption of the inserted construct or an effect of insertion site genomic context that countered EcR-based gene switch control. However, the other twenty-three plants formed large rosette leaves without flowering in 4 weeks implying that the transgenic FT gene was not expressed. For comparison, theft mutant plants would flower ~2 weeks later than wild type *Arabidopsis* plants that flower in ~4 weeks after planting under similar 16 hours long day conditions. These late flowering ID14 plants would be appropriate to test EcR-based gene switch controlled FT expression. For the ID16 control DNA construct, forty-three T1 transgenic plants were obtained. Forty-one of these flowered prematurely without rosette leaf formation in just 2 weeks after planting. Some plants set seeds in 4 weeks with short siliques. The siliques dried and opened in another ~2 weeks to expose the seeds inside. Representative photographs taken at 4 weeks after planting are shown in FIG. 4 to show ID14 plants (IP:FT on the left) and ID16 plants (35S:FT on the right).

Figure 15:
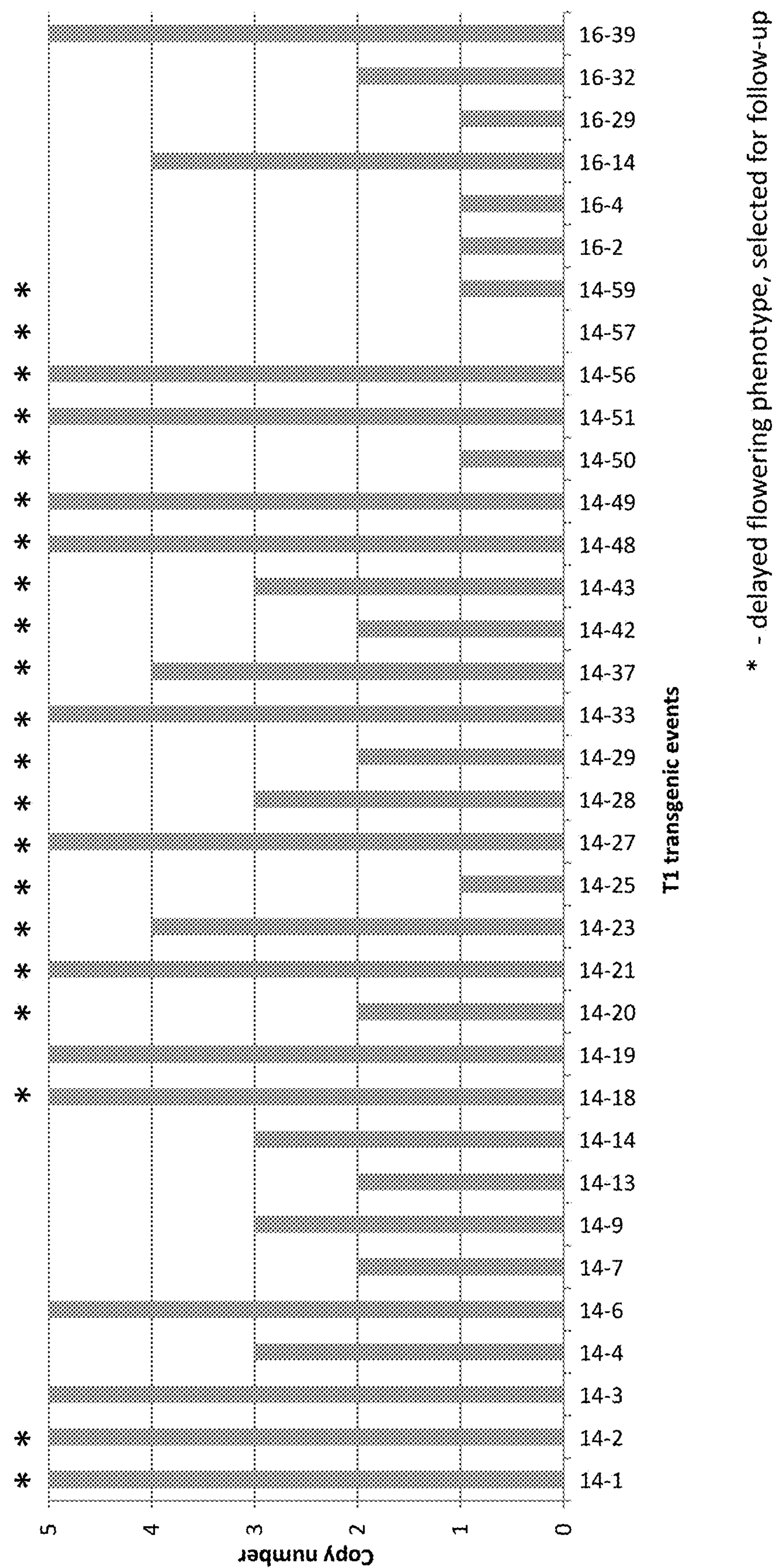
FIG. 15 shows the copy number of transgenes in transgenic T1 ID14 and ID16 plants determined by quantitative PCR. Transgenic plants that showed late flowering phenotype are indicated by an asterisk (*).

To gain early molecular characteristics of the transgenic events and also to validate some molecular assays we developed for the project, a subset of the ID14 and ID16 transgene T1 plants were sampled, depending on their availability, and preliminarily characterized for copy number by qPCR and FT gene expression by qRT-PCR. To estimate the copy numbers of the transgenic FT gene, TaqMan qPCR assays were designed using the phytoene desaturase gene (PDS) as the endogenous control to normalize the assay and the wild type *Arabidopsis* genomic DNA as the calibrator. Gene-specific qPCR primers and probes were designed, AtFT-F1/AtFT-R1/AtFT-T1 for FT gene and AtPDS-F1/AtPDS-R1/AtPDS-T1 for PDS gene. Genomic DNA extracted from leaf samples of the transgenic plants were analyzed by multiplex PCR with the above primers using a StepOne plus real time PCR system. Other cleaner transgene-specific qPCR assays such as the 35S-F2/35S-R1/35S-T1 targeting the 35S promoter, and Bar-F1/Bar-R1/Bar-T1 targeting the Bar selectable marker gene of the ID14 and ID16 DNA constructs were designed, validated, and used successfully to confirm the copy numbers of the transgenes obtained by the FT-specific qPCR. As shown in FIG. 15, both the ID14 (IP:FT) and ID16 (35S:FT) plants contained one or more copies of transgenic FT gene as determined by Bar-specific qPCR by using a single copy transgenic event as the calibrator. Events with 5 or more copies of the transgene were all counted as 5 since the qPCR assay was not accurate for high copy numbers. The endogenous 2 alleles of the FT gene were not counted in this assay for the sake of simplicity. Many ID plants flowered prematurely except for those indicated by * above the corresponding bars. There was no direct correlation between early flowering and the number of transgenic FT copies.

Figure 16:
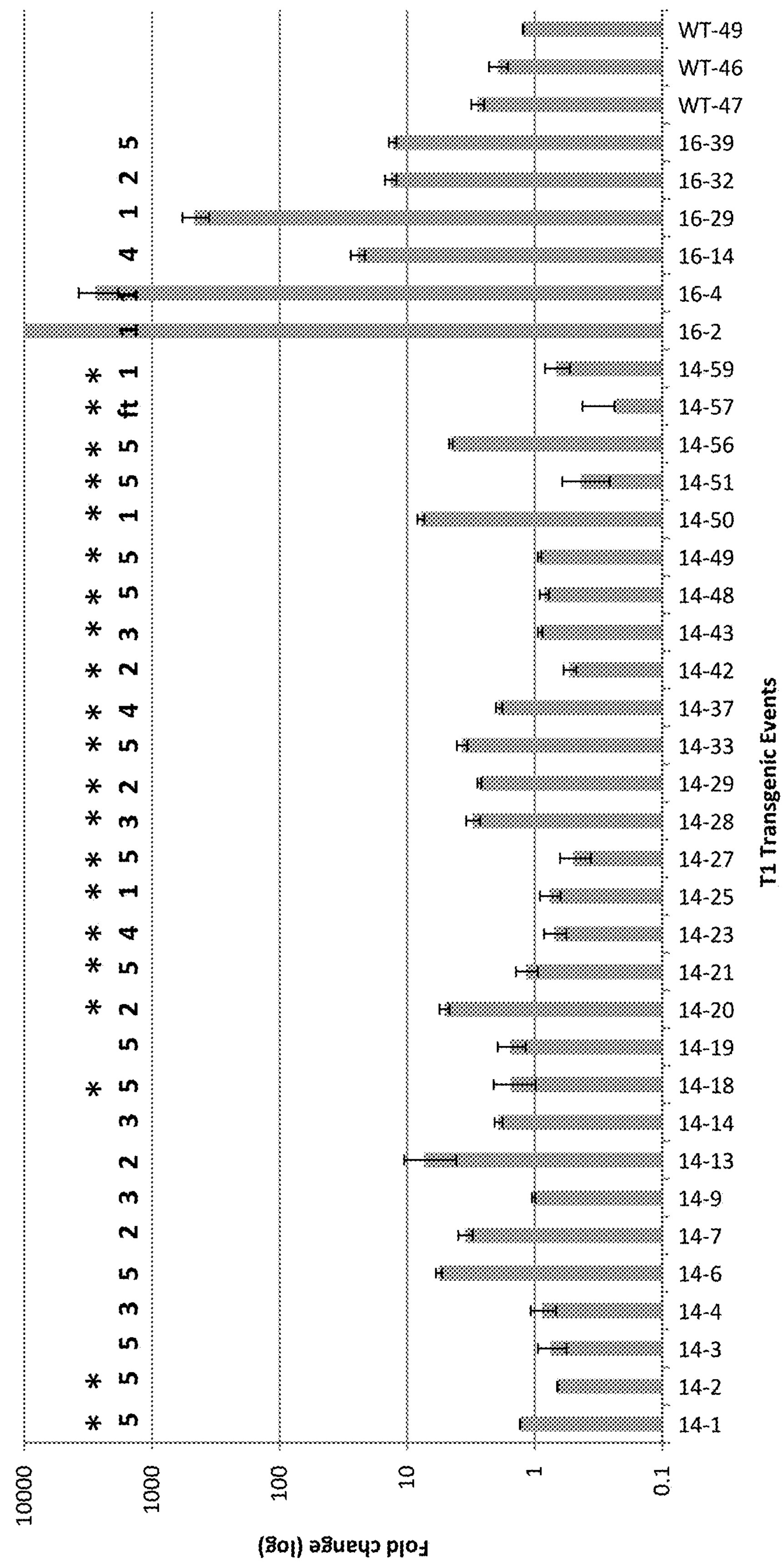
FIG. 16 shows baseline expression of FT gene in T1 transgenic (ID14 and ID16) and wild type *Arabidopsis* plants determined by quantitative RT-PCR. Transgene copy number is shown for each transgenic plants and the plants that showed late flowering phenotype are indicated by an asterisk (*).

The same subset of transgenic T1 plants was also characterized for FT gene expression in leaves by qRT-PCR as shown in FIG. 16. Total RNA was extracted from samples collected from rosette leave of flowering plants using a Qiagen RNA easy kit, treated with Qiagen DNaseI on column, and checked to be genomic DNA free by a simple PCR assay with primers AtPDS-F2/AtPDS-R2 targeting the endogenous PDS gene. The first cDNA was synthesized from the total RNA to be used as template for qRT-PCR analysis using a qScript cDNA master mix kit (Quanta Biosciences). The cDNA samples were analyzed by the same TaqMan qPCR assays with primers and probes, AtFT-F1/AtFT-R1/AtFT-T1 for the FT target gene and AtPDS-F1/AtPDS-R1/AtPDS-T1 for the endogenous control gene PDS with ft mutant *Arabidopsis* total cDNA as the calibrator. Some ID14 plants that did not flower prematurely (indicated by * above the bars) had similar level of FT expression as some of those plants that did flower prematurely. No positive correlations were found between the expression levels and transgenic FT copy numbers (indicated by the number above the bars). However, it was clear that most of the positive control 35S:FT plants (ID16) which flowered extremely prematurely did have higher levels of FT expression. Since the T1 plants developmental stages were not synchronized and only one time point was sampled due to the limitation of T1 plant materials, this qRT-PCR only served to demonstrate that the 35S:FT transgene in ID16 plants expressed FT gene at levels that were thousand times higher than in wild type or IP:FT (ID14) plants and likely led to extremely early flowering observed in ID16 plants.

It is clear that the late flowering phenotype of *Arabidopsis* ft mutant can be complemented by the ectopic expression of FT gene, as evidenced by extremely early flowering in 35S:FT plants (ID16) constitutively expressing the FT gene. Early flowering was also observed in some IP:FT plants (ID14) even without ligand application. The low level expression of FT gene in some ID14 plants was probably caused by complex transgene configuration that led to rearrangements and/or by position effect and was apparently sufficient for restoration of flowering in ft mutant. However, many ID14 T1 plants did not flower prematurely. These late flowering ID14 T1 plants were selected for further characterization at T2 generation to evaluate ability of the EcR switch to control flowering through conditioned complementation of ft mutation.

Example 8

Control Flowering Through Controlling the FT Gene Expression with an EcR-Based Gene Switch.

To get an early reading on the possibility of using the EcR-based gene switch to control flowering, a few selected ID14 T1 plants that did not flower within 3 weeks were sprayed with 2.5 μM methoxyfenozide ligand solution every other day for two weeks with aft mutant plant as the control. The treated ID14 plants started bolting within 5 days while the ft mutant plant did not. At day 11, the ID14 plants produced more flowers and pods while the ft mutant plant just started bolting. Though very preliminary, the results suggested that the EcR switch responded to the methoxyfenozide ligand induction and turned on FT expression.

T2 seeds were harvested from ID14 T1 plants and several experiments were designed to test if the EcR gene switch is tightly controlling the transgenic FT expression in the absence of the activator ligand, and if the switch can be easily turned on by applying the ligand to express enough FT to induce early flowering. T2 seeds from six independent ID14 lines (three with single copy of the transgene and three—with two copies) were planted along with wild-type *Arabidopsis* and ft mutant and grown under long day (16 hours) and short day (8 hours) photoperiods. Genotype of these T2 plants: homozygous, heterozygous, and null were assessed by TaqMan qPCR as described in Example 7 with the exception of utilizing only the Bar gene-specific primers and probes Bar-F1/Bar-R1/Bar-T1 and the same PDS endogenous control AtPDS-F1/AtPDS-R1AtPDS-T1. The T2 plants segregated the transgene as a single gene following the Mendelian inheritance.

The homozygous plants and null segregants that served as isogenic negative controls were subject to treatment with water (as a control) and 2 concentrations of methoxyfenozide: low (250 nM) and high (2.5 μM). Plants were treated in groups of 2 pots with 5 plants in each at short and long day photoperiods. Treatments were administered every other day starting from day 19 (long day) and 25 (short day) after planting and continued for about three weeks until all plants flowered.

Figure 17:
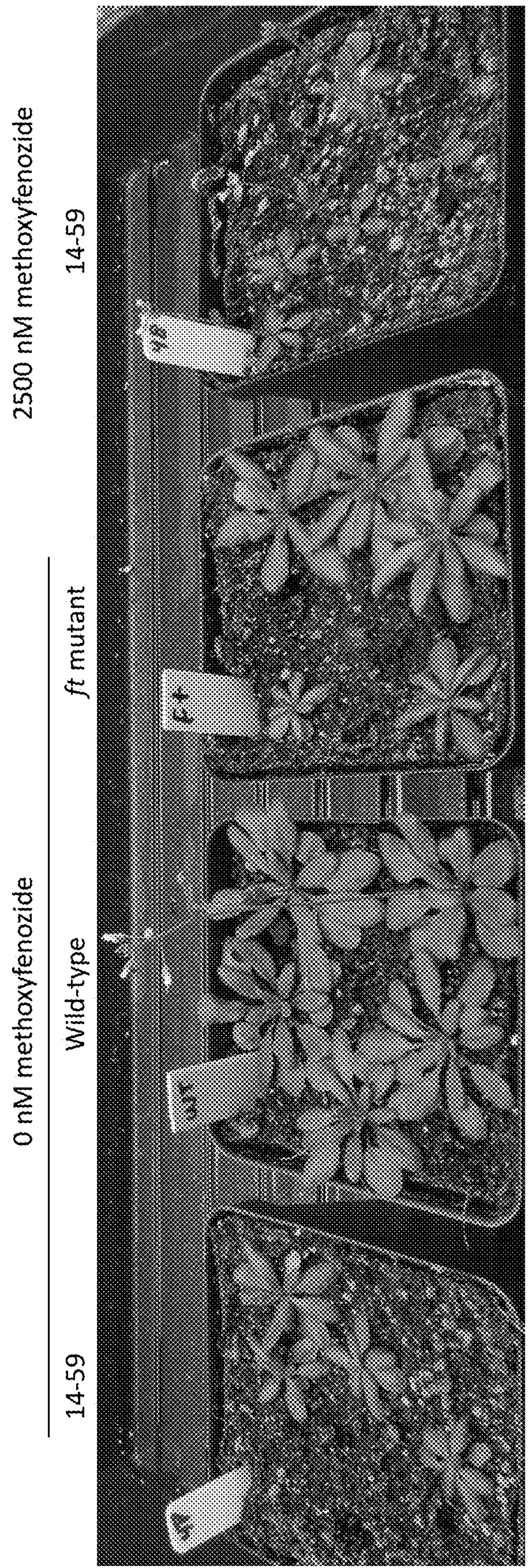
FIG. 17 shows controlled complementation of *Arabidopsis* ft mutation in ID14-59 T2 plants; The three pots on the left show untreated plants with controlled flowering plants (ID14) on the left, wild type plants in middle and late-flowering ft mutant plants on the right. The pot on the far right shows the controlled flowering plants treated with 2500 nM methoxyfenozide.

Induction of flowering with methoxyfenozide was clearly observed in most homozygous plants at both concentrations of the ligand. Five days after the first application the ID14 plants started to flower similarly to wild type control plants, while ft mutant and untreated ID14 plants did not flower as shown in FIG. 17. The homozygous T2 plants of one single-copy line (ID14-50) treated with either 250 or 2500 nM methoxyfenozide flowered two to ten days earlier than the wild type and 22 to 30 days earlier than ft mutant plants while the plants mock treated with water flowered at about the same time as the wild type and much earlier than ft mutant plants. As expected, the ID14-50 null segregant plants flowered at the same time as theft mutant plants—around 55 days after planting. Ligand dependent induction of flowering in homozygous ID14 T2 plants was observed under both short day and long day photoperiods. The two-copies ID14 lines showed results similar to single-copy lines.

ID14 T2 plants were maintained to maturity and T3 seeds were collected for further characterization of a selected single-copy line ID14-50. The homozygous and null segregant T3 plants along with *Arabidopsis* ft mutant plants were grown for three weeks before starting ligand application. Plants were divided in four groups in which up to twelve individual plants per genotype were counted. Each group was treated with different concentrations of methoxyfenozide (10, 50 and, 250 nM) and one group was mock treated (water). Treatments were applied every other day from day 17 (long day) or 24 (short day) for a period of approximately three weeks or until all plants flowered.

Figure 18:
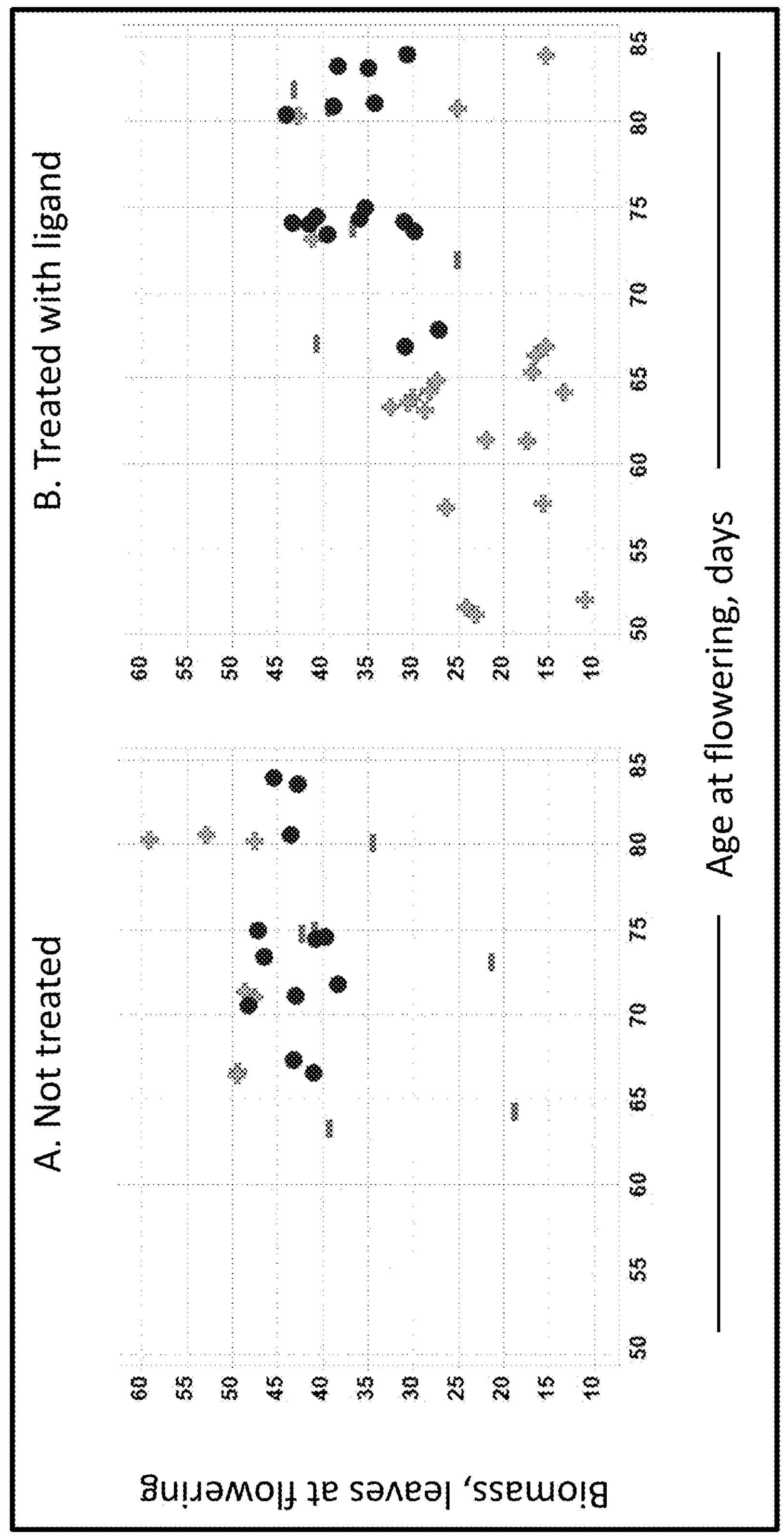
FIG. 18 documents observations done on *Arabidopsis* plants of 3 genotypes—homozygous single-copy transgenic T3 plants (ID14-50), ID14-50 null segregants and ft mutant plants—over period of 90 days after planting. For each plant the following 2 metrics were documented on the day when its first flower bud appeared—the age of the plant and the number of rosette leaves it has—and plotted as a marker on Age vs Number of Leaves axes as shown. Shape of the markers corresponds to each plant's genotype: black filled circles represent ft mutant plants, grey plus signs—ID14-50 homozygous T3 plants, and grey minus signs—ID14-50 nulls. Panel A shows plants in the control group treated with water. Panel B shows plants treated with methoxyfenozide (50-250 nM) every other day starting at day 24.
Figure 19:
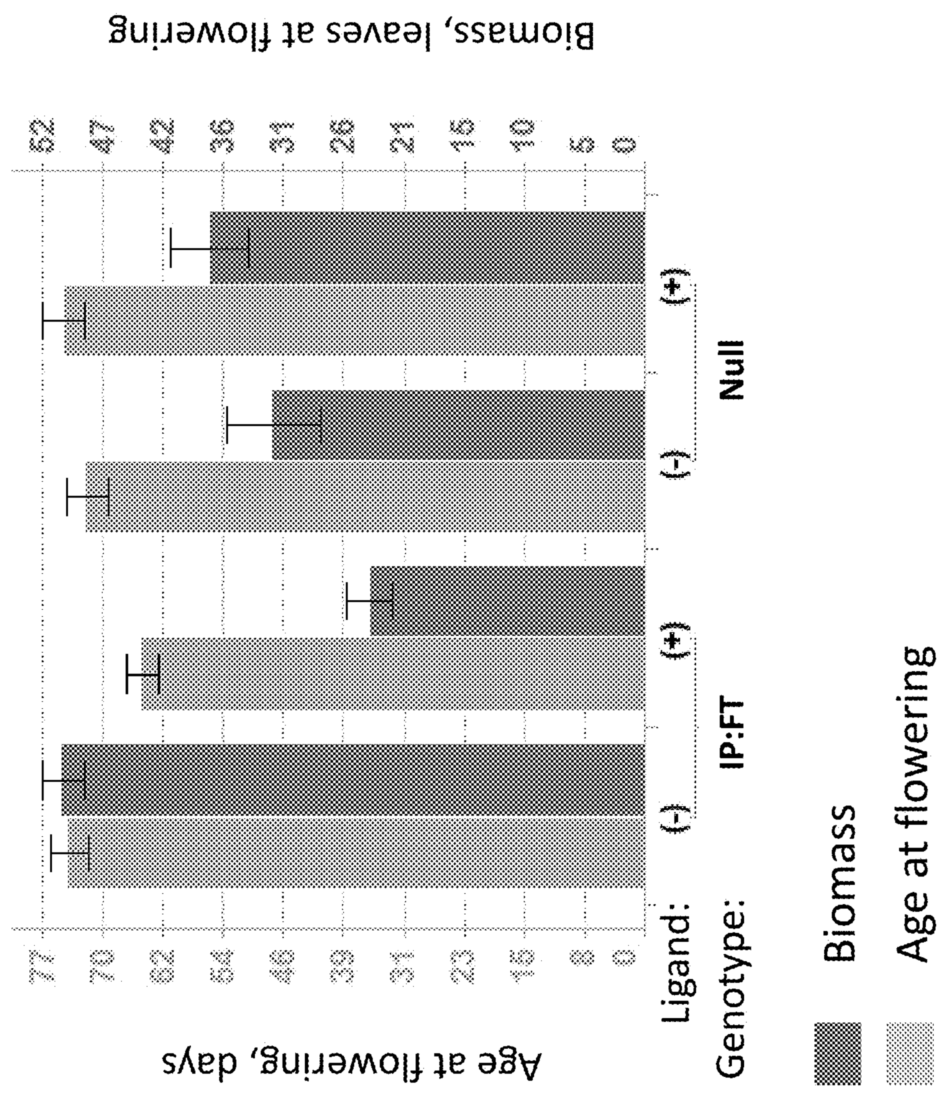
FIG. 19 shows the averages for the age and number of leaves at the start of the flowering for homozygous single-copy transgenic T3 plants (ID14-50) and ID14-50 null segregants shown in FIG. 18. The error bars are Standard Error of the Mean.

Plants were observed to document the age at the time of flowering (appearance of the first bud) and the number of rosette leaves when the first flower bud appears. The observation was done over a period of ninety days from the day of planting. In both short day and long day photoperiod, the homozygous T3 ID14-50 plants exposed to ligand started flowering as early as fourteen days before any null plants and ft mutants while the untreated plants flowered at a similar time with null and ft mutant plants as shown in FIG. 18. Looking at the number of rosette leaves as a proxy for biomass, only the homozygous T3 ID14-50 plants exposed to all ligand concentrations showed a strong decrease in biomass production at both photoperiods. This observation correlates nicely with early flowering as shown in FIG. 18 and FIG. 19.

FT expression was characterized at five time-points over the time-course of induction. One leaf per plant was collected at time-zero before ligand application corresponding to 17 and 24 days old plants in long and short day photoperiod, at one day after treatment started corresponding to 18 and 25 days old plants, four days after treatment started corresponding to 21 and 28 days old plants, seven days after ligand application started corresponding to 24 and 31 days old plants and, eleven days after treatment started corresponding to 28 and 35 days old plants for RNA extraction using a Qiagen RNA easy kit. First-strand cDNA was synthesized from the total RNA to be used as template for qRT-PCR analysis. qRT-PCR was set-up as previously described for T2 characterization. The homozygous ID14-50 plants showed low FT expression before ligand application which increases as early as one day post-treatment for all concentrations of methoxyfenozide in long day photoperiod and short day photoperiod (data not shown). For most homozygous plants FT expression stayed relatively high and to a similar level from day one to day seven post-treatment before going down a little by day eleven post-treatment. For all time points, tissue was collected at the end of a period of induction, right before treatment was re-applied. This data showed that the level of induction was persistent enough to keep FT level high to the next application of ligand. FT expression in mock-treated plants as well as null and mutant treated plants stayed very low for the most part over the eleven days of treatment. In all genotypes, there is a large variation in FT expression among individual plants in the groups of siblings.

TABLE 1

| Primer | Sequence | SEQ ID NO |
|---|---|---|
| AtPDS-F1 | CATCTGGAGGTTGTGAACTAATGG | 21 |
| AtPDS-R1 | TTGTTCTTGTCTTAAGCGCTTGA | 22 |
| AtPDS-T1 | 5' VIC-ACATAGCTTAGGGTTCC-3' MGBNFQ | 23 |
| AtFT-F1 | TTATGGCCAAAGAGAGGTGACTA | 24 |
| AtFT-R1 | CCAATCTCAACTCTTGGCTTGTT | 25 |
| AtFT-T1 | 5' 6FAM-TGGCTTGGATCTAAGGCCTTCTCA-ZEN-3'IBFQ | 26 |
| 35S-F2T | GATGTGATATCTCCACTGACGT | 27 |
| 35S-R1 | CGTGTCCTCTCCAAATGAAATGA | 28 |
| 35S-T1 | 5' 6FAM-CGCACAATCCCACTATCCTTCGCA-ZEN-3'IBFQ | 29 |
| Bar-F1 | GAGGTCGTCCGTCCACTC | 30 |
| Bar-R1 | GTCAACCACTACATCGAGACAAG | 31 |
| Bar-T1 | 5' 6FAM-CGGTTCCTGCGGCTCGGTAC-ZEN-3'IBFQ | 32 |
| AtPDS-F2 | TGTTTGGGAATGTTTCTGCGG | 33 |
| AtPDS-R2 | CTTCAAGCAACAGAGGTTTGTG | 34 |

Example 9

Transformation of Petunia to Downregulate the Chalcone Synthase Gene and Expression on Demand: Plants were generated to express interference RNA (RNAi) to downregulate the petunia chalcone synthase A (ChsA) gene (amino acid sequence SEQ ID NO:56). Dowregulation of the ChsA gene decreases the number of intact ChsA transcripts in the plant cells and thereby decreases anthocyanin production which resulted in a change in flower color from purple to white.

Figure 20:
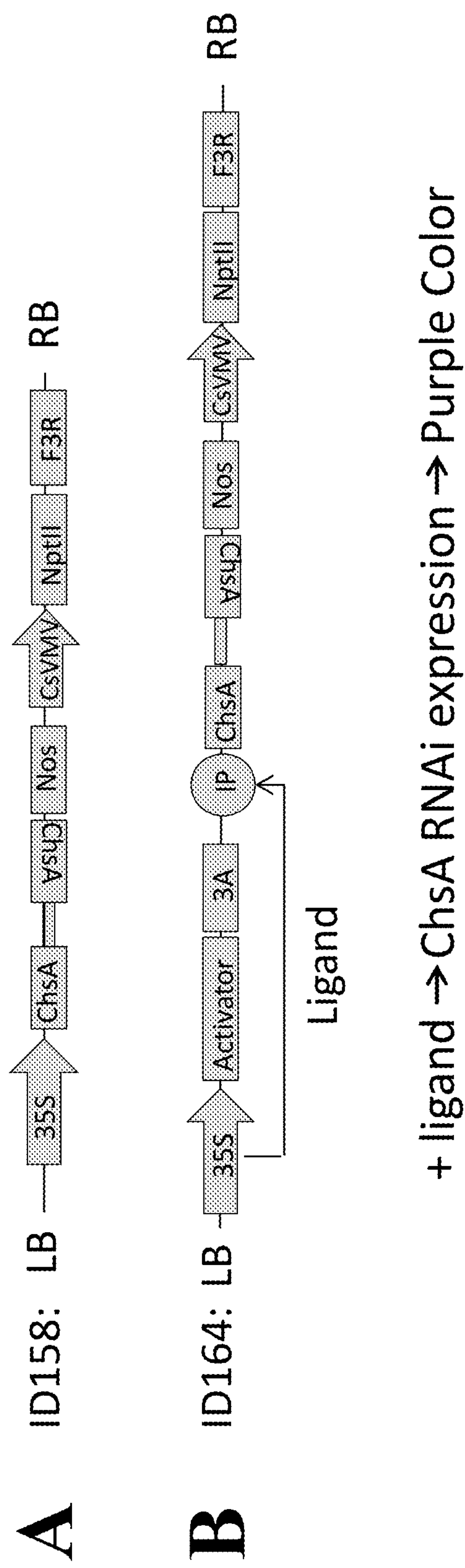
FIG. 20 shows constructs ID158 (SEQ ID NO:59) (Panel A) which constitutively expresses a chalcone synthase A (ChsA) hairpin transcript to down regulate ChsA through gene silencing and ID164 (SEQ ID NO:55) (Panel B) which expresses ChsA hairpin transcript (SEQ ID NO:64) under the control of the switch of the invention.

DNA construct ID158 (SEQ ID NO:59) (LB-35S:ChsA RNAi+CsVMV:NptII-RB) as shown in FIG. 20A was used as a positive control to transform wild-type Petunia hybrida variety V26. A 35S-CaMV promoter is driving the expression of a ChsA hairpin transcript (SEQ ID NO:64) (half hairpin is shown in SEQ ID NO:63) promoting targeted transcript degradation through gene silencing. The targeted region of ChsA is SEQ ID NO:62. CsVMV:NptII is used as the selectable marker gene for selecting transgenic plants with kanamycin antibiotic. To estimate the copy number of the transgene in TO transgenic plants, TaqMan qPCR assays were designed using the phytoene desaturase gene PDS as the endogenous control and a pre-characterized transgenic Petunia genomic DNA as the calibrator. Gene-specific qPCR primers and probes were designed, NptII-F1/NptII-R1/NptII-T1 for NptII gene and PhPDS-F1/PhPDS-R1/PhPDS-T1 for PDS gene. Genomic DNA extracted from leaf samples of the transgenic plants were analyzed by multiplex PCR with the above primers using a StepOne plus real time PCR system. Forty plants containing low copies of the transgene (two copies and below) were chosen to analyze correlation between ChsA transcript level and flower color. Total RNA was extracted from leaf samples of these 40 plants using a Qiagen RNA easy kit and checked to be genomic DNA free by a simple PCR assay targeting the endogenous PDS gene (PhPDS-F2/PhPDS-R2). The first cDNA was synthesized from the total RNA to be used as template for qRT-PCR analysis. qPCR primers and probes, PhChsA-F1/PhChsA-R1/PhChsA-T1 for the ChsA target gene and PhPDS-F1/PhPDS-R1/PhPDS-T1 for the endogenous control gene PDS were used with wild type Petunia total cDNAs as the calibrator. Plants containing ID158 DNA showed an array of flower color correlating with the level of ChsA transcript present in the plant cell as shown in FIG. 21. A wild-type plant was fixed to a ChsA transcript level of one. Most plants showing level of ChsA expression from one to 0.3 was dark purple color. Flowers from plants with ChsA transcript level from 0.3 to 0.06 were mostly variegated and plants with a really low ChsA transcript level (0.06 and below) were having predominantly white flowers. There were few biological exceptions showing a high level of ChsA transcripts with white flowers and vice versa.

Figure 22:
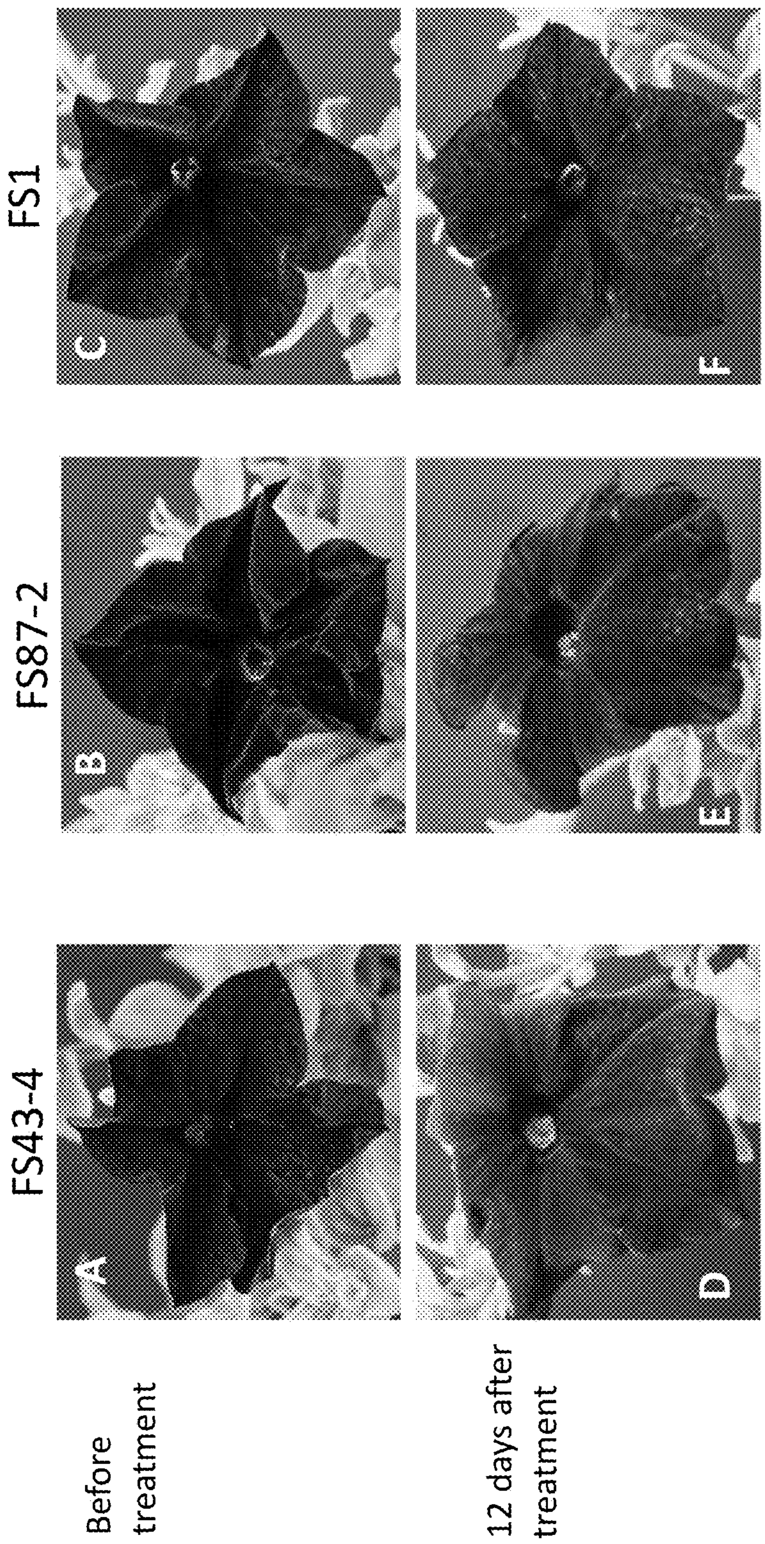
FIG. 22 shows FS:ChsA RNAi plants before treatment (top row): FS43-4 (Panel A), FS87-2 (Panel B) and FS1 (Panel C); and after treatment (bottom row): FS43-4 (Panel D), FS87-2 (Panel E) and FS1 (Panel F) with water (control treatment).
Figure 23:
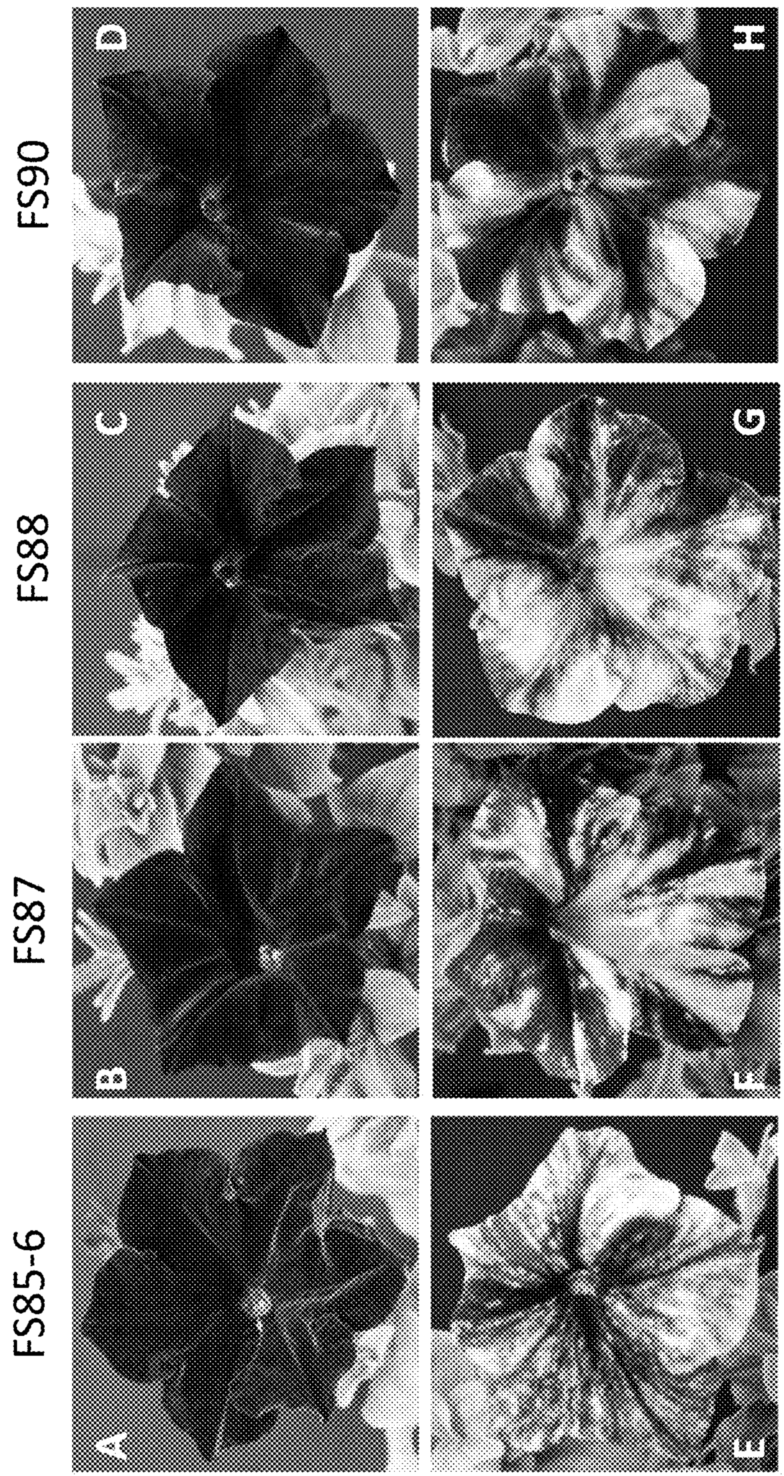
FIG. 23 shows FS:ChsA RNAi plants before treatment (top row): FS85-6 (Panel A), FS87 (Panel B), F88 (Panel C) and FS90 (Panel D); and 22 days after treatment (bottom row) FS85-6 (Panel E), FS87 (Panel F), FS88 (Panel G) and FS90 (Panel H) with 1 mM methoxyfenozide (Mtf).
Figure 24:
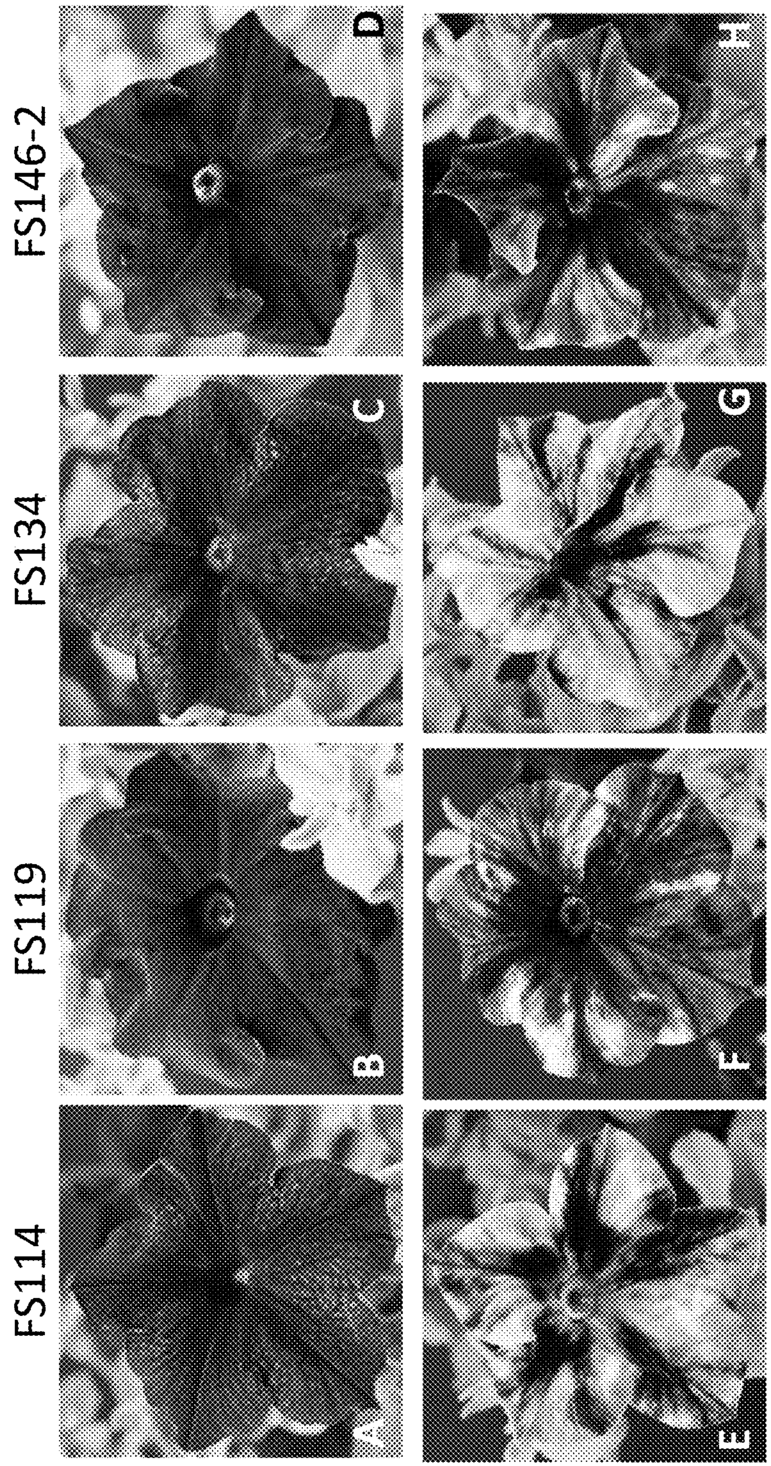
FIG. 24 shows FS:ChsA RNAi plants before treatment (top row): FS114 (Panel A), FS119 (Panel B), FS134 (Panel C) and FS146-2 (Panel D); and 6 days after treatment (bottom row) FS114 (Panel E), FS119 (Panel F), FS134 (Panel G) and FS146-2 (Panel H) with 2 mM methoxyfenozide (Mtf).
Figure 25:
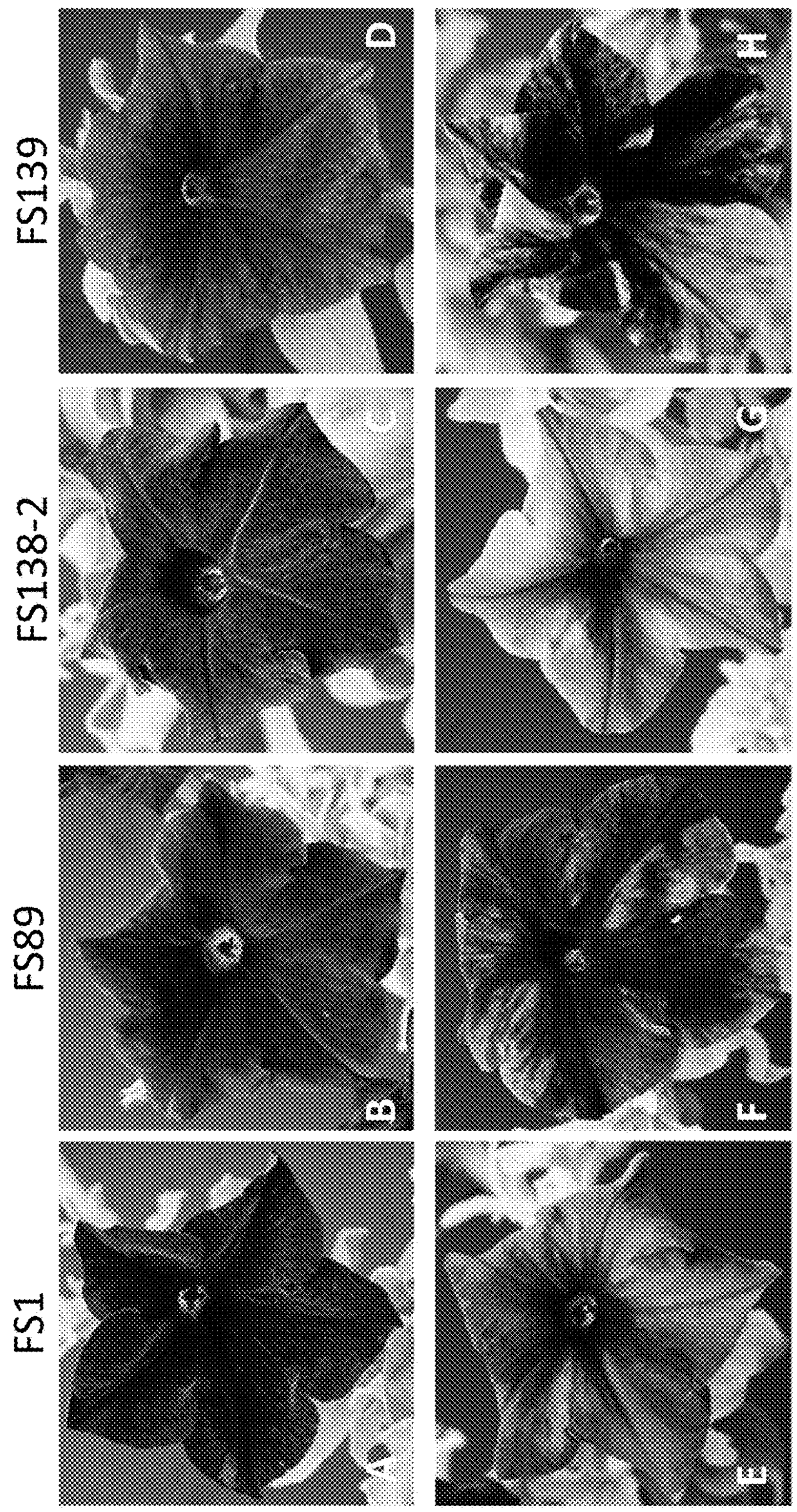
FIG. 25 shows FS:ChsA RNAi plants before treatment (top row): FS1 (Panel A), FS89 (Panel B), FS138-2 (Panel C) and FS139 (Panel D); and 4 days after treatment (bottom row) FS1 (Panel E), FS89 (Panel F), FS138-2 (Panel G) and FS139 (Panel H) with 5 mM methoxyfenozide.

DNA construct ID164 (LB-IP:ChsA RNAi+35S:AP+CsVMV:NptII-RB) (SEQ ID NO:55) containing both the inducible promoter (IP) composed of 5 GAL4 regulatory elements (GAL4-RE) placed upstream of the minimal CaMV-35S promoter and the multidomain activator (AP) protein gene (VGE(E68V/V184I/Y204E) under the control of CaMV-35S promoter is shown in FIG. 20B. ID164 (SEQ ID NO:55) was used to transform wild type (wt) Petunia hybrid variety V26. The chalcone synthase hairpin transcript will not be express until the activator ligand (methoxyfenozide; Mtf) is provided to mobilize the activator proteins for binding to the GAL4-RE and switching the inducible promoter FS on. Transgene copy number was assessed for 56 TO transgenic plants by Taqman assay. 84% were low copies (two copies and below), 12.5% were high copy (three copies and above) and, few plants were nulls. Before ligand application most (98%) plants were flowering as dark purple color. Plants were divided in five groups, each group being treated differently. Treatment occurred every other day at a rate of 30 ml per plant. Treatment is sprayed on plants (leaves and flowers). Water is used as a mock treatment while INTREPID® 2F insecticide (Mtf being the active ingredient) is used as a ligand treatment. Group one was mock treated. Group two was treated with 2.5 uM Mtf in INTREPID® 2F insecticide form. Group three was treated with 1 mM Mtf (highest recommended dose on ornamental plants for INTREPID® 2F). Group four was treated with 2 mM Mtf and group five treated with 5 mM Mtf. All plants mock treated keep their original flower color as seen in FIG. 22. However, plants treated with Mtf showed diverse flower color change depending on ligand concentration as shown in FIG. 23. Few plants treated with 2.5 uM (50%) showed flower color change from dark purple to light purple 10 days post-treatment. When increasing the ligand concentration to 1 mM, change in flower color, dark purple to variegate, was observed faster (7 days post-treatment) on 50% of plants as shown in FIG. 23. With 2 mM and 5 mM ligand, one application (2 days post-treatment) was sufficient to change flower color from dark purple to variegate as shown in FIG. 24 and FIG. 25, respectively. Decrease in ChsA gene expression level in treated plants compared to their higher level before ligand treatment correlates with their change in flower color as shown in FIG. 21.

Example 1

Assay for Agro-infiltration. Transient β-glucoronidase (GUS) expression, was modified from previously reported literature (Wroblewski et al. (2005) *Plant Biotechnol. J.* 3(2):259-273). Specifically, *Agrobacterium tumefaciens* strain EHA105 containing an appropriate plasmid for GUS expression was grown overnight to an OD600 of 0.8 and re-suspended in induction buffer with the following components: MS basal medium (Sigma-Aldrich), 10 mM $MgCl_2$, and 100 uM acetosyringone. After 4 hours, induced culture suspension was infiltrated into detached fully expanded petunia leaves (approximately 0.1 mL/leaf). Leaves were incubated in a humidity chamber at 28° C. for 3 days.

Histochemical X-gluc staining for GUS visualization. Leaf discs from Agro-infiltrated petunia leaves were submerged in GUS assay buffer: 10 mM EDTA (pH=8), 100 mM $NaH_2PO4$, 0.01% Triton X-100, 2 mM X-gluc (5-bromo-4-chloro-3-indolyl-β-D-glucuronic acid, cyclohexylammonium salt). Leaf discs were placed under vacuum for 5 minutes and then incubated at 37° C. for 24 hours. Leaf discs were then submerged in 95% ethanol and incubated at 37° C. for 24 hours to remove chlorophyll for easier visualization of X-gluc staining.

*Botrytis cinerea* isolation and inoculation. The plant pathogen was isolated from diseased strawberries displaying typical symptomology. A single spore colony was isolated using standard plant pathology methodologies and the ITSI—5.8S rDNA—ITSII locus was amplified and sequenced to validate its identity. The isolate used is 100% identical to more than 20 previously reported *B. cinerea* isolates in Genbank. For plant inoculation *B. cinerea* was grown on V8 Agar media under fluorescent light for 2 weeks until the typical grey mass of aerial spores was visible. A section of the colony was placed into 10 mL of sterile DI water and vortexed vigorously to dislodge spores. The resulting solution was filtered through a 70 micron mesh to yield a homogenous spore solution free of mycelia and agar media. The spore solution was spun down and washed 3× in sterile DI water and quantified using a hemocytometer. The solution was diluted in sterile DI water to a final concentration of 200,000 spores/ml. For petunia inoculations, detached leaves were wounded with a sterile forceps (approximately 0.5 mm abrasion) and the wounded site was inoculated with 10 uL of spore solution (2,000 spores/inoculation site). Three leaves/treatment and three wound sites/leaf were inoculated with spore solution for each assay.

Figure 32:
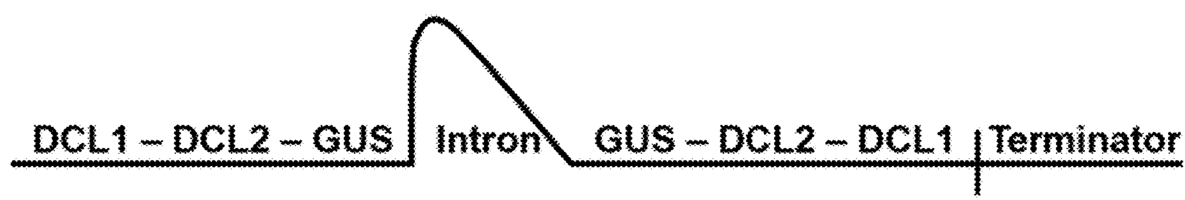
FIG. 32 shows a Dicer-like Glucuronidase hybrid hairpin (DCL1/DCL2/GUS Hairpin) (SEQ ID NO:35) construct that was developed for transgenic-based disease resistance in Petunias.

A Dicer-like Glucuronidase hybrid hairpin (DCL1/DCL2/GUS Hairpin) (SEQ ID NO:35) construct was developed for transgenic-based disease resistance in Petunias as shown in FIG. 32.

Cassettes for *Agrobacterium* Mediated Transformation. Two cassettes for *Agrobacterium*-mediated transformation of petunia were generated for constitutive and ligand inducible *Botrytis cinerea* resistance.

A. (LB-CsVMV:NPTII+35S: DCL1/DCL2/GUS hairpin-RB): Constitutive dsRNA expression (ID157)(SEQ ID NO:60).

B. (LB-CsVMV:NPTII+35S:Activator+IP:DCL1/DCL2/GUS hairpin-RB): Switch-controlled dsRNA expression (ID 163)(SEQ ID NO:57)

LB=Left Border

NPTII=Kanamycin Resistance gene

IP=Inducible Promoter

DCL1=*Botrytis cinerea* (Bc) Dicer Like Protein 1 partial

DCL2=Bc Dicer Like Protein 2 partial

GUS=β-glucoronidase (reporter gene) (encoding amino acid sequence SEQ ID NO:58), partial RB=Right Border Once may also generate cassettes for switch-controlled expression of anti-pest peptides. For example, an antifungal polypeptide with activity against *Botrytis cinerea* could be constructed with the antifungal peptide (AFP):

C. (LB-CsVMV:NPTII+35S:AFP-RB): constitutive AFP expression

D. (LB-CsVMV:NPTII+35S:Activator+IP:AFP-RB): Switch-controlled AFP Expression

LB=Left Border

NPTII=Kanamycin Resistance gene

IP=Inducible Promoter

AFP=*Botrytis cinerea* antifungal peptide

RB=Right Border

Petunia Transformation and Regeneration. Petunia variety V26 was transformed with the constructs A and B using *Agrobacterium tumefaciens* and regenerated using Kanamycin selection according to previously described protocols and standardized methodologies. The same strategy may also be used to transform Petunias with constructs C and D.

Event Characterizations. All event characterization for A and B was carried out using To plants. All plants were screened for the presence of the selectable NPTII marker and copy number within the genome was determined using QPCR.

Figure 26:
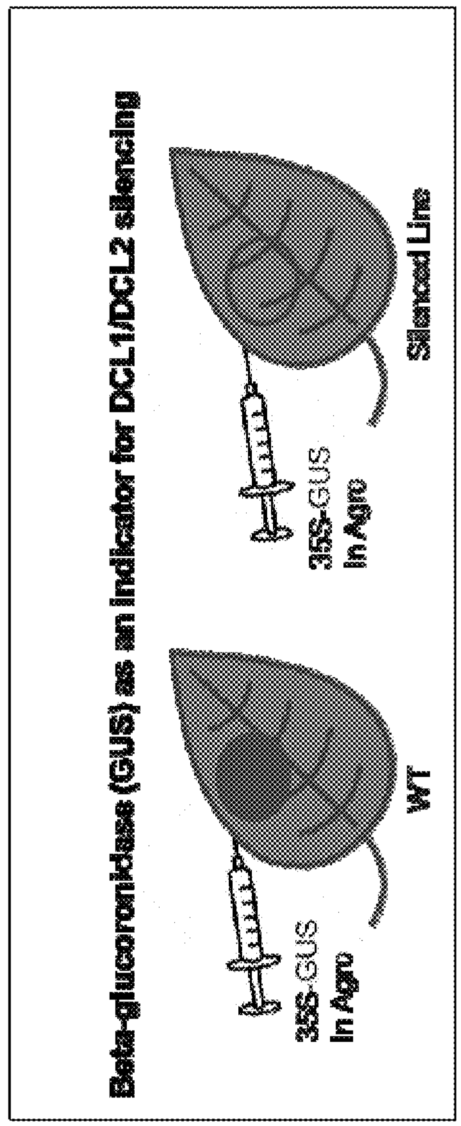
FIG. 26 shows expected outcome of Agro-infiltration on constitutively expressing DCL1/DCL2/GUS hairpin petunia lines. In wild-type plants, Agro-infiltration of a construct for constitutive expression of GUS and stained with X-gluc is expected to turn the leaf area blue (left), while in a DCL1/DCL2/GUS hairpin expressing plant, the Agro-infiltration a construct for constitutive expression of GUS and stained with X-gluc is expected to have no effect and no coloration change (right).
Figure 27:
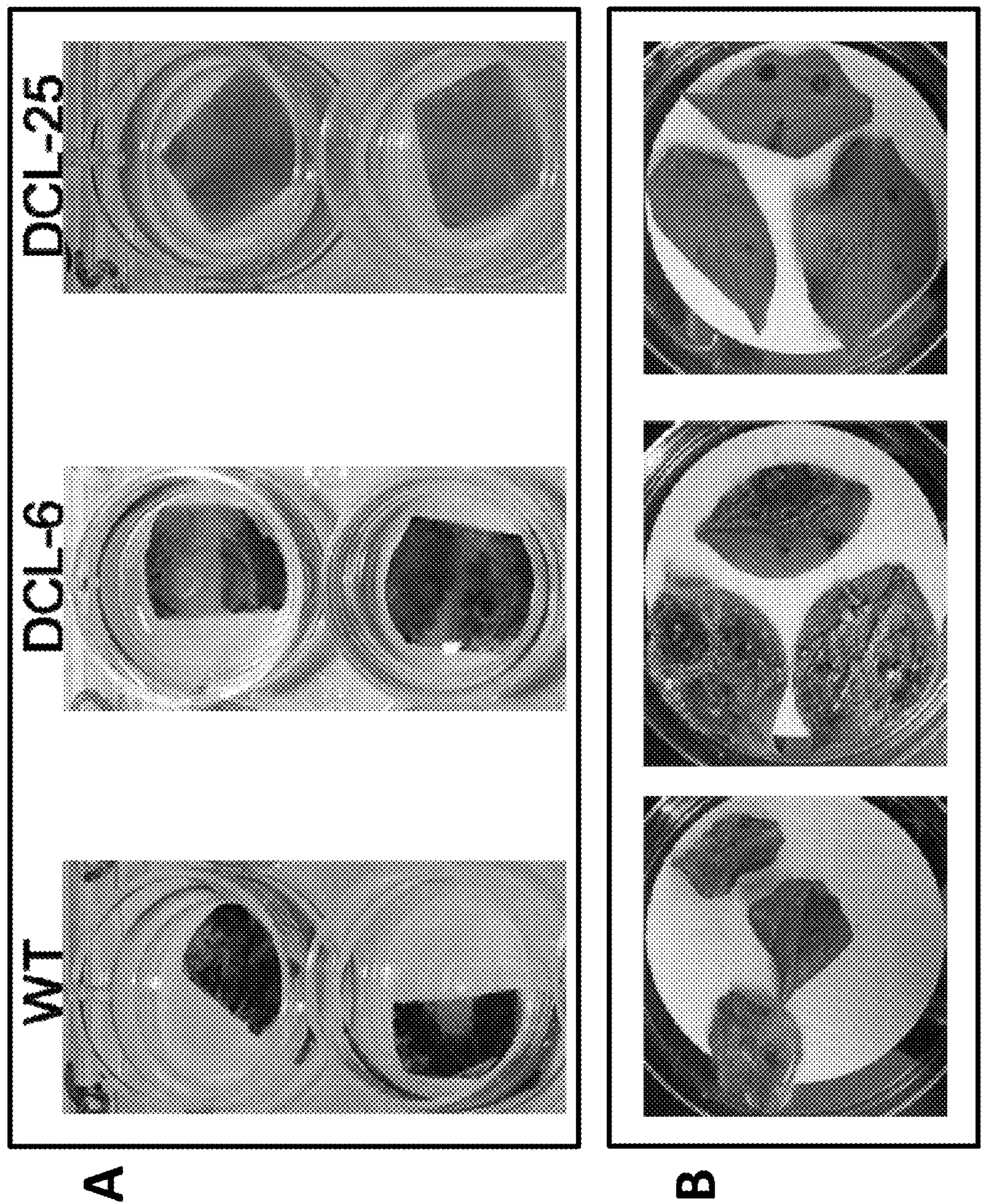
FIG. 27 shows characterization of constitutive DCL1/DCL2/GUS hairpin transformed petunia lines for GUS silencing and *Botrytis cinerea* disease resistance. Panel A: wild-type (WT) and transgenic DCL1/DCL2/GUS Hairpin Petunia events were infiltrated with *Agrobacterium* containing 35S-GUS and stained with X-gluc; the WT parental line showing full GUS expression; transgenic line DCL-6 which does not silence GUS expression (non-functional event); and line DCL-25 which shows complete GUS silencing; Panel B: inoculation of the same lines with *Botrytis cinerea.*

Constitutive hairpin expression for dsRNA synthesis targeting 2 *Botrytis cinerea* genes and the GUS reporter gene. A strategy for validating dsRNA expression through silencing of the reporter gene β-glucoronidase (GUS) was adapted from previous literature (Wroblewski et al. (2007) *Plant J.* 51:803-818). In our construct, the GUS fragment was fused to the previously-validated DCL1/DCL2 fragments for dsRNA expression. Silencing of GUS in transgenic Petunia lines was evaluated by transient *Agrobacterium tumefaciens* mediated expression through leaf infiltration as shown diagrammatically in FIG. 26. All lines were infiltrated with *Agrobacterium* containing a constitutively expressed GUS gene. Three days post-infiltration GUS expression was visualized using the histochemical X-gluc stain. Successful expression of the hairpin cassette would be expected to result in a lack of blue X-gluc staining as shown in FIG. 26. Multiple petunia transformation events were screened by infiltrating detached leaves with *Agrobacterium* and performing X-gluc staining. Selected lines were identified that blocked transient GUS expression (e.g., DCL-25) while other lines did not block GUS expression (e.g., DCL-6), presumably linked to hairpin expression activity. The results are shown in FIG. 27A. This colormetric screening technique is important for evaluating a HIGS hairpin cassette expression, as there is no endogenous plant gene targeted for down regulation that can be empirically measured to identify plant lines with successful dsRNA expression. Inoculation of the selected petunia lines with *Botrytis cinerea* spore solution showed a strong correlation between GUS silencing and disease resistance. As shown in FIG. 27B, there was a strong correlation between GUS silencing and disease resistance indicating both phenotypes are linked to initiation of RNAi through expression of the hairpin cassette shown above.

Constitutive expression of AFP. Transgenic petunia events transformed with the constitutively expressed an AFP cassette are screened by quantitative reverse-transcriptase PCR (qrtPCR) using the protocol as described in Example 7 and AFP specific primers are designed to determine the level of expression among independent lines.

When inoculated with *Botrytis cinerea* spores, AFP lines are expected to show disease resistance that should correlate to AFP expression levels while independent GFP transformed petunia lines should all be susceptible to *B. cinerea*.

Ligand inducible hairpin expression for dsRNA synthesis targeting two *Botrytis cinerea* genes and the GUS reporter gene. Ligand inducible expression of the DCL1/DCL2/GUS hairpin cassette was evaluated using the transient *Agrobacterium*-mediated GUS expression as described above only detached leaves were sprayed with 50 uM ligand or mock treated with water prior to Agro-infiltration. As shown in the cartoon on FIG. 28A, under ligand inducible hairpin expression we expected to see GUS silencing only following ligand application.

Figure 28:
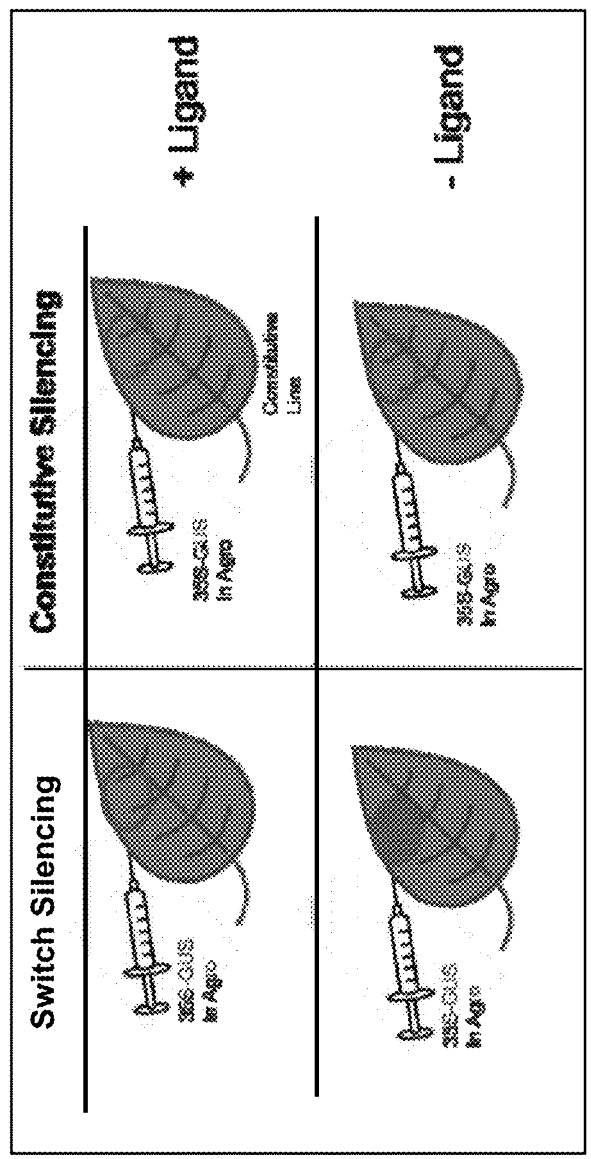
FIG. 28 shows ligand inducible GUS hairpin expression vs constitutive GUS hairpin expression when treated with ligand and Agro-infiltrated with GUS. Panel A: expected outcomes of inducible and constitutive expression; Panel B: experimental results of three petunia lines treated with ligand and Agro-infiltrated with GUS; constitutively silenced (DCL-25) and null event (DCL-6) showed no response to ligand application. Inducible hairpin line (DCL-8) shows GUS silencing (lack of blue color) only when treated with ligand.
Figure 28:
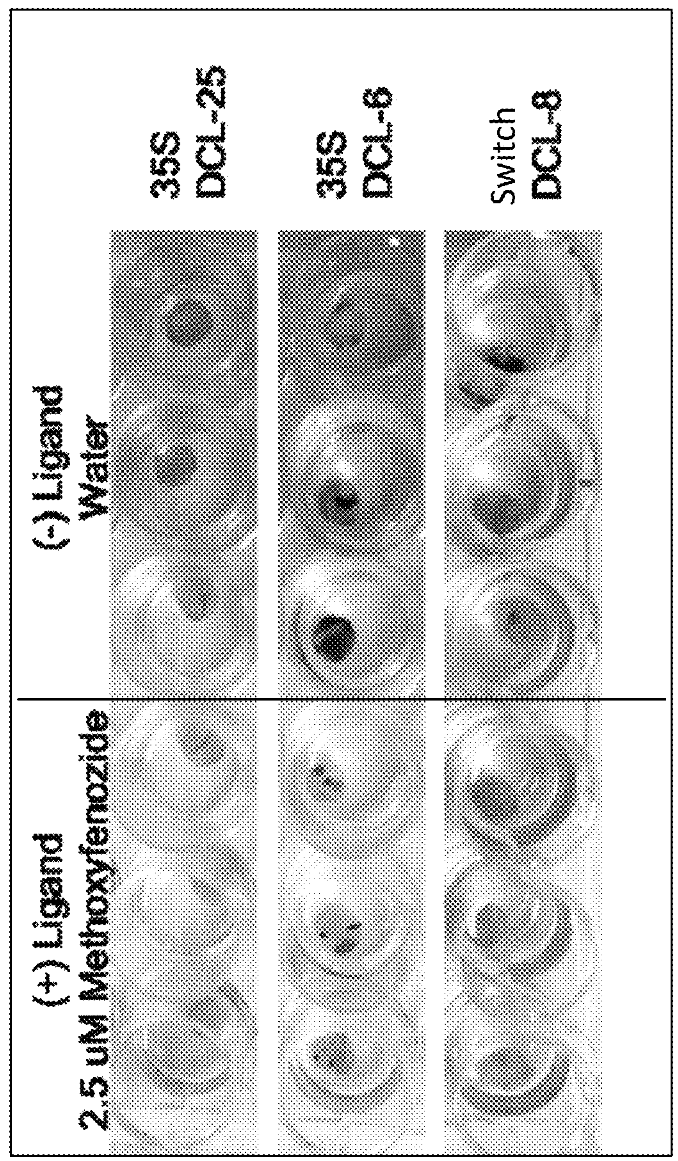

Eight independent Switch-DCL1/DCL2/GUS petunia lines were evaluated by detaching 6 leaves from each line and splitting into two treatments. One treatment was sprayed with 50 uM ligand while the other treatment was sprayed with water. At 2 days after the initial treatment, plants were treated again with 50 uM ligand or water. At 3 days after the initial treatment, plants were Agro-infiltrated in order to transiently express GUS. At 3 days after Agro-infiltration, plants were histochemical stained with X-gluc for visualization of GUS expression. Constitutive controls DCL-25 and DCL-6 analyzed in FIG. 27 did not show any ligand induced changes to GUS expression, while a single Switch DCL-8 line shown in FIG. 28B showed ligand induced GUS silencing as shown by the absence of blue staining.

Figure 29:
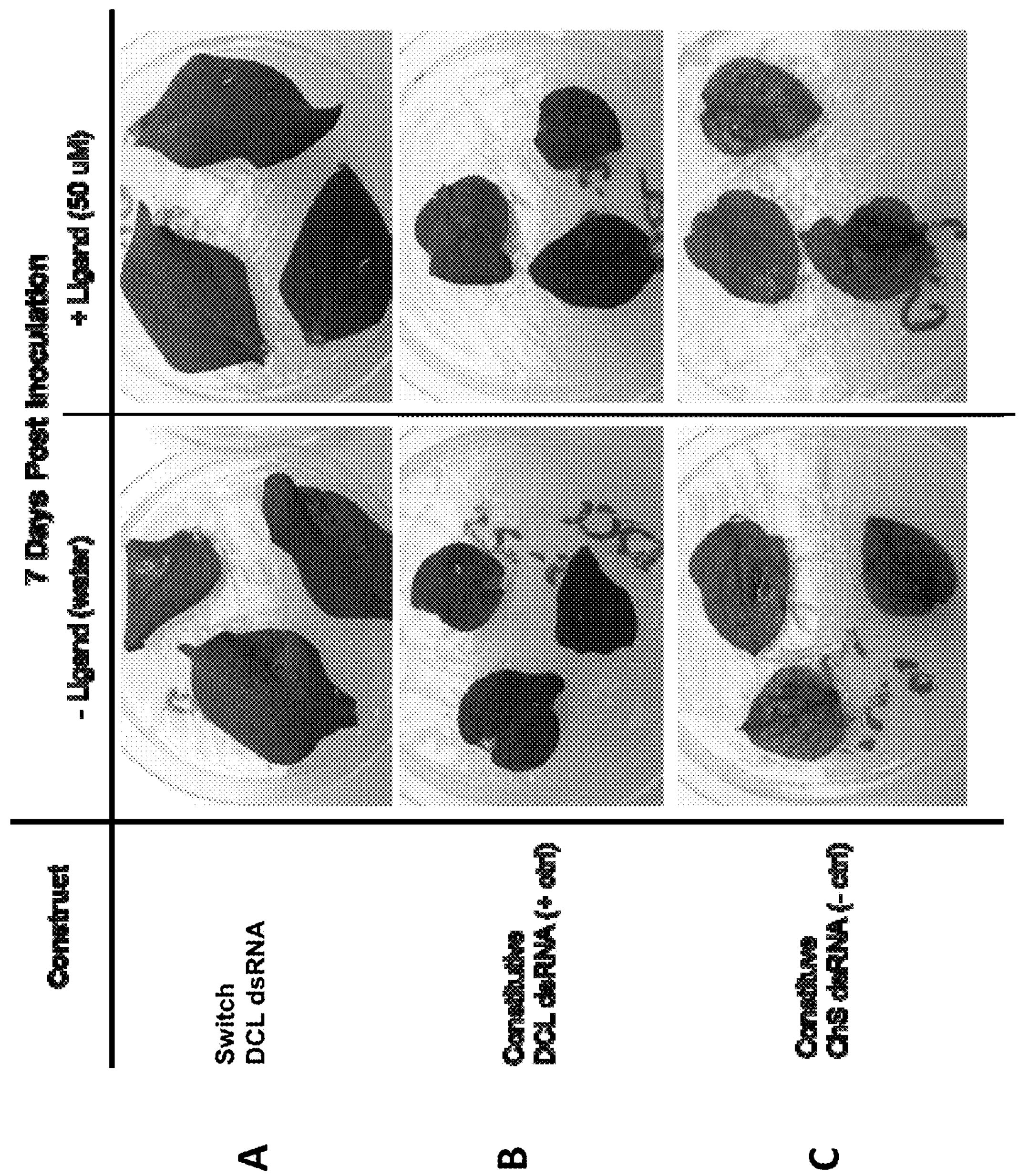
FIG. 29 shows Switch-DCL1/DCL2/GUS hairpin ligand-inducible *Botrytis cinerea* resistance. Plants were treated with 50 μM methoxyfenozide or control (water) and inoculated with *Botrytis cinerea* 3 days after treatment. Leaves were photographed seven days after pathogen inoculation; Row A shows a switch-controlled DCL dsRNA; Row B shows a constitutively expressing DCL dsRNA (a positive control); and Row C shows a constitutively expressing non-specific dsRNA (negative control for DCL).

For ligand inducible disease resistance screening, 6 leaves from each line were split into two treatments. One treatment was placed on 50 uM methoxyfenozide in 1% phytoagar (+Ligand) while the other treatment was placed on 1% phytoagar (−ligand). After 3 days all leaves were inoculated with *Botrytis cinerea* spore solution. As shown in FIG. 29, at 7 days after pathogen inoculation, the Switch-DCL1/DCL2/GUS hairpin line showed ligand induced disease resistance. The constitutive DCL1/DCL2/GUS hairpin line DCL-25 (+control) and non-specific dsRNA line (−control) showed no change in disease resistance in the presence or absence of ligand.

Figure 30:
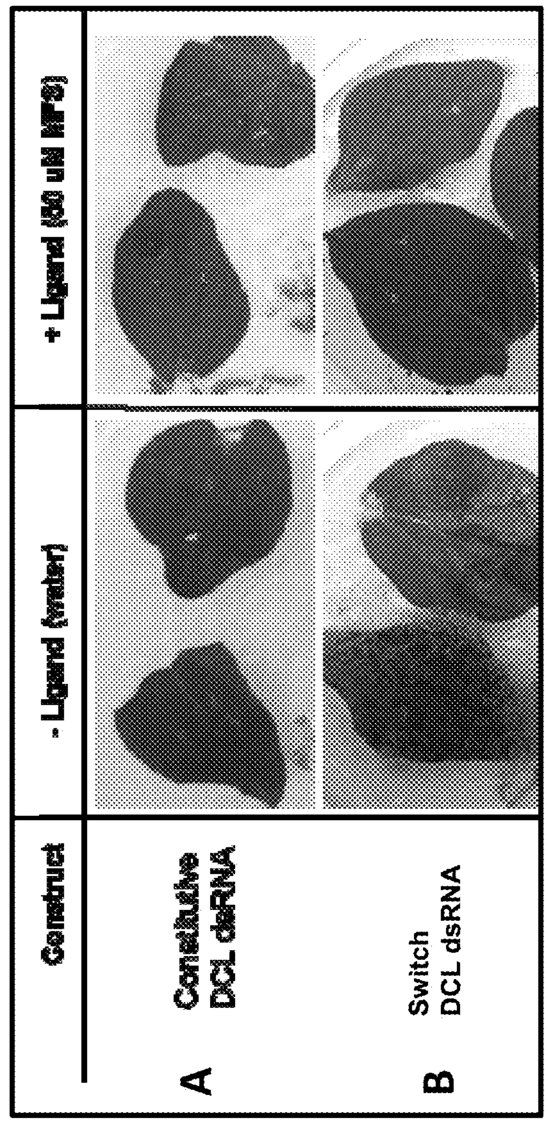
FIG. 30 shows a composite of switch-coupled constructs with ligand (50 μM methoxyfenozide) or control (water). Row A shows a constitutively-expressing DCL dsRNA (positive control); Row B shows a switch-controlled DCL dsRNA.

A composite of switch-coupled DCL constructs with ligand and in the absence of ligand is shown in FIG. 30.

Example 11

Figure 31:
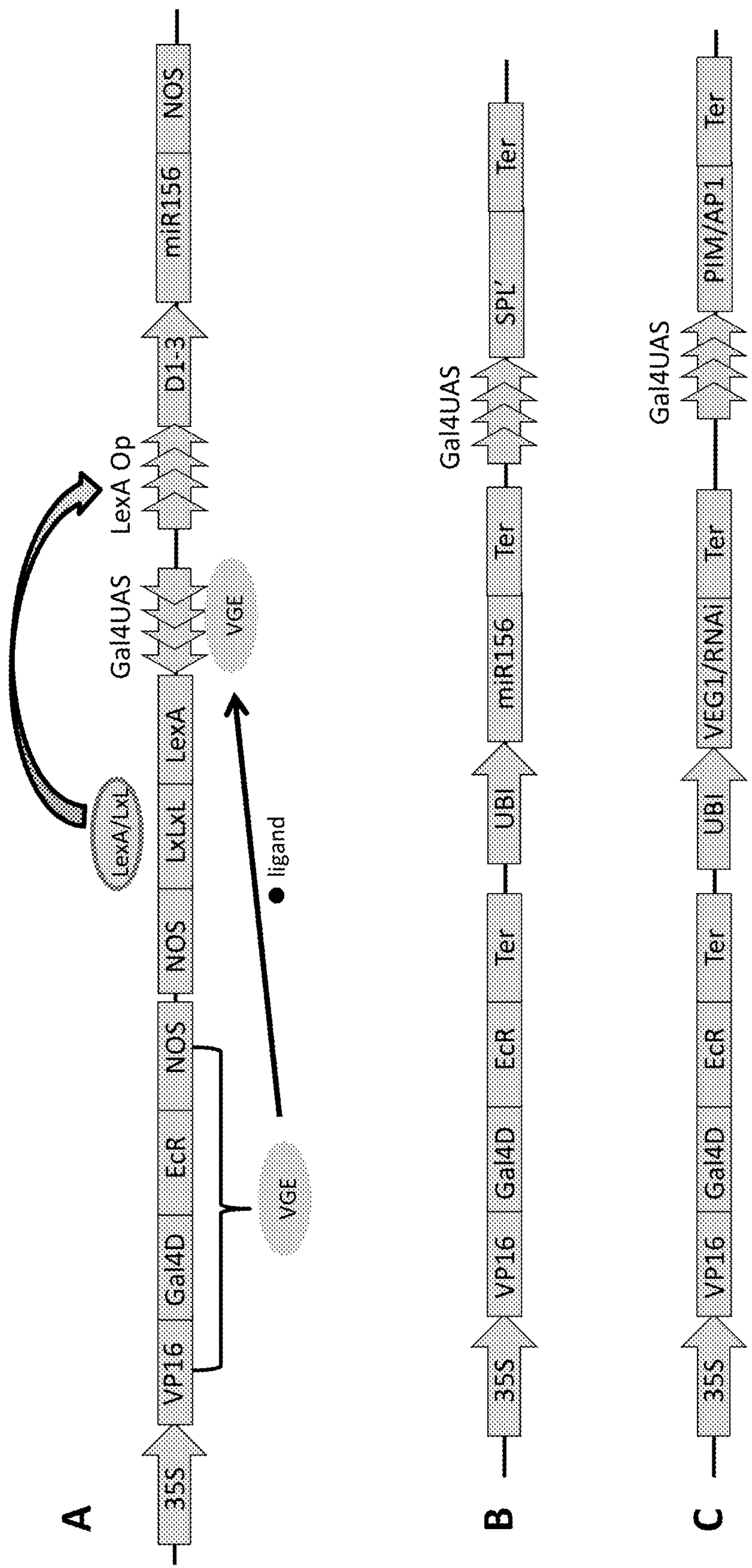
FIG. 31 shows constructs for increasing biomass. A: a control of flowering construct to allow constitutive expression of miR156 (SEQ ID NO:61), an miRNA that represses the expression of SPL flowering gene(s) and a gene switch with a repression domain (LxLxL) such that when ligand is present miR156 is repressed and flowering occurs; B: a control of flowering construct to allow constitutive expression of miR156, however, in the presence of ligand, the switch leads to expression of SPL' which is a modified SPL with nucleotide changes that encode the same amino acid sequences but make the gene resistant to miR156 silencing, thereby leading to flowering in the presence of ligand; C: a control of flowering construct to allow constitutive expression of Veg1/RNAi which silences the VEG1 gene, but in the presence of ligand, the gene switch leads to expression of PIM/AP1 and restores flowering.

FIG. 31 shows three constructs that illustrate a strategy to increase biomass in plants. In FIG. 31A, a construct is shown to allow constitutive expression of miR156 (SEQ ID NO:61), an miRNA that effectively silences the SPL flowering gene. The construct also contains a gene switch with a repression domain (LxLxL) in place of the activation domain such that when ligand is present, miR156 is repressed by the expression of LexA/with its LxLxL domain and flowering occurs (Wang, J-W (2009) *Cell* 138:738-749). Thus, in this example, one may grow the plants to allow increased biomass by inhibition of flowering until flowering is desired. Thereupon, application of the chemical ligand of the gene switch represses the miR156 inhibition and flowering is restored.

FIG. 31B shows a construct that allows constitutive expression of miR156, however, in this arrangement, in the presence of ligand, the switch leads to expression of SPL' which is a modified SPL flowering gene with nucleotide changes (which encode the same amino acid sequence) that make it resistant to miR156 silencing, thereby leading to flowing in the presence of ligand through expression of the engineered SPL'. Thus, in this example, one may grow the plants to allow increased biomass by inhibition of flowering until flowering is desired. Application of the chemical ligand at the appropriate time allows the gene switch-controlled SPL' gene to be expressed and flowering is restored.

In FIG. 31C, the construct allows constitutive expression of Veg1/RNAi which silences the VEG1 flowering gene, but in the presence of ligand, the gene switch leads to expression of PIM (AP1) and restores flowering. Thus, in this example, one may grow the plants to allow increased biomass by inhibition of flowering until flowering is desired. Thereupon, application of the chemical ligand of the gene switch overrides VEG1 inhibition and flowering is restored.

The invention claimed is:

1. One or more vectors or polynucleotides comprising:

(a) a polynucleotide encoding a VGEvy gene switch, comprising:

(i) a transactivation domain;

(ii) a DNA-binding domain; and (iii) a ligand-binding domain having an amino acid sequence of SEQ ID NO:2;

(b) a nucleic acid which controls one or more traits in a plant; and (c) a regulatory element operably connected 5' of (b), wherein the VGEvy gene switch induces expression of (b) in the presence of a chemical ligand.

2. The one or more vectors or polynucleotides of claim 1, wherein said one or more traits comprises one or more of flowering, drought resistance, herbicide resistance, pest resistance, diseases resistance, type of floral color, intensity of floral color, floral aroma, accumulation of specific nutrients, taste, aroma, color, taste, nutritional value, or expression of an exogenous gene.

3. The one or more vectors or polynucleotides of claim 2, wherein said nucleic acid controls flowering and comprises a polynucleotide encoding a full-length polypeptide, or biologically active fragment thereof, of one or more of Gigantea (GI), Nuclear Factor Y (NFY), Constans (CO), protein farnesyltransferase (PFT), Agamous-Like 15 (AGL15), Flowering Locus T (FT), Twin Sister of FT (TSF), bZIP transcription factor (FD), Apetalal (AP1), Suppressor of Overexpression of CO1 (SOC1), Agamous-Like 24 (AGL24); Leafy (LFY), or Squamosa Promoter Binding Protein-Like 3a (SPL3).

4. The one or more vectors or polynucleotides of claim 1, wherein said DNA-binding domain comprises one or more of a Gal4 binding domain, a LexA binding domain, a transcription factor binding domain, a Group H nuclear receptor member binding domain, a steroid/thyroid hormone nuclear receptor superfamily member binding domain, a bacterial LacZ binding domain, an EcR binding domain, an ARF, a bZIP, a homeodomain family of a DNA binding domain, or synthetic DNA-binding protein.

5. The one or more vectors or polynucleotides of claim 1, wherein said transactivation domain comprises one or more of a Group H nuclear receptor member transactivation domain, steroid/thyroid hormone nuclear receptor transactivation domain, synthetic or chimeric transactivation domain, polyglutamine transactivation domain, basic or acidic amino acid transactivation domain, a VP16 transactivation domain, a GAL4 transactivation domain, an NF-κB transactivation domain, a BP64 transactivation domain, a B42 acidic transactivation domain (B42AD), a p53 transactivation domain, a p65 transactivation domain (p65AD), an EDLL acidic transactivation domain from AP2/ERF, a glutamine-rich transactivation domain, an ARFs or CONSTANS protein transactivation domain, a proline-rich domain transactivation domain from bZIP, or an analog, combination, or modification thereof.

6. The one or more vectors or polynucleotides of claim 1, wherein said DNA-binding domain is a GAL4 transcription factor DNA-binding domain and/or wherein said transactivation domain is (i) derived from a Sarcoma Virus 40 (SV40) transcriptional transactivation domain or (ii) comprises a herpes virus VP16 transcriptional transactivation domain.

7. The one or more vectors or polynucleotides of claim 1, wherein said VGEvy gene switch comprises the polypeptide sequence of SEQ ID NO:1.

8. The one or more vectors or polynucleotides of claim 1, wherein said chemical ligand is methoxyfenozide or diacylhydrazine.

9. The one or more vectors or polynucleotides of claim 1, wherein said regulatory element comprises (i) a recognition site for the DNA-binding domain of said VGEvy gene switch and (ii) a promoter.

10. A plant comprising one or more vectors or polynucleotides of claim 1.

11. The plant of claim 10, wherein all or a portion of the one or more vectors or polynucleotides is integrated into the plant genome.

12. The plant of claim 11, wherein said plant is a dicot.

13. A method of controlling or regulating flowering in a plant comprising introducing one or more vectors or polynucleotides of claim 1 into said plant.

14. The method of claim 13, further comprising contacting said plant with a non-steroidal chemical ligand wherein said chemical ligand is diacylhydrazine or methoxyfenozide.

15. The plant of claim 11, wherein said plant is a monocot.

16. The method of claim 13, wherein the plant is alfalfa sprouts, apples, apricots, artichokes, Asian pears, asparagus, atemoyas, avocados, bamboo shoots, bananas, beans, bean sprouts, beets, belgian endive, bitter melons, bell peppers, blackberries, blueberries, bok choy, boniato, boysenberries, broccoflowers, broccoli, broccolini, brussels sprouts, butter lettuce, cabbage, cantaloupe, carambola, carrots, casaba melons, cauliflower, celery, chayotes, cherimoyas, cherries, coconuts, coffee, collard greens, corn, cranberries, cucumbers, dates, eggplant, endive, escarole, feijoa, fennel, figs, garlic, gooseberries, grapefruit, grapes, green beans, green onions, collard greens, mustard greens, guava, hominy, honeydew melons, horned melons, iceberg lettuce, Jerusalem artichokes, jicama, kale, kiwifruit, kohlrabi, kumquats, leeks, lemons, lettuce, lima beans, limes, longan, loquats, lychees, mandarins, malangas, mandarin marijuana, oranges, mangos, mulberries, mushrooms, napas, nectarines, okra, onions, oranges, papayas, parsnip, passion fruits, pawpaws, peaches, peanut, pears, sugar snap peas, green peas, peppers, persimmons, pineapples, plantains, plums, pomegranates, potatoes, prickly pears, pummelos, pumpkins, quince, radicchio, radishes, raspberries, red cabbage, rhubarb, romaine lettuce, rutabaga, shallots, snow peas, soybeans, spinach, sprouts, squash, strawberries, string beans, sweet potatoes, tangelo, tangerines, tomatillo, tomatoes, turnip, ugli fruit, watermelons, water chestnuts, watercress, waxed beans, yams, yellow squash, yuca/cassava, or zucchini squash.

* * * * *

SEQUENCE LISTING

```
<160> NUMBER OF SEQ ID NOS: 64

<210> SEQ ID NO 1
<211> LENGTH: 584
<212> TYPE: PRT
<213> ORGANISM: Artificial Sequence
<220> FEATURE:
<223> OTHER INFORMATION: Chimeric polypeptide gene switch
<220> FEATURE:
<221> NAME/KEY: MISC_FEATURE
<222> LOCATION: (1)..(93)
<223> OTHER INFORMATION: "V" region; acidic transcriptional
      transactivator domain derived from SV40 virus (Simian virus 40);
      also referred to as a transactivation domain (TAD).
<220> FEATURE:
```

```
<221> NAME/KEY: MISC_FEATURE
<222> LOCATION: (94)..(95)
<223> OTHER INFORMATION: GG (gly-gly) linker
<220> FEATURE:
<221> NAME/KEY: MISC_FEATURE
<222> LOCATION: (96)..(242)
<223> OTHER INFORMATION: "G" region; DNA-binding domain (DBD)
<220> FEATURE:
<221> NAME/KEY: MISC_FEATURE
<222> LOCATION: (243)..(249)
<223> OTHER INFORMATION: GGSRRIS (gly-gly-ser-arg-arg-ile-ser) linker
<220> FEATURE:
<221> NAME/KEY: MISC_FEATURE
<222> LOCATION: (250)..(584)
<223> OTHER INFORMATION: "E" region; mutation substituted ecdysone
      receptor ligand binding domain Evy (E68V/V184I/Y204E)

<400> SEQUENCE: 1

Met Ala Pro Pro Thr Asp Val Ser Leu Gly Asp Glu Leu His Leu Asp
1               5                   10                  15

Gly Glu Asp Val Ala Met Ala His Ala Asp Ala Leu Asp Asp Phe Asp
            20                  25                  30

Leu Asp Met Leu Gly Asp Gly Asp Ser Pro Gly Pro Gly Phe Thr Pro
        35                  40                  45

His Asp Ser Ala Pro Tyr Gly Ala Leu Asp Met Ala Asp Phe Glu Phe
    50                  55                  60

Glu Gln Met Phe Thr Asp Ala Leu Gly Ile Asp Glu Tyr Gly Gly Lys
65                  70                  75                  80

Leu Leu Gly Thr Ser Arg Arg Ile Ser Gly Gly Glu Phe Gly Gly Met
                85                  90                  95

Lys Leu Leu Ser Ser Ile Glu Gln Ala Cys Asp Ile Cys Arg Leu Lys
            100                 105                 110

Lys Leu Lys Cys Ser Lys Glu Lys Pro Lys Cys Ala Lys Cys Leu Lys
        115                 120                 125

Asn Asn Trp Glu Cys Arg Tyr Ser Pro Lys Thr Lys Arg Ser Pro Leu
    130                 135                 140

Thr Arg Ala His Leu Thr Glu Val Glu Ser Arg Leu Glu Arg Leu Glu
145                 150                 155                 160

Gln Leu Phe Leu Leu Ile Phe Pro Arg Glu Asp Leu Asp Met Ile Leu
                165                 170                 175

Lys Met Asp Ser Leu Gln Asp Ile Lys Ala Leu Leu Thr Gly Leu Phe
            180                 185                 190

Val Gln Asp Asn Val Asn Lys Asp Ala Val Thr Asp Arg Leu Ala Ser
        195                 200                 205

Val Glu Thr Asp Met Pro Leu Thr Leu Arg Gln His Arg Ile Ser Ala
    210                 215                 220

Thr Ser Ser Ser Glu Glu Ser Ser Asn Lys Gly Gln Arg Gln Leu Thr
225                 230                 235                 240

Val Ser Gly Gly Ser Arg Arg Ile Ser Arg Pro Glu Cys Val Val Pro
                245                 250                 255

Glu Thr Gln Cys Ala Met Lys Arg Lys Glu Lys Lys Ala Gln Lys Glu
            260                 265                 270

Lys Asp Lys Leu Pro Val Ser Thr Thr Thr Val Asp Asp His Met Pro
        275                 280                 285

Pro Ile Met Gln Cys Glu Pro Pro Pro Pro Glu Ala Ala Arg Ile His
    290                 295                 300

Glu Val Val Pro Arg Phe Leu Ser Asp Lys Leu Leu Val Thr Asn Arg
305                 310                 315                 320
```

```
Gln Lys Asn Ile Pro Gln Leu Thr Ala Asn Gln Gln Phe Leu Ile Ala
                325                 330                 335

Arg Leu Ile Trp Tyr Gln Asp Gly Tyr Glu Gln Pro Ser Asp Glu Asp
            340                 345                 350

Leu Lys Arg Ile Thr Gln Thr Trp Gln Gln Ala Asp Asp Glu Asn Glu
        355                 360                 365

Glu Ser Asp Thr Pro Phe Arg Gln Ile Thr Glu Met Thr Ile Leu Thr
    370                 375                 380

Val Gln Leu Ile Val Glu Phe Ala Lys Gly Leu Pro Gly Phe Ala Lys
385                 390                 395                 400

Ile Ser Gln Pro Asp Gln Ile Thr Leu Leu Lys Ala Cys Ser Ser Glu
                405                 410                 415

Val Met Met Leu Arg Val Ala Arg Arg Tyr Asp Ala Ala Ser Asp Ser
            420                 425                 430

Ile Leu Phe Ala Asn Asn Gln Ala Tyr Thr Arg Asp Asn Tyr Arg Lys
        435                 440                 445

Ala Gly Met Ala Glu Val Ile Glu Asp Leu Leu His Phe Cys Arg Cys
    450                 455                 460

Met Tyr Ser Met Ala Leu Asp Asn Ile His Tyr Ala Leu Leu Thr Ala
465                 470                 475                 480

Val Val Ile Phe Ser Asp Arg Pro Gly Leu Glu Gln Pro Gln Leu Val
                485                 490                 495

Glu Glu Ile Gln Arg Tyr Tyr Leu Asn Thr Leu Arg Ile Tyr Ile Leu
            500                 505                 510

Asn Gln Leu Ser Gly Ser Ala Arg Ser Ser Val Ile Tyr Gly Lys Ile
        515                 520                 525

Leu Ser Ile Leu Ser Glu Leu Arg Thr Leu Gly Met Gln Asn Ser Asn
    530                 535                 540

Met Cys Ile Ser Leu Lys Leu Lys Asn Arg Lys Leu Pro Pro Phe Leu
545                 550                 555                 560

Glu Glu Ile Trp Asp Val Ala Asp Met Ser His Thr Gln Pro Pro Pro
                565                 570                 575

Ile Leu Glu Ser Pro Thr Asn Leu
            580
```

<210> SEQ ID NO 2
<211> LENGTH: 335
<212> TYPE: PRT
<213> ORGANISM: Artificial Sequence
<220> FEATURE:
<223> OTHER INFORMATION: Polypeptide Gene Switch
<220> FEATURE:
<221> NAME/KEY: MISC_FEATURE
<222> LOCATION: (68)..(68)
<223> OTHER INFORMATION: Position at which E (Glu) in wild-type ecdysone receptor ligand binding domain is substituted with V (Val).
<220> FEATURE:
<221> NAME/KEY: MISC_FEATURE
<222> LOCATION: (184)..(184)
<223> OTHER INFORMATION: Position at which V (Val) in wild-type ecdysone receptor ligand binding domain is substituted with I (Ile).
<220> FEATURE:
<221> NAME/KEY: MISC_FEATURE
<222> LOCATION: (204)..(204)
<223> OTHER INFORMATION: Position at which Y (Tyr) in wild-type ecdysone receptor ligand binding domain is substituted with E (Glu).

<400> SEQUENCE: 2

```
Arg Pro Glu Cys Val Val Pro Glu Thr Gln Cys Ala Met Lys Arg Lys
1               5                   10                  15
```

```
Glu Lys Lys Ala Gln Lys Glu Lys Asp Lys Leu Pro Val Ser Thr Thr
            20                  25                  30

Thr Val Asp Asp His Met Pro Pro Ile Met Gln Cys Glu Pro Pro Pro
        35                  40                  45

Pro Glu Ala Ala Arg Ile His Glu Val Val Pro Arg Phe Leu Ser Asp
    50                  55                  60

Lys Leu Leu Val Thr Asn Arg Gln Lys Asn Ile Pro Gln Leu Thr Ala
65                  70                  75                  80

Asn Gln Gln Phe Leu Ile Ala Arg Leu Ile Trp Tyr Gln Asp Gly Tyr
                85                  90                  95

Glu Gln Pro Ser Asp Glu Asp Leu Lys Arg Ile Thr Gln Thr Trp Gln
            100                 105                 110

Gln Ala Asp Asp Glu Asn Glu Glu Ser Asp Thr Pro Phe Arg Gln Ile
        115                 120                 125

Thr Glu Met Thr Ile Leu Thr Val Gln Leu Ile Val Glu Phe Ala Lys
    130                 135                 140

Gly Leu Pro Gly Phe Ala Lys Ile Ser Gln Pro Asp Gln Ile Thr Leu
145                 150                 155                 160

Leu Lys Ala Cys Ser Ser Glu Val Met Met Leu Arg Val Ala Arg Arg
                165                 170                 175

Tyr Asp Ala Ala Ser Asp Ser Ile Leu Phe Ala Asn Asn Gln Ala Tyr
            180                 185                 190

Thr Arg Asp Asn Tyr Arg Lys Ala Gly Met Ala Glu Val Ile Glu Asp
        195                 200                 205

Leu Leu His Phe Cys Arg Cys Met Tyr Ser Met Ala Leu Asp Asn Ile
    210                 215                 220

His Tyr Ala Leu Leu Thr Ala Val Val Ile Phe Ser Asp Arg Pro Gly
225                 230                 235                 240

Leu Glu Gln Pro Gln Leu Val Glu Glu Ile Gln Arg Tyr Tyr Leu Asn
                245                 250                 255

Thr Leu Arg Ile Tyr Ile Leu Asn Gln Leu Ser Gly Ser Ala Arg Ser
            260                 265                 270

Ser Val Ile Tyr Gly Lys Ile Leu Ser Ile Leu Ser Glu Leu Arg Thr
        275                 280                 285

Leu Gly Met Gln Asn Ser Asn Met Cys Ile Ser Leu Lys Leu Lys Asn
    290                 295                 300

Arg Lys Leu Pro Pro Phe Leu Glu Glu Ile Trp Asp Val Ala Asp Met
305                 310                 315                 320

Ser His Thr Gln Pro Pro Pro Ile Leu Glu Ser Pro Thr Asn Leu
                325                 330                 335
```

<210> SEQ ID NO 3
<211> LENGTH: 13176
<212> TYPE: DNA
<213> ORGANISM: Artificial Sequence
<220> FEATURE:
<223> OTHER INFORMATION: Polynucleotide Vector
<220> FEATURE:
<221> NAME/KEY: misc_feature
<222> LOCATION: (223)..(774)
<223> OTHER INFORMATION: Complement Phosphinothricin N-acetyltransferase
<220> FEATURE:
<221> NAME/KEY: misc_feature
<222> LOCATION: (792)..(1090)
<223> OTHER INFORMATION: Complement NOS Promoter
<220> FEATURE:
<221> NAME/KEY: misc_feature
<222> LOCATION: (1123)..(1146)
<223> OTHER INFORMATION: attB1

```
<220> FEATURE:
<221> NAME/KEY: misc_feature
<222> LOCATION: (1177)..(1471)
<223> OTHER INFORMATION: Complement E9 Terminator
<220> FEATURE:
<221> NAME/KEY: misc_feature
<222> LOCATION: (1478)..(2005)
<223> OTHER INFORMATION: Complement At-FT
<220> FEATURE:
<221> NAME/KEY: misc_feature
<222> LOCATION: (2019)..(2236)
<223> OTHER INFORMATION: Complement RS Promoter
<220> FEATURE:
<221> NAME/KEY: misc_feature
<222> LOCATION: (2252)..(2812)
<223> OTHER INFORMATION: Complement 3A Terminator
<220> FEATURE:
<221> NAME/KEY: misc_feature
<222> LOCATION: (2819)..(4579)
<223> OTHER INFORMATION: VGEvy (E68V/V184I/Y204E)
<220> FEATURE:
<221> NAME/KEY: misc_feature
<222> LOCATION: (4594)..(5242)
<223> OTHER INFORMATION: Complement35S Promoter
<220> FEATURE:
<221> NAME/KEY: misc_feature
<222> LOCATION: (5797)..(6483)
<223> OTHER INFORMATION: Resolvase

<400> SEQUENCE: 3

taactataac ggtcctaagg tagcgacgta cgaattcggg ggatctggat tttagtactg     60

gattttggtt ttaggaatta gaaattttat tgatagaagt attttacaaa tacaaataca    120

tactaagggt ttcttatatg ctcaacacat gagcgaaacc ctataggaac cctaattccc    180

ttatctggga actactcaca cattattatg gagaaactcg agttagatct cggtgacggg    240

caggaccgga cggggcggta ccggcaggct gaagtccagc tgccagaaac ccacgtcatg    300

ccagttcccg tgcttgaagc cggccgcccg cagcatgccg cggggggcat atccgagcgc    360

ctcgtgcatg cgcacgctcg ggtcgttggg cagcccgatg acagcgacca cgctcttgaa    420

gccctgtgcc tccagggact tcagcaggtg ggtgtagagc gtggagccca gtcccgtccg    480

ctggtggcgg ggggagacgt acacggtcga ctcggccgtc cagtcgtagg cgttgcgtgc    540

cttccagggg cccgcgtagg cgatgccggc gacctcgccg tccacctcgg cgacgagcca    600

gggatagcgc tcccgcagac ggacgaggtc gtccgtccac tcctgcggtt cctgcggctc    660

ggtacggaag ttgaccgtgc ttgtctcgat gtagtggttg acgatggtgc agaccgccgg    720

catgtccgcc tcggtggcac ggcggatgtc ggccgggcgt cgttctgggc tcatttttgc    780

tccagatccg gtgcagatta tttggattga gagtgaatat gagactctaa ttggataccg    840

aggggaattt atggaacgtc agtggagcat ttttgacaag aaatatttgc tagctgatag    900

tgaccttagg cgacttttga acgcgcaata atggtttctg acgtatgtgc ttagctcatt    960

aaactccaga aacccgcggc tgagtggctc cttcaacgtt gcggttctgt cagttccaaa   1020

cgtaaaacgg cttgtcccgc gtcatcggcg ggggtcataa cgtgactccc ttaattctcc   1080

gctcatgatc agattgtcgt ttcccgcctt ggcgcgccat cacaagtttg tacaaaaaag   1140

caggctccga attcgccctt ggcgcgcctc ggaccggttt gggatgtttt actcctcata   1200

ttaacttcgg tcattagagg ccacgatttg acacattttt actcaaaaca aaatgtttgc   1260

atatctctta taatttcaaa ttcaacacac aacaaataag agaaaaaaca aataatatta   1320

atttgagaat gaacaaaagg accatatcat tcattaactc ttctccatcc atttccattt   1380

cacagttcga tagcgaaaac cgaataaaaa acacagtaaa ttacaagcac aacaaatggt   1440
```

```
acaagaaaaa cagttttccc aatgccataa tatcgatcta aagtcttctt cctccgcagc   1500
cactctccct ctgacaattg tagaaaactg cggccacggg aaggccgaga ttgtagatct   1560
cagcaaactc gcgagtgttg aagttctggc gccaccctgg tgcatacact gtttgcctgc   1620
caagctgtcg aaacaatata aacacgacac gatgaattcc tgcagtggga cttggatttt   1680
cgtaacacac aatctcattg ccaaaggttg ttccagttgt agcagggata tcagtcacca   1740
accaatggag atattctcgg aggtgagggt tgctaggact tggaacatct ggatccacca   1800
taaccaaagt atagaagttc ctgaggtctt ctccaccaat ctcaactctt ggcttgtttt   1860
gaacctgaga aggccttaga tccaagccat tagtcacctc tctttggcca taagtaacct   1920
ttagagtgat tgatctatta aacggatcaa gaacgtctcc aacaactctg cttactataa   1980
gagggtctct tatatttata gacatctttg cctgcaggac cggaatgcca agctggaatt   2040
cgagctcctg cagctcgaag atccaagctt cgtgtcctct ccaaatgaaa tgaacttcct   2100
tatatagagg aagggtcttg ctctagtgtc tccgctcgga ggacagtact ccgctcggag   2160
gacagtactc cgctcggagg acagtactcc gctcggagga cagtactccg ctcggaggac   2220
agtactccga gaattcagcg gccgcctcga gctcagctag aataattatc agacaaatat   2280
tgagattctg gtatatcaag aaaaaatgtt ctattttggt ggtaagagag attcatcaag   2340
tccaataaaa actacaaaca tgatttgaaa attgcagaaa ggaaagtgaa taaatgttga   2400
cacaaaaagc ctatactgta cttaacttga ttgcataatt acttgatcat agactcatag   2460
taaacttgat tacacagata agtgaagaaa caaaccaatt caagacataa ccaaagagag   2520
gtgaaagact gttttatatg tctaacattg caccttaata tcacactgtt agttcctttc   2580
ttacttaaat tcaacccatt aaagtaaaaa caacagataa taataatttg agaatgaaca   2640
aaaggaccat atcatttatt aactcttatc catccatttg cattttgatg tccgaaaaca   2700
aaaactgaaa gaacacagta aattacaagc agaacaaatg atagaagaaa acagcttttc   2760
caatgccata atactcaaac ttagtaggat tctggtgtgt gggcaatgaa acatcgattc   2820
agagattcgt gggggactca aggataggcg gcggttgggt gtgcgacatg tccgccacat   2880
cccaaatctc ctcaaggaaa ggcggcagct ttctgttctt gagcttgagg gagatgcaca   2940
tgttggagtt ttgcattccg agcgtgcgta gctcagagag gattgagagg atcttgccgt   3000
atatgacgga cgaacgcgcc gaaccggaaa gttggttcag gatatagatg cggagcgtat   3060
tcaggtagta ccgctggatt tcctccacca gttgcggctg ctccaaccct ggccggtcag   3120
aaaagatgac gacagccgtg agcagcgcgt aatggatgtt gtccaacgcc atagagtaca   3180
tgcaccggca gaagtgcagt agatcctcga tgacttcggc catgccagcc ttgcggtagt   3240
tatccctggt gtacgcttgg ttgttagcga acagaatact gtcggaggcc gcatcgtatc   3300
gtcgcgcgac tcggagcatc attacctcac ttgagcaagc cttgagcagc gtaatttgat   3360
ctggctggct gatcttggcg aaccctggca atcccttagc gaactccacg ataagttgga   3420
ccgtgaggat agtcatctcc gtgatctggc ggaagggagt gtccgattct tcgttttcat   3480
cgtccgcttg ctgccacgtc tgcgtaatcc ttttaagatc ctcatcagaa ggctgctcgt   3540
acccgtcttg ataccagatg agcctggcga taaggaactg ctggttggct gtcaactggg   3600
ggatgttttt ctgccggttt gtcaccaaca gcttgtcgga gagaaacctt gggacaacct   3660
cgtgaatcct tgctgcttca ggaggtggag gttcacactg cataatgggc ggcatgtggt   3720
cgtccaccgt cgtcgtgctg acaggcagtt tgtccttctc cttctgtgct ttcttctctt   3780
tccgcttcat ggcgcactga gtctcgggta ctacgcactc aggccgtgat attctcctag   3840
```

```
acccgcccga tacagtcaac tgtctttgac ctttgttact actctcctcc gatgatgatg   3900
tcgcacttat tctatgctgt ctcaatgtta gaggcatatc agtctccact gaagccaatc   3960
tatctgtgac ggcatccttg ttcacattat cttgtacaaa taatccggta agaagtgctt   4020
ttatatcctg taaagaatcc attttcaaaa tcatgtcaag gtcctccctt ggaaaaatca   4080
gtagaaatag ctgttccagt ctttctagcc ttgattccac ttctgtcaga tgtgccctag   4140
tcagcggaga ccttttggtt ttgggagagt agcgacactc ccagttgttc ttcagacact   4200
tggcgcactt cggtttttct ttggagcact tgagcttttt aagtcggcaa atatcgcagg   4260
cttgttcgat agaagaaagt agcttcatcc cgccgaactc cccgcctgat attcttctgg   4320
aggttccaag caacttccca ccgtactcgt caattccaag ggcatcggta aacatctgct   4380
caaactcgaa gtcggccata tccagagcgc cgtagggggc ggagtcgtgg ggggtaaatc   4440
ccggacctgg ggaatccccg tcccccaaca tgtccagatc gaaatcgtct agcgcgtcag   4500
cgtgagccat cgccacgtcc tcgccgtcta agtggagttc gtcccccagg ctgacatcgg   4560
tcgggggggc catggtggcg ctagccctgc aggtctggag gatctgctag agtcagcttg   4620
tcgcgtgtcc tctccaaatg aaatgaactt ccttatatag aggaagggtc ttgcgaagga   4680
tagtgggatt gtgcgtcatc ccttacgtca gtggagatat cacatcaatc cacttgcttt   4740
gaagacgtgg ttggaacgtc ttctttttcc acgatgctcc tcgtgggtgg gggtccatct   4800
ttgggaccac tgtcggcaga ggcatcttca acgatggcct ttcctttatc gcaatgatgg   4860
catttgtagg agccaccttc cttttccact atcttcacaa taaagtgaca gatagctggg   4920
caatggaatc cgaggaggtt tccggatatt accctttgtt gaaaagtctc acatcggacc   4980
atcacatcaa tccacttgct ttgaagacgt ggttggaacg tcttcttttt ccacgatgct   5040
cctcgtgggt gggggtccat ctttgggacc actgtcggca gaggcatctt caacgatggc   5100
ctttccttta tcgcaatgat ggcatttgta ggagccacct tccttttcca ctatcttcac   5160
aataaagtga cagatagctg ggcaatggaa tccgaggagg tttccggata ttaccctttg   5220
ttgaaaagtc tcacatcgga ccacgcgtca cagttgaggt atttcggatc gtggcgatcg   5280
caagggcgaa ttcgacccag ctttcttgta caaagtggtg atcggtccgg ttcggctgcg   5340
gccgcattac cctgttatcc ctatagatct ttaactatga ctctcttaag gtagccaaat   5400
tccggaacgc gccgaagttt aaacgactta atcagctaat acaaactatc agtgtttgac   5460
aggatatatt ggcgggtaaa cctaagagaa aagagcgttt attagaataa tcggatattt   5520
aaaagggcgt gaaaaggttt atccgttcgt ccatttgtat gtgcatgcca accacagggt   5580
tcccctcggg atcaaagtac tttgatccaa cccctccgct gctatagtgc agtcggcttc   5640
tgacgttcag tgcagccgtc ttctgaaaac gacatgtcgc acaagtccta agttacgcga   5700
caggctgccg ccctgccctt ttcctggcgt tttcttgtcg cgtgttttag tcgcataaag   5760
tagaatactt gcgactagaa ccggagacat tacgccatga acaagagcgc cgccgctggc   5820
ctgctgggct atgcccgcgt cagcaccgac gaccaggact tgaccaacca acgggccgaa   5880
ctgcacgcgg ccggctgcac caagctgttt tccgagaaga tcaccggcac caggcgcgac   5940
cgcccggagc tggccaggat gcttgaccac ctacgccctg gcgacgttgt gacagtgacc   6000
aggctagacc gcctggcccg cagcacccgc gacctactgg acattgccga gcgcatccag   6060
gaggccggcg cgggcctgcg tagcctggca gagccgtggg ccgacaccac cacgccggcc   6120
ggccgcatgg tgttgaccgt gttcgccggc attgccgagt tcgagcgttc cctaatcatc   6180
```

-continued

```
gaccgcaccc ggagcgggcg cgaggccgcc aaggcccgag gcgtgaagtt tggccccgc    6240
cctaccctca ccccggcaca gatcgcgcac gcccgcgagc tgatcgacca ggaaggccgc   6300
accgtgaaag aggcggctgc actgcttggc gtgcatcgct cgaccctgta ccgcgcactt   6360
gagcgcagcg aggaagtgac gcccaccgag gccaggcggc gcggtgcctt ccgtgaggac   6420
gcattgaccg aggccgacgc cctggctgct gctgagaatg aacgccaaga ggaacaagca   6480
tgaaaccgca ccaggacggc caggacgaac cgtttttcat taccgaagag atcgaggcgg   6540
agatgatcgc ggccgggtac gtgttcgagc cgcccgcgca cgtctcaacc gtgcggctgc   6600
atgaaatcct ggccggtttg tctgatgcca agctggcggc ctggccggcc agcttggccg   6660
ctgaagaaac cgagcgccgc cgtctaaaaa ggtgatgtgt atttgagtaa aacagcttgc   6720
gtcatgcggt cgctgcgtat atgatgcgat gagtaaataa acaaatacgc aaggggaacg   6780
catgaaggtt atcgctgtac ttaaccagaa aggcgggtca ggcaagacga ccatcgcaac   6840
ccatctagcc cgcgccctgc aactcgccgg ggccgatgtt ctgttagtcg attccgatcc   6900
ccagggcagt gcccgcgatt gggcggccgt gcgggaagat caaccgctaa ccgttgtcgg   6960
catcgaccgc ccgacgattg accgcgacgt gaaggccatc ggccggcgcg acttcgtagt   7020
gatcgacgga gcgccccagg cggcggactt ggctgtgtcc gcgatcaagg cagccgactt   7080
cgtgctgatt ccggtgcagc caagccctta cgacatatgg gccaccgccg acctggtgga   7140
gctggttaag cagcgcattg aggtcacgga tggaaggcta caagcggcct ttgtcgtgtc   7200
gcgggcgatc aaaggcacgc gcatcggcgg tgaggttgcc gaggcgctgg ccgggtacga   7260
gctgcccatt cttgagtccc gtatcacgca gcgcgtgagc tacccaggca ctgccgccgc   7320
cggcacaacc gttcttgaat cagaacccga gggcgacgct gcccgcgagg tccaggcgct   7380
ggccgctgaa attaaatcaa aactcatttg agttaatgag gtaaagagaa aatgagcaaa   7440
agcacaaaca cgctaagtgc cggccgtccg agcgcacgca gcagcaaggc tgcaacgttg   7500
gccagcctgg cagacacgcc agccatgaag cgggtcaact ttcagttgcc ggcggaggat   7560
cacaccaagc tgaagatgta cgcggtacgc caaggcaaga ccattaccga gctgctatct   7620
gaatacatcg cgcagctacc agagtaaatg agcaaatgaa taaatgagta gatgaatttt   7680
agcggctaaa ggaggcggca tggaaaatca agaacaacca ggcaccgacg ccgtggaatg   7740
ccccatgtgt ggaggaacgg gcggttggcc aggcgtaagc ggctgggttg cctgccggcc   7800
ctgcaatggc actggaaccc ccaagcccga ggaatcggcg tgagcggtcg caaaccatcc   7860
ggcccggtac aaatcggcgc ggcgctgggt gatgacctgg tggagaagtt gaaggccgcg   7920
caggccgccc agcggcaacg catcgaggca gaagcacgcc ccggtgaatc gtggcaagct   7980
gctgctgatc gaatccgcaa agaatcccgg caaccgccgg cagccggtgc gccgtcgatt   8040
aggaagccgc ccaagggcga cgagcaacca gatttttcg ttccgatgct ctatgacgtg    8100
ggcacccgcg atagtcgcag catcatggac gtggccgttt tccgtctgtc gaagcgtgac   8160
cgacgagctg gcgaggtgat ccgctacgag cttccagacg ggcacgtaga ggtttccgca   8220
gggccggccg gcatggccag tgtgtgggat tacgacctgg tactgatggc ggtttcccat   8280
ctaaccgaat ccatgaaccg ataccgggaa gggaagggag acaagcccgg ccgcgtgttc   8340
cgtccacacg ttgcggacgt actcaagttc tgccggcgag ccgatggcgg aaagcagaaa   8400
gacgacctgg tagaaacctg cattcggtta aacaccacgc acgttgccat gcagcgtacc   8460
aagaaggcca agaacggccg cctggtgacg gtatccgagg gtgaagcctt gattagccgc   8520
tacaagatcg taaagagcga aaccgggcgg ccggagtaca tcgagatcga actggctgat   8580
```

-continued

```
tggatgtacc gcgagatcac agaaggcaag aacccggacg tgctgacggt tcaccccgat   8640
tactttttga tcgaccccgg catcggccgt tttctctacc gcctggcacg ccgcgccgca   8700
ggcaaggcag aagccagatg gttgttcaag acgatctacg aacgcagtgg cagcgccgga   8760
gagttcaaga agttctgttt caccgtgcgc aagctgatcg ggtcaaatga cctgccggag   8820
tacgatttga aggaggaggc ggggcaggct ggcccgatcc tagtcatgcg ctaccgcaac   8880
ctgatcgagg gcgaagcatc cgccggttcc taatgtacgg agcagatgct agggcaaatt   8940
gccctagcag gggaaaaagg tcgaaaaggt ctctttcctg tggatagcac gtacattggg   9000
aacccaaagc cgtacattgg gaaccggaac ccgtacattg ggaacccaaa gccgtacatt   9060
gggaaccggt cacacatgta agtgactgat ataaaagaga aaaaaggcga tttttccgcc   9120
taaaactctt taaaacttat taaaactctt aaaacccgcc tggcctgtgc ataactgtct   9180
ggccagcgca cagccgaaga gctgcaaaaa gcgcctaccc ttcggtcgct gcgctcccta   9240
cgccccgccg cttcgcgtcg gcctatcacg gccgctggcc gctcaaaaat ggctggccta   9300
cggccaggca atctaccagg gcgcggacaa gccgcgccgt cgccactcga ccgccggcgc   9360
ccacatcaag gcaccctgcc tcgcgcgttt cggtgatgac ggtgaaaacc tctgacacat   9420
gcagctcccg gagacggtca cagcttgtct gtaagcggat gccgggagca gacaagcccg   9480
tcagggcgcg tcagcgggtg ttggcgggtg tcggggcgca gccatgaccc agtcacgtag   9540
cgatagcgga gtgtatactg gcttaactat gcggcatcag agcagattgt actgagagtg   9600
caccatatgc ggtgtgaaat accgcacaga tgcgtaagga gaaaataccg catcaggcgc   9660
tcttccgctt cctcgctcac tgactcgctg cgctcggtcg ttcggctgcg gcgagcggta   9720
tcagctcact caaaggcggt aatacggtta tccacagaat caggggataa cgcaggaaag   9780
aacatgtgag caaaaggcca gcaaaaggcc aggaaccgta aaaaggccgc gttgctggcg   9840
tttttccata ggctccgccc ccctgacgag catcacaaaa atcgacgctc aagtcagagg   9900
tggcgaaacc cgacaggact ataaagatac caggcgtttc cccctggaag ctccctcgtg   9960
cgctctcctg ttccgaccct gccgcttacc ggatacctgt ccgcctttct cccttcggga  10020
agcgtggcgc tttctcatag ctcacgctgt aggtatctca gttcggtgta ggtcgttcgc  10080
tccaagctgg gctgtgtgca cgaacccccc gttcagcccg accgctgcgc cttatccggt  10140
aactatcgtc ttgagtccaa cccggtaaga cacgacttat cgccactggc agcagccact  10200
ggtaacagga ttagcagagc gaggtatgta ggcggtgcta cagagttctt gaagtggtgg  10260
cctaactacg gctacactag aaggacagta tttggtatct gcgctctgct gaagccagtt  10320
accttcggaa aaagagttgg tagctcttga tccggcaaac aaaccaccgc tggtagcggt  10380
ggtttttttg tttgcaagca gcagattacg cgcagaaaaa aaggatctca agaagatcct  10440
ttgatctttt ctacggggtc tgacgctcag tgctgatgaa tcccctaatg atttttatca  10500
aaatcattaa gttaaggtag atacacatct tgtcatatga tcaaatggtt tcgccaaaaa  10560
tcaataatca gacaacaaaa tgtgcgaact cgatatttta cacgactctc tttaccaatt  10620
ctgccccgaa ttacacttaa aacgactcaa cagcttaacg ttggcttgcc acgccttact  10680
tgactgtaaa actctcactc ttaccgaact tggccgtaac ctgccaacca aagcgagaac  10740
aaaacataac atcaaacgaa tcgaccgatt gttaggtaat cgtcacctcc acaaagagcg  10800
actcgctgta taccgttggc atgctagctt tatctgttcg ggcaatacga tgcccattgt  10860
acttgttgac tggtctgata tccgtgagca aaaacggctt atggtattgc gagcttcagt  10920
```

```
cgcactacac ggtcgttctg ttactcttta tgagaaagcg ttcccgcttt cagagcaatg  10980
ttcaaagaaa gctcatgacc aatttctagc cgaccttgcg agcattctac cgagtaacac  11040
cacaccgctc attgtcagtg atgctggctt taaagtgcca tggtataaat ccgttgagaa  11100
gctgggttgg tactggttaa gtcgagtaag aggaaaagta caatatgcag acctaggagc  11160
ggaaaactgg aaacctatca gcaacttaca tgatatgtca tctagtcact caaagacttt  11220
aggctataag aggctgacta aaagcaatcc aatctcatgc caaattctat tgtataaatc  11280
tcgctctaaa ggccgaaaaa atcagcgctc gacacggact cattgtcacc acccgtcacc  11340
taaaatctac tcagcgtcgg caaaggagcc atggattcta gcaactaact tacctgttga  11400
aattcgaaca cccaaacaac ttgttaatat ctattcgaag cgaatgcaga ttgaagaaac  11460
cttccgagac ttgaaaagtc ctgcctacgg actaggccta cgccatagcc gaacgagcag  11520
ctcagagcgt tttgatatca tgctgctaat cgccctgatg cttcaactaa catgttggct  11580
tgcgggcgtt catgctcaga aacaaggttg ggacaagcac ttccaggcta acacagtcag  11640
aaatcgaaac gtactctcaa cagttcgctt aggcatggaa gttttgcggc attctggcta  11700
cacaataaca agggaagact cactcgtggc tgcaaccctg cttactcaaa atctattcac  11760
acatggttac gttttgggga aattatgagg ggatctctca gcgctcagtg gaacgaaaac  11820
tcacgttaag ggattttggt catgcattct aggtactaaa acaattcatc cagtaaaata  11880
taatatttta ttttctccca atcaggcttg atccccagta agtcaaaaaa tagctcgaca  11940
tactgttctt ccccgatatc ctccctgatc gaccggacgc agaaggcaat gtcataccac  12000
ttgtccgccc tgccgcttct cccaagatca ataaagccac ttactttgcc atctttcaca  12060
aagatgttgc tgtctcccag gtcgccgtgg gaaaagacaa gttcctcttc gggcttttcc  12120
gtctttaaaa aatcatacag ctcgcgcgga tctttaaatg gagtgtcttc ttcccagttt  12180
tcgcaatcca catcggccag atcgttattc agtaagtaat ccaattcggc taagcggctg  12240
tctaagctat tcgtataggg acaatccgat atgtcgatgg agtgaaagag cctgatgcac  12300
tccgcataca gctcgataat cttttcaggg ctttgttcat cttcatactc ttccgagcaa  12360
aggacgccat cggcctcact catgagcaga ttgctccagc catcatgccg ttcaaagtgc  12420
aggacctttg gaacaggcag ctttccttcc agccatagca tcatgtcctt ttcccgttcc  12480
acatcatagg tggtcccttt ataccggctg tccgtcattt ttaaatatag gttttcattt  12540
tctcccacca gcttatatac cttagcagga gacattcctt ccgtatcttt tacgcagcgg  12600
tatttttcga tcagtttttt caattccggt gatattctca ttttagccat ttattatttc  12660
cttcctcttt tctacagtat ttaaagatac cccaagaagc taattataac aagacgaact  12720
ccaattcact gttccttgca ttctaaaacc ttaaatacca gaaaacagct tttcaaagt   12780
tgttttcaaa gttggcgtat aacatagtat cgacggagcc gattttgaaa ccgcggtgat  12840
cacaggcagc aacgctctgt catcgttaca atcaacatgc taccctccgc gagatcatcc  12900
gtgtttcaaa cccggcagct tagttgccgt tcttccgaat agcatcggta acatgagcaa  12960
agtctgccgc cttacaacgg ctctcccgct gacgccgtcc cggactgatg ggctgcctgt  13020
atcgagtggt gattttgtgc cgagctgccg gtcggggagc tgttggctgg ctggtggcag  13080
gatatattgt ggtgtaaaca aattgacgct tagacaactt aataacacat tgcggacgtt  13140
tttaatgtac tgaattaacg ccgaattaat gtcgac                            13176
```

<210> SEQ ID NO 4
<211> LENGTH: 10601

<212> TYPE: DNA
<213> ORGANISM: Artificial Sequence
<220> FEATURE:
<223> OTHER INFORMATION: Polynucleotide Vector
<220> FEATURE:
<221> NAME/KEY: misc_feature
<222> LOCATION: (33)..(222)
<223> OTHER INFORMATION: Complement CaMV 35S Terminator
<220> FEATURE:
<221> NAME/KEY: misc_feature
<222> LOCATION: (223)..(774)
<223> OTHER INFORMATION: Complement Bar
<220> FEATURE:
<221> NAME/KEY: misc_feature
<222> LOCATION: (792)..(1090)
<223> OTHER INFORMATION: Complement NOS Promoter
<220> FEATURE:
<221> NAME/KEY: misc_feature
<222> LOCATION: (1177)..(1471)
<223> OTHER INFORMATION: Complement E9 Terminator
<220> FEATURE:
<221> NAME/KEY: misc_feature
<222> LOCATION: (2720)..(2743)
<223> OTHER INFORMATION: Complement attB2
<220> FEATURE:
<221> NAME/KEY: misc_feature
<222> LOCATION: (3222)..(3908)
<223> OTHER INFORMATION: Resolvase

<400> SEQUENCE: 4
taactataac ggtcctaagg tagcgacgta cgaattcggg ggatctggat tttagtactg 60
gattttggtt ttaggaatta gaaattttat tgatagaagt attttacaaa tacaaataca 120
tactaagggt ttcttatatg ctcaacacat gagcgaaacc ctataggaac cctaattccc 180
ttatctggga actactcaca cattattatg gagaaactcg agttagatct cggtgacggg 240
caggaccgga cggggcggta ccggcaggct gaagtccagc tgccagaaac ccacgtcatg 300
ccagttcccg tgcttgaagc cggccgcccg cagcatgccg cggggggcat atccgagcgc 360
ctcgtgcatg cgcacgctcg ggtcgttggg cagcccgatg acagcgacca cgctcttgaa 420
gccctgtgcc tccagggact tcagcaggtg ggtgtagagc gtggagccca gtcccgtccg 480
ctggtggcgg ggggagacgt acacggtcga ctcggccgtc cagtcgtagg cgttgcgtgc 540
cttccagggg cccgcgtagg cgatgccggc gacctcgccg tccacctcgg cgacgagcca 600
gggatagcgc tcccgcagac ggacgaggtc gtccgtccac tcctgcggtt cctgcggctc 660
ggtacggaag ttgaccgtgc ttgtctcgat gtagtggttg acgatggtgc agaccgccgg 720
catgtccgcc tcggtggcac ggcggatgtc ggccgggcgt cgttctgggc tcatttttgc 780
tccagatccg gtgcagatta tttggattga gagtgaatat gagactctaa ttggataccg 840
aggggaattt atggaacgtc agtggagcat ttttgacaag aaatatttgc tagctgatag 900
tgaccttagg cgacttttga acgcgcaata atggtttctg acgtatgtgc ttagctcatt 960
aaactccaga aacccgcggc tgagtggctc cttcaacgtt gcggttctgt cagttccaaa 1020
cgtaaaacgg cttgtcccgc gtcatcggcg ggggtcataa cgtgactccc ttaattctcc 1080
gctcatgatc agattgtcgt ttcccgcctt ggcgcgccat cacaagtttg tacaaaaaag 1140
caggctccga attcgccctt ggcgcgcctc ggaccggttt gggatgtttt actcctcata 1200
ttaacttcgg tcattagagg ccacgatttg acacattttt actcaaaaca aaatgtttgc 1260
atatctctta taatttcaaa ttcaacacac aacaaataag agaaaaaaca aataatatta 1320
atttgagaat gaacaaaagg accatatcat tcattaactc ttctccatcc atttccattt 1380
cacagttcga tagcgaaaac cgaataaaaa acacagtaaa ttacaagcac aacaaatggt 1440

```
acaagaaaaa cagttttccc aatgccataa tatcgatcta aagtcttctt cctccgcagc   1500
cactctccct ctgacaattg tagaaaactg cggccacggg aaggccgaga ttgtagatct   1560
cagcaaactc gcgagtgttg aagttctggc gccaccctgg tgcatacact gtttgcctgc   1620
caagctgtcg aaacaatata aacacgacac gatgaattcc tgcagtggga cttggatttt   1680
cgtaacacac aatctcattg ccaaaggttg ttccagttgt agcagggata tcagtcacca   1740
accaatggag atattctcgg aggtgagggt tgctaggact tggaacatct ggatccacca   1800
taaccaaagt atagaagttc ctgaggtctt ctccaccaat ctcaactctt ggcttgtttt   1860
gaacctgaga aggccttaga tccaagccat tagtcacctc tctttggcca taagtaacct   1920
ttagagtgat tgatctatta aacggatcaa gaacgtctcc aacaactctg cttactataa   1980
gagggtctct tatatttata gacatctttg cctgcaggtc tggaggatct gctagagtca   2040
gcttgtcgcg tgtcctctcc aaatgaaatg aacttcctta tatagaggaa gggtcttgcg   2100
aaggatagtg ggattgtgcg tcatccctta cgtcagtgga gatatcacat caatccactt   2160
gctttgaaga cgtggttgga acgtcttctt tttccacgat gctcctcgtg ggtgggggtc   2220
catctttggg accactgtcg gcagaggcat cttcaacgat ggcctttcct ttatcgcaat   2280
gatggcattt gtaggagcca ccttcctttt ccactatctt cacaataaag tgacagatag   2340
ctgggcaatg gaatccgagg aggtttccgg atattaccct ttgttgaaaa gtctcacatc   2400
ggaccatcac atcaatccac ttgctttgaa gacgtggttg gaacgtcttc tttttccacg   2460
atgctcctcg tgggtggggg tccatctttg ggaccactgt cggcagaggc atcttcaacg   2520
atggcctttc ctttatcgca atgatggcat ttgtaggagc caccttcctt ttccactatc   2580
ttcacaataa agtgacagat agctgggcaa tggaatccga ggaggtttcc ggatattacc   2640
ctttgttgaa aagtctcaca tcggaccacg cgtcacagtt gaggtatttc ggatcgtggc   2700
gatcgcaagg gcgaattcga cccagctttc ttgtacaaag tggtgatcgg tccggttcgg   2760
ctgcggccgc attaccctgt tatccctata gatctttaac tatgactctc ttaaggtagc   2820
caaattccgg aacgcgccga agtttaaacg acttaatcag ctaatacaaa ctatcagtgt   2880
ttgacaggat atattggcgg gtaaacctaa gagaaaagag cgtttattag aataatcgga   2940
tatttaaaag ggcgtgaaaa ggtttatccg ttcgtccatt tgtatgtgca tgccaaccac   3000
agggttcccc tcgggatcaa agtactttga tccaacccct ccgctgctat agtgcagtcg   3060
gcttctgacg ttcagtgcag ccgtcttctg aaaacgacat gtcgcacaag tcctaagtta   3120
cgcgacaggc tgccgccctg cccttttcct ggcgttttct tgtcgcgtgt tttagtcgca   3180
taaagtagaa tacttgcgac tagaaccgga gacattacgc catgaacaag agcgccgccg   3240
ctggcctgct gggctatgcc cgcgtcagca ccgacgacca ggacttgacc aaccaacggg   3300
ccgaactgca cgcggccggc tgcaccaagc tgttttccga gaagatcacc ggcaccaggc   3360
gcgaccgccc ggagctggcc aggatgcttg accacctacg ccctggcgac gttgtgacag   3420
tgaccaggct agaccgcctg gcccgcagca cccgcgacct actggacatt gccgagcgca   3480
tccaggaggc cggcgcgggc ctgcgtagcc tggcagagcc gtgggccgac accaccacgc   3540
cggccggccg catggtgttg accgtgttcg ccggcattgc cgagttcgag cgttccctaa   3600
tcatcgaccg cacccggagc gggcgcgagg ccgccaaggc ccgaggcgtg aagtttggcc   3660
cccgccctac cctcaccccg gcacagatcg cgcacgcccg cgagctgatc gaccaggaag   3720
gccgcaccgt gaaagaggcg gctgcactgc ttggcgtgca tcgctcgacc ctgtaccgcg   3780
cacttgagcg cagcgaggaa gtgacgccca ccgaggccag gcggcgcggt gccttccgtg   3840
```

```
aggacgcatt gaccgaggcc gacgccctgg ctgctgctga gaatgaacgc caagaggaac   3900
aagcatgaaa ccgcaccagg acggccagga cgaaccgttt ttcattaccg aagagatcga   3960
ggcggagatg atcgcggccg ggtacgtgtt cgagccgccc gcgcacgtct caaccgtgcg   4020
gctgcatgaa atcctggccg gtttgtctga tgccaagctg gcggcctggc cggccagctt   4080
ggccgctgaa gaaaccgagc gccgccgtct aaaaaggtga tgtgtatttg agtaaaacag   4140
cttgcgtcat gcggtcgctg cgtatatgat gcgatgagta aataaacaaa tacgcaaggg   4200
gaacgcatga aggttatcgc tgtacttaac cagaaaggcg ggtcaggcaa gacgaccatc   4260
gcaacccatc tagcccgcgc cctgcaactc gccggggccg atgttctgtt agtcgattcc   4320
gatccccagg gcagtgcccg cgattgggcg gccgtgcggg aagatcaacc gctaaccgtt   4380
gtcggcatcg accgcccgac gattgaccgc gacgtgaagg ccatcggccg gcgcgacttc   4440
gtagtgatcg acggagcgcc ccaggcggcg gacttggctg tgtccgcgat caaggcagcc   4500
gacttcgtgc tgattccggt gcagccaagc ccttacgaca tatgggccac cgccgacctg   4560
gtggagctgg ttaagcagcg cattgaggtc acggatggaa ggctacaagc ggcctttgtc   4620
gtgtcgcggg cgatcaaagg cacgcgcatc ggcggtgagg ttgccgaggc gctggccggg   4680
tacgagctgc ccattcttga gtcccgtatc acgcagcgcg tgagctaccc aggcactgcc   4740
gccgccggca caaccgttct tgaatcagaa cccgagggcg acgctgcccg cgaggtccag   4800
gcgctggccg ctgaaattaa atcaaaactc atttgagtta atgaggtaaa gagaaaatga   4860
gcaaaagcac aaacacgcta agtgccggcc gtccgagcgc acgcagcagc aaggctgcaa   4920
cgttggccag cctggcagac acgccagcca tgaagcgggt caactttcag ttgccggcgg   4980
aggatcacac caagctgaag atgtacgcgg tacgccaagg caagaccatt accgagctgc   5040
tatctgaata catcgcgcag ctaccagagt aaatgagcaa atgaataaat gagtagatga   5100
attttagcgg ctaaaggagg cggcatggaa aatcaagaac aaccaggcac cgacgccgtg   5160
gaatgcccca tgtgtggagg aacgggcggt tggccaggcg taagcggctg ggttgcctgc   5220
cggccctgca atggcactgg aacccccaag cccgaggaat cggcgtgagc ggtcgcaaac   5280
catccggccc ggtacaaatc ggcgcggcgc tgggtgatga cctggtggag aagttgaagg   5340
ccgcgcaggc cgcccagcgg caacgcatcg aggcagaagc acgccccggt gaatcgtggc   5400
aagctgctgc tgatcgaatc cgcaaagaat cccggcaacc gccggcagcc ggtgcgccgt   5460
cgattaggaa gccgcccaag ggcgacgagc aaccagattt tttcgttccg atgctctatg   5520
acgtgggcac ccgcgatagt cgcagcatca tggacgtggc cgttttccgt ctgtcgaagc   5580
gtgaccgacg agctggcgag gtgatccgct acgagcttcc agacgggcac gtagaggttt   5640
ccgcagggcc ggccggcatg gccagtgtgt gggattacga cctggtactg atggcggttt   5700
cccatctaac cgaatccatg aaccgatacc gggaagggaa gggagacaag cccggccgcg   5760
tgttccgtcc acacgttgcg gacgtactca agttctgccg gcgagccgat ggcggaaagc   5820
agaaagacga cctggtagaa acctgcattc ggttaaacac cacgcacgtt gccatgcagc   5880
gtaccaagaa ggccaagaac ggccgcctgg tgacggtatc cgagggtgaa gccttgatta   5940
gccgctacaa gatcgtaaag agcgaaaccg ggcggccgga gtacatcgag atcgaactgg   6000
ctgattggat gtaccgcgag atcacagaag gcaagaaccc ggacgtgctg acggttcacc   6060
ccgattactt tttgatcgac cccggcatcg gccgttttct ctaccgcctg gcacgccgcg   6120
ccgcaggcaa ggcagaagcc agatggttgt tcaagacgat ctacgaacgc agtggcagcg   6180
```

-continued

```
ccggagagtt caagaagttc tgtttcaccg tgcgcaagct gatcgggtca aatgacctgc   6240
cggagtacga tttgaaggag gaggcggggc aggctggccc gatcctagtc atgcgctacc   6300
gcaacctgat cgagggcgaa gcatccgccg gttcctaatg tacggagcag atgctagggc   6360
aaattgccct agcaggggaa aaaggtcgaa aaggtctctt tcctgtggat agcacgtaca   6420
ttgggaaccc aaagccgtac attgggaacc ggaacccgta cattgggaac ccaaagccgt   6480
acattgggaa ccggtcacac atgtaagtga ctgatataaa agagaaaaaa ggcgattttt   6540
ccgcctaaaa ctctttaaaa cttattaaaa ctcttaaaac ccgcctggcc tgtgcataac   6600
tgtctggcca gcgcacagcc gaagagctgc aaaaagcgcc tacccttcgg tcgctgcgct   6660
ccctacgccc cgccgcttcg cgtcggccta tcacggccgc tggccgctca aaaatggctg   6720
gcctacggcc aggcaatcta ccagggcgcg gacaagccgc gccgtcgcca ctcgaccgcc   6780
ggcgcccaca tcaaggcacc ctgcctcgcg cgtttcggtg atgacggtga aaacctctga   6840
cacatgcagc tcccggagac ggtcacagct tgtctgtaag cggatgccgg gagcagacaa   6900
gcccgtcagg gcgcgtcagc gggtgttggc gggtgtcggg gcgcagccat gacccagtca   6960
cgtagcgata gcggagtgta tactggctta actatgcggc atcagagcag attgtactga   7020
gagtgcacca tatgcggtgt gaaataccgc acagatgcgt aaggagaaaa taccgcatca   7080
ggcgctcttc cgcttcctcg ctcactgact cgctgcgctc ggtcgttcgg ctgcggcgag   7140
cggtatcagc tcactcaaag gcggtaatac ggttatccac agaatcaggg gataacgcag   7200
gaaagaacat gtgagcaaaa ggccagcaaa aggccaggaa ccgtaaaaag gccgcgttgc   7260
tggcgttttt ccataggctc cgcccccctg acgagcatca caaaaatcga cgctcaagtc   7320
agaggtggcg aaacccgaca ggactataaa gataccaggc gtttccccct ggaagctccc   7380
tcgtgcgctc tcctgttccg accctgccgc ttaccggata cctgtccgcc tttctccctt   7440
cgggaagcgt ggcgctttct catagctcac gctgtaggta tctcagttcg gtgtaggtcg   7500
ttcgctccaa gctgggctgt gtgcacgaac cccccgttca gcccgaccgc tgcgccttat   7560
ccggtaacta tcgtcttgag tccaacccgg taagacacga cttatcgcca ctggcagcag   7620
ccactggtaa caggattagc agagcgaggt atgtaggcgg tgctacagag ttcttgaagt   7680
ggtggcctaa ctacggctac actagaagga cagtatttgg tatctgcgct ctgctgaagc   7740
cagttacctt cggaaaaaga gttggtagct cttgatccgg caaacaaacc accgctggta   7800
gcggtggttt ttttgtttgc aagcagcaga ttacgcgcag aaaaaaagga tctcaagaag   7860
atcctttgat cttttctacg gggtctgacg ctcagtgctg atgaatcccc taatgatttt   7920
tatcaaaatc attaagttaa ggtagataca catcttgtca tatgatcaaa tggtttcgcc   7980
aaaaatcaat aatcagacaa caaaatgtgc gaactcgata ttttacacga ctctctttac   8040
caattctgcc ccgaattaca cttaaaacga ctcaacagct taacgttggc ttgccacgcc   8100
ttacttgact gtaaaactct cactcttacc gaacttggcc gtaacctgcc aaccaaagcg   8160
agaacaaaac ataacatcaa acgaatcgac cgattgttag gtaatcgtca cctccacaaa   8220
gagcgactcg ctgtataccg ttggcatgct agctttatct gttcgggcaa tacgatgccc   8280
attgtacttg ttgactggtc tgatatccgt gagcaaaaac ggcttatggt attgcgagct   8340
tcagtcgcac tacacggtcg ttctgttact ctttatgaga aagcgttccc gctttcagag   8400
caatgttcaa agaaagctca tgaccaattt ctagccgacc ttgcgagcat tctaccgagt   8460
aacaccacac cgctcattgt cagtgatgct ggctttaaag tgccatggta taaatccgtt   8520
gagaagctgg gttggtactg gttaagtcga gtaagaggaa aagtacaata tgcagaccta   8580
```

```
ggagcggaaa actggaaacc tatcagcaac ttacatgata tgtcatctag tcactcaaag   8640

actttaggct ataagaggct gactaaaagc aatccaatct catgccaaat tctattgtat   8700

aaatctcgct ctaaaggccg aaaaaatcag cgctcgacac ggactcattg tcaccacccg   8760

tcacctaaaa tctactcagc gtcggcaaag gagccatgga ttctagcaac taacttacct   8820

gttgaaattc gaacacccaa acaacttgtt aatatctatt cgaagcgaat gcagattgaa   8880

gaaaccttcc gagacttgaa aagtcctgcc tacggactag gcctacgcca tagccgaacg   8940

agcagctcag agcgttttga tatcatgctg ctaatcgccc tgatgcttca actaacatgt   9000

tggcttgcgg gcgttcatgc tcagaaacaa ggttgggaca agcacttcca ggctaacaca   9060

gtcagaaatc gaaacgtact ctcaacagtt cgcttaggca tggaagtttt gcggcattct   9120

ggctacacaa taacaaggga agactcactc gtggctgcaa ccctgcttac tcaaaatcta   9180

ttcacacatg gttacgtttt ggggaaatta tgaggggatc tctcagcgct cagtggaacg   9240

aaaactcacg ttaagggatt ttggtcatgc attctaggta ctaaaacaat tcatccagta   9300

aaatataata ttttattttc tcccaatcag gcttgatccc cagtaagtca aaaaatagct   9360

cgacatactg ttcttccccg atatcctccc tgatcgaccg gacgcagaag gcaatgtcat   9420

accacttgtc cgccctgccg cttctcccaa gatcaataaa gccacttact ttgccatctt   9480

tcacaaagat gttgctgtct cccaggtcgc cgtgggaaaa gacaagttcc tcttcgggct   9540

tttccgtctt taaaaaatca tacagctcgc gcggatcttt aaatggagtg tcttcttccc   9600

agttttcgca atccacatcg gccagatcgt tattcagtaa gtaatccaat tcggctaagc   9660

ggctgtctaa gctattcgta tagggacaat ccgatatgtc gatggagtga aagagcctga   9720

tgcactccgc atacagctcg ataatctttt cagggctttg ttcatcttca tactcttccg   9780

agcaaaggac gccatcggcc tcactcatga gcagattgct ccagccatca tgccgttcaa   9840

agtgcaggac ctttggaaca ggcagctttc cttccagcca tagcatcatg tccttttccc   9900

gttccacatc ataggtggtc cctttatacc ggctgtccgt catttttaaa tataggtttt   9960

cattttctcc caccagctta tataccttag caggagacat tccttccgta tcttttacgc  10020

agcggtattt ttcgatcagt tttttcaatt ccggtgatat tctcatttta gccatttatt  10080

atttccttcc tcttttctac agtatttaaa gataccccaa gaagctaatt ataacaagac  10140

gaactccaat tcactgttcc ttgcattcta aaaccttaaa taccagaaaa cagcttttc   10200

aaagttgttt tcaaagttgg cgtataacat agtatcgacg gagccgattt tgaaaccgcg  10260

gtgatcacag gcagcaacgc tctgtcatcg ttacaatcaa catgctaccc tccgcgagat  10320

catccgtgtt tcaaacccgg cagcttagtt gccgttcttc cgaatagcat cggtaacatg  10380

agcaaagtct gccgccttac aacggctctc ccgctgacgc cgtcccggac tgatgggctg  10440

cctgtatcga gtggtgattt tgtgccgagc tgccggtcgg ggagctgttg gctggctggt  10500

ggcaggatat attgtggtgt aaacaaattg acgcttagac aacttaataa cacattgcgg  10560

acgtttttaa tgtactgaat taacgccgaa ttaatgtcga c                     10601
```

<210> SEQ ID NO 5
<211> LENGTH: 552
<212> TYPE: DNA
<213> ORGANISM: Streptomyces hygroscopicus

<400> SEQUENCE: 5

```
ttagatctcg gtgacgggca ggaccggacg gggcggtacc ggcaggctga agtccagctg     60
```

```
ccagaaaccc acgtcatgcc agttcccgtg cttgaagccg gccgcccgca gcatgccgcg    120

gggggcatat ccgagcgcct cgtgcatgcg cacgctcggg tcgttgggca gcccgatgac    180

agcgaccacg ctcttgaagc cctgtgcctc cagggacttc agcaggtggg tgtagagcgt    240

ggagcccagt cccgtccgct ggtggcgggg ggagacgtac acggtcgact cggccgtcca    300

gtcgtaggcg ttgcgtgcct tccaggggcc cgcgtaggcg atgccggcga cctcgccgtc    360

cacctcggcg acgagccagg gatagcgctc ccgcagacgg acgaggtcgt ccgtccactc    420

ctgcggttcc tgcggctcgg tacggaagtt gaccgtgctt gtctcgatgt agtggttgac    480

gatggtgcag accgccggca tgtccgcctc ggtggcacgg cggatgtcgg ccgggcgtcg    540

ttctgggctc at                                                        552


<210> SEQ ID NO 6
<211> LENGTH: 299
<212> TYPE: DNA
<213> ORGANISM: Agrobacterium tumefaciens

<400> SEQUENCE: 6

tgcagattat ttggattgag agtgaatatg agactctaat tggataccga ggggaattta     60

tggaacgtca gtggagcatt tttgacaaga aatatttgct agctgatagt gaccttaggc    120

gacttttgaa cgcgcaataa tggtttctga cgtatgtgct tagctcatta aactccagaa    180

acccgcggct gagtggctcc ttcaacgttg cggttctgtc agttccaaac gtaaaacggc    240

ttgtcccgcg tcatcggcgg gggtcataac gtgactccct taattctccg ctcatgatc     299


<210> SEQ ID NO 7
<211> LENGTH: 24
<212> TYPE: DNA
<213> ORGANISM: Escherichia coli

<400> SEQUENCE: 7

caagtttgta caaaaaagca ggct                                            24


<210> SEQ ID NO 8
<211> LENGTH: 528
<212> TYPE: DNA
<213> ORGANISM: Arabidopsis thaliana

<400> SEQUENCE: 8

ctaaagtctt cttcctccgc agccactctc cctctgacaa ttgtagaaaa ctgcggccac     60

gggaaggccg agattgtaga tctcagcaaa ctcgcgagtg ttgaagttct ggcgccaccc    120

tggtgcatac actgtttgcc tgccaagctg tcgaaacaat ataaacacga cacgatgaat    180

tcctgcagtg ggacttggat tttcgtaaca cacaatctca ttgccaaagg ttgttccagt    240

tgtagcaggg atatcagtca ccaaccaatg gagatattct cggaggtgag ggttgctagg    300

acttggaaca tctggatcca ccataaccaa agtatagaag ttcctgaggt cttctccacc    360

aatctcaact cttggcttgt tttgaacctg agaaggcctt agatccaagc cattagtcac    420

ctctctttgg ccataagtaa cctttagagt gattgatcta ttaaacggat caagaacgtc    480

tccaacaact ctgcttacta taagagggtc tcttatattt atagacat                 528


<210> SEQ ID NO 9
<211> LENGTH: 51
<212> TYPE: DNA
<213> ORGANISM: Cauliflower mosaic virus

<400> SEQUENCE: 9
```

```
aacttcctta tatagaggaa gggtcttgcg aaggatagtg ggattgtgcg t              51


<210> SEQ ID NO 10
<211> LENGTH: 93
<212> TYPE: DNA
<213> ORGANISM: Saccharomyces cerevisiae

<400> SEQUENCE: 10

tggagatatc acatcaatcc acttgctttg aagacgtggt tggaacgtct tctttttcca     60

cgatgctcct cgtgggtggg ggtccatctt tgg                                  93


<210> SEQ ID NO 11
<211> LENGTH: 1761
<212> TYPE: DNA
<213> ORGANISM: Artificial Sequence
<220> FEATURE:
<223> OTHER INFORMATION: Encodes a Chimeric Sequence Forming Monopartite
      Gene Switch Polypeptide

<400> SEQUENCE: 11

gccaaattcc ggaacgcgcc gaagtttaaa cgacttaatc agctaataca aactatcagt     60

gtttgacagg atatattggc gggtaaacct aagagaaaag agcgtttatt agaataatcg    120

gatatttaaa agggcgtgaa aaggtttatc cgttcgtcca tttgtatgtg catgccaacc    180

acagggttcc cctcgggatc aaagtacttt gatccaaccc ctccgctgct atagtgcagt    240

cggcttctga cgttcagtgc agccgtcttc tgaaaacgac atgtcgcaca agtcctaagt    300

tacgcgacag gctgccgccc tgcccttttc ctggcgtttt cttgtcgcgt gttttagtcg    360

cataaagtag aatacttgcg actagaaccg gagacattac gccatgaaca agagcgccgc    420

cgctggcctg ctgggctatg cccgcgtcag caccgacgac caggacttga ccaaccaacg    480

ggccgaactg cacgcggccg gctgcaccaa gctgttttcc gagaagatca ccggcaccag    540

gcgcgaccgc ccggagctgg ccaggatgct tgaccaccta cgccctggcg acgttgtgac    600

agtgaccagg ctagaccgcc tggcccgcag cacccgcgac ctactggaca ttgccgagcg    660

catccaggag gccggcgcgg gcctgcgtag cctggcagag ccgtgggccg acaccaccac    720

gccggccggc cgcatggtgt tgaccgtgtt cgccggcatt gccgagttcg agcgttccct    780

aatcatcgac cgcacccgga gcgggcgcga ggccgccaag gcccgaggcg tgaagtttgg    840

cccccgccct accctcaccc cggcacagat cgcgcacgcc cgcgagctga tcgaccagga    900

aggccgcacc gtgaaagagg cggctgcact gcttggcgtg catcgctcga ccctgtaccg    960

cgcacttgag cgcagcgagg aagtgacgcc caccgaggcc aggcggcgcg gtgccttccg   1020

tgaggacgca ttgaccgagg ccgacgccct ggctgctgct gagaatgaac gccaagagga   1080

acaagcatga aaccgcacca ggacggccag gacgaaccgt ttttcattac cgaagagatc   1140

gaggcggaga tgatcgcggc cgggtacgtg ttcgagccgc ccgcgcacgt ctcaaccgtg   1200

cggctgcatg aaatcctggc cggtttgtct gatgccaagc tggcggcctg gccggccagc   1260

ttggccgctg aagaaaccga gcgccgccgt ctaaaaaggt gatgtgtatt tgagtaaaac   1320

agcttgcgtc atgcggtcgc tgcgtatatg atgcgatgag taaataaaca aatacgcaag   1380

gggaacgcat gaaggttatc gctgtactta accagaaagg cgggtcaggc aagacgacca   1440

tcgcaaccca tctagcccgc gccctgcaac tcgccggggc cgatgttctg ttagtcgatt   1500

ccgatcccca gggcagtgcc cgcgattggg cggccgtgcg ggaagatcaa ccgctaaccg   1560

ttgtcggcat cgaccgcccg acgattgacc gcgacgtgaa ggccatcggc cggcgcgact   1620
```

```
tcgtagtgat cgacggagcg ccccaggcgg cggacttggc tgtgtccgcg atcaaggcag   1680

ccgacttcgt gctgattccg gtgcagccaa gcccttacga catatgggcc accgccgacc   1740

tggtggagct ggttaagcag c                                             1761
```

<210> SEQ ID NO 12
<211> LENGTH: 24
<212> TYPE: DNA
<213> ORGANISM: Escherichia coli

<400> SEQUENCE: 12

```
caaatcggcg cggcgctggg tgat                                            24
```

<210> SEQ ID NO 13
<211> LENGTH: 2507
<212> TYPE: DNA
<213> ORGANISM: Arabidopsis thaliana

<400> SEQUENCE: 13

```
acaaattaaa gaagcagaaa caaaaacaag taaaacagaa acaatcaaca cagagaaacc     60

acctgtttgt tcaagatcaa agatgtctat aaatataaga gaccctctta tagtaagcag    120

agttgttgga gacgttcttg atccgtttaa tagatcaatc actctaaagg ttacttatgg    180

ccaaagagag gtgactaatg gcttggatct aaggccttct caggttcaaa acaagccaag    240

agttgagatt ggtggagaag acctcaggaa cttctatact ttggttcttt cacttgaact    300

ccccttttgtc tcttttcttc tttagtttct tcagtgcttc ttacaccttc ttttttaaaa    360

tagaaattat tttccttttt tggggtatac tgaaaatatt tcttgggcat gcagagacct    420

tggttaaaaa tgccccacgc tttccttttc tctgtttttt tatgatttat ttggttttac    480

tttatgatac ccaaatcaaa aactaattta tatttcattt cttttttcat gaagatggac    540

ccataaaaata tttcttccta tcctaaatta aatagagata aatttatgat ctatcccaaa    600

tttttccac caacttcttg cataagtgat tattatttag gataagaatc ttgggatttt    660

tctttgttcc tcctacctaa taatttaatt tgcatttgtt tttttttgtt ttttttaag    720

tataattttt tactatactt tgaaaatggc atttttgaaa tatccttttt gctaattaaa    780

atatctgcaa aaagatatag aaaattgatg ttcattaaaa caaatatata tattgatgaa    840

tctctgttgt ggaatatttg aaaactgttt gaataaggat attctgatat tcaagccagc    900

ctttaagata ctctctgcta tatatagaca tgtagctact accttttttc tattcatagt    960

tttcttcttc tttcttgtgt tatctcattt tccaaacttc aaaaaagaaa aagaaaaaaa   1020

gaccttttgc tttcttgatt tctttgaaaa tgataatctt atcttcttat aattcttcgt   1080

cttatttgtt taatgaaggt tatggtggat ccagatgttc caagtcctag caaccctcac   1140

ctccgagaat atctccattg gtttgtgcac taactcaact ctttaattaa ttcactttta   1200

agttatagca tagctcaaac atgttgctcg aattatatat atagacactc aactacacat   1260

gtaaaactgg acatgtattt tggatacttt gaaattgagt agatcactta taacttaaga   1320

ctcaaacatt ttacatttaa tagaaggaga catataaaat caacttcgag agtgcgatgc   1380

atcaatttgt ctcccaaaaa agcccacacc caagctaaat tgacatattt tgttcaaaaa   1440

ctttactatg tgtaatgtaa atatgtatta tgtatgtctg tgtattttac tgatcgcaca   1500

tagattctat agaatgtata ggacgtgact tgaactaaga tttgtttttt tcactttaaa   1560

gtggtctttg tacgggaata tcattgagct taaaatagcc tgatgacatc atcattgttc   1620
```

```
cttgaagtga gcaggactag gtttcctgtt atatcacttt ttatttttat ttatatattc   1680
atgcacttga atgttattgc atgttttgct agtcacttgc actagtaatc taggaattag   1740
ttacgttgct attatttttt tgtaagaaaa taaagtttaa gtagcatttc aattctgtca   1800
aaaaaagaag tagcatttca attatgttgt ggtgccatag cttaaacatg tgtatggcta   1860
tctctcatta caggttggtg actgatatcc ctgctacaac tggaacaacc tttggtgagt   1920
tttattctat atattagatc gctaggtgtt agaaatatag aaaggtatat gaaatagcct   1980
aattaattag ttactagcta gaaaattcac atgttttgat gaacttttta tttttcaggc   2040
aatgagattg tgtgttacga aaatccaagt cccactgcag gaattcatcg tgtcgtgttt   2100
atattgtttc gacagcttgg caggcaaaca gtgtatgcac cagggtggcg ccagaacttc   2160
aacactcgcg agtttgctga gatctacaat ctcggccttc ccgtggccgc agttttctac   2220
aattgtcaga gggagagtgg ctgcggagga agaagacttt agatggcttc ttcctttata   2280
accaattgat attgcatact ctgatgagat ttatgcatct atagtatttt aatttaataa   2340
ccattttatg atacgagtaa cgaacggtga tgatgcctat agtagttcaa tatataagtg   2400
tgtaataaaa atgagagggg gaggaaaatg agagtgtttt acttatatag tgtgtgatgc   2460
gataattata ttaatctaca tgaaatgaag tgttatattt atacttt                 2507
```

<210> SEQ ID NO 14
<211> LENGTH: 855
<212> TYPE: DNA
<213> ORGANISM: Arabidopsis thaliana

<400> SEQUENCE: 14

```
acaaattaaa gaagcagaaa caaaaacaag taaaacagaa acaatcaaca cagagaaacc     60
acctgtttgt tcaagatcaa agatgtctat aaatataaga gaccctctta tagtaagcag    120
agttgttgga gacgttcttg atccgtttaa tagatcaatc actctaaagg ttacttatgg    180
ccaaagagag gtgactaatg gcttggatct aaggccttct caggttcaaa acaagccaag    240
agttgagatt ggtggagaag acctcaggaa cttctatact ttggttatgg tggatccaga    300
tgttccaagt cctagcaacc ctcacctccg agaatatctc cattggttgg tgactgatat    360
ccctgctaca actggaacaa cctttggcaa tgagattgtg tgttacgaaa atccaagtcc    420
cactgcagga attcatcgtg tcgtgtttat attgtttcga cagcttggca ggcaaacagt    480
gtatgcacca gggtggcgcc agaacttcaa cactcgcgag tttgctgaga tctacaatct    540
cggccttccc gtggccgcag ttttctacaa ttgtcagagg gagagtggct gcggaggaag    600
aagactttag atggcttctt cctttataac caattgatat tgcatactct gatgagattt    660
atgcatctat agtattttaa tttaataacc attttatgat acgagtaacg aacggtgatg    720
atgcctatag tagttcaata tataagtgtg taataaaaat gagaggggga ggaaaatgag    780
agtgttttac ttatatagtg tgtgatgcga taattatatt aatctacatg aaatgaagtg    840
ttatatttat acttt                                                     855
```

<210> SEQ ID NO 15
<211> LENGTH: 528
<212> TYPE: DNA
<213> ORGANISM: Arabidopsis thaliana

<400> SEQUENCE: 15

```
atgtctataa atataagaga ccctcttata gtaagcagag ttgttggaga cgttcttgat     60
ccgtttaata gatcaatcac tctaaaggtt acttatggcc aaagagaggt gactaatggc    120
```

```
ttggatctaa ggccttctca ggttcaaaac aagccaagag ttgagattgg tggagaagac    180

ctcaggaact tctatacttt ggttatggtg gatccagatg ttccaagtcc tagcaaccct    240

cacctccgag aatatctcca ttggttggtg actgatatcc ctgctacaac tggaacaacc    300

tttggcaatg agattgtgtg ttacgaaaat ccaagtccca ctgcaggaat tcatcgtgtc    360

gtgtttatat tgtttcgaca gcttggcagg caaacagtgt atgcaccagg gtggcgccag    420

aacttcaaca ctcgcgagtt tgctgagatc tacaatctcg gccttcccgt ggccgcagtt    480

ttctacaatt gtcagaggga gagtggctgc ggaggaagaa gactttag                 528
```

<210> SEQ ID NO 16
<211> LENGTH: 1056
<212> TYPE: DNA
<213> ORGANISM: Arabidopsis thaliana

<400> SEQUENCE: 16

```
atggcggcga tttcaggcat ctcctctggt acgttgacga tttcacggcc tttggttact     60

cttcgacgct ctagagccgc cgtttcgtac agctcctctc accgattgct tcatcatctt    120

cctctctctt ctcgtcgtct gctattaagg aacaatcatc gagtccaagc aacgattttg    180

caagacgatg aagagaaagt ggtggtggag gaatcgttta aagccgagac ttctactggt    240

acagaaccac ttgaggagcc aaatatgagt tcttcttcaa ctagtgcttt tgagacatgg    300

atcatcaagc ttgagcaagg agtgaatgtt ttccttacag actcggttat taagatactt    360

gacactttgt atcgtgaccg aacatatgca aggttctttg ttcttgagac aattgctaga    420

gtgccttatt ttgcgtttat gtctgtgcta catatgtatg agacctttgg ttggtggagg    480

agagcagatt atttgaaagt acactttgct gagagctgga atgaaatgca tcacttgctc    540

ataatggaag aattgggtgg aaattcttgg tggtttgatc gttttctggc tcagcacata    600

gcaaccttct actacttcat gacagtgttc ttgtatatct taagccctag aatggcatat    660

cacttttcgg aatgtgtgga gagtcatgca tatgagactt atgataaatt tctcaaggcc    720

agtggagagg agttgaagaa tatgcctgca ccggatatcg cagtaaaata ctatacggga    780

ggtgacttgt acttatttga tgagttccaa acatcaagaa ctcccaatac tcgaagacca    840

gtaatagaaa atctatacga tgtgtttgtg aacataagag atgatgaagc agaacactgc    900

aagacaatga gagcttgtca gactctaggc agtctgcgtt ctccacactc cattttagaa    960

gatgatgata ctgaagaaga atcagggtgt gttgttcctg aggaggctca ttgcgaaggt   1020

attgtagact gcctcaagaa atccattaca agttaa                             1056
```

<210> SEQ ID NO 17
<211> LENGTH: 149
<212> TYPE: PRT
<213> ORGANISM: Bacillus amyloliquefaciens

<400> SEQUENCE: 17

```
Met Lys Lys Arg Leu Ser Trp Ile Ser Val Cys Leu Leu Val Leu Val
1               5                   10                  15

Ser Ala Ala Gly Met Leu Phe Ser Thr Ala Ala Lys Thr Glu Thr Ser
            20                  25                  30

Ser His Lys Ala His Thr Glu Ala Gln Val Ile Asn Thr Phe Asp Gly
        35                  40                  45

Val Ala Asp Tyr Leu Gln Thr Tyr His Lys Leu Pro Asp Asn Tyr Ile
    50                  55                  60
```

```
Thr Lys Ser Glu Ala Gln Ala Leu Gly Trp Val Ala Ser Lys Gly Asn
65                  70                  75                  80

Leu Ala Asp Val Ala Pro Gly Lys Ser Ile Gly Gly Asp Ile Phe Ser
                85                  90                  95

Asn Arg Glu Gly Lys Leu Pro Gly Lys Ser Gly Arg Thr Trp Arg Glu
            100                 105                 110

Ala Asp Ile Asn Tyr Thr Ser Gly Phe Arg Asn Ser Asp Arg Ile Leu
        115                 120                 125

Tyr Ser Ser Asp Trp Leu Ile Tyr Lys Thr Thr Asp His Tyr Gln Thr
    130                 135                 140

Phe Thr Lys Ile Arg
145


<210> SEQ ID NO 18
<211> LENGTH: 101
<212> TYPE: PRT
<213> ORGANISM: Bacillus amyloliquefaciens

<400> SEQUENCE: 18

Met Glu Ile Val Ile Ile Asp Gly Lys Asp Val Thr Ser Thr Glu Ala
1               5                   10                  15

Leu His Arg Ile Leu Lys Asp Gln Leu Asp Phe Pro Asp Phe Tyr Gly
            20                  25                  30

Glu Asn Leu Asn Ala Leu Trp Asp Cys Leu Thr Gly Trp Ile Glu Tyr
        35                  40                  45

Pro Leu Thr Leu Val Trp Lys Asn Phe Glu Ile Ser Gln Lys Glu Leu
    50                  55                  60

Gly Ser Asp Ala Asp Asp Val Leu Glu Leu Phe Gln Glu Ala Gln Ala
65                  70                  75                  80

Glu Leu Asp Gly Glu Phe Phe Ile Gln Ile Asp Gln Pro Ser Ala Gly
                85                  90                  95

Thr Thr Asp Arg His
            100


<210> SEQ ID NO 19
<211> LENGTH: 513
<212> TYPE: PRT
<213> ORGANISM: Choristoneura fumiferana

<400> SEQUENCE: 19

Met Asp Leu Lys His Glu Val Ala Tyr Arg Gly Val Leu Pro Gly Gln
1               5                   10                  15

Val Lys Ala Glu Pro Gly Val His Asn Gly Gln Val Asn Gly His Val
            20                  25                  30

Arg Asp Trp Met Ala Gly Gly Ala Gly Ala Asn Ser Pro Ser Pro Gly
        35                  40                  45

Ala Val Ala Gln Pro Gln Pro Asn Asn Gly Tyr Ser Ser Pro Leu Ser
    50                  55                  60

Ser Gly Ser Tyr Gly Pro Tyr Ser Pro Asn Gly Lys Ile Gly Arg Glu
65                  70                  75                  80

Glu Leu Ser Pro Ala Ser Ser Ile Asn Gly Cys Ser Thr Asp Gly Glu
                85                  90                  95

Ala Arg Arg Gln Lys Lys Gly Pro Ala Pro Arg Gln Gln Glu Glu Leu
            100                 105                 110

Cys Leu Val Cys Gly Asp Arg Ala Ser Gly Tyr His Tyr Asn Ala Leu
        115                 120                 125
```

```
Thr Cys Glu Gly Cys Lys Gly Phe Phe Arg Arg Ser Val Thr Lys Asn
    130                 135                 140

Ala Val Tyr Ile Cys Lys Phe Gly His Ala Cys Glu Met Asp Met Tyr
145                 150                 155                 160

Met Arg Arg Lys Cys Gln Glu Cys Arg Leu Lys Lys Cys Leu Ala Val
                165                 170                 175

Gly Met Arg Pro Glu Cys Val Val Pro Glu Thr Gln Cys Ala Met Lys
            180                 185                 190

Arg Lys Glu Lys Lys Ala Gln Lys Glu Lys Asp Lys Leu Pro Val Ser
        195                 200                 205

Thr Thr Thr Val Asp Asp His Met Pro Pro Ile Met Gln Cys Glu Pro
    210                 215                 220

Pro Pro Pro Glu Ala Ala Arg Ile His Glu Val Val Pro Arg Phe Leu
225                 230                 235                 240

Ser Asp Lys Leu Leu Glu Thr Asn Arg Gln Lys Asn Ile Pro Gln Leu
                245                 250                 255

Thr Ala Asn Gln Gln Phe Leu Ile Ala Arg Leu Ile Trp Tyr Gln Asp
            260                 265                 270

Gly Tyr Glu Gln Pro Ser Asp Glu Asp Leu Lys Arg Ile Thr Gln Thr
        275                 280                 285

Trp Gln Gln Ala Asp Asp Glu Asn Glu Glu Ser Asp Thr Pro Phe Arg
    290                 295                 300

Gln Ile Thr Glu Met Thr Ile Leu Thr Val Gln Leu Ile Val Glu Phe
305                 310                 315                 320

Ala Lys Gly Leu Pro Gly Phe Ala Lys Ile Ser Gln Pro Asp Gln Ile
                325                 330                 335

Thr Leu Leu Lys Ala Cys Ser Ser Glu Val Met Met Leu Arg Val Ala
            340                 345                 350

Arg Arg Tyr Asp Ala Ala Ser Asp Ser Val Leu Phe Ala Asn Asn Gln
        355                 360                 365

Ala Tyr Thr Arg Asp Asn Tyr Arg Lys Ala Gly Met Ala Tyr Val Ile
    370                 375                 380

Glu Asp Leu Leu His Phe Cys Arg Cys Met Tyr Ser Met Ala Leu Asp
385                 390                 395                 400

Asn Ile His Tyr Ala Leu Leu Thr Ala Val Val Ile Phe Ser Asp Arg
                405                 410                 415

Pro Gly Leu Glu Gln Pro Gln Leu Val Glu Glu Ile Gln Arg Tyr Tyr
            420                 425                 430

Leu Asn Thr Leu Arg Ile Tyr Ile Leu Asn Gln Leu Ser Gly Ser Ala
        435                 440                 445

Arg Ser Ser Val Ile Tyr Gly Lys Ile Leu Ser Ile Leu Ser Glu Leu
    450                 455                 460

Arg Thr Leu Gly Met Gln Asn Ser Asn Met Cys Ile Ser Leu Lys Leu
465                 470                 475                 480

Lys Asn Arg Lys Leu Pro Pro Phe Leu Glu Glu Ile Trp Asp Val Ala
                485                 490                 495

Asp Met Ser His Thr Gln Pro Pro Pro Ile Leu Glu Ser Pro Thr Asn
            500                 505                 510

Leu
```

<210> SEQ ID NO 20
<211> LENGTH: 879
<212> TYPE: PRT
<213> ORGANISM: Drosophila melanogaster

<400> SEQUENCE: 20

```
Met Lys Arg Arg Trp Ser Asn Asn Gly Gly Phe Met Arg Leu Pro Glu
1               5                   10                  15

Glu Ser Ser Ser Glu Val Thr Ser Ser Ser Asn Gly Leu Val Leu Pro
            20                  25                  30

Ser Gly Val Asn Met Ser Pro Ser Ser Leu Asp Ser His Asp Tyr Cys
        35                  40                  45

Asp Gln Asp Leu Trp Leu Cys Gly Asn Glu Ser Gly Ser Phe Gly Gly
    50                  55                  60

Ser Asn Gly His Gly Leu Ser Gln Gln Gln Gln Ser Val Ile Thr Leu
65                  70                  75                  80

Ala Met His Gly Cys Ser Ser Thr Leu Pro Ala Gln Thr Thr Ile Ile
                85                  90                  95

Pro Ile Asn Gly Asn Ala Asn Gly Asn Gly Gly Ser Thr Asn Gly Gln
            100                 105                 110

Tyr Val Pro Gly Ala Thr Asn Leu Gly Ala Leu Ala Asn Gly Met Leu
        115                 120                 125

Asn Gly Gly Phe Asn Gly Met Gln Gln Gln Ile Gln Asn Gly His Gly
    130                 135                 140

Leu Ile Asn Ser Thr Thr Pro Ser Thr Pro Thr Thr Pro Leu His Leu
145                 150                 155                 160

Gln Gln Asn Leu Gly Gly Ala Gly Gly Gly Gly Ile Gly Gly Met Gly
                165                 170                 175

Ile Leu His His Ala Asn Gly Thr Pro Asn Gly Leu Ile Gly Val Val
            180                 185                 190

Gly Gly Gly Gly Gly Val Gly Leu Gly Val Gly Gly Gly Gly Val Gly
        195                 200                 205

Gly Leu Gly Glu Gln His Thr Pro Arg Ser Asp Ser Val Asn Ser Ile
    210                 215                 220

Ser Ser Gly Arg Asp Asp Leu Ser Pro Ser Ser Ser Leu Asn Gly Tyr
225                 230                 235                 240

Ser Ala Asn Glu Ser Cys Asp Ala Lys Lys Ser Lys Lys Gly Pro Ala
                245                 250                 255

Pro Arg Val Gln Glu Glu Leu Cys Leu Val Cys Gly Asp Arg Ala Ser
            260                 265                 270

Gly Tyr His Tyr Asn Ala Leu Thr Cys Glu Gly Cys Lys Gly Phe Phe
        275                 280                 285

Arg Arg Ser Val Thr Lys Ser Ala Val Tyr Cys Cys Lys Phe Gly Arg
    290                 295                 300

Ala Cys Glu Met Asp Met Tyr Met Arg Arg Lys Cys Gln Glu Cys Arg
305                 310                 315                 320

Leu Lys Lys Cys Leu Ala Val Gly Gly Glu Arg Pro Glu Cys Val Val
                325                 330                 335

Pro Glu Asn Gln Cys Ala Met Lys Arg Arg Glu Lys Lys Ala Gln Lys
            340                 345                 350

Glu Lys Asp Lys Met Thr Thr Ser Pro Ser Ser Gln His Gly Gly Asn
        355                 360                 365

Gly Ser Leu Ala Ser Gly Gly Gly Gln Asp Phe Val Lys Lys Glu Ile
    370                 375                 380

Leu Asp Leu Met Thr Cys Glu Pro Pro Gln His Ala Thr Ile Pro Leu
385                 390                 395                 400

Leu Pro Asp Glu Ile Leu Ala Lys Cys Gln Ala Arg Asn Ile Pro Ser
```

```
                405                 410                 415

Leu Thr Tyr Asn Gln Leu Ala Val Ile Tyr Lys Leu Ile Trp Tyr Gln
            420                 425                 430

Asp Gly Tyr Glu Gln Pro Ser Glu Glu Asp Leu Arg Arg Ile Met Ser
        435                 440                 445

Gln Pro Asp Glu Asn Glu Ser Gln Thr Asp Val Ser Phe Arg His Ile
    450                 455                 460

Thr Glu Ile Thr Ile Leu Thr Val Gln Leu Ile Val Glu Phe Ala Lys
465                 470                 475                 480

Gly Leu Pro Ala Phe Thr Lys Ile Pro Gln Glu Asp Gln Ile Thr Leu
                485                 490                 495

Leu Lys Ala Cys Ser Ser Glu Val Met Met Leu Arg Met Ala Arg Arg
            500                 505                 510

Tyr Asp His Ser Ser Asp Ser Ile Phe Phe Ala Asn Asn Arg Ser Tyr
        515                 520                 525

Thr Arg Asp Ser Tyr Lys Met Ala Gly Met Ala Asp Asn Ile Glu Asp
    530                 535                 540

Leu Leu His Phe Cys Arg Gln Met Phe Ser Met Lys Val Asp Asn Val
545                 550                 555                 560

Glu Tyr Ala Leu Leu Thr Ala Ile Val Ile Phe Ser Asp Arg Pro Gly
                565                 570                 575

Leu Glu Lys Ala Gln Leu Val Glu Ala Ile Gln Ser Tyr Tyr Ile Asp
            580                 585                 590

Thr Leu Arg Ile Tyr Ile Leu Asn Arg His Cys Gly Asp Ser Met Ser
        595                 600                 605

Leu Val Phe Tyr Ala Lys Leu Leu Ser Ile Leu Thr Glu Leu Arg Thr
    610                 615                 620

Leu Gly Asn Gln Asn Ala Glu Met Cys Phe Ser Leu Lys Leu Lys Asn
625                 630                 635                 640

Arg Lys Leu Pro Lys Phe Leu Glu Glu Ile Trp Asp Val His Ala Ile
                645                 650                 655

Pro Pro Ser Val Gln Ser His Leu Gln Ile Thr Gln Glu Glu Asn Glu
            660                 665                 670

Arg Leu Glu Arg Ala Glu Arg Met Arg Ala Ser Val Gly Gly Ala Ile
        675                 680                 685

Thr Ala Gly Ile Asp Cys Asp Ser Ala Ser Thr Ser Ala Ala Ala Ala
    690                 695                 700

Ala Ala Gln His Gln Pro Gln Pro Gln Pro Gln Pro Gln Pro Ser Ser
705                 710                 715                 720

Leu Thr Gln Asn Asp Ser Gln His Gln Thr Gln Pro Gln Leu Gln Pro
                725                 730                 735

Gln Leu Pro Pro Gln Leu Gln Gly Gln Leu Gln Pro Gln Leu Gln Pro
            740                 745                 750

Gln Leu Gln Thr Gln Leu Gln Pro Gln Ile Gln Pro Gln Pro Gln Leu
        755                 760                 765

Leu Pro Val Ser Ala Pro Val Pro Ala Ser Val Thr Ala Pro Gly Ser
    770                 775                 780

Leu Ser Ala Val Ser Thr Ser Ser Glu Tyr Met Gly Gly Ser Ala Ala
785                 790                 795                 800

Ile Gly Pro Ile Thr Pro Ala Thr Thr Ser Ser Ile Thr Ala Ala Val
                805                 810                 815

Thr Ala Ser Ser Thr Thr Ser Ala Val Pro Met Gly Asn Gly Val Gly
            820                 825                 830
```

```
Val Gly Val Gly Val Gly Gly Asn Val Ser Met Tyr Ala Asn Ala Gln
        835                 840                 845

Thr Ala Met Ala Leu Met Gly Val Ala Leu His Ser His Gln Glu Gln
    850                 855                 860

Leu Ile Gly Gly Val Ala Val Lys Ser Glu His Ser Thr Thr Ala
865                 870                 875


<210> SEQ ID NO 21
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 21

catctggagg ttgtgaacta atgg                                            24


<210> SEQ ID NO 22
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 22

ttgttcttgt cttaagcgct tga                                             23


<210> SEQ ID NO 23
<211> LENGTH: 18
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(1)
<223> OTHER INFORMATION: Conjugated to VIC(R) reporter dye
<220> FEATURE:
<221> NAME/KEY: misc_feature
<222> LOCATION: (18)..(18)
<223> OTHER INFORMATION: Conjugated to minor groove binder
      non-fluorescent quencher (MGBNFQ)

<400> SEQUENCE: 23

acatagcttt agggttcc                                                   18


<210> SEQ ID NO 24
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 24

ttatggccaa agagaggtga cta                                             23


<210> SEQ ID NO 25
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 25

ccaatctcaa ctcttggctt gtt                                             23
```

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<223> OTHER INFORMATION: Conjugated to internal ZEN(R) Quencher
<220> FEATURE:
<221> NAME/KEY: misc_feature
<222> LOCATION: (1)..(1)
<223> OTHER INFORMATION: Conjugated to 6-carboxyfluorescein (FAM(R)) Reporter dye
<220> FEATURE:
<221> NAME/KEY: misc_feature
<222> LOCATION: (24)..(24)
<223> OTHER INFORMATION: Conjugated to Iowa Black FQ (IBFQ) Quencher

<400> SEQUENCE: 26
tggcttggat ctaaggcctt ctca 24

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 27
gatgtgatat ctccactgac gt 22

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 28
cgtgtcctct ccaaatgaaa tga 23

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<223> OTHER INFORMATION: Conjugated to internal ZEN(R) Quencher
<220> FEATURE:
<221> NAME/KEY: misc_feature
<222> LOCATION: (1)..(1)
<223> OTHER INFORMATION: Conjugated to 6-carboxyfluorescein (FAM(R)) Reporter dye
<220> FEATURE:
<221> NAME/KEY: misc_feature
<222> LOCATION: (24)..(24)
<223> OTHER INFORMATION: Conjugated to Iowa Black FQ (IBFQ) Quencher

<400> SEQUENCE: 29
cgcacaatcc cactatcctt cgca 24

<210> SEQ ID NO 30
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 30
gaggtcgtcc gtccactc 18

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 31
gtcaaccact acatcgagac aag 23

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<223> OTHER INFORMATION: Conjugated to internal ZEN(R) Quencher
<220> FEATURE:
<221> NAME/KEY: misc_feature
<222> LOCATION: (1)..(1)
<223> OTHER INFORMATION: Conjugated to 6-carboxyfluorescein (FAM(R)) Reporter dye
<220> FEATURE:
<221> NAME/KEY: misc_feature
<222> LOCATION: (20)..(20)
<223> OTHER INFORMATION: Conjugated to Iowa Black FQ (IBFQ) Quencher

<400> SEQUENCE: 32
cggttcctgc ggctcggtac 20

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 33
tgtttgggaa tgtttctgcg g 21

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 34
cttcaagcaa cagaggtttg tg 22

<210> SEQ ID NO 35
<211> LENGTH: 2442
<212> TYPE: DNA
<213> ORGANISM: botrytis cinerea

<400> SEQUENCE: 35
tgcaggactc ttgagtactt tcgccagctc acgttgactt ttttcgctat cactcctttt 60
tagtgtcaaa acgtaggggt cttcgaaaat gttgagactt tgcacaatct ttctcaggct 120
cgccacagtt ttcgtcacga tgatatttga ctctggggta tagtagataa tagatagaag 180

```
tggtagcttt actcgaaggc gaagatctgc tcgatgtatt tttggcgtgc agcaaatggc    240
atccgtccag atctggtcaa cacaccaaga tcctagagtt ctactggctt ctgtcccaaa    300
tacaaatggc ttccgaaaga taggattgtc ttttagaagc gggagcattt gaagataaag    360
aggagtattg aatttcgggc ccaagggatc atagtaggca agagtctcag gtttaccttt    420
gattgagtac tgcagcaagc tgggatcttc tgcagtacat atttgactgt gtagcaaacc    480
ttcaagttct tccgcatcgg cgtggtgtag agcattacgc tgcgatggat tccggcatag    540
ttaaagaaat catggaagta agactgcttt ttcttgccgt tttcgtcggt aatcaccatt    600
cccggcggga tagtctgcca gttcagttcg ttgttcacac aaacggtgat acgtacactt    660
ttcccggcaa taacatacgg cgtgacatcg gcttcaaatg gcgtatagcc gccctgatgc    720
tccatcactt cctgattatt gacccacact ttgccgtaat gagtgaccgc atcgaaacgc    780
agcacgatac gctggcctgc ccaacctttc ggtataaaga cttcgcgctg ataccagacg    840
ttgcccgcat aattacgaat atctgcatcg gcgaactgat cgttaaaact gcctggcaca    900
gcaattgccc ggctttcttg taacgcgctt tcccaccaac gctggtatac ctgccttgtg    960
gtaagcctcc ttcagtcctt cccctttcaa aggtcataaa cgctaaagca ctactcaaaa   1020
tttattactc atttttgagg aatcgtgaca aaccataaaa cattgacgaa agatctaata   1080
atatcatatt tttacaatct tttcacctcg tgaacaccta ttgtataaaa agacagatat   1140
attggttttt atttaagtta ttttacatga aataagcatt ttaattttgt gattgtgcag   1200
atgtgtttaa ccacgtggta taccagcgtt ggtgggaaag cgcgttacaa gaaagccggg   1260
caattgctgt gccaggcagt tttaacgatc agttcgccga tgcagatatt cgtaattatg   1320
cgggcaacgt ctggtatcag cgcgaagtct ttataccgaa aggttgggca ggccagcgta   1380
tcgtgctgcg tttcgatgcg gtcactcatt acggcaaagt gtgggtcaat aatcaggaag   1440
tgatggagca tcagggcggc tatacgccat ttgaagccga tgtcacgccg tatgttattg   1500
ccgggaaaag tgtacgtatc accgtttgtg tgaacaacga actgaactgg cagactatcc   1560
cgccgggaat ggtgattacc gacgaaaacg gcaagaaaaa gcagtcttac ttccatgatt   1620
tctttaacta tgccggaatc catcgcagcg taatgctcta caccacgccg atgcggaaga   1680
acttgaaggt ttgctacaca gtcaaatatg tactgcagaa gatcccagct tgctgcagta   1740
ctcaatcaaa ggtaaacctg agactcttgc ctactatgat cccttgggcc cgaaattcaa   1800
tactcctctt tatcttcaaa tgctcccgct tctaaaagac aatcctatct ttcggaagcc   1860
atttgtattt gggacagaag ccagtagaac tctaggatct tggtgtgttg accagatctg   1920
gacggatgcc atttgctgca cgccaaaaat acatcgagca gatcttcgcc ttcgagtaaa   1980
gctaccactt ctatctatta tctactatac cccagagtca aatatcatcg tgacgaaaac   2040
tgtggcgagc ctgagaaaga ttgtgcaaag tctcaacatt ttcgaagacc cctacgtttt   2100
gacactaaaa aggagtgata gcgaaaaaag tcaacgtgag ctggcgaaag tactcaagag   2160
tcctgcagga tcgatgactt cccgatcgtt caaacatttg gcaataaagt ttcttaagat   2220
tgaatcctgt tgccggtctt gcgatgatta tcatataatt tctgttgaat tacgttaagc   2280
atgtaataat taacatgtaa tgcatgacgt tatttatgag atgggttttt atgattagag   2340
tcccgcaatt atacatttaa tacgcgatag aaaacaaaat atagcgcgca aactaggata   2400
aattatcgcg cgcggtgtca tctatgttac tagatcgggg ct                      2442
```

<210> SEQ ID NO 36
<211> LENGTH: 175

```
<212> TYPE: PRT
<213> ORGANISM: Arabidopsis thaliana

<400> SEQUENCE: 36

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175


<210> SEQ ID NO 37
<211> LENGTH: 9
<212> TYPE: PRT
<213> ORGANISM: Arabidopsis thaliana

<400> SEQUENCE: 37

Thr Glu Leu Arg Leu Gly Leu Pro Gly
1               5


<210> SEQ ID NO 38
<211> LENGTH: 9
<212> TYPE: PRT
<213> ORGANISM: Arabidopsis thaliana

<400> SEQUENCE: 38

Thr Glu Leu Arg Leu Gly Leu Pro Glu
1               5


<210> SEQ ID NO 39
<211> LENGTH: 9
<212> TYPE: PRT
<213> ORGANISM: Arabidopsis thaliana

<400> SEQUENCE: 39

Thr Glu Leu Cys Leu Gly Leu Pro Gly
1               5


<210> SEQ ID NO 40
<211> LENGTH: 9
<212> TYPE: PRT
<213> ORGANISM: Arabidopsis thaliana

<400> SEQUENCE: 40
```

Thr Glu Leu Thr Leu Gly Leu Pro Gly
1 5

<210> SEQ ID NO 41
<211> LENGTH: 9
<212> TYPE: PRT
<213> ORGANISM: Arabidopsis thaliana

<400> SEQUENCE: 41

Thr Glu Leu Thr Leu Ala Leu Pro Gly
1 5

<210> SEQ ID NO 42
<211> LENGTH: 9
<212> TYPE: PRT
<213> ORGANISM: Arabidopsis thaliana

<400> SEQUENCE: 42

Thr Asp Leu Arg Leu Gly Leu Ser Phe
1 5

<210> SEQ ID NO 43
<211> LENGTH: 9
<212> TYPE: PRT
<213> ORGANISM: Arabidopsis thaliana

<400> SEQUENCE: 43

Thr Glu Leu Asp Leu Ala Leu Gly Leu
1 5

<210> SEQ ID NO 44
<211> LENGTH: 9
<212> TYPE: PRT
<213> ORGANISM: Arabidopsis thaliana

<400> SEQUENCE: 44

Ser Glu Leu Glu Leu Gly Leu Gly Leu
1 5

<210> SEQ ID NO 45
<211> LENGTH: 9
<212> TYPE: PRT
<213> ORGANISM: Arabidopsis thaliana

<400> SEQUENCE: 45

Met Glu Leu Asp Leu Gly Leu Ser Leu
1 5

<210> SEQ ID NO 46
<211> LENGTH: 9
<212> TYPE: PRT
<213> ORGANISM: Arabidopsis thaliana

<400> SEQUENCE: 46

Ile Glu Leu Gly Leu Thr Leu Ser Leu
1 5

<210> SEQ ID NO 47
<211> LENGTH: 9
<212> TYPE: PRT
<213> ORGANISM: Arabidopsis thaliana

<400> SEQUENCE: 47

Ile Asp Leu Gly Leu Asp Leu Arg Thr
1 5

<210> SEQ ID NO 48
<211> LENGTH: 9
<212> TYPE: PRT
<213> ORGANISM: Arabidopsis thaliana

<400> SEQUENCE: 48

Val Asn Leu Ser Leu Ser Leu Thr Phe
1               5

<210> SEQ ID NO 49
<211> LENGTH: 9
<212> TYPE: PRT
<213> ORGANISM: Arabidopsis thaliana

<400> SEQUENCE: 49

Lys Lys Leu Glu Leu Lys Leu Gly Pro
1               5

<210> SEQ ID NO 50
<211> LENGTH: 9
<212> TYPE: PRT
<213> ORGANISM: Arabidopsis thaliana

<400> SEQUENCE: 50

Lys Lys Leu Glu Leu Arg Leu His Arg
1               5

<210> SEQ ID NO 51
<211> LENGTH: 9
<212> TYPE: PRT
<213> ORGANISM: Arabidopsis thaliana

<400> SEQUENCE: 51

Lys Arg Leu Glu Leu Arg Leu Ala Pro
1               5

<210> SEQ ID NO 52
<211> LENGTH: 9
<212> TYPE: PRT
<213> ORGANISM: Nicotiana tabacum

<400> SEQUENCE: 52

Ile Asp Leu Asp Leu Asn Leu Ala Pro
1               5

<210> SEQ ID NO 53
<211> LENGTH: 9
<212> TYPE: PRT
<213> ORGANISM: Arabidopsis thaliana

<400> SEQUENCE: 53

Leu Asp Leu Glu Leu Asn Leu Pro Pro
1               5

<210> SEQ ID NO 54
<211> LENGTH: 9
<212> TYPE: PRT
<213> ORGANISM: Arabidopsis thaliana

<400> SEQUENCE: 54

Gln Asp Leu Asp Leu Glu Leu Arg Leu
1               5

<210> SEQ ID NO 55
<211> LENGTH: 14669
<212> TYPE: DNA
<213> ORGANISM: Artificial Sequence
<220> FEATURE:
<223> OTHER INFORMATION: ID164 Vector

<400> SEQUENCE: 55

```
taactataac ggtcctaagg tagcgacgta cgtgcggagg gacactatca atcgtagctc     60
gagtttgata tccaaaatag acgagaacaa taagcaaaaa ctcttagttt tgaaataaat    120
caacaatccc gagggttgtc acatatacat caaaaacgaa aatccatata gcaaaaaaaa    180
actctaaatt accgttcgac aaaaaagaaa actgataaga catttgctaa acattaaaaa    240
tcgattcaga agaactcgtc aagaaggcga tagaaggcga tgcgctgcga atcgggagcg    300
gcgataccgt aaagcacgag gaagcggtca gcccattcgc cgccaagctc ttcagcaata    360
tcacgggtag ccaacgctat gtcctgatac ctatcagcca caccaagcct tccacagtcg    420
atgaatccag aaaagcggcc attttccacc atgatattcg gcaagcaggc atcgccatgg    480
gtcacgacga gatcctcgcc gtctggcatc ctcgccttga gcctggcgaa cagttcggct    540
ggcgcgagcc cctgatgctc ttcgtccaga tcatcctgat cgacaagacc ggcttccatc    600
cgagtacgtg ctcgctcgat gcgatgtttc gcttggtggt cgaatgggca ggtagccgga    660
tcaagcgtat gcagccgccg cattgcatca gccatgatgg atactttctc ggcaggagca    720
aggtgagatg acaggagatc ctgccccggc acttcgccca atagcagcca gtcccttccc    780
gcttcagtga caacgtcgag cacagcagcg caaggaacgc ccgtcgtggc cagccacgat    840
agccgcgctg cctcgtcttg aagttcattc agggcaccgg acaggtcggt cttgacaaaa    900
agaactggcc ttccctgcgc tgacagccgg aacacggcgg catcagagca gccgattgtc    960
tgttgtgccc agtcatagcc gaatagcctc tccacccaag cggccggaga acctgcgtgc   1020
aatccatctt gttcaatcat gtttaaacta ccaccacgga gacggagcac gagatggaga   1080
gttgactcct tctggatgtt gtagtcggca agagtacgac catcctcaag ctgctttccg   1140
gcgaaaatca aacgctgctg gtctgggga atcccttcct tgtcctggat cttggctttg    1200
acattgtcga tggtgtcgga agactcaacc tctagggtga tcgtcttccc cgttaaggtc   1260
ttcacgaaga tctgcatttt tgcgctagcc cgaaaagcac acaatgccct gcaggcaaac   1320
ttacaaattt ctctgaagtt gtatcctcag tacttcaaag aaaatagctt acaccaaatt   1380
ttttcttgtt ttcacaaatg ccgaacttgg ttccttatat aggaaaactc aagggcaaaa   1440
atgacacgga aaaatataaa aggataagta gtgggggata agattccttt gtgataaggt   1500
tactttccgc ccttacattt tccaccttac atgtgtcctc tatgtctctt tcacaatcac   1560
cgaccttatc ttcttctttt cattgttgtc gtcagtgctt acgtcttcaa gattcttttc   1620
ttcgcctggt tcttcttttt caatttctat gtattcttct tcgtattctg gcagtatagg   1680
atcttgtatc tgtacattct tcatttttga acataggttg aatatgtgcc gcatattgat   1740
ctgcttcttg ctgagttcac ataatacttc catagttttt cccgtaaaca ttggattctt   1800
gatgctacat cttggataat taccttctga cgcgtcatga gaagttcact cgtgacgaag   1860
ggcgcgccat cacaagtttg tacaaaaaag caggctccga attcgccctt ggcgcgcctc   1920
ggaccgcgtt gctcacgtta cagctccatt cctcgagccc cgatctagta acatagatga   1980
caccgcgcgc gataatttat cctagtttgc gcgctatatt ttgttttcta tcgcgtatta   2040
aatgtataat tgcgggactc taatcataaa aacccatctc ataaataacg tcatgcatta   2100
```

```
catgttaatt attacatgct taacgtaatt caacagaaat tatatgataa tcatcgcaag   2160
accggcaaca ggattcaatc ttaagaaact ttattgccaa atgtttgaac gatcgggaag   2220
tcatcgatat cctgcagggc aacactgtgg aggacaacag tctcaactgt tagcccaggc   2280
ccaaatccaa aaagaacacc ccactcaagc ccttcaccag tagttcctaa accttctttg   2340
gctgaggcct ttctcatttc atccaaaata aacagtacac aagcacttga catgttacca   2400
tagtcactta acacattcct tgtagcctta agtttctcgg gctttaggcc caactttatt   2460
tcaacttggt ccaaaattgc aggcccacct ggatgagcaa tccagaatag agagttccaa   2520
tcagaaatgc ccaaaggttt aaatgcttcc tcaaggctct tctcaatatt ttttgagatc   2580
agcccaggaa catctttgag taagtggaat gtaagcccaa cttcacggag atggccatca   2640
atagcaccat ggctatctgg gagaagagtt tgggctgctg aaacgagctc gaacaaaggc   2700
ctctcgactc ctggaattgg atcagaacct ataatgatcg cgcctgcccc atcaccaaaa   2760
agggcttggc caactaaact atccacacgt ggttaaacac atctgcacaa tcacaaaatt   2820
aaaatgctta tttcatgtaa aataacttaa ataaaaacca atatatctgt ctttttatac   2880
aataggtgtt cacgaggtga aaagattgta aaaatatgat attattagat ctttcgtcaa   2940
tgttttatgg tttgtcacga ttcctcaaaa atgagtaata aattttgagt agtgctttag   3000
cgtttatgac ctttgaaagg ggaaggactg aaggaggctt accacaaggc aggtagtgtg   3060
gatagtttag ttggccaagc cctttttggt gatggggcag gcgcgatcat tataggttct   3120
gatccaattc caggagtcga gaggcctttg ttcgagctcg tttcagcagc ccaaactctt   3180
ctcccagata gccatggtgc tattgatggc catctccgtg aagttgggct tacattccac   3240
ttactcaaag atgttcctgg gctgatctca aaaaatattg agaagagcct tgaggaagca   3300
tttaaacctt tgggcatttc tgattggaac tctctattct ggattgctca tccaggtggg   3360
cctgcaattt tggaccaagt tgaaataaag ttgggcctaa agcccgagaa acttaaggct   3420
acaaggaatg tgttaagtga ctatggtaac atgtcaagtg cttgtgtact gtttattttg   3480
gatgaaatga gaaaggcctc agccaaagaa ggtttaggaa ctactggtga agggcttgag   3540
tggggtgttc tttttggatt tgggcctggg ctaacagttg agactgttgt cctccacagt   3600
gttgccctgc aggaccggaa tgccaagctg gaattcgagc tcctgcagct cgaagatcca   3660
agcttcgtgt cctctccaaa tgaaatgaac ttccttatat agaggaaggg tcttgctcta   3720
gtgtctccgc tcggaggaca gtactccgct cggaggacag tactccgctc ggaggacagt   3780
actccgctcg gaggacagta ctccgctcgg aggacagtac tccgagaatt cagcggccgc   3840
ctcgagctca gctagaataa ttatcagaca aatattgaga ttctggtata tcaagaaaaa   3900
atgttctatt ttggtggtaa gagagattca tcaagtccaa taaaaactac aaacatgatt   3960
tgaaaattgc agaaaggaaa gtgaataaat gttgacacaa aaagcctata ctgtacttaa   4020
cttgattgca taattacttg atcatagact catagtaaac ttgattacac agataagtga   4080
agaaacaaac caattcaaga cataaccaaa gagaggtgaa agactgtttt atatgtctaa   4140
cattgcacct taatatcaca ctgttagttc ctttcttact taaattcaac ccattaaagt   4200
aaaaacaaca gataataata atttgagaat gaacaaaagg accatatcat ttattaactc   4260
ttatccatcc atttgcattt tgatgtccga aaacaaaaac tgaaagaaca cagtaaatta   4320
caagcagaac aaatgataga agaaaacagc ttttccaatg ccataatact caaacttagt   4380
aggattctgg tgtgtgggca atgaaacatc gattcagaga ttcgtggggg actcaaggat   4440
aggcggcggt tgggtgtgcg acatgtccgc cacatcccaa atctcctcaa ggaaaggcgg   4500
```

```
cagctttctg ttcttgagct tgagggagat gcacatgttg gagttttgca ttccgagcgt   4560
gcgtagctca gagaggattg agaggatctt gccgtatatg acggacgaac gcgccgaacc   4620
ggaaagttgg ttcaggatat agatgcggag cgtattcagg tagtaccgct ggatttcctc   4680
caccagttgc ggctgctcca accctggccg gtcagaaaag atgacgacag ccgtgagcag   4740
cgcgtaatgg atgttgtcca acgccataga gtacatgcac cggcagaagt gcagtagatc   4800
ctcgatgact tcggccatgc cagccttgcg gtagttatcc ctggtgtacg cttggttgtt   4860
agcgaacaga atactgtcgg aggccgcatc gtatcgtcgc gcgactcgga gcatcattac   4920
ctcacttgag caagccttga gcagcgtaat ttgatctggc tggctgatct tggcgaaccc   4980
tggcaatccc ttagcgaact ccacgataag ttggaccgtg aggatagtca tctccgtgat   5040
ctggcggaag ggagtgtccg attcttcgtt ttcatcgtcc gcttgctgcc acgtctgcgt   5100
aatcctttta agatcctcat cagaaggctg ctcgtacccg tcttgatacc agatgagcct   5160
ggcgataagg aactgctggt tggctgtcaa ctgggggatg tttttctgcc ggtttgtcac   5220
caacagcttg tcggagagaa accttgggac aacctcgtga atccttgctg cttcaggagg   5280
tggaggttca cactgcataa tgggcggcat gtggtcgtcc accgtcgtcg tgctgacagg   5340
cagtttgtcc ttctccttct gtgctttctt ctctttccgc ttcatggcgc actgagtctc   5400
gggtactacg cactcaggcc gtgatattct cctagacccg cccgatacag tcaactgtct   5460
ttgacctttg ttactactct cctccgatga tgatgtcgca cttattctat gctgtctcaa   5520
tgttagaggc atatcagtct ccactgaagc caatctatct gtgacggcat ccttgttcac   5580
attatcttgt acaaataatc cggtaagaag tgcttttata tcctgtaaag aatccatttt   5640
caaaatcatg tcaaggtcct cccttggaaa aatcagtaga aatagctgtt ccagtctttc   5700
tagccttgat tccacttctg tcagatgtgc cctagtcagc ggagaccttt tggttttggg   5760
agagtagcga cactcccagt tgttcttcag acacttggcg cacttcggtt tttctttgga   5820
gcacttgagc tttttaagtc ggcaaatatc gcaggcttgt tcgatagaag aaagtagctt   5880
catcccgccg aactccccgc ctgatattct tctggaggtt ccaagcaact tcccaccgta   5940
ctcgtcaatt ccaagggcat cggtaaacat ctgctcaaac tcgaagtcgg ccatatccag   6000
agcgccgtag gggcggagt cgtgggggt aaatcccgga cctggggaat ccccgtcccc   6060
caacatgtcc agatcgaaat cgtctagcgc gtcagcgtga gccatcgcca cgtcctcgcc   6120
gtctaagtgg agttcgtccc ccaggctgac atcggtcggg ggggccatgg tggcgctagc   6180
cctgcaggtc tggaggatct gctagagtca gcttgtcgcg tgtcctctcc aaatgaaatg   6240
aacttcctta tatagaggaa gggtcttgcg aaggatagtg ggattgtgcg tcatccctta   6300
cgtcagtgga gatatcacat caatccactt gctttgaaga cgtggttgga acgtcttctt   6360
tttccacgat gctcctcgtg ggtgggggtc catctttggg accactgtcg gcagaggcat   6420
cttcaacgat ggcctttcct ttatcgcaat gatggcattt gtaggagcca ccttcctttt   6480
ccactatctt cacaataaag tgacagatag ctgggcaatg gaatccgagg aggtttccgg   6540
atattaccct ttgttgaaaa gtctcacatc ggaccatcac atcaatccac ttgctttgaa   6600
gacgtggttg gaacgtcttc tttttccacg atgctcctcg tgggtggggg tccatctttg   6660
ggaccactgt cggcagaggc atcttcaacg atggcctttc ctttatcgca atgatggcat   6720
ttgtaggagc caccttcctt ttccactatc ttcacaataa agtgacagat agctgggcaa   6780
tggaatccga ggaggtttcc ggatattacc ctttgttgaa aagtctcaca tcggaccacg   6840
```

-continued

```
cgtcacagtt gaggtatttc ggatcgtggc gatcgcaagg gcgaattcga cccagctttc   6900
ttgtacaaag tggtgatcgg tccggttcgg ctgcggccgc attaccctgt tatccctaat   6960
ctcgtttaac tatgactctc ttaaggtagc caaattccgg aaaacgactt aatcagctaa   7020
tacaaactat cagtgtttga caggatatat tggcgggtaa acctaagaga aaagagcgtt   7080
tattagaata atcggatatt taaaagggcg tgaaaaggtt tatccgttcg tccatttgta   7140
tgtgcatgcg gctggggcga gcaccagacg gagcaccgcc aggatcacga gccatatcct   7200
gacgaatggg ttctcgtcca acgccccttt atcgacagta tgtgaatttg cagtgtggcc   7260
gcgatcaacg cacactggcc ttgggtctga agggtgatct tcaaaacgaa cccccgtctt   7320
ggtggtcagt gtgatgggca catcgcttac tcctcagtca ccctttgagc cagataatta   7380
agaggcaaat gcaattggct caggctgcca tcgtcccccc gtgcgaaacc tgcacgtccg   7440
cgtcaaagaa ataaccggca cctcttgctg tttttatcag ttgagggctt gacggatcag   7500
cctcaagttt gcggcgcagc ctcaaaatga gaacatctat actcctgtca taaacctcct   7560
cgtcgcgtac tcgactggca atgagaagtt gctcgcgcga tagaacgtcg cggggtttct   7620
ctaaaaacgc gaggagaaga ttgaactcac ctgccgtaag tttcacctca ccgccagctt   7680
cggacatcaa gcgacgttgc ctgagattaa gtgtccagtc agtaaaacaa aaagaccgtc   7740
ggtctttgga gcggacaacg ttggggcgca cgcgcaaggc aacccgaatg cgtgctagaa   7800
actctctgat actgaacggc ttagcgataa aatcacttgc tcctagctca agtgcaacaa   7860
ctttatccgt ctcctcaagg cggtcgccac tgataattat gattggaata tcagactttg   7920
ccgccagatt acgaacgatc tcaagcccat cttcacgacc taaatctaga tcaacaacca   7980
cgacatcgac cgtcgcggaa gagagtactc ttgtgaactg ggtgctgtcg gctaccgcgg   8040
tcactttgaa ggcgtggatc gtaaggtatt caataataag atgccgcata gcgacgtcgt   8100
catcgacaag aagaacgtgt ttcaacggct cacctttcaa tctaaaatct gaacccttgt   8160
tcacagcgct tgagaaattt tcacgtgaag gatgtacaat catctccagc taaatgggca   8220
gttcgtcaga attgcggctg accgcggatg acaaaaatgc gaaccaagta tttcaatttt   8280
atgacaaaaa ttctcaatcg ttgttacaag tgaaacgctt cgaggttaca gctactattg   8340
atttaggaga tcgcctatgg tctcgccccg gcgtcgtgcg tccgccgcga gccgcatgcc   8400
aaccacaggg ttcccctcgg gatcaaagta ctttgatcca acccctccgc tgctatagtg   8460
cagtcggctt ctgacgttca gtgcagccgt cttctgaaaa cgacatgtcg cacaagtcct   8520
aagttacgcg acaggctgcc gccctgccct tttcctggcg ttttcttgtc gcgtgtttta   8580
gtcgcataaa gtagaatact tgcgactaga accggagaca ttacgccatg aacaagagcg   8640
ccgccgctgg cctgctgggc tatgcccgcg tcagcaccga cgaccaggac ttgaccaacc   8700
aacgggccga actgcacgcg gccggctgca ccaagctgtt ttccgagaag atcaccggca   8760
ccaggcgcga ccgcccggag ctggccagga tgcttgacca cctacgccct ggcgacgttg   8820
tgacagtgac caggctagac cgcctggccc gcagcacccg cgacctactg gacattgccg   8880
agcgcatcca ggaggccggc gcgggcctgc gtagcctggc agagccgtgg gccgacacca   8940
ccacgccggc cggccgcatg gtgttgaccg tgttcgccgg cattgccgag ttcgagcgtt   9000
ccctaatcat cgaccgcacc cggagcgggc gcgaggccgc caaggcccga ggcgtgaagt   9060
ttggcccccg ccctaccctc accccggcac agatcgcgca cgcccgcgag ctgatcgacc   9120
aggaaggccg caccgtgaaa gaggcggctg cactgcttgg cgtgcatcgc tcgaccctgt   9180
accgcgcact tgagcgcagc gaggaagtga cgcccaccga ggccaggcgg cgcggtgcct   9240
```

```
tccgtgagga cgcattgacc gaggccgacg ccctggctgc tgctgagaat gaacgccaag    9300
aggaacaagc atgaaaccgc accaggacgg ccaggacgaa ccgtttttca ttaccgaaga    9360
gatcgaggcg gagatgatcg cggccgggta cgtgttcgag ccgcccgcgc acgtctcaac    9420
cgtgcggctg catgaaatcc tggccggttt gtctgatgcc aagctggcgg cctggccggc    9480
cagcttggcc gctgaagaaa ccgagcgccg ccgtctaaaa aggtgatgtg tatttgagta    9540
aaacagcttg cgtcatgcgg tcgctgcgta tatgatgcga tgagtaaata aacaaatacg    9600
caaggggaac gcatgaaggt tatcgctgta cttaaccaga aaggcgggtc aggcaagacg    9660
accatcgcaa cccatctagc ccgcgccctg caactcgctg gggccgatgt tctgttagtc    9720
gattccgatc cccagggcag tgcccgcgat tgggcggccg tgcgggaaga tcaaccgcta    9780
accgttgtcg gcatcgaccg cccgacgatt gaccgcgacg tgaaggccat cggccggcgc    9840
gacttcgtag tgatcgacgg agcgccccag gcggcggact tggctgtgtc cgcgatcaag    9900
gcagccgact tcgtgctgat tccggtgcag ccaagccctt acgacatatg ggccaccgcc    9960
gacctggtgg agctggttaa gcagcgcatt gaggtcacgg atggaaggct acaagcggcc   10020
tttgtcgtgt cgcgggcgat caaaggcacg cgcatcggcg gtgaggttgc cgaggcgctg   10080
gccgggtacg agctgcccat tcttgagtcc cgtatcacgc agcgcgtgag ctacccaggc   10140
actgccgccg ccggcacaac cgttctttaa tcagaacccg agggcgacgc tgcccgcgag   10200
gtccaggcgc tggccgctga aattaaatca aaactcattt gagttaatga ggtaaagaga   10260
aaatgagcaa aagcacaaac acgctaagtg ccggccgtcc gagcgcacgc agcagcaagg   10320
ctgcaacgtt ggccagcctg gcagacacgc cagccatgaa gcgggtcaac tttcagttgc   10380
cggcggagga tcacaccaag ctgaagatgt acgcggtacg ccaaggcaag accattaccg   10440
agctgctatc tgaatacatc gcgcagctac cagagtaaat gagcaaatga ataaatgagt   10500
agatgaattt tagcggctaa aggaggcggc atggaaaatc aagaacaacc aggcaccgac   10560
gccgtggaat gccccatgtg tggaggaacg ggcggttggc caggcgtaag cggctgggtt   10620
gcctgccggc cctgcaatgg cactggaacc cccaagcccg aggaatcggc gtgagcggtc   10680
gcaaaccatc cggcccggta caaatcggcg cggcgctggg tgatgacctg gtggagaagt   10740
tgaaggccgc gcaggccgcc cagcggcaac gcatcgaggc agaagcacgc cccggtgaat   10800
cgtggcaagc tgctgctgat cgaatccgca aagaatcccg gcaaccgccg gcagccggtg   10860
cgccgtcgat taggaagccg cccaagggcg acgagcaacc agattttttc gttccgatgc   10920
tctatgacgt gggcacccgc gatagtcgca gcatcatgga cgtggccgtt ttccgtctgt   10980
cgaagcgtga ccgacgagct ggcgaggtga tccgctacga gcttccagac gggcacgtag   11040
aggtttccgc agggccggcc ggcatggcca gtgtgtggga ttacgacctg gtactgatgg   11100
cggtttccca tctaaccgaa tccatgaacc gataccggga agggaaggga gacaagcccg   11160
gccgcgtgtt ccgtccacac gttgcggacg tactcaagtt ctgccggcga gccgatggcg   11220
gaaagcagaa agacgacctg gtagaaacct gcattcggtt aaacaccacg cacgttgcca   11280
tgcagcgtac caagaaggcc aagaacggcc gcctggtgac ggtatccgag ggtgaagcct   11340
tgattagccg ctacaagatc gtaaagagcg aaaccgggcg gccggagtac atcgagatcg   11400
aactggctga ttggatgtac cgcgagatca cagaaggcaa gaacccggac gtgctgacgg   11460
ttcaccccga ttactttttg atcgaccccg gcatcggccg ttttctctac cgcctggcac   11520
gccgcgccgc aggcaaggca gaagccagat ggttgttcaa gacgatctac gaacgcagtg   11580
```

```
gcagcgccgg agagttcaag aagttctgtt tcaccgtgcg caagctgatc gggtcaaatg  11640
acctgccgga gtacgatttg aaggaggagg cggggcaggc tggcccgatc ctagtcatgc  11700
gctaccgcaa cctgatcgag ggcgaagcat ccgccggttc ctaatgtacg gagcagatgc  11760
tagggcaaat tgccctagca ggggaaaaag gtcgaaaagg tctctttcct gtggatagca  11820
cgtacattgg gaacccaaag ccgtacattg ggaaccggaa cccgtacatt gggaacccaa  11880
agccgtacat tgggaaccgg tcacacatgt aagtgactga tataaaagag aaaaaaggcg  11940
atttttccgc ctaaaactct ttaaaactta ttaaaactct taaaacccgc ctggcctgtg  12000
cataactgtc tggccagcgc acagccgaag agctgcaaaa agcgcctacc cttcggtcgc  12060
tgcgctccct acgccccgcc gcttcgcgtc ggcctatcac ggccgctggc cgctcaaaaa  12120
tggctggcct acggccaggc aatctaccag ggcgcggaca agccgcgccg tcgccactcg  12180
accgccggcg cccacatcaa ggcaccctgc ctcgcgcgtt tcggtgatga cggtgaaaac  12240
ctctgacaca tgcagctccc ggagacggtc acagcttgtc tgtaagcgga tgccgggagc  12300
agacaagccc gtcagggcgc gtcagcgggt gttggcgggt gtcggggcgc agccatgacc  12360
cagtcacgta gcgatagcgg agtgtatact ggcttaacta tgcggcatca gagcagattg  12420
tactgagagt gcaccatatg cggtgtgaaa taccgcacag atgcgtaagg agaaaatacc  12480
gcatcaggcg ctcttccgct tcctcgctca ctgactcgct gcgctcggtc gttcggctgc  12540
ggcgagcggt atcagctcac tcaaaggcgg taatacggtt atccacagaa tcaggggata  12600
acgcaggaaa gaacatgtga gcaaaaggcc agcaaaaggc caggaaccgt aaaaaggccg  12660
cgttgctggc gtttttccat aggctccgcc cccctgacga gcatcacaaa aatcgacgct  12720
caagtcagag gtggcgaaac ccgacaggac tataaagata ccaggcgttt ccccctggaa  12780
gctccctcgt gcgctctcct gttccgaccc tgccgcttac cggatacctg tccgcctttc  12840
tcccttcggg aagcgtggcg ctttctcata gctcacgctg taggtatctc agttcggtgt  12900
aggtcgttcg ctccaagctg ggctgtgtgc acgaaccccc cgttcagccc gaccgctgcg  12960
ccttatccgg taactatcgt cttgagtcca acccggtaag acacgactta tcgccactgg  13020
cagcagccac tggtaacagg attagcagag cgaggtatgt aggcggtgct acagagttct  13080
tgaagtggtg gcctaactac ggctacacta gaaggacagt atttggtatc tgcgctctgc  13140
tgaagccagt taccttcgga aaaagagttg gtagctcttg atccggcaaa caaaccaccg  13200
ctggtagcgg tggttttttt gtttgcaagc agcagattac gcgcagaaaa aaaggatctc  13260
aagaagatcc tttgatcttt tctacggggt ctgacgctca gtggaacgaa aactcacgtt  13320
aagggatttt ggtcatgcat tctaggtact aaaacaattc atccagtaaa atataatatt  13380
ttattttctc ccaatcaggc ttgatcccca gtaagtcaaa aaatagctcg acatactgtt  13440
cttccccgat atcctccctg atcgaccgga cgcagaaggc aatgtcatac cacttgtccg  13500
ccctgccgct tctcccaaga tcaataaagc cacttacttt gccatctttc acaaagatgt  13560
tgctgtctcc caggtcgccg tgggaaaaga caagttcctc ttcgggcttt tccgtcttta  13620
aaaaatcata cagctcgcgc ggatctttaa atggagtgtc ttcttcccag ttttcgcaat  13680
ccacatcggc cagatcgtta ttcagtaagt aatccaattc ggctaagcgg ctgtctaagc  13740
tattcgtata gggacaatcc gatatgtcga tggagtgaaa gagcctgatg cactccgcat  13800
acagctcgat aatcttttca gggctttgtt catcttcata ctcttccgag caaaggacgc  13860
catcggcctc actcatgagc agattgctcc agccatcatg ccgttcaaag tgcaggacct  13920
ttggaacagg cagctttcct tccagccata gcatcatgtc cttttcccgt tccacatcat  13980
```

```
aggtggtccc tttataccgg ctgtccgtca tttttaaata taggttttca ttttctccca  14040

ccagcttata taccttagca ggagacattc cttccgtatc ttttacgcag cggtattttt  14100

cgatcagttt tttcaattcc ggtgatattc tcattttagc catttattat ttccttcctc  14160

ttttctacag tatttaaaga taccccaaga agctaattat aacaagacga actccaattc  14220

actgttcctt gcattctaaa accttaaata ccagaaaaca gctttttcaa agttgttttc  14280

aaagttggcg tataacatag tatcgacgga gccgattttg aaaccgcggt gatcacaggc  14340

agcaacgctc tgtcatcgtt acaatcaaca tgctaccctc cgcgagatca tccgtgtttc  14400

aaacccggca gcttagttgc cgttcttccg aatagcatcg gtaacatgag caaagtctgc  14460

cgccttacaa cggctctccc gctgacgccg tcccggactg atgggctgcc tgtatcgagt  14520

ggtgattttg tgccgagctg ccggtcgggg agctgttggc tggctggtgg caggatatat  14580

tgtggtgtaa acaaattgac gcttagacaa cttaataaca cattgcggac gtttttaatg  14640

tactgaatta acgccgaatt aatgtcgac                                    14669
```

<210> SEQ ID NO 56
<211> LENGTH: 389
<212> TYPE: PRT
<213> ORGANISM: Petunia axillaris

<400> SEQUENCE: 56

```
Met Val Thr Val Glu Glu Tyr Arg Lys Ala Gln Arg Ala Glu Gly Pro
1               5                   10                  15

Ala Thr Val Met Ala Ile Gly Thr Ala Thr Pro Thr Asn Cys Val Asp
            20                  25                  30

Gln Ser Thr Tyr Pro Asp Tyr Tyr Phe Arg Ile Thr Asn Ser Glu His
        35                  40                  45

Lys Thr Asp Leu Lys Glu Lys Phe Lys Arg Met Cys Glu Lys Ser Met
    50                  55                  60

Ile Lys Lys Arg Tyr Met His Leu Thr Glu Glu Ile Leu Lys Glu Asn
65                  70                  75                  80

Pro Ser Met Cys Glu Tyr Met Ala Pro Ser Leu Asp Ala Arg Gln Asp
                85                  90                  95

Ile Val Val Val Glu Val Pro Lys Leu Gly Lys Glu Ala Ala Gln Lys
            100                 105                 110

Ala Ile Lys Glu Trp Gly Gln Pro Lys Ser Lys Ile Thr His Leu Phe
        115                 120                 125

Phe Cys Thr Thr Ser Gly Val Asp Met Pro Gly Cys Asp Tyr Gln Leu
    130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Asn Asp Thr His Leu Asp Ser
        195                 200                 205

Leu Val Gly Gln Ala Leu Phe Gly Asp Gly Ala Gly Ala Ile Ile Ile
    210                 215                 220

Gly Ser Asp Pro Ile Pro Gly Val Glu Arg Pro Leu Phe Glu Leu Val
225                 230                 235                 240

Ser Ala Ala Gln Thr Leu Leu Pro Asp Ser His Gly Ala Ile Asp Gly
```

```
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Glu Glu Ala Phe Lys
        275                 280                 285

Pro Leu Gly Ile Ser Asp Trp Asn Ser Leu Phe Trp Ile Ala His Pro
    290                 295                 300

Gly Gly Pro Ala Ile Leu Asp Gln Val Glu Ile Lys Leu Gly Leu Lys
305                 310                 315                 320

Pro Glu Lys Leu Lys Ala Thr Arg Asn Val Leu Ser Asp Tyr Gly Asn
                325                 330                 335

Met Ser Ser Ala Cys Val Leu Phe Ile Leu Asp Glu Met Arg Lys Ala
            340                 345                 350

Ser Ala Lys Glu Gly Leu Gly Thr Thr Gly Glu Gly Leu Glu Trp Gly
        355                 360                 365

Val Leu Phe Gly Phe Gly Pro Gly Leu Thr Val Glu Thr Val Val Leu
    370                 375                 380

His Ser Val Ala Thr
385
```

<210> SEQ ID NO 57
<211> LENGTH: 15457
<212> TYPE: DNA
<213> ORGANISM: Artificial Sequence
<220> FEATURE:
<223> OTHER INFORMATION: Vector ID163

<400> SEQUENCE: 57

```
taactataac ggtcctaagg tagcgacgta cgtgcggagg gacactatca atcgtagctc     60

gagtttgata tccaaaatag acgagaacaa taagcaaaaa ctcttagttt tgaaataaat    120

caacaatccc gagggttgtc acatatacat caaaaacgaa aatccatata gcaaaaaaaa    180

actctaaatt accgttcgac aaaaaagaaa actgataaga catttgctaa acattaaaaa    240

tcgattcaga agaactcgtc aagaaggcga tagaaggcga tgcgctgcga atcgggagcg    300

gcgataccgt aaagcacgag gaagcggtca gcccattcgc cgccaagctc ttcagcaata    360

tcacgggtag ccaacgctat gtcctgatac ctatcagcca caccaagcct tccacagtcg    420

atgaatccag aaaagcggcc attttccacc atgatattcg gcaagcaggc atcgccatgg    480

gtcacgacga gatcctcgcc gtctggcatc ctcgccttga gcctggcgaa cagttcggct    540

ggcgcgagcc cctgatgctc ttcgtccaga tcatcctgat cgacaagacc ggcttccatc    600

cgagtacgtg ctcgctcgat gcgatgtttc gcttggtggt cgaatgggca ggtagccgga    660

tcaagcgtat gcagccgccg cattgcatca gccatgatgg atactttctc ggcaggagca    720

aggtgagatg acaggagatc ctgccccggc acttcgccca atagcagcca gtcccttccc    780

gcttcagtga caacgtcgag cacagcagcg caaggaacgc ccgtcgtggc cagccacgat    840

agccgcgctg cctcgtcttg aagttcattc agggcaccgg acaggtcggt cttgacaaaa    900

agaactggcc ttccctgcgc tgacagccgg aacacggcgg catcagagca gccgattgtc    960

tgttgtgccc agtcatagcc gaatagcctc tccacccaag cggccggaga acctgcgtgc   1020

aatccatctt gttcaatcat gtttaaacta ccaccacgga gacggagcac gagatggaga   1080

gttgactcct tctggatgtt gtagtcggca agagtacgac catcctcaag ctgctttccg   1140

gcgaaaatca aacgctgctg gtctggggga atcccttcct tgtcctggat cttggctttg   1200
```

```
acattgtcga tggtgtcgga agactcaacc tctagggtga tcgtcttccc cgttaaggtc   1260
ttcacgaaga tctgcatttt tgcgctagcc cgaaaagcac acaatgccct gcaggcaaac   1320
ttacaaattt ctctgaagtt gtatcctcag tacttcaaag aaaatagctt acaccaaatt   1380
ttttcttgtt ttcacaaatg ccgaacttgg ttccttatat aggaaaactc aagggcaaaa   1440
atgacacgga aaaatataaa aggataagta gtgggggata agattccttt gtgataaggt   1500
tactttccgc ccttacattt tccaccttac atgtgtcctc tatgtctctt tcacaatcac   1560
cgaccttatc ttcttctttt cattgttgtc gtcagtgctt acgtcttcaa gattcttttc   1620
ttcgcctggt tcttcttttt caatttctat gtattcttct tcgtattctg gcagtatagg   1680
atcttgtatc tgtacattct tcatttttga acataggttg aatatgtgcc gcatattgat   1740
ctgcttcttg ctgagttcac ataatacttc catagttttt cccgtaaaca ttggattctt   1800
gatgctacat cttggataat taccttctga cgcgtcatga gaagttcact cgtgacgaag   1860
ggcgcgccat cacaagtttg tacaaaaaag caggctccga attcgccctt ggcgcgcctc   1920
ggaccgcgtt gctcacgtta cagctccatt cctcgagccc cgatctagta acatagatga   1980
caccgcgcgc gataatttat cctagtttgc gcgctatatt ttgttttcta tcgcgtatta   2040
aatgtataat tgcgggactc taatcataaa aacccatctc ataaataacg tcatgcatta   2100
catgttaatt attacatgct taacgtaatt caacagaaat tatatgataa tcatcgcaag   2160
accggcaaca ggattcaatc ttaagaaact ttattgccaa atgtttgaac gatcgggaag   2220
tcatcgatac ctgcaggact cttgagtact ttcgccagct cacgttgact tttttcgcta   2280
tcactccttt ttagtgtcaa aacgtagggg tcttcgaaaa tgttgagact ttgcacaatc   2340
tttctcaggc tcgccacagt tttcgtcacg atgatatttg actctggggt atagtagata   2400
atagatagaa gtggtagctt tactcgaagg cgaagatctg ctcgatgtat ttttggcgtg   2460
cagcaaatgg catccgtcca gatctggtca acacaccaag atcctagagt tctactggct   2520
tctgtcccaa atacaaatgg cttccgaaag ataggattgt cttttagaag cgggagcatt   2580
tgaagataaa gaggagtatt gaatttcggg cccaagggat catagtaggc aagagtctca   2640
ggtttacctt tgattgagta ctgcagcaag ctgggatctt ctgcagtaca tatttgactg   2700
tgtagcaaac cttcaagttc ttccgcatcg gcgtggtgta gagcattacg ctgcgatgga   2760
ttccggcata gttaaagaaa tcatggaagt aagactgctt tttcttgccg ttttcgtcgg   2820
taatcaccat tcccggcggg atagtctgcc agttcagttc gttgttcaca caaacggtga   2880
tacgtacact tttcccggca ataacatacg gcgtgacatc ggcttcaaat ggcgtatagc   2940
cgccctgatg ctccatcact tcctgattat tgacccacac tttgccgtaa tgagtgaccg   3000
catcgaaacg cagcacgata cgctggcctg cccaaccttt cggtataaag acttcgcgct   3060
gataccagac gttgcccgca taattacgaa tatctgcatc ggcgaactga tcgttaaaac   3120
tgcctggcac agcaattgcc cggctttctt gtaacgcgct ttcccaccaa cgctggtata   3180
cacacgtggt taaacacatc tgcacaatca caaaattaaa atgcttattt catgtaaaat   3240
aacttaaata aaaaccaata tatctgtctt tttatacaat aggtgttcac gaggtgaaaa   3300
gattgtaaaa atatgatatt attagatctt tcgtcaatgt tttatggttt gtcacgattc   3360
ctcaaaaatg agtaataaat tttgagtagt gctttagcgt ttatgacctt tgaaagggga   3420
aggactgaag gaggcttacc acaaggcagg tataccagcg ttggtgggaa agcgcgttac   3480
aagaaagccg ggcaattgct gtgccaggca gttttaacga tcagttcgcc gatgcagata   3540
ttcgtaatta tgcgggcaac gtctggtatc agcgcgaagt ctttataccg aaaggttggg   3600
```

```
caggccagcg tatcgtgctg cgtttcgatg cggtcactca ttacggcaaa gtgtgggtca   3660
ataatcagga agtgatggag catcagggcg gctatacgcc atttgaagcc gatgtcacgc   3720
cgtatgttat tgccgggaaa agtgtacgta tcaccgtttg tgtgaacaac gaactgaact   3780
ggcagactat cccgccggga atggtgatta ccgacgaaaa cggcaagaaa aagcagtctt   3840
acttccatga tttctttaac tatgccggaa tccatcgcag cgtaatgctc tacaccacgc   3900
cgatgcggaa gaacttgaag gtttgctaca cagtcaaata tgtactgcag aagatcccag   3960
cttgctgcag tactcaatca aaggtaaacc tgagactctt gcctactatg atcccttggg   4020
cccgaaattc aatactcctc tttatcttca aatgctcccg cttctaaaag acaatcctat   4080
ctttcggaag ccatttgtat ttgggacaga agccagtaga actctaggat cttggtgtgt   4140
tgaccagatc tggacggatg ccatttgctg cacgccaaaa atacatcgag cagatcttcg   4200
ccttcgagta aagctaccac ttctatctat tatctactat accccagagt caaatatcat   4260
cgtgacgaaa actgtggcga gcctgagaaa gattgtgcaa agtctcaaca ttttcgaaga   4320
cccctacgtt ttgacactaa aaaggagtga tagcgaaaaa agtcaacgtg agctggcgaa   4380
agtactcaag agtcctgcag gaccggaatg ccaagctgga attcgagctc ctgcagctcg   4440
aagatccaag cttcgtgtcc tctccaaatg aaatgaactt ccttatatag aggaagggtc   4500
ttgctctagt gtctccgctc ggaggacagt actccgctcg gaggacagta ctccgctcgg   4560
aggacagtac tccgctcgga ggacagtact ccgctcggag gacagtactc cgagaattca   4620
gcggccgcct cgagctcagc tagaataatt atcagacaaa tattgagatt ctggtatatc   4680
aagaaaaaat gttctatttt ggtggtaaga gagattcatc aagtccaata aaaactacaa   4740
acatgatttg aaaattgcag aaaggaaagt gaataaatgt tgacacaaaa agcctatact   4800
gtacttaact tgattgcata attacttgat catagactca tagtaaactt gattacacag   4860
ataagtgaag aaacaaacca attcaagaca taaccaaaga gaggtgaaag actgttttat   4920
atgtctaaca ttgcacctta atatcacact gttagttcct ttcttactta aattcaaccc   4980
attaaagtaa aaacaacaga taataataat ttgagaatga acaaaaggac catatcattt   5040
attaactctt atccatccat ttgcattttg atgtccgaaa acaaaaactg aaagaacaca   5100
gtaaattaca agcagaacaa atgatagaag aaaacagctt ttccaatgcc ataatactca   5160
aacttagtag gattctggtg tgtgggcaat gaaacatcga ttcagagatt cgtgggggac   5220
tcaaggatag gcggcggttg ggtgtgcgac atgtccgcca catcccaaat ctcctcaagg   5280
aaaggcggca gctttctgtt cttgagcttg agggagatgc acatgttgga gttttgcatt   5340
ccgagcgtgc gtagctcaga gaggattgag aggatcttgc cgtatatgac ggacgaacgc   5400
gccgaaccgg aaagttggtt caggatatag atgcggagcg tattcaggta gtaccgctgg   5460
atttcctcca ccagttgcgg ctgctccaac cctggccggt cagaaaagat gacgacagcc   5520
gtgagcagcg cgtaatggat gttgtccaac gccatagagt acatgcaccg gcagaagtgc   5580
agtagatcct cgatgacttc ggccatgcca gccttgcggt agttatccct ggtgtacgct   5640
tggttgttag cgaacagaat actgtcggag gccgcatcgt atcgtcgcgc gactcggagc   5700
atcattacct cacttgagca agccttgagc agcgtaattt gatctggctg gctgatcttg   5760
gcgaaccctg gcaatccctt agcgaactcc acgataagtt ggaccgtgag gatagtcatc   5820
tccgtgatct ggcggaaggg agtgtccgat tcttcgtttt catcgtccgc ttgctgccac   5880
gtctgcgtaa tccttttaag atcctcatca gaaggctgct cgtacccgtc ttgataccag   5940
```

```
atgagcctgg cgataaggaa ctgctggttg gctgtcaact gggggatgtt tttctgccgg   6000
tttgtcacca acagcttgtc ggagagaaac cttgggacaa cctcgtgaat ccttgctgct   6060
tcaggaggtg gaggttcaca ctgcataatg ggcggcatgt ggtcgtccac cgtcgtcgtg   6120
ctgacaggca gtttgtcctt ctccttctgt gctttcttct ctttccgctt catggcgcac   6180
tgagtctcgg gtactacgca ctcaggccgt gatattctcc tagacccgcc cgatacagtc   6240
aactgtcttt gacctttgtt actactctcc tccgatgatg atgtcgcact tattctatgc   6300
tgtctcaatg ttagaggcat atcagtctcc actgaagcca atctatctgt gacggcatcc   6360
ttgttcacat tatcttgtac aaataatccg gtaagaagtg cttttatatc ctgtaaagaa   6420
tccattttca aaatcatgtc aaggtcctcc cttggaaaaa tcagtagaaa tagctgttcc   6480
agtctttcta gccttgattc cacttctgtc agatgtgccc tagtcagcgg agaccttttg   6540
gttttgggag agtagcgaca ctcccagttg ttcttcagac acttggcgca cttcggtttt   6600
tctttggagc acttgagctt tttaagtcgg caaatatcgc aggcttgttc gatagaagaa   6660
agtagcttca tcccgccgaa ctccccgcct gatattcttc tggaggttcc aagcaacttc   6720
ccaccgtact cgtcaattcc aagggcatcg gtaaacatct gctcaaactc gaagtcggcc   6780
atatccagag cgccgtaggg ggcggagtcg tggggggtaa atcccggacc tggggaatcc   6840
ccgtccccca acatgtccag atcgaaatcg tctagcgcgt cagcgtgagc catcgccacg   6900
tcctcgccgt ctaagtggag ttcgtccccc aggctgacat cggtcggggg ggccatggtg   6960
gcgctagccc tgcaggtctg gaggatctgc tagagtcagc ttgtcgcgtg tcctctccaa   7020
atgaaatgaa cttccttata tagaggaagg gtcttgcgaa ggatagtggg attgtgcgtc   7080
atcccttacg tcagtggaga tatcacatca atccacttgc tttgaagacg tggttggaac   7140
gtcttctttt tccacgatgc tcctcgtggg tgggggtcca tctttgggac cactgtcggc   7200
agaggcatct tcaacgatgg cctttccttt atcgcaatga tggcatttgt aggagccacc   7260
ttccttttcc actatcttca caataaagtg acagatagct gggcaatgga atccgaggag   7320
gtttccggat attacccttt gttgaaaagt ctcacatcgg accatcacat caatccactt   7380
gctttgaaga cgtggttgga acgtcttctt tttccacgat gctcctcgtg ggtgggggtc   7440
catctttggg accactgtcg gcagaggcat cttcaacgat ggcctttcct ttatcgcaat   7500
gatggcattt gtaggagcca ccttcctttt ccactatctt cacaataaag tgacagatag   7560
ctgggcaatg gaatccgagg aggtttccgg atattaccct ttgttgaaaa gtctcacatc   7620
ggaccacgcg tcacagttga ggtatttcgg atcgtggcga tcgcaagggc gaattcgacc   7680
cagctttctt gtacaaagtg gtgatcggtc cggttcggct gcggccgcat taccctgtta   7740
tccctaatct cgtttaacta tgactctctt aaggtagcca aattccggaa aacgacttaa   7800
tcagctaata caaactatca gtgtttgaca ggatatattg gcgggtaaac ctaagagaaa   7860
agagcgttta ttagaataat cggatattta aaagggcgtg aaaaggttta tccgttcgtc   7920
catttgtatg tgcatgcggc tggggcgagc accagacgga gcaccgccag gatcacgagc   7980
catatcctga cgaatgggtt ctcgtccaac gcccctttat cgacagtatg tgaatttgca   8040
gtgtggccgc gatcaacgca cactggcctt gggtctgaag ggtgatcttc aaaacgaacc   8100
cccgtcttgg tggtcagtgt gatgggcaca tcgcttactc ctcagtcacc ctttgagcca   8160
gataattaag aggcaaatgc aattggctca ggctgccatc gtcccccccgt gcgaaacctg   8220
cacgtccgcg tcaaagaaat aaccggcacc tcttgctgtt tttatcagtt gagggcttga   8280
cggatcagcc tcaagtttgc ggcgcagcct caaaatgaga acatctatac tcctgtcata   8340
```

```
aacctcctcg tcgcgtactc gactggcaat gagaagttgc tcgcgcgata gaacgtcgcg   8400
gggtttctct aaaaacgcga ggagaagatt gaactcacct gccgtaagtt tcacctcacc   8460
gccagcttcg gacatcaagc gacgttgcct gagattaagt gtccagtcag taaaacaaaa   8520
agaccgtcgg tctttggagc ggacaacgtt ggggcgcacg cgcaaggcaa cccgaatgcg   8580
tgctagaaac tctctgatac tgaacggctt agcgataaaa tcacttgctc ctagctcaag   8640
tgcaacaact ttatccgtct cctcaaggcg gtcgccactg ataattatga ttggaatatc   8700
agactttgcc gccagattac gaacgatctc aagcccatct tcacgaccta aatctagatc   8760
aacaaccacg acatcgaccg tcgcggaaga gagtactctt gtgaactggg tgctgtcggc   8820
taccgcggtc actttgaagg cgtggatcgt aaggtattca ataataagat gccgcatagc   8880
gacgtcgtca tcgacaagaa gaacgtgttt caacggctca cctttcaatc taaaatctga   8940
acccttgttc acagcgcttg agaaattttc acgtgaagga tgtacaatca tctccagcta   9000
aatgggcagt tcgtcagaat tgcggctgac cgcggatgac aaaaatgcga accaagtatt   9060
tcaattttat gacaaaaatt ctcaatcgtt gttacaagtg aaacgcttcg aggttacagc   9120
tactattgat ttaggagatc gcctatggtc tcgccccggc gtcgtgcgtc cgccgcgagc   9180
cgcatgccaa ccacagggtt cccctcggga tcaaagtact ttgatccaac ccctccgctg   9240
ctatagtgca gtcggcttct gacgttcagt gcagccgtct tctgaaaacg acatgtcgca   9300
caagtcctaa gttacgcgac aggctgccgc cctgcccttt tcctggcgtt ttcttgtcgc   9360
gtgttttagt cgcataaagt agaatacttg cgactagaac cggagacatt acgccatgaa   9420
caagagcgcc gccgctggcc tgctgggcta tgcccgcgtc agcaccgacg accaggactt   9480
gaccaaccaa cgggccgaac tgcacgcggc cggctgcacc aagctgtttt ccgagaagat   9540
caccggcacc aggcgcgacc gcccggagct ggccaggatg cttgaccacc tacgccctgg   9600
cgacgttgtg acagtgacca ggctagaccg cctggcccgc agcacccgcg acctactgga   9660
cattgccgag cgcatccagg aggccggcgc gggcctgcgt agcctggcag agccgtgggc   9720
cgacaccacc acgccggccg gccgcatggt gttgaccgtg ttcgccggca ttgccgagtt   9780
cgagcgttcc ctaatcatcg accgcacccg gagcgggcgc gaggccgcca aggcccgagg   9840
cgtgaagttt ggcccccgcc ctaccctcac cccggcacag atcgcgcacg cccgcgagct   9900
gatcgaccag gaaggccgca ccgtgaaaga ggcggctgca ctgcttggcg tgcatcgctc   9960
gaccctgtac cgcgcacttg agcgcagcga ggaagtgacg cccaccgagg ccaggcggcg  10020
cggtgccttc cgtgaggacg cattgaccga ggccgacgcc ctggctgctg ctgagaatga  10080
acgccaagag gaacaagcat gaaaccgcac caggacggcc aggacgaacc gtttttcatt  10140
accgaagaga tcgaggcgga gatgatcgcg gccgggtacg tgttcgagcc gcccgcgcac  10200
gtctcaaccg tgcggctgca tgaaatcctg gccggtttgt ctgatgccaa gctggcggcc  10260
tggccggcca gcttggccgc tgaagaaacc gagcgccgcc gtctaaaaag gtgatgtgta  10320
tttgagtaaa acagcttgcg tcatgcggtc gctgcgtata tgatgcgatg agtaaataaa  10380
caaatacgca aggggaacgc atgaaggtta tcgctgtact taaccagaaa ggcgggtcag  10440
gcaagacgac catcgcaacc catctagccc gcgccctgca actcgctggg gccgatgttc  10500
tgttagtcga ttccgatccc cagggcagtg cccgcgattg ggcggccgtg cgggaagatc  10560
aaccgctaac cgttgtcggc atcgaccgcc cgacgattga ccgcgacgtg aaggccatcg  10620
gccggcgcga cttcgtagtg atcgacggag cgccccaggc ggcggacttg gctgtgtccg  10680
```

```
cgatcaaggc agccgacttc gtgctgattc cggtgcagcc aagcccttac gacatatggg  10740
ccaccgccga cctggtggag ctggttaagc agcgcattga ggtcacggat ggaaggctac  10800
aagcggcctt tgtcgtgtcg cgggcgatca aaggcacgcg catcggcggt gaggttgccg  10860
aggcgctggc cgggtacgag ctgcccattc ttgagtcccg tatcacgcag cgcgtgagct  10920
acccaggcac tgccgccgcc ggcacaaccg ttctttaatc agaacccgag ggcgacgctg  10980
cccgcgaggt ccaggcgctg gccgctgaaa ttaaatcaaa actcatttga gttaatgagg  11040
taaagagaaa atgagcaaaa gcacaaacac gctaagtgcc ggccgtccga gcgcacgcag  11100
cagcaaggct gcaacgttgg ccagcctggc agacacgcca gccatgaagc gggtcaactt  11160
tcagttgccg gcggaggatc acaccaagct gaagatgtac gcggtacgcc aaggcaagac  11220
cattaccgag ctgctatctg aatacatcgc gcagctacca gagtaaatga gcaaatgaat  11280
aaatgagtag atgaatttta gcggctaaag gaggcggcat ggaaaatcaa gaacaaccag  11340
gcaccgacgc cgtggaatgc cccatgtgtg gaggaacggg cggttggcca ggcgtaagcg  11400
gctgggttgc ctgccggccc tgcaatggca ctggaacccc caagcccgag gaatcggcgt  11460
gagcggtcgc aaaccatccg gcccggtaca aatcggcgcg gcgctgggtg atgacctggt  11520
ggagaagttg aaggccgcgc aggccgccca gcggcaacgc atcgaggcag aagcacgccc  11580
cggtgaatcg tggcaagctg ctgctgatcg aatccgcaaa gaatcccggc aaccgccggc  11640
agccggtgcg ccgtcgatta ggaagccgcc caagggcgac gagcaaccag atttttcgt  11700
tccgatgctc tatgacgtgg gcacccgcga tagtcgcagc atcatggacg tggccgtttt  11760
ccgtctgtcg aagcgtgacc gacgagctgg cgaggtgatc cgctacgagc ttccagacgg  11820
gcacgtagag gtttccgcag ggccggccgg catggccagt gtgtgggatt acgacctggt  11880
actgatggcg gtttcccatc taaccgaatc catgaaccga taccgggaag ggaagggaga  11940
caagcccggc cgcgtgttcc gtccacacgt tgcggacgta ctcaagttct gccggcgagc  12000
cgatggcgga aagcagaaag acgacctggt agaaacctgc attcggttaa acaccacgca  12060
cgttgccatg cagcgtacca agaaggccaa gaacggccgc ctggtgacgg tatccgaggg  12120
tgaagccttg attagccgct acaagatcgt aaagagcgaa accgggcggc cggagtacat  12180
cgagatcgaa ctggctgatt ggatgtaccg cgagatcaca gaaggcaaga acccggacgt  12240
gctgacggtt caccccgatt actttttgat cgaccccggc atcggccgtt ttctctaccg  12300
cctggcacgc cgcgccgcag gcaaggcaga agccagatgg ttgttcaaga cgatctacga  12360
acgcagtggc agcgccggag agttcaagaa gttctgtttc accgtgcgca agctgatcgg  12420
gtcaaatgac ctgccggagt acgatttgaa ggaggaggcg gggcaggctg gcccgatcct  12480
agtcatgcgc taccgcaacc tgatcgaggg cgaagcatcc gccggttcct aatgtacgga  12540
gcagatgcta gggcaaattg ccctagcagg ggaaaaaggt cgaaaaggtc tctttcctgt  12600
ggatagcacg tacattggga acccaaagcc gtacattggg aaccggaacc cgtacattgg  12660
gaacccaaag ccgtacattg ggaaccggtc acacatgtaa gtgactgata taaaagagaa  12720
aaaaggcgat ttttccgcct aaaactcttt aaaacttatt aaaactctta aaacccgcct  12780
ggcctgtgca taactgtctg gccagcgcac agccgaagag ctgcaaaaag cgcctaccct  12840
tcggtcgctg cgctccctac gccccgccgc ttcgcgtcgg cctatcacgg ccgctggccg  12900
ctcaaaaatg gctggcctac ggccaggcaa tctaccaggg cgcggacaag ccgcgccgtc  12960
gccactcgac cgccggcgcc cacatcaagg caccctgcct cgcgcgtttc ggtgatgacg  13020
gtgaaaacct ctgacacatg cagctcccgg agacggtcac agcttgtctg taagcggatg  13080
```

```
ccgggagcag acaagcccgt cagggcgcgt cagcgggtgt tggcgggtgt cggggcgcag  13140
ccatgaccca gtcacgtagc gatagcggag tgtatactgg cttaactatg cggcatcaga  13200
gcagattgta ctgagagtgc accatatgcg gtgtgaaata ccgcacagat gcgtaaggag  13260
aaaataccgc atcaggcgct cttccgcttc ctcgctcact gactcgctgc gctcggtcgt  13320
tcggctgcgg cgagcggtat cagctcactc aaaggcggta atacggttat ccacagaatc  13380
aggggataac gcaggaaaga acatgtgagc aaaaggccag caaaaggcca ggaaccgtaa  13440
aaaggccgcg ttgctggcgt ttttccatag gctccgcccc cctgacgagc atcacaaaaa  13500
tcgacgctca agtcagaggt ggcgaaaccc gacaggacta taaagatacc aggcgtttcc  13560
ccctggaagc tccctcgtgc gctctcctgt tccgaccctg ccgcttaccg gatacctgtc  13620
cgcctttctc ccttcgggaa gcgtggcgct ttctcatagc tcacgctgta ggtatctcag  13680
ttcggtgtag gtcgttcgct ccaagctggg ctgtgtgcac gaaccccccg ttcagcccga  13740
ccgctgcgcc ttatccggta actatcgtct tgagtccaac ccggtaagac acgacttatc  13800
gccactggca gcagccactg gtaacaggat tagcagagcg aggtatgtag gcggtgctac  13860
agagttcttg aagtggtggc ctaactacgg ctacactaga aggacagtat ttggtatctg  13920
cgctctgctg aagccagtta ccttcggaaa aagagttggt agctcttgat ccggcaaaca  13980
aaccaccgct ggtagcggtg gtttttttgt ttgcaagcag cagattacgc gcagaaaaaa  14040
aggatctcaa gaagatcctt tgatcttttc tacggggtct gacgctcagt ggaacgaaaa  14100
ctcacgttaa gggattttgg tcatgcattc taggtactaa aacaattcat ccagtaaaat  14160
ataatatttt attttctccc aatcaggctt gatccccagt aagtcaaaaa atagctcgac  14220
atactgttct tccccgatat cctccctgat cgaccggacg cagaaggcaa tgtcatacca  14280
cttgtccgcc ctgccgcttc tcccaagatc aataaagcca cttactttgc catctttcac  14340
aaagatgttg ctgtctccca ggtcgccgtg ggaaaagaca agttcctctt cgggcttttc  14400
cgtctttaaa aaatcataca gctcgcgcgg atctttaaat ggagtgtctt cttcccagtt  14460
ttcgcaatcc acatcggcca gatcgttatt cagtaagtaa tccaattcgg ctaagcggct  14520
gtctaagcta ttcgtatagg gacaatccga tatgtcgatg gagtgaaaga gcctgatgca  14580
ctccgcatac agctcgataa tcttttcagg gctttgttca tcttcatact cttccgagca  14640
aaggacgcca tcggcctcac tcatgagcag attgctccag ccatcatgcc gttcaaagtg  14700
caggaccttt ggaacaggca gctttccttc cagccatagc atcatgtcct tttcccgttc  14760
cacatcatag gtggtccctt tataccggct gtccgtcatt tttaaatata ggttttcatt  14820
ttctcccacc agcttatata ccttagcagg agacattcct tccgtatctt ttacgcagcg  14880
gtatttttcg atcagttttt tcaattccgg tgatattctc attttagcca tttattattt  14940
ccttcctctt ttctacagta tttaaagata ccccaagaag ctaattataa caagacgaac  15000
tccaattcac tgttccttgc attctaaaac cttaaatacc agaaaacagc tttttcaaag  15060
ttgttttcaa agttggcgta taacatagta tcgacggagc cgattttgaa accgcggtga  15120
tcacaggcag caacgctctg tcatcgttac aatcaacatg ctaccctccg cgagatcatc  15180
cgtgtttcaa acccggcagc ttagttgccg ttcttccgaa tagcatcggt aacatgagca  15240
aagtctgccg ccttacaacg gctctcccgc tgacgccgtc ccggactgat gggctgcctg  15300
tatcgagtgg tgattttgtg ccgagctgcc ggtcggggag ctgttggctg gctggtggca  15360
ggatatattg tggtgtaaac aaattgacgc ttagacaact taataacaca ttgcggacgt  15420
```

```
ttttaatgta ctgaattaac gccgaattaa tgtcgac                          15457

<210> SEQ ID NO 58
<211> LENGTH: 602
<212> TYPE: PRT
<213> ORGANISM: Escherichia coli

<400> SEQUENCE: 58

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Gln Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365
```

```
Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Val His Gly Asn Ile Ser Pro Leu Ala Glu Ala Thr Arg
            420                 425                 430

Lys Leu Asp Pro Thr Arg Pro Ile Thr Cys Val Asn Val Met Phe Cys
        435                 440                 445

Asp Ala His Thr Asp Thr Ile Ser Asp Leu Phe Asp Val Leu Cys Leu
    450                 455                 460

Asn Arg Tyr Tyr Gly Trp Tyr Val Gln Ser Gly Asp Leu Glu Thr Ala
465                 470                 475                 480

Glu Lys Val Leu Glu Lys Glu Leu Leu Ala Trp Gln Glu Lys Leu His
                485                 490                 495

Gln Pro Ile Ile Ile Thr Glu Tyr Gly Val Asp Thr Leu Ala Gly Leu
            500                 505                 510

His Ser Met Tyr Thr Asp Met Trp Ser Glu Glu Tyr Gln Cys Ala Trp
        515                 520                 525

Leu Asp Met Tyr His Arg Val Phe Asp Arg Val Ser Ala Val Val Gly
    530                 535                 540

Glu Gln Val Trp Asn Phe Ala Asp Phe Ala Thr Ser Gln Gly Ile Leu
545                 550                 555                 560

Arg Val Gly Gly Asn Lys Lys Gly Ile Phe Thr Arg Asp Arg Lys Pro
                565                 570                 575

Lys Ser Ala Ala Phe Leu Leu Gln Lys Arg Trp Thr Gly Met Asn Phe
            580                 585                 590

Gly Glu Lys Pro Gln Gln Gly Gly Lys Gln
        595                 600
```

```
<210> SEQ ID NO 59
<211> LENGTH: 12143
<212> TYPE: DNA
<213> ORGANISM: Artificial Sequence
<220> FEATURE:
<223> OTHER INFORMATION: Polynucleotide Vector

<400> SEQUENCE: 59

taactataac ggtcctaagg tagcgacgta cgtgcggagg gacactatca atcgtagctc     60

gagtttgata tccaaaatag acgagaacaa taagcaaaaa ctcttagttt tgaaataaat    120

caacaatccc gagggttgtc acatatacat caaaaacgaa aatccatata gcaaaaaaaa    180

actctaaatt accgttcgac aaaaaagaaa actgataaga catttgctaa acattaaaaa    240

tcgattcaga agaactcgtc aagaaggcga tagaaggcga tgcgctgcga atcgggagcg    300

gcgataccgt aaagcacgag gaagcggtca gcccattcgc cgccaagctc ttcagcaata    360

tcacgggtag ccaacgctat gtcctgatac ctatcagcca caccaagcct tccacagtcg    420

atgaatccag aaaagcggcc attttccacc atgatattcg gcaagcaggc atcgccatgg    480

gtcacgacga gatcctcgcc gtctggcatc ctcgccttga gcctggcgaa cagttcggct    540

ggcgcgagcc cctgatgctc ttcgtccaga tcatcctgat cgacaagacc ggcttccatc    600

cgagtacgtg ctcgctcgat gcgatgtttc gcttggtggt cgaatgggca ggtagccgga    660

tcaagcgtat gcagccgccg cattgcatca gccatgatgg atactttctc ggcaggagca    720
```

```
aggtgagatg acaggagatc ctgccccggc acttcgccca atagcagcca gtcccttccc    780
gcttcagtga caacgtcgag cacagcagcg caaggaacgc ccgtcgtggc cagccacgat    840
agccgcgctg cctcgtcttg aagttcattc agggcaccgg acaggtcggt cttgacaaaa    900
agaactggcc ttccctgcgc tgacagccgg aacacggcgg catcagagca gccgattgtc    960
tgttgtgccc agtcatagcc gaatagcctc tccacccaag cggccggaga acctgcgtgc   1020
aatccatctt gttcaatcat gtttaaacta ccaccacgga gacggagcac gagatggaga   1080
gttgactcct tctggatgtt gtagtcggca agagtacgac catcctcaag ctgctttccg   1140
gcgaaaatca aacgctgctg gtctggggga atcccttcct tgtcctggat cttggctttg   1200
acattgtcga tggtgtcgga agactcaacc tctagggtga tcgtcttccc cgttaaggtc   1260
ttcacgaaga tctgcatttt tgcgctagcc cgaaaagcac acaatgccct gcaggcaaac   1320
ttacaaattt ctctgaagtt gtatcctcag tacttcaaag aaaatagctt acaccaaatt   1380
ttttcttgtt ttcacaaatg ccgaacttgg ttccttatat aggaaaactc aagggcaaaa   1440
atgacacgga aaaatataaa aggataagta gtgggggata agattccttt gtgataaggt   1500
tactttccgc ccttacattt tccaccttac atgtgtcctc tatgtctctt tcacaatcac   1560
cgaccttatc ttcttctttt cattgttgtc gtcagtgctt acgtcttcaa gattcttttc   1620
ttcgcctggt tcttcttttt caatttctat gtattcttct tcgtattctg gcagtatagg   1680
atcttgtatc tgtacattct tcatttttga acataggttg aatatgtgcc gcatattgat   1740
ctgcttcttg ctgagttcac ataatacttc catagttttt cccgtaaaca ttggattctt   1800
gatgctacat cttggataat taccttctga cgcgtcatga gaagttcact cgtgacgaag   1860
ggcgcgccat cacaagtttg tacaaaaaag caggctccga attcgccctt gcgatcgccg   1920
gaccgctcga gcccgggcgg ccgcagccga accggaccgc gttgctcacg ttacagctcc   1980
attcctcgag ccccgatcta gtaacataga tgacaccgcg cgcgataatt tatcctagtt   2040
tgcgcgctat attttgtttt ctatcgcgta ttaaatgtat aattgcggga ctctaatcat   2100
aaaaacccat ctcataaata acgtcatgca ttacatgtta attattacat gcttaacgta   2160
attcaacaga aattatatga taatcatcgc aagaccggca acaggattca atcttaagaa   2220
actttattgc caaatgtttg aacgatcggg aagtcatcga tatcctgcag ggcaacactg   2280
tggaggacaa cagtctcaac tgttagccca ggcccaaatc caaaaagaac accccactca   2340
agcccttcac cagtagttcc taaaccttct ttggctgagg cctttctcat ttcatccaaa   2400
ataaacagta cacaagcact tgacatgtta ccatagtcac ttaacacatt ccttgtagcc   2460
ttaagtttct cgggctttag gcccaacttt atttcaactt ggtccaaaat tgcaggccca   2520
cctggatgag caatccagaa tagagagttc caatcagaaa tgcccaaagg tttaaatgct   2580
tcctcaaggc tcttctcaat attttttgag atcagcccag gaacatcttt gagtaagtgg   2640
aatgtaagcc caacttcacg gagatggcca tcaatagcac catggctatc tgggagaaga   2700
gtttgggctg ctgaaacgag ctcgaacaaa ggcctctcga ctcctggaat tggatcagaa   2760
cctataatga tcgcgcctgc cccatcacca aaaagggctt ggccaactaa actatccaca   2820
cgtggttaaa cacatctgca caatcacaaa attaaaatgc ttatttcatg taaaataact   2880
taaataaaaa ccaatatatc tgtcttttta tacaataggt gttcacgagg tgaaaagatt   2940
gtaaaaatat gatattatta gatctttcgt caatgtttta tggtttgtca cgattcctca   3000
aaaatgagta ataaattttg agtagtgctt tagcgtttat gacctttgaa aggggaagga   3060
ctgaaggagg cttaccacaa ggcaggtagt gtggatagtt tagttggcca agcccttttt   3120
```

```
ggtgatgggg caggcgcgat cattataggt tctgatccaa ttccaggagt cgagaggcct   3180
ttgttcgagc tcgtttcagc agcccaaact cttctcccag atagccatgg tgctattgat   3240
ggccatctcc gtgaagttgg gcttacattc cacttactca aagatgttcc tgggctgatc   3300
tcaaaaaata ttgagaagag ccttgaggaa gcatttaaac ctttgggcat ttctgattgg   3360
aactctctat tctggattgc tcatccaggt gggcctgcaa ttttggacca agttgaaata   3420
aagttgggcc taaagcccga gaaacttaag gctacaagga atgtgttaag tgactatggt   3480
aacatgtcaa gtgcttgtgt actgtttatt ttggatgaaa tgagaaaggc ctcagccaaa   3540
gaaggtttag gaactactgg tgaagggctt gagtggggtg ttcttttttgg atttgggcct   3600
gggctaacag ttgagactgt tgtcctccac agtgttgccc tgcaggtctg gaggatctgc   3660
tagagtcagc ttgtcgcgtg tcctctccaa atgaaatgaa cttccttata tagaggaagg   3720
gtcttgcgaa ggatagtggg attgtgcgtc atcccttacg tcagtggaga tatcacatca   3780
atccacttgc tttgaagacg tggttggaac gtcttctttt tccacgatgc tcctcgtggg   3840
tgggggtcca tctttgggac cactgtcggc agaggcatct tcaacgatgg cctttccttt   3900
atcgcaatga tggcatttgt aggagccacc ttccttttcc actatcttca caataaagtg   3960
acagatagct gggcaatgga atccgaggag gtttccggat attacccttt gttgaaaagt   4020
ctcacatcgg accatcacat caatccactt gctttgaaga cgtggttgga acgtcttctt   4080
tttccacgat gctcctcgtg ggtgggggtc catctttggg accactgtcg gcagaggcat   4140
cttcaacgat ggcctttcct ttatcgcaat gatggcattt gtaggagcca ccttcctttt   4200
ccactatctt cacaataaag tgacagatag ctgggcaatg gaatccgagg aggtttccgg   4260
atattaccct ttgttgaaaa gtctcacatc ggaccacgcg tcacagttga ggtatttcgg   4320
atcgtggcga tcgctatccc caggcgcgcc aagggcgaat tcgacccagc tttcttgtac   4380
aaagtggtga tcggtccggt tcggctgcgg ccgcattacc ctgttatccc taatctcgtt   4440
taactatgac tctcttaagg tagccaaatt ccggaaaacg acttaatcag ctaatacaaa   4500
ctatcagtgt ttgacaggat atattggcgg gtaaacctaa gagaaaagag cgtttattag   4560
aataatcgga tatttaaaag ggcgtgaaaa ggtttatccg ttcgtccatt tgtatgtgca   4620
tgcggctggg gcgagcacca gacggagcac cgccaggatc acgagccata tcctgacgaa   4680
tgggttctcg tccaacgccc ctttatcgac agtatgtgaa tttgcagtgt ggccgcgatc   4740
aacgcacact ggccttgggt ctgaagggtg atcttcaaaa cgaacccccg tcttggtggt   4800
cagtgtgatg ggcacatcgc ttactcctca gtcacccttt gagccagata attaagaggc   4860
aaatgcaatt ggctcaggct gccatcgtcc ccccgtgcga aacctgcacg tccgcgtcaa   4920
agaaataacc ggcacctctt gctgttttta tcagttgagg gcttgacgga tcagcctcaa   4980
gtttgcggcg cagcctcaaa atgagaacat ctatactcct gtcataaacc tcctcgtcgc   5040
gtactcgact ggcaatgaga agttgctcgc gcgatagaac gtcgcggggt ttctctaaaa   5100
acgcgaggag aagattgaac tcacctgccg taagtttcac ctcaccgcca gcttcggaca   5160
tcaagcgacg ttgcctgaga ttaagtgtcc agtcagtaaa acaaaaagac cgtcggtctt   5220
tggagcggac aacgttgggg cgcacgcgca aggcaacccg aatgcgtgct agaaactctc   5280
tgatactgaa cggcttagcg ataaaatcac ttgctcctag ctcaagtgca acaactttat   5340
ccgtctcctc aaggcggtcg ccactgataa ttatgattgg aatatcagac tttgccgcca   5400
gattacgaac gatctcaagc ccatcttcac gacctaaatc tagatcaaca accacgacat   5460
```

```
cgaccgtcgc ggaagagagt actcttgtga actgggtgct gtcggctacc gcggtcactt   5520
tgaaggcgtg gatcgtaagg tattcaataa taagatgccg catagcgacg tcgtcatcga   5580
caagaagaac gtgtttcaac ggctcacctt tcaatctaaa atctgaaccc ttgttcacag   5640
cgcttgagaa attttcacgt gaaggatgta caatcatctc cagctaaatg ggcagttcgt   5700
cagaattgcg gctgaccgcg gatgacaaaa atgcgaacca agtatttcaa ttttatgaca   5760
aaaattctca atcgttgtta caagtgaaac gcttcgaggt tacagctact attgatttag   5820
gagatcgcct atggtctcgc cccggcgtcg tgcgtccgcc gcgagccgca tgccaaccac   5880
agggttcccc tcgggatcaa agtactttga tccaacccct ccgctgctat agtgcagtcg   5940
gcttctgacg ttcagtgcag ccgtcttctg aaaacgacat gtcgcacaag tcctaagtta   6000
cgcgacaggc tgccgccctg cccttttcct ggcgttttct tgtcgcgtgt tttagtcgca   6060
taaagtagaa tacttgcgac tagaaccgga gacattacgc catgaacaag agcgccgccg   6120
ctggcctgct gggctatgcc cgcgtcagca ccgacgacca ggacttgacc aaccaacggg   6180
ccgaactgca cgcggccggc tgcaccaagc tgttttccga gaagatcacc ggcaccaggc   6240
gcgaccgccc ggagctggcc aggatgcttg accacctacg ccctggcgac gttgtgacag   6300
tgaccaggct agaccgcctg gcccgcagca cccgcgacct actggacatt gccgagcgca   6360
tccaggaggc cggcgcgggc ctgcgtagcc tggcagagcc gtgggccgac accaccacgc   6420
cggccggccg catggtgttg accgtgttcg ccggcattgc cgagttcgag cgttccctaa   6480
tcatcgaccg cacccggagc gggcgcgagg ccgccaaggc ccgaggcgtg aagtttggcc   6540
cccgccctac cctcaccccg gcacagatcg cgcacgcccg cgagctgatc gaccaggaag   6600
gccgcaccgt gaaagaggcg gctgcactgc ttggcgtgca tcgctcgacc ctgtaccgcg   6660
cacttgagcg cagcgaggaa gtgacgccca ccgaggccag gcggcgcggt gccttccgtg   6720
aggacgcatt gaccgaggcc gacgccctgg ctgctgctga gaatgaacgc caagaggaac   6780
aagcatgaaa ccgcaccagg acggccagga cgaaccgttt ttcattaccg aagagatcga   6840
ggcggagatg atcgcggccg ggtacgtgtt cgagccgccc gcgcacgtct caaccgtgcg   6900
gctgcatgaa atcctggccg gtttgtctga tgccaagctg gcggcctggc cggccagctt   6960
ggccgctgaa gaaaccgagc gccgccgtct aaaaaggtga tgtgtatttg agtaaaacag   7020
cttgcgtcat gcggtcgctg cgtatatgat gcgatgagta aataaacaaa tacgcaaggg   7080
gaacgcatga aggttatcgc tgtacttaac cagaaaggcg ggtcaggcaa gacgaccatc   7140
gcaacccatc tagcccgcgc cctgcaactc gctggggccg atgttctgtt agtcgattcc   7200
gatccccagg gcagtgcccg cgattgggcg gccgtgcggg aagatcaacc gctaaccgtt   7260
gtcggcatcg accgcccgac gattgaccgc gacgtgaagg ccatcggccg gcgcgacttc   7320
gtagtgatcg acggagcgcc ccaggcggcg gacttggctg tgtccgcgat caaggcagcc   7380
gacttcgtgc tgattccggt gcagccaagc ccttacgaca tatgggccac cgccgacctg   7440
gtggagctgg ttaagcagcg cattgaggtc acggatggaa ggctacaagc ggcctttgtc   7500
gtgtcgcggg cgatcaaagg cacgcgcatc ggcggtgagg ttgccgaggc gctggccggg   7560
tacgagctgc ccattcttga gtcccgtatc acgcagcgcg tgagctaccc aggcactgcc   7620
gccgccggca caaccgttct ttaatcagaa cccgagggcg acgctgcccg cgaggtccag   7680
gcgctggccg ctgaaattaa atcaaaactc atttgagtta atgaggtaaa gagaaaatga   7740
gcaaaagcac aaacacgcta agtgccggcc gtccgagcgc acgcagcagc aaggctgcaa   7800
cgttggccag cctggcagac acgccagcca tgaagcgggt caactttcag ttgccggcgg   7860
```

```
aggatcacac caagctgaag atgtacgcgg tacgccaagg caagaccatt accgagctgc   7920
tatctgaata catcgcgcag ctaccagagt aaatgagcaa atgaataaat gagtagatga   7980
attttagcgg ctaaaggagg cggcatggaa aatcaagaac aaccaggcac cgacgccgtg   8040
gaatgcccca tgtgtggagg aacgggcggt tggccaggcg taagcggctg ggttgcctgc   8100
cggccctgca atggcactgg aacccccaag cccgaggaat cggcgtgagc ggtcgcaaac   8160
catccggccc ggtacaaatc ggcgcggcgc tgggtgatga cctggtggag aagttgaagg   8220
ccgcgcaggc cgcccagcgg caacgcatcg aggcagaagc acgccccggt gaatcgtggc   8280
aagctgctgc tgatcgaatc cgcaaagaat cccggcaacc gccggcagcc ggtgcgccgt   8340
cgattaggaa gccgcccaag ggcgacgagc aaccagattt tttcgttccg atgctctatg   8400
acgtgggcac ccgcgatagt cgcagcatca tggacgtggc cgttttccgt ctgtcgaagc   8460
gtgaccgacg agctggcgag gtgatccgct acgagcttcc agacgggcac gtagaggttt   8520
ccgcagggcc ggccggcatg gccagtgtgt gggattacga cctggtactg atggcggttt   8580
cccatctaac cgaatccatg aaccgatacc gggaagggaa gggagacaag cccggccgcg   8640
tgttccgtcc acacgttgcg gacgtactca agttctgccg gcgagccgat ggcggaaagc   8700
agaaagacga cctggtagaa acctgcattc ggttaaacac cacgcacgtt gccatgcagc   8760
gtaccaagaa ggccaagaac ggccgcctgg tgacggtatc cgagggtgaa gccttgatta   8820
gccgctacaa gatcgtaaag agcgaaaccg ggcggccgga gtacatcgag atcgaactgg   8880
ctgattggat gtaccgcgag atcacagaag gcaagaaccc ggacgtgctg acggttcacc   8940
ccgattactt tttgatcgac cccggcatcg gccgttttct ctaccgcctg gcacgccgcg   9000
ccgcaggcaa ggcagaagcc agatggttgt tcaagacgat ctacgaacgc agtggcagcg   9060
ccggagagtt caagaagttc tgtttcaccg tgcgcaagct gatcgggtca aatgacctgc   9120
cggagtacga tttgaaggag gaggcggggc aggctggccc gatcctagtc atgcgctacc   9180
gcaacctgat cgagggcgaa gcatccgccg gttcctaatg tacggagcag atgctagggc   9240
aaattgccct agcaggggaa aaaggtcgaa aaggtctctt tcctgtggat agcacgtaca   9300
ttgggaaccc aaagccgtac attgggaacc ggaacccgta cattgggaac ccaaagccgt   9360
acattgggaa ccggtcacac atgtaagtga ctgatataaa agagaaaaaa ggcgattttt   9420
ccgcctaaaa ctctttaaaa cttattaaaa ctcttaaaac ccgcctggcc tgtgcataac   9480
tgtctggcca gcgcacagcc gaagagctgc aaaaagcgcc tacccttcgg tcgctgcgct   9540
ccctacgccc cgccgcttcg cgtcggccta tcacggccgc tggccgctca aaaatggctg   9600
gcctacggcc aggcaatcta ccagggcgcg gacaagccgc gccgtcgcca ctcgaccgcc   9660
ggcgcccaca tcaaggcacc ctgcctcgcg cgtttcggtg atgacggtga aaacctctga   9720
cacatgcagc tcccggagac ggtcacagct tgtctgtaag cggatgccgg gagcagacaa   9780
gcccgtcagg gcgcgtcagc gggtgttggc gggtgtcggg gcgcagccat gacccagtca   9840
cgtagcgata gcggagtgta tactggctta actatgcggc atcagagcag attgtactga   9900
gagtgcacca tatgcggtgt gaaataccgc acagatgcgt aaggagaaaa taccgcatca   9960
ggcgctcttc cgcttcctcg ctcactgact cgctgcgctc ggtcgttcgg ctgcggcgag  10020
cggtatcagc tcactcaaag gcggtaatac ggttatccac agaatcaggg gataacgcag  10080
gaaagaacat gtgagcaaaa ggccagcaaa aggccaggaa ccgtaaaaag gccgcgttgc  10140
tggcgttttt ccataggctc cgcccccctg acgagcatca caaaaatcga cgctcaagtc  10200
```

```
agaggtggcg aaacccgaca ggactataaa gataccaggc gtttccccct ggaagctccc  10260

tcgtgcgctc tcctgttccg accctgccgc ttaccggata cctgtccgcc tttctccctt  10320

cgggaagcgt ggcgctttct catagctcac gctgtaggta tctcagttcg gtgtaggtcg  10380

ttcgctccaa gctgggctgt gtgcacgaac cccccgttca gcccgaccgc tgcgccttat  10440

ccggtaacta tcgtcttgag tccaacccgg taagacacga cttatcgcca ctggcagcag  10500

ccactggtaa caggattagc agagcgaggt atgtaggcgg tgctacagag ttcttgaagt  10560

ggtggcctaa ctacggctac actagaagga cagtatttgg tatctgcgct ctgctgaagc  10620

cagttacctt cggaaaaaga gttggtagct cttgatccgg caaacaaacc accgctggta  10680

gcggtggttt ttttgtttgc aagcagcaga ttacgcgcag aaaaaaagga tctcaagaag  10740

atcctttgat cttttctacg gggtctgacg ctcagtggaa cgaaaactca cgttaaggga  10800

ttttggtcat gcattctagg tactaaaaca attcatccag taaaatataa tattttattt  10860

tctcccaatc aggcttgatc cccagtaagt caaaaaatag ctcgacatac tgttcttccc  10920

cgatatcctc cctgatcgac cggacgcaga aggcaatgtc ataccacttg tccgccctgc  10980

cgcttctccc aagatcaata aagccactta ctttgccatc tttcacaaag atgttgctgt  11040

ctcccaggtc gccgtgggaa aagacaagtt cctcttcggg cttttccgtc tttaaaaaat  11100

catacagctc gcgcggatct ttaaatggag tgtcttcttc ccagttttcg caatccacat  11160

cggccagatc gttattcagt aagtaatcca attcggctaa gcggctgtct aagctattcg  11220

tatagggaca atccgatatg tcgatggagt gaaagagcct gatgcactcc gcatacagct  11280

cgataatctt ttcagggctt tgttcatctt catactcttc cgagcaaagg acgccatcgg  11340

cctcactcat gagcagattg ctccagccat catgccgttc aaagtgcagg acctttggaa  11400

caggcagctt tccttccagc catagcatca tgtccttttc ccgttccaca tcataggtgg  11460

tccctttata ccggctgtcc gtcattttta aatataggtt ttcattttct cccaccagct  11520

tatatacctt agcaggagac attccttccg tatcttttac gcagcggtat ttttcgatca  11580

gtttttcaa ttccggtgat attctcattt tagccattta ttatttcctt cctcttttct  11640

acagtattta aagatacccc aagaagctaa ttataacaag acgaactcca attcactgtt  11700

ccttgcattc taaaacctta aataccagaa aacagctttt tcaaagttgt tttcaaagtt  11760

ggcgtataac atagtatcga cggagccgat tttgaaaccg cggtgatcac aggcagcaac  11820

gctctgtcat cgttacaatc aacatgctac cctccgcgag atcatccgtg tttcaaaccc  11880

ggcagcttag ttgccgttct tccgaatagc atcggtaaca tgagcaaagt ctgccgcctt  11940

acaacggctc tcccgctgac gccgtcccgg actgatgggc tgcctgtatc gagtggtgat  12000

tttgtgccga gctgccggtc ggggagctgt tggctggctg gtggcaggat atattgtggt  12060

gtaaacaaat tgacgcttag acaacttaat aacacattgc ggacgttttt aatgtactga  12120

attaacgccg aattaatgtc gac                                          12143
```

<210> SEQ ID NO 60
<211> LENGTH: 12931
<212> TYPE: DNA
<213> ORGANISM: Artificial Sequence
<220> FEATURE:
<223> OTHER INFORMATION: Polynucleotide Vector

<400> SEQUENCE: 60

```
taactataac ggtcctaagg tagcgacgta cgtgcggagg gacactatca atcgtagctc     60

gagtttgata tccaaaatag acgagaacaa taagcaaaaa ctcttagttt tgaaataaat    120
```

```
caacaatccc gagggttgtc acatatacat caaaaacgaa aatccatata gcaaaaaaaa    180
actctaaatt accgttcgac aaaaaagaaa actgataaga catttgctaa acattaaaaa    240
tcgattcaga agaactcgtc aagaaggcga tagaaggcga tgcgctgcga atcgggagcg    300
gcgataccgt aaagcacgag gaagcggtca gcccattcgc cgccaagctc ttcagcaata    360
tcacgggtag ccaacgctat gtcctgatac ctatcagcca caccaagcct tccacagtcg    420
atgaatccag aaaagcggcc attttccacc atgatattcg gcaagcaggc atcgccatgg    480
gtcacgacga gatcctcgcc gtctggcatc ctcgccttga gcctggcgaa cagttcggct    540
ggcgcgagcc cctgatgctc ttcgtccaga tcatcctgat cgacaagacc ggcttccatc    600
cgagtacgtg ctcgctcgat gcgatgtttc gcttggtggt cgaatgggca ggtagccgga    660
tcaagcgtat gcagccgccg cattgcatca gccatgatgg atactttctc ggcaggagca    720
aggtgagatg acaggagatc ctgccccggc acttcgccca atagcagcca gtcccttccc    780
gcttcagtga caacgtcgag cacagcagcg caaggaacgc ccgtcgtggc cagccacgat    840
agccgcgctg cctcgtcttg aagttcattc agggcaccgg acaggtcggt cttgacaaaa    900
agaactggcc ttccctgcgc tgacagccgg aacacggcgg catcagagca gccgattgtc    960
tgttgtgccc agtcatagcc gaatagcctc tccacccaag cggccggaga acctgcgtgc   1020
aatccatctt gttcaatcat gtttaaacta ccaccacgga gacggagcac gagatggaga   1080
gttgactcct tctggatgtt gtagtcggca agagtacgac catcctcaag ctgctttccg   1140
gcgaaaatca aacgctgctg gtctggggga atcccttcct tgtcctggat cttggctttg   1200
acattgtcga tggtgtcgga agactcaacc tctagggtga tcgtcttccc cgttaaggtc   1260
ttcacgaaga tctgcatttt tgcgctagcc cgaaaagcac acaatgccct gcaggcaaac   1320
ttacaaattt ctctgaagtt gtatcctcag tacttcaaag aaaatagctt acaccaaatt   1380
ttttcttgtt ttcacaaatg ccgaacttgg ttccttatat aggaaaactc aagggcaaaa   1440
atgacacgga aaaatataaa aggataagta gtgggggata agattccttt gtgataaggt   1500
tactttccgc ccttacattt tccaccttac atgtgtcctc tatgtctctt tcacaatcac   1560
cgaccttatc ttcttctttt cattgttgtc gtcagtgctt acgtcttcaa gattcttttc   1620
ttcgcctggt tcttcttttt caatttctat gtattcttct tcgtattctg gcagtatagg   1680
atcttgtatc tgtacattct tcatttttga acataggttg aatatgtgcc gcatattgat   1740
ctgcttcttg ctgagttcac ataatacttc catagttttt cccgtaaaca ttggattctt   1800
gatgctacat cttggataat taccttctga cgcgtcatga gaagttcact cgtgacgaag   1860
ggcgcgccat cacaagtttg tacaaaaaag caggctccga attcgccctt gcgatcgccg   1920
gaccgctcga gcccgggcgg ccgcagccga accggaccgc gttgctcacg ttacagctcc   1980
attcctcgag ccccgatcta gtaacataga tgacaccgcg cgcgataatt tatcctagtt   2040
tgcgcgctat attttgtttt ctatcgcgta ttaaatgtat aattgcggga ctctaatcat   2100
aaaaacccat ctcataaata acgtcatgca ttacatgtta attattacat gcttaacgta   2160
attcaacaga aattatatga taatcatcgc aagaccggca acaggattca atcttaagaa   2220
actttattgc caaatgtttg aacgatcggg aagtcatcga tacctgcagg actcttgagt   2280
actttcgcca gctcacgttg actttttttcg ctatcactcc tttttagtgt caaaacgtag   2340
gggtcttcga aaatgttgag actttgcaca atctttctca ggctcgccac agttttcgtc   2400
acgatgatat ttgactctgg ggtatagtag ataatagata gaagtggtag ctttactcga   2460
```

```
aggcgaagat ctgctcgatg tatttttggc gtgcagcaaa tggcatccgt ccagatctgg   2520
tcaacacacc aagatcctag agttctactg gcttctgtcc caaatacaaa tggcttccga   2580
aagataggat tgtcttttag aagcgggagc atttgaagat aaagaggagt attgaatttc   2640
gggcccaagg gatcatagta ggcaagagtc tcaggtttac ctttgattga gtactgcagc   2700
aagctgggat cttctgcagt acatatttga ctgtgtagca aaccttcaag ttcttccgca   2760
tcggcgtggt gtagagcatt acgctgcgat ggattccggc atagttaaag aaatcatgga   2820
agtaagactg ctttttcttg ccgttttcgt cggtaatcac cattcccggc gggatagtct   2880
gccagttcag ttcgttgttc acacaaacgg tgatacgtac acttttcccg gcaataacat   2940
acggcgtgac atcggcttca aatggcgtat agccgccctg atgctccatc acttcctgat   3000
tattgaccca cactttgccg taatgagtga ccgcatcgaa acgcagcacg atacgctggc   3060
ctgcccaacc tttcggtata aagacttcgc gctgatacca gacgttgccc gcataattac   3120
gaatatctgc atcggcgaac tgatcgttaa aactgcctgg cacagcaatt gcccggcttt   3180
cttgtaacgc gctttcccac caacgctggt atacacacgt ggttaaacac atctgcacaa   3240
tcacaaaatt aaaatgctta tttcatgtaa aataacttaa ataaaaacca atatatctgt   3300
ctttttatac aataggtgtt cacgaggtga aaagattgta aaaatatgat attattagat   3360
ctttcgtcaa tgttttatgg tttgtcacga ttcctcaaaa atgagtaata aattttgagt   3420
agtgctttag cgtttatgac ctttgaaagg ggaaggactg aaggaggctt accacaaggc   3480
aggtatacca gcgttggtgg gaaagcgcgt tacaagaaag ccgggcaatt gctgtgccag   3540
gcagttttaa cgatcagttc gccgatgcag atattcgtaa ttatgcgggc aacgtctggt   3600
atcagcgcga agtctttata ccgaaaggtt gggcaggcca gcgtatcgtg ctgcgtttcg   3660
atgcggtcac tcattacggc aaagtgtggg tcaataatca ggaagtgatg gagcatcagg   3720
gcggctatac gccatttgaa gccgatgtca cgccgtatgt tattgccggg aaaagtgtac   3780
gtatcaccgt ttgtgtgaac aacgaactga actggcagac tatcccgccg ggaatggtga   3840
ttaccgacga aaacggcaag aaaaagcagt cttacttcca tgatttcttt aactatgccg   3900
gaatccatcg cagcgtaatg ctctacacca cgccgatgcg gaagaacttg aaggtttgct   3960
acacagtcaa atatgtactg cagaagatcc cagcttgctg cagtactcaa tcaaaggtaa   4020
acctgagact cttgcctact atgatccctt gggcccgaaa ttcaatactc ctctttatct   4080
tcaaatgctc ccgcttctaa aagacaatcc tatctttcgg aagccatttg tatttgggac   4140
agaagccagt agaactctag gatcttggtg tgttgaccag atctggacgg atgccatttg   4200
ctgcacgcca aaaatacatc gagcagatct tcgccttcga gtaaagctac cacttctatc   4260
tattatctac tataccccag agtcaaatat catcgtgacg aaaactgtgg cgagcctgag   4320
aaagattgtg caaagtctca acattttcga agacccctac gttttgacac taaaaaggag   4380
tgatagcgaa aaaagtcaac gtgagctggc gaaagtactc aagagtcctg caggtctgga   4440
ggatctgcta gagtcagctt gtcgcgtgtc ctctccaaat gaaatgaact tccttatata   4500
gaggaagggt cttgcgaagg atagtgggat tgtgcgtcat cccttacgtc agtggagata   4560
tcacatcaat ccacttgctt tgaagacgtg gttggaacgt cttctttttc cacgatgctc   4620
ctcgtgggtg ggggtccatc tttgggacca ctgtcggcag aggcatcttc aacgatggcc   4680
tttcctttat cgcaatgatg gcatttgtag gagccacctt ccttttccac tatcttcaca   4740
ataaagtgac agatagctgg gcaatggaat ccgaggaggt ttccggatat taccctttgt   4800
tgaaaagtct cacatcggac catcacatca atccacttgc tttgaagacg tggttggaac   4860
```

```
gtcttctttt tccacgatgc tcctcgtggg tgggggtcca tctttgggac cactgtcggc   4920
agaggcatct tcaacgatgg cctttccttt atcgcaatga tggcatttgt aggagccacc   4980
ttccttttcc actatcttca caataaagtg acagatagct gggcaatgga atccgaggag   5040
gtttccggat attacccttt gttgaaaagt ctcacatcgg accacgcgtc acagttgagg   5100
tatttcggat cgtggcgatc gctatcccca ggcgcgccaa gggcgaattc gacccagctt   5160
tcttgtacaa agtggtgatc ggtccggttc ggctgcggcc gcattaccct gttatcccta   5220
atctcgttta actatgactc tcttaaggta gccaaattcc ggaaaacgac ttaatcagct   5280
aatacaaact atcagtgttt gacaggatat attggcgggt aaacctaaga gaaaagagcg   5340
tttattagaa taatcggata tttaaaaggg cgtgaaaagg tttatccgtt cgtccatttg   5400
tatgtgcatg cggctggggc gagcaccaga cggagcaccg ccaggatcac gagccatatc   5460
ctgacgaatg ggttctcgtc caacgcccct ttatcgacag tatgtgaatt tgcagtgtgg   5520
ccgcgatcaa cgcacactgg ccttgggtct gaagggtgat cttcaaaacg aaccccccgtc   5580
ttggtggtca gtgtgatggg cacatcgctt actcctcagt caccctttga gccagataat   5640
taagaggcaa atgcaattgg ctcaggctgc catcgtcccc ccgtgcgaaa cctgcacgtc   5700
cgcgtcaaag aaataaccgg cacctcttgc tgtttttatc agttgagggc ttgacggatc   5760
agcctcaagt ttgcggcgca gcctcaaaat gagaacatct atactcctgt cataaacctc   5820
ctcgtcgcgt actcgactgg caatgagaag ttgctcgcgc gatagaacgt cgcggggttt   5880
ctctaaaaac gcgaggagaa gattgaactc acctgccgta agtttcacct caccgccagc   5940
ttcggacatc aagcgacgtt gcctgagatt aagtgtccag tcagtaaaac aaaaagaccg   6000
tcggtctttg gagcggacaa cgttggggcg cacgcgcaag gcaacccgaa tgcgtgctag   6060
aaactctctg atactgaacg gcttagcgat aaaatcactt gctcctagct caagtgcaac   6120
aactttatcc gtctcctcaa ggcggtcgcc actgataatt atgattggaa tatcagactt   6180
tgccgccaga ttacgaacga tctcaagccc atcttcacga cctaaatcta gatcaacaac   6240
cacgacatcg accgtcgcgg aagagagtac tcttgtgaac tgggtgctgt cggctaccgc   6300
ggtcactttg aaggcgtgga tcgtaaggta ttcaataata agatgccgca tagcgacgtc   6360
gtcatcgaca agaagaacgt gtttcaacgg ctcacctttc aatctaaaat ctgaaccctt   6420
gttcacagcg cttgagaaat tttcacgtga aggatgtaca atcatctcca gctaaatggg   6480
cagttcgtca gaattgcggc tgaccgcgga tgacaaaaat gcgaaccaag tatttcaatt   6540
ttatgacaaa aattctcaat cgttgttaca agtgaaacgc ttcgaggtta cagctactat   6600
tgatttagga gatcgcctat ggtctcgccc cggcgtcgtg cgtccgccgc gagccgcatg   6660
ccaaccacag ggttcccctc gggatcaaag tactttgatc caacccctcc gctgctatag   6720
tgcagtcggc ttctgacgtt cagtgcagcc gtcttctgaa aacgacatgt cgcacaagtc   6780
ctaagttacg cgacaggctg ccgccctgcc cttttcctgg cgttttcttg tcgcgtgttt   6840
tagtcgcata aagtagaata cttgcgacta gaaccggaga cattacgcca tgaacaagag   6900
cgccgccgct ggcctgctgg gctatgcccg cgtcagcacc gacgaccagg acttgaccaa   6960
ccaacgggcc gaactgcacg cggccggctg caccaagctg ttttccgaga agatcaccgg   7020
caccaggcgc gaccgcccgg agctggccag gatgcttgac cacctacgcc ctggcgacgt   7080
tgtgacagtg accaggctag accgcctggc ccgcagcacc cgcgacctac tggacattgc   7140
cgagcgcatc caggaggccg gcgcgggcct gcgtagcctg gcagagccgt gggccgacac   7200
```

```
caccacgccg gccggccgca tggtgttgac cgtgttcgcc ggcattgccg agttcgagcg   7260
ttccctaatc atcgaccgca cccggagcgg gcgcgaggcc gccaaggccc gaggcgtgaa   7320
gtttggcccc cgccctaccc tcaccccggc acagatcgcg cacgcccgcg agctgatcga   7380
ccaggaaggc cgcaccgtga aagaggcggc tgcactgctt ggcgtgcatc gctcgaccct   7440
gtaccgcgca cttgagcgca gcgaggaagt gacgcccacc gaggccaggc ggcgcggtgc   7500
cttccgtgag gacgcattga ccgaggccga cgccctggct gctgctgaga atgaacgcca   7560
agaggaacaa gcatgaaacc gcaccaggac ggccaggacg aaccgttttt cattaccgaa   7620
gagatcgagg cggagatgat cgcggccggg tacgtgttcg agccgcccgc gcacgtctca   7680
accgtgcggc tgcatgaaat cctggccggt ttgtctgatg ccaagctggc ggcctggccg   7740
gccagcttgg ccgctgaaga aaccgagcgc cgccgtctaa aaaggtgatg tgtatttgag   7800
taaaacagct tgcgtcatgc ggtcgctgcg tatatgatgc gatgagtaaa taaacaaata   7860
cgcaagggga acgcatgaag gttatcgctg tacttaacca gaaaggcggg tcaggcaaga   7920
cgaccatcgc aacccatcta gcccgcgccc tgcaactcgc tggggccgat gttctgttag   7980
tcgattccga tccccagggc agtgcccgcg attgggcggc cgtgcgggaa gatcaaccgc   8040
taaccgttgt cggcatcgac cgcccgacga ttgaccgcga cgtgaaggcc atcggccggc   8100
gcgacttcgt agtgatcgac ggagcgcccc aggcggcgga cttggctgtg tccgcgatca   8160
aggcagccga cttcgtgctg attccggtgc agccaagccc ttacgacata tgggccaccg   8220
ccgacctggt ggagctggtt aagcagcgca ttgaggtcac ggatggaagg ctacaagcgg   8280
cctttgtcgt gtcgcgggcg atcaaaggca cgcgcatcgg cggtgaggtt gccgaggcgc   8340
tggccgggta cgagctgccc attcttgagt cccgtatcac gcagcgcgtg agctacccag   8400
gcactgccgc cgccggcaca accgttcttt aatcagaacc cgagggcgac gctgcccgcg   8460
aggtccaggc gctggccgct gaaattaaat caaaactcat ttgagttaat gaggtaaaga   8520
gaaaatgagc aaaagcacaa acacgctaag tgccggccgt ccgagcgcac gcagcagcaa   8580
ggctgcaacg ttggccagcc tggcagacac gccagccatg aagcgggtca actttcagtt   8640
gccggcggag gatcacacca agctgaagat gtacgcggta cgccaaggca agaccattac   8700
cgagctgcta tctgaataca tcgcgcagct accagagtaa atgagcaaat gaataaatga   8760
gtagatgaat tttagcggct aaaggaggcg gcatggaaaa tcaagaacaa ccaggcaccg   8820
acgccgtgga atgccccatg tgtggaggaa cgggcggttg gccaggcgta agcggctggg   8880
ttgcctgccg gccctgcaat ggcactggaa cccccaagcc cgaggaatcg gcgtgagcgg   8940
tcgcaaacca tccggcccgg tacaaatcgg cgcggcgctg ggtgatgacc tggtggagaa   9000
gttgaaggcc gcgcaggccg cccagcggca acgcatcgag gcagaagcac gccccggtga   9060
atcgtggcaa gctgctgctg atcgaatccg caaagaatcc cggcaaccgc cggcagccgg   9120
tgcgccgtcg attaggaagc cgcccaaggg cgacgagcaa ccagattttt tcgttccgat   9180
gctctatgac gtgggcaccc gcgatagtcg cagcatcatg gacgtggccg ttttccgtct   9240
gtcgaagcgt gaccgacgag ctggcgaggt gatccgctac gagcttccag acgggcacgt   9300
agaggtttcc gcagggccgg ccggcatggc cagtgtgtgg gattacgacc tggtactgat   9360
ggcggtttcc catctaaccg aatccatgaa ccgataccgg gaagggaagg gagacaagcc   9420
cggccgcgtg ttccgtccac acgttgcgga cgtactcaag ttctgccggc gagccgatgg   9480
cggaaagcag aaagacgacc tggtagaaac ctgcattcgg ttaaacacca cgcacgttgc   9540
catgcagcgt accaagaagg ccaagaacgg ccgcctggtg acggtatccg agggtgaagc   9600
```

```
cttgattagc cgctacaaga tcgtaaagag cgaaaccggg cggccggagt acatcgagat    9660
cgaactggct gattggatgt accgcgagat cacagaaggc aagaacccgg acgtgctgac    9720
ggttcacccc gattactttt tgatcgaccc cggcatcggc cgttttctct accgcctggc    9780
acgccgcgcc gcaggcaagg cagaagccag atggttgttc aagacgatct acgaacgcag    9840
tggcagcgcc ggagagttca agaagttctg tttcaccgtg cgcaagctga tcgggtcaaa    9900
tgacctgccg gagtacgatt tgaaggagga ggcggggcag gctggcccga tcctagtcat    9960
gcgctaccgc aacctgatcg agggcgaagc atccgccggt tcctaatgta cggagcagat   10020
gctagggcaa attgccctag caggggaaaa aggtcgaaaa ggtctctttc ctgtggatag   10080
cacgtacatt gggaacccaa agccgtacat tgggaaccgg aacccgtaca ttgggaaccc   10140
aaagccgtac attgggaacc ggtcacacat gtaagtgact gatataaaag agaaaaaagg   10200
cgatttttcc gcctaaaact ctttaaaact tattaaaact cttaaaaccc gcctggcctg   10260
tgcataactg tctggccagc gcacagccga agagctgcaa aaagcgccta cccttcggtc   10320
gctgcgctcc ctacgccccg ccgcttcgcg tcggcctatc acggccgctg gccgctcaaa   10380
aatggctggc ctacggccag gcaatctacc agggcgcgga caagccgcgc cgtcgccact   10440
cgaccgccgg cgcccacatc aaggcaccct gcctcgcgcg tttcggtgat gacggtgaaa   10500
acctctgaca catgcagctc ccggagacgg tcacagcttg tctgtaagcg gatgccggga   10560
gcagacaagc ccgtcagggc gcgtcagcgg gtgttggcgg gtgtcggggc gcagccatga   10620
cccagtcacg tagcgatagc ggagtgtata ctggcttaac tatgcggcat cagagcagat   10680
tgtactgaga gtgcaccata tgcggtgtga aataccgcac agatgcgtaa ggagaaaata   10740
ccgcatcagg cgctcttccg cttcctcgct cactgactcg ctgcgctcgg tcgttcggct   10800
gcggcgagcg gtatcagctc actcaaaggc ggtaatacgg ttatccacag aatcagggga   10860
taacgcagga aagaacatgt gagcaaaagg ccagcaaaag gccaggaacc gtaaaaaggc   10920
cgcgttgctg gcgtttttcc ataggctccg cccccctgac gagcatcaca aaaatcgacg   10980
ctcaagtcag aggtggcgaa acccgacagg actataaaga taccaggcgt ttccccctgg   11040
aagctccctc gtgcgctctc ctgttccgac cctgccgctt accggatacc tgtccgcctt   11100
tctcccttcg ggaagcgtgg cgctttctca tagctcacgc tgtaggtatc tcagttcggt   11160
gtaggtcgtt cgctccaagc tgggctgtgt gcacgaaccc cccgttcagc ccgaccgctg   11220
cgccttatcc ggtaactatc gtcttgagtc caacccggta agacacgact tatcgccact   11280
ggcagcagcc actggtaaca ggattagcag agcgaggtat gtaggcggtg ctacagagtt   11340
cttgaagtgg tggcctaact acggctacac tagaaggaca gtatttggta tctgcgctct   11400
gctgaagcca gttaccttcg gaaaaagagt tggtagctct tgatccggca aacaaaccac   11460
cgctggtagc ggtggttttt ttgtttgcaa gcagcagatt acgcgcagaa aaaaaggatc   11520
tcaagaagat cctttgatct tttctacggg gtctgacgct cagtggaacg aaaactcacg   11580
ttaagggatt ttggtcatgc attctaggta ctaaaacaat tcatccagta aaatataata   11640
ttttattttc tcccaatcag gcttgatccc cagtaagtca aaaaatagct cgacatactg   11700
ttcttccccg atatcctccc tgatcgaccg gacgcagaag gcaatgtcat accacttgtc   11760
cgccctgccg cttctcccaa gatcaataaa gccacttact ttgccatctt tcacaaagat   11820
gttgctgtct cccaggtcgc cgtgggaaaa gacaagttcc tcttcgggct tttccgtctt   11880
taaaaaatca tacagctcgc gcggatcttt aaatggagtg tcttcttccc agttttcgca   11940
```

```
atccacatcg gccagatcgt tattcagtaa gtaatccaat tcggctaagc ggctgtctaa  12000

gctattcgta tagggacaat ccgatatgtc gatggagtga aagagcctga tgcactccgc  12060

atacagctcg ataatctttt cagggctttg ttcatcttca tactcttccg agcaaaggac  12120

gccatcggcc tcactcatga gcagattgct ccagccatca tgccgttcaa agtgcaggac  12180

ctttggaaca ggcagctttc cttccagcca tagcatcatg tccttttccc gttccacatc  12240

ataggtggtc cctttatacc ggctgtccgt catttttaaa tataggtttt cattttctcc  12300

caccagctta tataccttag caggagacat tccttccgta tcttttacgc agcggtattt  12360

ttcgatcagt tttttcaatt ccggtgatat tctcatttta gccatttatt atttccttcc  12420

tcttttctac agtatttaaa gataccccaa gaagctaatt ataacaagac gaactccaat  12480

tcactgttcc ttgcattcta aaaccttaaa taccagaaaa cagctttttc aaagttgttt  12540

tcaaagttgg cgtataacat agtatcgacg gagccgattt tgaaaccgcg gtgatcacag  12600

gcagcaacgc tctgtcatcg ttacaatcaa catgctaccc tccgcgagat catccgtgtt  12660

tcaaacccgg cagcttagtt gccgttcttc cgaatagcat cggtaacatg agcaaagtct  12720

gccgccttac aacggctctc ccgctgacgc cgtcccggac tgatgggctg cctgtatcga  12780

gtggtgattt tgtgccgagc tgccggtcgg ggagctgttg gctggctggt ggcaggatat  12840

attgtggtgt aaacaaattg acgcttagac aacttaataa cacattgcgg acgtttttaa  12900

tgtactgaat taacgccgaa ttaatgtcga c                                 12931
```

<210> SEQ ID NO 61
<211> LENGTH: 82
<212> TYPE: DNA
<213> ORGANISM: Arabidopsis thaliana

<400> SEQUENCE: 61

```
tgacagaaga gagtgagcac acaaaggcaa tttgcatatc attgcacttg cttctcttgc     60

gtgctcactg ctctttctgt ca                                              82
```

<210> SEQ ID NO 62
<211> LENGTH: 180
<212> TYPE: PRT
<213> ORGANISM: Petunia axillaris

<400> SEQUENCE: 62

```
Asp Ser Leu Val Gly Gln Ala Leu Phe Gly Asp Gly Ala Gly Ala Ile
1               5                   10                  15

Ile Ile Gly Ser Asp Pro Ile Pro Gly Val Glu Arg Pro Leu Phe Glu
            20                  25                  30

Leu Val Ser Ala Ala Gln Thr Leu Leu Pro Asp Ser His Gly Ala Ile
        35                  40                  45

Asp Gly His Leu Arg Glu Val Gly Leu Thr Phe His Leu Leu Lys Asp
    50                  55                  60

Val Pro Gly Leu Ile Ser Lys Asn Ile Glu Lys Ser Leu Glu Glu Ala
65                  70                  75                  80

Phe Lys Pro Leu Gly Ile Ser Asp Trp Asn Ser Leu Phe Trp Ile Ala
                85                  90                  95

His Pro Gly Gly Pro Ala Ile Leu Asp Gln Val Glu Ile Lys Leu Gly
            100                 105                 110

Leu Lys Pro Glu Lys Leu Lys Ala Thr Arg Asn Val Leu Ser Asp Tyr
        115                 120                 125

Gly Asn Met Ser Ser Ala Cys Val Leu Phe Ile Leu Asp Glu Met Arg
```

```
    130                 135                 140

Lys Ala Ser Ala Lys Glu Gly Leu Gly Thr Thr Gly Glu Gly Leu Glu
145                 150                 155                 160

Trp Gly Val Leu Phe Gly Phe Gly Pro Gly Leu Thr Val Glu Thr Val
                165                 170                 175

Val Leu His Ser
            180


<210> SEQ ID NO 63
<211> LENGTH: 547
<212> TYPE: DNA
<213> ORGANISM: Petunia axillaris

<400> SEQUENCE: 63

gcaacactgt ggaggacaac agtctcaact gttagcccag gcccaaatcc aaaaagaaca     60

ccccactcaa gcccttcacc agtagttcct aaaccttctt tggctgaggc ctttctcatt    120

tcatccaaaa taaacagtac acaagcactt gacatgttac catagtcact taacacattc    180

cttgtagcct taagtttctc gggctttagg cccaacttta tttcaacttg gtccaaaatt    240

gcaggcccac ctggatgagc aatccagaat agagagttcc aatcagaaat gcccaaaggt    300

ttaaatgctt cctcaaggct cttctcaata ttttttgaga tcagcccagg aacatctttg    360

agtaagtgga atgtaagccc aacttcacgg agatggccat caatagcacc atggctatct    420

gggagaagag tttgggctgc tgaaacgagc tcgaacaaag gcctctcgac tcctggaatt    480

ggatcagaac ctataatgat cgcgcctgcc ccatcaccaa aaagggcttg gccaactaaa    540

ctatcca                                                              547


<210> SEQ ID NO 64
<211> LENGTH: 1094
<212> TYPE: DNA
<213> ORGANISM: Petunia axillaris

<400> SEQUENCE: 64

gcaacactgt ggaggacaac agtctcaact gttagcccag gcccaaatcc aaaaagaaca     60

ccccactcaa gcccttcacc agtagttcct aaaccttctt tggctgaggc ctttctcatt    120

tcatccaaaa taaacagtac acaagcactt gacatgttac catagtcact taacacattc    180

cttgtagcct taagtttctc gggctttagg cccaacttta tttcaacttg gtccaaaatt    240

gcaggcccac ctggatgagc aatccagaat agagagttcc aatcagaaat gcccaaaggt    300

ttaaatgctt cctcaaggct cttctcaata ttttttgaga tcagcccagg aacatctttg    360

agtaagtgga atgtaagccc aacttcacgg agatggccat caatagcacc atggctatct    420

gggagaagag tttgggctgc tgaaacgagc tcgaacaaag gcctctcgac tcctggaatt    480

ggatcagaac ctataatgat cgcgcctgcc ccatcaccaa aaagggcttg gccaactaaa    540

ctatccatgg atagtttagt tggccaagcc ctttttggtg atggggcagg cgcgatcatt    600

ataggttctg atccaattcc aggagtcgag aggcctttgt tcgagctcgt ttcagcagcc    660

caaactcttc tcccagatag ccatggtgct attgatggcc atctccgtga agttgggctt    720

acattccact tactcaaaga tgttcctggg ctgatctcaa aaaatattga gaagagcctt    780

gaggaagcat ttaaaccttt gggcatttct gattggaact ctctattctg gattgctcat    840

ccaggtgggc ctgcaatttt ggaccaagtt gaaataaagt tgggcctaaa gcccgagaaa    900

cttaaggcta caaggaatgt gttaagtgac tatggtaaca tgtcaagtgc ttgtgtactg    960
```

-continued

```
tttattttgg atgaaatgag aaaggcctca gccaaagaag gtttaggaac tactggtgaa    1020

gggcttgagt ggggtgttct ttttggattt gggcctgggc taacagttga gactgttgtc    1080

ctccacagtg ttgc                                                      1094
```